(12) United States Patent
Abelin et al.

(10) Patent No.: US 11,965,892 B2
(45) Date of Patent: *Apr. 23, 2024

(54) HLA-BASED METHODS AND COMPOSITIONS AND USES THEREOF

(71) Applicant: BioNTech US Inc., Cambridge, MA (US)

(72) Inventors: Jennifer Grace Abelin, Boston, MA (US); Rob Carl Oslund, Brookline, MA (US); Nir Hacohen, Brookline, MA (US); Dominik Barthelme, Belmont, MA (US); Michael Rooney, Boston, MA (US)

(73) Assignee: BioNTech US Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/484,918

(22) PCT Filed: Feb. 12, 2018

(86) PCT No.: PCT/US2018/017849
§ 371 (c)(1),
(2) Date: Aug. 9, 2019

(87) PCT Pub. No.: WO2018/148671
PCT Pub. Date: Aug. 16, 2018

(65) Prior Publication Data
US 2020/0096521 A1    Mar. 26, 2020

Related U.S. Application Data

(60) Provisional application No. 62/461,162, filed on Feb. 20, 2017, provisional application No. 62/457,978, filed on Feb. 12, 2017.

(51) Int. Cl.
*G16B 20/30* (2019.01)
*A61K 35/12* (2015.01)
(Continued)

(52) U.S. Cl.
CPC ......... *G01N 33/6878* (2013.01); *A61K 35/12* (2013.01); *A61K 39/0011* (2013.01);
(Continued)

(58) Field of Classification Search
CPC ........ G16B 20/30; G16B 30/00; G16B 40/00; G16B 40/20
See application file for complete search history.

(56) References Cited

U.S. PATENT DOCUMENTS 798,739 A    9/1905  Machlet
4,588,585 A   5/1986  Mark et al.
(Continued)

FOREIGN PATENT DOCUMENTS

WO    WO-2005085323 A2    9/2005
WO    WO-2016128060 A1    8/2016
(Continued)

OTHER PUBLICATIONS

Burr, Marian L., et al., MHC class I molecules are preferentially ubiquitinated on endoplasmic reticular luminal residues during HRD1 ubiquitin E3 ligase-mediated dislocation, PNAS, vol. 110, No. 35, Aug. 27, 2013, pp. 14290-14295.
(Continued)

*Primary Examiner* — Olivia M. Wise
(74) *Attorney, Agent, or Firm* — Wilson Sonsini Goodrich & Rosati

(57) ABSTRACT

Systems, compositions, and methods for isolating HLA-peptides from cells. A universal platform and methods for profiling the HLA-peptidome, enabling identification of
(Continued)

endogenously presented HLA-peptides from cell lines expressing any possible class I or II construct.

21 Claims, 24 Drawing Sheets

Specification includes a Sequence Listing.

(51) Int. Cl.
　　A61K 39/00　　(2006.01)
　　A61K 39/39　　(2006.01)
　　G01N 33/68　　(2006.01)
　　G16B 20/20　　(2019.01)
　　G16B 30/00　　(2019.01)
　　G16B 35/10　　(2019.01)
　　G16B 35/20　　(2019.01)
　　G16B 40/00　　(2019.01)
　　G16B 40/20　　(2019.01)
　　C40B 40/02　　(2006.01)
　　C40B 40/10　　(2006.01)

(52) U.S. Cl.
　　CPC ............. *A61K 39/39* (2013.01); *G16B 20/20* (2019.02); *G16B 20/30* (2019.02); *G16B 30/00* (2019.02); *G16B 35/10* (2019.02); *G16B 35/20* (2019.02); *G16B 40/00* (2019.02); *G16B 40/20* (2019.02); *A61K 2039/5154* (2013.01); *C40B 40/02* (2013.01); *C40B 40/10* (2013.01)

(56) References Cited

U.S. PATENT DOCUMENTS

| | | |
|---|---|---|
| 4,703,004 A | 10/1987 | Hopp et al. |
| 4,751,180 A | 6/1988 | Cousens et al. |
| 4,851,341 A | 7/1989 | Hopp et al. |
| 4,935,233 A | 6/1990 | Bell et al. |
| 5,126,132 A | 6/1992 | Rosenberg |
| 5,185,146 A | 2/1993 | Altenburger |
| 5,443,983 A | 8/1995 | Ochoa et al. |
| 5,506,121 A | 4/1996 | Skerra et al. |
| 5,623,584 A | 4/1997 | Kurumida |
| 5,635,363 A | 6/1997 | Altman et al. |
| 5,658,785 A | 8/1997 | Johnson |
| 5,686,281 A | 11/1997 | Roberts |
| 5,723,584 A | 3/1998 | Schatz |
| 5,766,920 A | 6/1998 | Babbitt et al. |
| 5,833,975 A | 11/1998 | Paoletti et al. |
| 5,841,828 A | 11/1998 | Gordon et al. |
| 5,843,728 A | 12/1998 | Seed et al. |
| 5,846,827 A | 12/1998 | Celis et al. |
| 5,874,239 A | 2/1999 | Schatz |
| 5,906,936 A | 5/1999 | Eshhar et al. |
| 5,912,170 A | 6/1999 | Seed et al. |
| 5,912,172 A | 6/1999 | Eshhar et al. |
| 5,932,433 A | 8/1999 | Schatz |
| 5,942,235 A | 8/1999 | Paoletti |
| 5,994,136 A | 11/1999 | Naldini et al. |
| 6,004,811 A | 12/1999 | Seed et al. |
| 6,013,516 A | 1/2000 | Verma et al. |
| 6,090,393 A | 7/2000 | Fischer |
| 6,156,567 A | 12/2000 | Fischer |
| 6,165,782 A | 12/2000 | Naldini et al. |
| 6,194,207 B1 | 2/2001 | Bell et al. |
| 6,251,385 B1 | 6/2001 | Terman |
| 6,255,073 B1 | 7/2001 | Cai et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,392,013 B1 | 5/2002 | Seed et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,537,540 B1 | 3/2003 | Burstein et al. |
| 6,537,594 B1 | 3/2003 | Paoletti et al. |
| 6,753,162 B1 | 6/2004 | Seed et al. |
| 6,780,407 B1 | 8/2004 | Paoletti et al. |
| 6,793,926 B1 | 9/2004 | Rasty et al. |
| 6,869,794 B2 | 3/2005 | Vogels et al. |
| 6,893,865 B1 | 5/2005 | Lockert et al. |
| 6,913,922 B1 | 7/2005 | Bout et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,115,391 B1 | 10/2006 | Chen et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,198,784 B2 | 4/2007 | Kingsman et al. |
| 7,255,862 B1 | 8/2007 | Tartaglia et al. |
| 7,259,015 B2 | 8/2007 | Kingsman et al. |
| 7,303,910 B2 | 12/2007 | Bebbington et al. |
| 7,351,581 B2 | 4/2008 | Aulakh |
| 7,399,838 B2 | 7/2008 | Reiter |
| 7,741,465 B1 | 6/2010 | Eshhar et al. |
| 7,985,739 B2 | 7/2011 | Kay et al. |
| 8,088,379 B2 | 1/2012 | Robbins et al. |
| 8,211,422 B2 | 7/2012 | Eshhar et al. |
| 8,227,432 B2 | 7/2012 | Hackett et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 8,999,937 B2 | 4/2015 | Srinivasan |
| 9,101,584 B2 | 8/2015 | June et al. |
| 9,102,760 B2 | 8/2015 | June et al. |
| 9,102,761 B2 | 8/2015 | June et al. |
| 9,862,927 B2 | 1/2018 | Banchereau et al. |
| 10,055,540 B2 | 8/2018 | Yelensky et al. |
| 11,183,272 B2 * | 11/2021 | Rooney ................. G16B 40/10 |
| 11,650,211 B2 | 5/2023 | Abelin et al. |
| 2004/0013648 A1 | 1/2004 | Kingsman et al. |
| 2006/0258607 A1 | 11/2006 | Jarosch et al. |
| 2007/0025970 A1 | 2/2007 | Kingsman et al. |
| 2007/0134197 A1 | 6/2007 | Eichner et al. |
| 2008/0254008 A1 | 10/2008 | Dropulic et al. |
| 2009/0111106 A1 | 4/2009 | Mitrophanous et al. |
| 2009/0130134 A1 | 5/2009 | Pancre et al. |
| 2011/0293571 A1 | 12/2011 | Widdowson et al. |
| 2012/0295960 A1 | 11/2012 | Palfi et al. |
| 2013/0071414 A1 | 3/2013 | Dotti et al. |
| 2014/0178438 A1 | 6/2014 | Sahin et al. |
| 2015/0031566 A1 | 1/2015 | Napper et al. |
| 2017/0199961 A1 | 7/2017 | Yelensky et al. |
| 2017/0212984 A1 | 7/2017 | Yelensky et al. |
| 2022/0199198 A1 | 6/2022 | Rooney et al. |

FOREIGN PATENT DOCUMENTS

| | | |
|---|---|---|
| WO | WO-2017184590 A1 | 10/2017 |
| WO | WO-2018005559 A1 | 1/2018 |
| WO | WO-2018195357 A1 | 10/2018 |
| WO | WO-2018208856 A1 | 11/2018 |
| WO | WO-2019178081 A1 | 9/2019 |

OTHER PUBLICATIONS

Cherryholmes et al., Current methods of epitope identification for cancer vaccine design, Vaccine 2015, vol. 33, pp. 7408-7414 (Year: 2015).

International Search Report and Written Opinion dated May 19, 2020, for PCT/US2019/068084.

(56) References Cited

OTHER PUBLICATIONS

Non-Final Office Action dated Jun. 10, 2020, for U.S. Appl. No. 16/692,544.
Shraibman, et al., "Identification of Tumor Antigens Among the HLA Peptidomes of Glioblastoma Tumors and Plasma" (2019)Molecular & Cellular Proteomics 18, 12545-1268.
Prilliman, et al., "Large-scale production of class I bound peptides: assigning a signature to HLA-B*1501" (1997) Immunogenetics 45: 379-385.
Bassani-Sternberg et al., Mass Spectrometry of Human Leukocyte Antigen Class I Peptidomes Reveals Strong Effects of Protein Abundance and Turnover on Antigen Presentation, Mol Cell Proteomics, 14:658-673 (2015).
Caron et al., Analysis of MHC immunopeptidomes using mass spectrometry, Mol Cell Proteomics (2015), doi: 10.1074/mcp.0115. 052431.
Cobbold et al., MHC class I-associated phosphopeptides are the targets of memory-like immunity in leukemia, Sci Trans Med. Sep. 18, 2013;5(203).
Horig, et al. 2000. Phase I clinical trial of a recombinant canarypoxvirus (ALVAC) vaccine expressing human carcinoembryonic antigen and the B7.1 co-stimulatory molecule. Cancer Immunol Immunother 49:504-514.
Leitner, W.W., et al., Immune responses induced by intramuscular or gene gun injection of protective deoxyribonucleic acid vaccines that express the circumsporozoite protein from Plasmodium berghei malaria parasites, J Immunol Dec. 15, 1997, 159(12)6112-6119.
Mandl et al., Immunotherapy with MVA-BN®-HER2 induces HER-2-specific Th1 immunity and alters the intratumoral balance of effector and regulatory T cells, Cancer Immunol Immunother. Jan. 2012; 61(1): 19-29.
Maratea et al., "Deletion and fusion analysis of the phage ØX174 lysis gene E," Gene, 40:39-46, 1985.
Marshall, et al. 2000. Phase I study in advanced cancer patients of a diversified prime-and- boost vaccination protocol using recombinant vaccinia virus and recombinant nonreplicating avipox virus to elicit anti-carcinoembryonic antigen immune responses. J Clin Oncol 18:3964-3973.
Martin, et al. GAP domains responsible for ras p21-dependent inhibition of muscarinic atrial K+ channel currents. Science. Jan. 10, 1992;255(5041):192-4.
Matsushita et al, Cancer exome analysis reveals a T-cell-dependent mechanism of cancer immunoediting, Nature 482:400 (2012).
Medzihradszky KF and Chalkley RJ, Lessons in de novo Peptide Sequencing by Tandem Mass Spectrometry ,Mass Spectrom Rev. Jan.-Feb. 2015;34(1):43-63.
Merrifield et al. Solid Phase Peptide Synthesis I. J Am Chem Soc 85:2149-2154 (1963).
Merrifield, Solid Phase Synthesis, Science 232:341-347 (1986).
Meyer, H. et al., (1991), Mapping of deletions in the genome of the highly attenuated vaccinia virus MVA and their influence on virulence, J. Gen. Virol. 72, 1031-1038.
Miller et al. Construction and properties of retrovirus packaging cells based on gibbon ape leukemia virus. J Virol. 65(5):2220-2224 (1991).
Mor, et al., (1995), Complexity of the cytokine and antibody response elicited by immunizing mice with Plasmodium yoelii circumsporozoite protein plasmid DNA, The Journal of Immunology 155 (4): 2039-2046.
Moss, Reflections on the Early Development of Poxvirus Vectors, Vaccine. 2013; 31(39):4220-4222.
Murphy, J. R. et al., "Genetic construction, expression, and melanoma-selective cytotoxicity of a diptheria toxin-related α-melanocyte-stimulating hormone fusion protein," PNAS US.A., 83(21):8258-8262 (1986).
Musey, L. et al. HIV-1 vaccination administered intramuscularly can induce both systemic and mucosal T cell immunity in HIV-1-uninfected individuals. J Immunol 2003;171:1094-101.
Paborsky, et al., Mammalian cell transient expression of tissue factor for the production of antigen, Protein Engineering, 3:547-53.
Paoletti, E. 1996. Applications of pox virus vectors to vaccination: an update. Proc Natl Acad Sci U S A 93:11349-11353.
Rammensee et al., "SYFPEITHI: database for MHC ligands and peptide motifs," Immunogenetics, Nov. 1999 vol. 50 p. 213-219.
Rammensee HG. "Chemistry of peptides associated with MHC class I and class II molecules," Curr Opin Immunol. Feb. 1995;7(1):85-96.
Rasmussen, Michael, Uncovering the Peptide-Binding Specificities of HLA-C: A General Strategy to Determine the Specificity of Any MHC Class I Molecule, The Journal of Immunology, 2014, pp. 4790-4802.
Robinson et al., "Integrative clinical genomics of advanced prostate cancer," Cell 2015; 161(5):1215-1228.
Roche and Furuta, The ins and outs of MHC class II-mediated antigen processing and presentation, Nat Rev Immunol. Apr. 2015 ; 15(4): 203-216. doi:10.1038/nri3818.
Rolph et al., Recombinant viruses as vaccines and immunological tools. Curr Opin Immunol 9:517-524, 1997.
Rossjohn, J., 2015,Annu Rev Immunol. 2015;33:169-200. {doi: 10.1146/annurev-immunol-032414-112334. Epub Dec. 10, 2014}.
Sampson et al, Immunologic escape after prolonged progression-free survival with epidermal growth factor receptor variant III peptide vaccination in patients with newly diagnosed glioblastoma J Clin Oncol. 28:4722-4729 (2010).
Schmidt et al., Molecular interaction between the Strep-tag affinity peptide and its cognate target, streptavidin, J. Mol. Biol., 255(5):753-766, 1996.
Sharei, et al. A vector-free microfluidic platform for intracellular delivery. Proc Natl Acad Sci U S A. Feb. 5, 2013; 110(6): 2082-2087.
Skinner et al. Use of the Glu-Glu-Phe C-terminal epitope for rapid purification of the catalytic domain of normal and mutant ras GTPase-activating proteins. J. Biol. Chem. 266:15163-15166 (1991).
Skinner, W. S., et al., Isolation and Identification of Paralytic Peptides from Hemolymph of the Lepidopteran insects manduca sexta, Spodoptera exigua, and Heliothis virescens, J. Biological Chemistry, vol. 266, No. 20, Jul. 15, 1991, pp. 12873-12877.
Sommerfelt et al., Receptor interference groups of 20 retroviruses plating on human cells.(1990) Virol. 176:58-59.
Stern, L. J. et al. Crystal structure of the human class II MHC protein HLA-DR1 complexed with an influenza virus peptide. Nature 368, 215-221, doi: 10.1038/368215a0 (1994).
Trolle et al., "The Length Distribution of Class 1-Restricted T Cell Epitopes Is Determined by Both Peptide Supply and MHC Allele-Specific Binding Preference," J Immunol (2016), doi: 10.4049/jimmunol.1501721.
Unanue et al., (2016), Variations in MHC Class II Antigen Processing and Presentation in Health and Disease, Annual Review of Immunology, vol. 34, 265-297.
Verardi et al., A vaccinia virus renaissance New vaccine and immunotherapeutic uses after smallpox eradication, Hum Vaccin Immunother. Jul. 2012;8(7):961-70.
Vita et al., The immune epitope database (IEDB) 3.0, Nucleic Acids Res, 43:D405-D412 (2015).
Wahl et al., [43] Molecular hybridization of immobilized nucleic acids: Theoretical concepts and practical considerations, Methods in enzymology, Academic Press, 152:399-407 (1987).
Weiner et al., (1999), Genetic Vaccines, Scientific American 281 (1): 34-41.
Wilson et al Formation of infectious hybrid virions with gibbon ape leukemia virus and human T-cell leukemia virus retroviral envelope glycoproteins and the gag and pol proteins of Moloney murine leukemia virus. J Virol 63(5):2374-2378 (1989).
Yang, J. et al., In vivo biotinylation of the major histocompatibility complex (MHC) class II/peptide complex by coexpression of BirA enzyme for the generation of MHC class II/tetramers, Hum Immunol., Jul. 2004;65(7):692-9.
Zarling AL., 2006, Identification of class I MHC-associated phosphopeptides as targets for cancer immunotherapy, PNAS Oct. 3, 2006 103 (40) 14889-14894.
Zarling AL., et al.,2000, Phosphorylated Peptides Are Naturally Processed and Presented by Major Histocompatibility Complex Class I Molecules in Vivo, J. Exp Med., 192(12): 1755-1762.

(56) References Cited

OTHER PUBLICATIONS

"Berger, et al., "MHC class II transport at a glance" (2009) Journal of Cell Science 122, p. 1- 4".
DeLuca, Patrick P. et al., Parenteral Drug-Delivery Systems, Pharmaceutics and Pharmacy Practice, J.B. Lippincott Company, Philadelphia, PA, Banker and Chalmers, eds., pp. 238-250(1982).
"Sercarz, et al., "MHC-Guided processing: Binding of Large Antigen Fragments" Nature-Immunology (2003) vol. 3, p. 621-629".
"Hickman, et la., "Mining the plasma immunopeptidome for cancer peptides as biomarkers and beyond" (2010) PNAS vol. 107 No. 44, p. 18747-18748".
"Kim, et al., "Divergent paths for the selection of immunodominant epitopes from distinct antigenic sources" (2014) Nature Communications, pp. 1-16".
"Pathak, et al., "Endocytic Recycling is Required for the Presentation of an Exogenous Peptide via MHC Class II Molecules" (2000) Traffic 1: 561-569".
Shraibman, B. et al., "Identification of Tumor Antigens Among the HLA Peptidomes of Glioblastoma Tumors and Plasma," Molecular & Cellular Proteomics, 2019, vol. 18, pp. 1255-1268.
Prilliman, K. et al., "Large-scale production of class I bound peptides: assigning a signature to HLA-B*1501," Immunogenetics, 1997, vol. 45, pp. 379-385.
Abelin et al. (2017). Mass Spectrometry Profiling of HLA-Associated Peptidomes in Mono-allelic Cells Enables More Accurate Epitope Prediction. Immunity 46, 315-326.
Alarcon et al., DNA vaccines: technology and application as anti-parasite and anti-microbial agents, Advances in Parasitology, 42:343-410 (1999).
Alvarez et al., Computational Tools for the Identification and Interpretation of Sequence Motifs in Immunopeptidomes. Proteomics 18, 1700252 (2018).
Andreatta et al., GibbsCluster: unsupervised clustering and alignment of peptide sequences. Nucleic Acids Res. 45, W458-W463 (2017).
Archila et al., Tetramer-Guided Epitope Mapping: A Rapid Approach to Identify HLA-Restricted T-Cell Epitopes from Composite Allergens. In Food Allergens: Methods and Protocols, J. Lin, and M. Alcocer, eds. (New York, NY: Springer New York), pp. 199-209 (2017).
Ayers et al., IFN-γ-related mRNA profile predicts clinical response to PD-1 blockade. J. Clin. Invest. 127, 2930-2940 (2017).
Barra C., Footprints of antigen processing boost MHC class II natural ligand predictions. Genome Med. 10, 84 (2018).
Bozzacco et al., Mass spectrometry analysis and quantitation of peptides presented on the MHC II molecules of mouse spleen dendritic cells. J. Proteome Res. 10, 5016-5030 (2011).
Braendstrup et al., "MHC Class II Tetramers Made from Isolated Recombinant α and β Chains Refolded with Affinity-Tagged Peptides," PLoS One vol. 8, No. 9 (2013).
Bulik-Sullivan et al., Deep learning using tumor HLA peptide mass spectrometry datasets improves neoantigen identification. Nat. Biotechnol (2018).
Butler et al., Integrating single-cell transcriptomic data across different conditions, technologies, and species. Nat. Biotechnol. 36, 411 (2018).
Cancer Genome Atlas Network. Genomic Classification of Cutaneous Melanoma. Cell 161, 1681-1696 (2015).
Carithers et al., A Novel Approach to High-Quality Postmortem Tissue Procurement: The GTEx Project. Biopreservation Biobanking 13, 311-319 (2015).
Castello et al., Insights into RNA Biology from an Atlas of Mammalian mRNA-Binding Proteins. Cell 149, 1393-1406 (2012).
Cheng et al., SCRATCH: a protein structure and structural feature prediction server. Nucleic Acids Res. 33, W72-W76 (2005).
Chiang et al., A dendritic cell vaccine pulsed with autologous hypochlorous acid-oxidized ovarian cancer lysate primes effective broad antitumor immunity: from bench to bedside. Clin Cancer Res 19(17):4801-4815 (2013).

Chong et al., High-throughput and Sensitive Immunopeptidomics Platform Reveals Profound Interferonγ-Mediated Remodeling of the Human Leukocyte Antigen (HLA) Ligandome. Mol. Cell. Proteomics MCP 17, 533-548 (2018).
Clement et al., The Dendritic Cell Major Histocompatibility Complex II (MHC II) Peptidome Derives from a Variety of Processing Pathways and Includes Peptides with a Broad Spectrum of HLA-DM Sensitivity. J. Biol. Chem. 291, 5576-5595 (2016).
Constantino et al. (2012). Class II MHC Self-Antigen Presentation in Human B and T Lymphocytes. PLoS One 7, e29805 (2012).
Deniger et al., T-cell Responses TP53 Hotspot Mutations and Neoantigens Expressed by Human Ovarian Cancers, Clin Cancer Res., 24, 5562 (2018).
Dobin et al., Star: Ultrafast Universal RNA-Seq Aligner, Bioinformatics, Oct. 25, 2012, 29:15-21.
Emens et al., The interplay of immunotherapy and chemotherapy: harnessing potential synergies. Cancer Immunol. Res. 3, 436-443 (2015).
Encode project consortium et al., an integrated encyclopedia of DNA elements in the human genome. Nature. Sep. 6, 2012;489(7414):57-74. doi: 10.1038/nature11247.
Graham et al., Antigen discovery and specification of immunodominance hierarchies for MHCII-restricted epitopes, Nature Medicine, vol. 24, Nov. 2018, pp. 1762-1772.
He et al., Delving Deep into Rectifiers: Surpassing Human-Level Performance on ImageNet Classification. In the IEEE International Conference on Computer Vision (ICCV) (2015).
Henikoff et al. Amino acid substitution matrices from protein blocks. PNAS USA 89(22):10915-10919 (1992).
Hinton, G.E., Rectified linear units improve restricted boltzmann machines vinod nair (2010).
Hoff et al., "Proteome Sampling by the HLA Class I Antigen Processing Pathway", PLoS Computational Biology, vol. 8, Issue 5, p. 1-9 (2012).
Hoof et al., Proteome Sampling by the HLA Class I Antigen Processing Pathway. PLoS Comput Biol 8, e1002517 (2012).
Hortin et al., High-Abundance Polypeptides of the Human Plasma Proteome Comprising the Top 4 Logs of Polypeptide Abundance. Clin. Chem. 54, 1608 (2008).
Hunt et al., Characterization of peptides bound to the class I MHC molecule HLA-A2.1 by mass spectrometry, Science, 255:1261-1263 (1992).
International Search Report dated Apr. 30, 2018 for PCT/US18/017849.
Ioffe et al., Batch Normalization: Accelerating Deep Network Training by Reducing Internal Covariate Shift. Eprint ArXiv150203167 arXiv:1502.03167 (2015).
Jerby-Arnon et al., A Cancer Cell Program Promotes T Cell Exclusion and Resistance to Checkpoint Blockade. Cell 175, 984-997.e24 (2018).
Justesen et al., Functional recombinant MHC class II molecules and high-throughput peptide-binding assays. Immunome Res. 5, 2-2 (2009).
Karosiene et al., NetMHCIIpan-3.0, a common pan-specific MHC class II prediction method including all three human MHC class II isotypes, HLA-DR, HLA-DP and HLA-DQ. Immunogenetics 65 (2013).
Kent et al., The Human Genome Browser at UCSC. Genome Res. 12:996-1006 (2002).
Kenter et al., Vaccination against HPV-16 oncoproteins for vulvar intraepithelial neoplasia, New England Journal of Medicine, 361(19): 1838-1847 (2009).
Khodadoust et al., Antigen presentation profiling reveals recognition of lymphoma immunoglobulin neoantigens, Nature 543, 723-727 (2017).
Kim et al., Derivation of an amino acid similarity matrix for peptide:MHC binding and its application as a Bayesian prior. BMC Bioinformatics 10, 1-11 (2009).
Kreiter et al., Mutant MHC class II epitopes drive therapeutic immune responses to cancer. Nature 520, 692-696 (2015).
Kronke et al., Lenalidomide causes selective degradation of IKZF1 and IKZF3 in multiple myeloma cells. Science. 343(6168):301-5 (2014).

(56) References Cited

OTHER PUBLICATIONS

Kronke et al., Lenalidomide induces ubiquitination and degradation of CK1alpha in del(5q) MDS. Nature. 523(7559):183-188 (2015).
Krutzik et al, Fluorescent cell barcoding for multiplex flow cytometry. Curr. Protoc. Cytom. Chapter 6, Unit-6.31 (2011).
Lecun et al., Backpropagation Applied to Handwritten Zip Code Recognition. Neural Comput. 1, 541-551 (1989).
Li et al., The Sequence Alignment/Map format and SAMtools, Bioinformatics, 25(16):2078-2079 (2009).
Li et al., Reference component analysis of single-cell transcriptomes elucidates cellular heterogeneity in human colorectal tumors. Nat. Genet. 49, 708 (2017).
Loffler et al., Mapping the HLA Ligandome of Colorectal Cancer Reveals an Imprint of Malignant Cell Transformation. Cancer Res. 78, 4627 (2018).
Alvaro-Benito et al., Quantification of HLA-DM-Dependent Major Histocompatibility Complex of Class II Immunopeptidomes by the Peptide Landscape Antigenic Epitope Alignment Utility. Front. Immunol. 9, 872 (2018).
Magnan, et al., SSpro/ACCpro 5: almost perfect prediction of protein secondary structure and relative solvent accessibility using profiles, machine learning and structural similarity. Bioinforma. Oxf. Engl. 30, 2592-2597 (2014).
McGranahan et al., Allele-Specific HLA Loss and Immune Escape in Lung Cancer Evolution. Cell 171, 1259-1271.e11 (2017).
Mommen et al., "Expanding the detectable HLA peptide repertoire using electron-transfer/higher-energy collision dissociation (EThcD)," PNAS III, 4507-4512 (2014).
Nanaware et al., HLA-DO Modulates the Diversity of the MHC-II Self-peptidome. Mol. Amp Cell. Proteomics 18, 490 (2019).
Bassani-Sternberg et al. Direct identification of clinically relevant neoepitopes presented on native human melanoma tissue by mass spectrometry. Nat. Commun. 7, 13404 (2016).
Nesbeth et al., CD4+ T cells elicit host immune responses to MHC class II-negative ovarian cancer through CCL5 secretion and CD40-mediated licensing of dendritic cells. J Immunol 184(10):5654-5662 (2010).
Nielsen et al., NN-align. An artificial neural network-based alignment algorithm for MHC class II peptide binding prediction. BMC Bioinformatics. Sep. 18, 2009;10:296.
Oates et al., D(2)P(2): database of disordered protein predictions, Nucleic Acids Res, 41:D508-D516 (2013).
Ong et al., Stable isotope labeling by amino acids in cell culture, SILAC, as a simple and accurate approach to expression proteomics. Mol Cell Proteomics 1(5):376-386 (2002).
Ooi et al., Dominant protection from HLA-linked autoimmunity by antigen-specific regulatory T cells. Nature 545, 243-247 (2017).
Ossendorp et al., Specific T Helper Cell Requirement for Optimal Induction of Cytotoxic T Lymphocytes against Major Histocompatibility Complex Class II Negative Tumors. J. Exp. Med. 187, 693 (1998).
Ott et al., An immunogenic personal neoantigen vaccine for patients with melanoma. Nature 547, 217 (2017).
Pacis et al., Gene activation precedes DNA demethylation in response to infection in human dendritic cells. BioRxiv 358531 (2018).
Paul et al., Determination of a Predictive Cleavage Motif for Eluted Major Histocompatibility Complex Class II Ligands. Front. Immunol. 9, 1795 (2018).
Puram et al., Single-Cell Transcriptomic Analysis of Primary and Metastatic Tumor Ecosystems in Head and Neck Cancer. Cell 171, 1611-1624.e24 (2017).
Quezada et al., Tumor-reactive CD4+ T cells develop cytotoxic activity and eradicate large established melanoma after transfer into lymphopenic hosts. J. Exp. Med. 207, 637 (2010).
Rappsilber et al., Protocol for micro-purification, enrichment, prefractionation and storage of peptides for proteomics using StageTips, Nat Protoc, 2(8):1896-1906 (2007).

Riberdy et al., HLA-DR molecules from an antigen-processing mutant cell line are associated with invariant chain peptides. Nature 360, 474 (1992).
Rock et al., Present Yourself! By MHC Class I and MHC Class II Molecules. Trends Immunol. 37, 724-737 (2016).
Rose et al. Highly Multiplexed Quantitative Mass Spectrometry Analysis of Ubiquitylomes. Cell Syst. 3, 395-403.e4 (2016).
Sade-Feldman et al., Resistance to checkpoint blockade therapy through inactivation of antigen presentation. Nat. Commun. 8, 1136 (2017).
Sahin et al., Personalized RNA mutanome vaccines mobilize polyspecific therapeutic immunity against cancer, Nature, 547(7662):222-226 (2017).
Saxena et al., Re-Emergence of Dendritic Cell Vaccines for Cancer Treatment. Trends Cancer 4, 119-137 (2018).
Shao, XM, High-throughput prediction of MCH Class I and Class II neoantigens with MHCnuggests, Cancer Immun Research, Dec. 23, 2019, pp. 1-34.
Sidney et al., Measurement of MHC/peptide interactions by gel filtration or monoclonal antibody capture. Curr. Protoc. Immunol. Chapter 18, Unit-18.3 (2013).
Netzel-Arnett et al., Sequence Specificities of Human fibroblast and Neutrophil Collagenases, Biol. Chem.,266:15173, (1991).
Srivastava et al., Dropout: a simple way to prevent neural networks from overfilling. Journal of Machine earning Research 15.1: 1929-1958 (2014).
Thorvaldsdottir et al., Integrative Genomics Viewer (IGV): high-performance genomics data visualization and exploration. Brief. Bioinform. 14, 178-192 (2013).
Tirosh et al. Dissecting the multicellular ecosystem of metastatic melanoma by single-cell RNA-seq. Science 352, 189 (2016).
Touw et al., A series of PDB-related databanks for everyday needs. Nucleic Acids Res. 43, D364-D368 (2015).
Tran et al. Cancer Immunotherapy Based on Mutation-Specific CD4+ T Cells in a Patient with Epithelial Cancer. Science 344, 641 (2014).
Udeshi et al., Methods for quantification of in vivo changes in protein ubiquitination following proteasome and deubiquitinase inhibition, Mot Cell Proteomics, 11:148-159 (2012).
Van Lith et al., HLA-DP, HLA-DQ, and HLA-DR have different requirements for invariant chain and HLA-DM. J. Biol. Chem. 285, 40800-40808 (2010).
Vita et al., The Immune Epitope Database (IEDB): 2018 update. Nucleic Acids Res. gky1006-gky1006 (2018).
Yadav et al, Transformations of the macromolecular landscape at mitochondria during DNA-damage-induced apoptotic cell death. Cell Death Amp Dis. 5, e1453 (2014).
Yang et al., Multiplex mapping of CD4 T cell epitopes using class II tetramers. Clin. Immunol. 120, 21-32 (2006).
Yates et al. Genenames.org: the HGNC and VGNC resources in 2017. Nucleic Acids Res. 45, D619-D625 (2016).
Yin et al., Evaluating the Role of HLA-DM in MHC Class II-Peptide Association Reactions. J. Immunol. 195, 706 (2015).
Yoshihara et al., Inferring tumour purity and stromal and immune cell admixture from expression data: Nature communications 4:2612 (2013).
Yost et al., Clonal replacement of tumor-specific T cells following PD-1 blockade. Nat. Med (2019).
Zacharakis et al., Immune recognition of somatic mutations leading to complete durable regression in metastatic breast cancer. Nat. Med. 24, 724-730 (2018).
Zhang et al., "Machine learning competition in immunology—Prediction of HLA class I binding peptides," Journal of Immunological Methods vol. 374, No. 1-2, pp. 1-4 (2011).
Andreatta et al.: Accurate pan-specific prediction of peptide-MHC class II binding affinity with improved binding core identification. Immunogenetics 67(0):641-650 (2015).
Bersesng et al.: Different binding motifs of the celiac disease-associated HLA molecules DQ2.5, DQ2.2, and DQ7.5 revealed by relative quantitative proteomics of endogenous peptide repertoires. Immunogenetics 67, 73-84 (2015).
Carter et al.: Absolute quantification of somatic DNA alterations in human cancer. Nat Biotechnol 30:413-421 (2012).

(56) References Cited

OTHER PUBLICATIONS

Johnson et al.: Melanoma-specific MHC-II expression represents a tumour-autonomous phenotype and predicts response to anti-PD-1/PD-L1 therapy. Nat. Commun. 7:10582 pp. 1-10 (2016).

Lambrechts et al.: Phenotype molding of stromal cells in the lung tumor microenvironment. Nat. Med. 24:1277-1289 (2018).

R Core Team (2021). R: A language and environment for statistical computing. R Foundation for Statistical Computing, Vienna, Austria. URL: https://www.R-project.org/. homepage provided (3 pages); obtained online on Sep. 11, 2023.

Robinson et al.: The IPD and IMGT/HLA database: allele variant databases. Nucleic Acids Res. 43:D423-D431 (2015).

Roche et al.: Formation of a nine-subunit complex by HLA class II glycoproteins and the invariant chain. Nature 354:392 (1991).

Shraibman et al.: "Identification of Tumor Antigens Among the HLA Peptidomes of Glioblastoma Tumors and Plasma" Molecular & Cellular Proteomics 18.6, p. 1255-1268.

Sidney et al.: Measurement of MHC/Peptide Interactions by Gel Filtration Curr Prot Immunol, 31(1):18.3.1-18.3.19 (1999).

Singapore Application No. 11202106678P Written Opinion dated Sep. 25, 2023.

\* cited by examiner

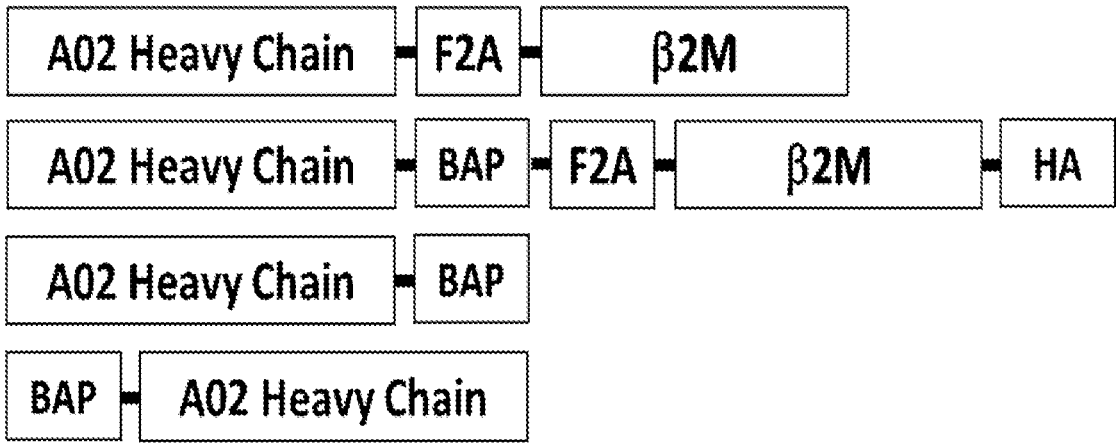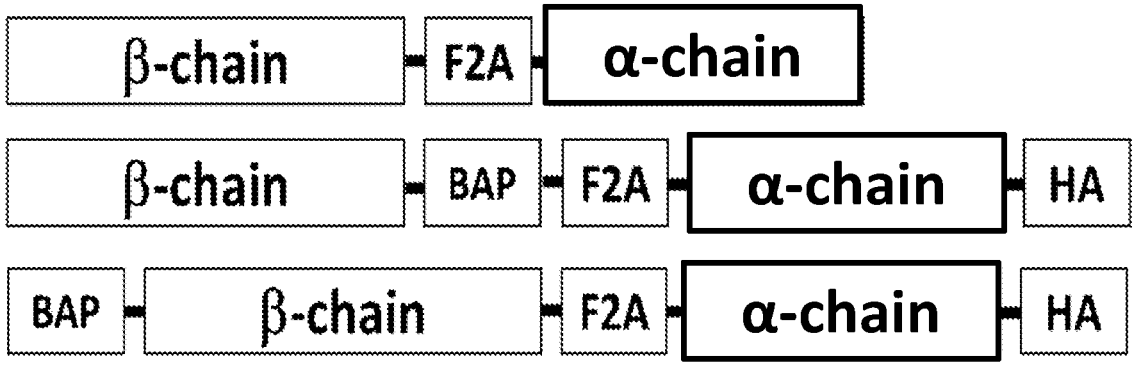
FIG. 2

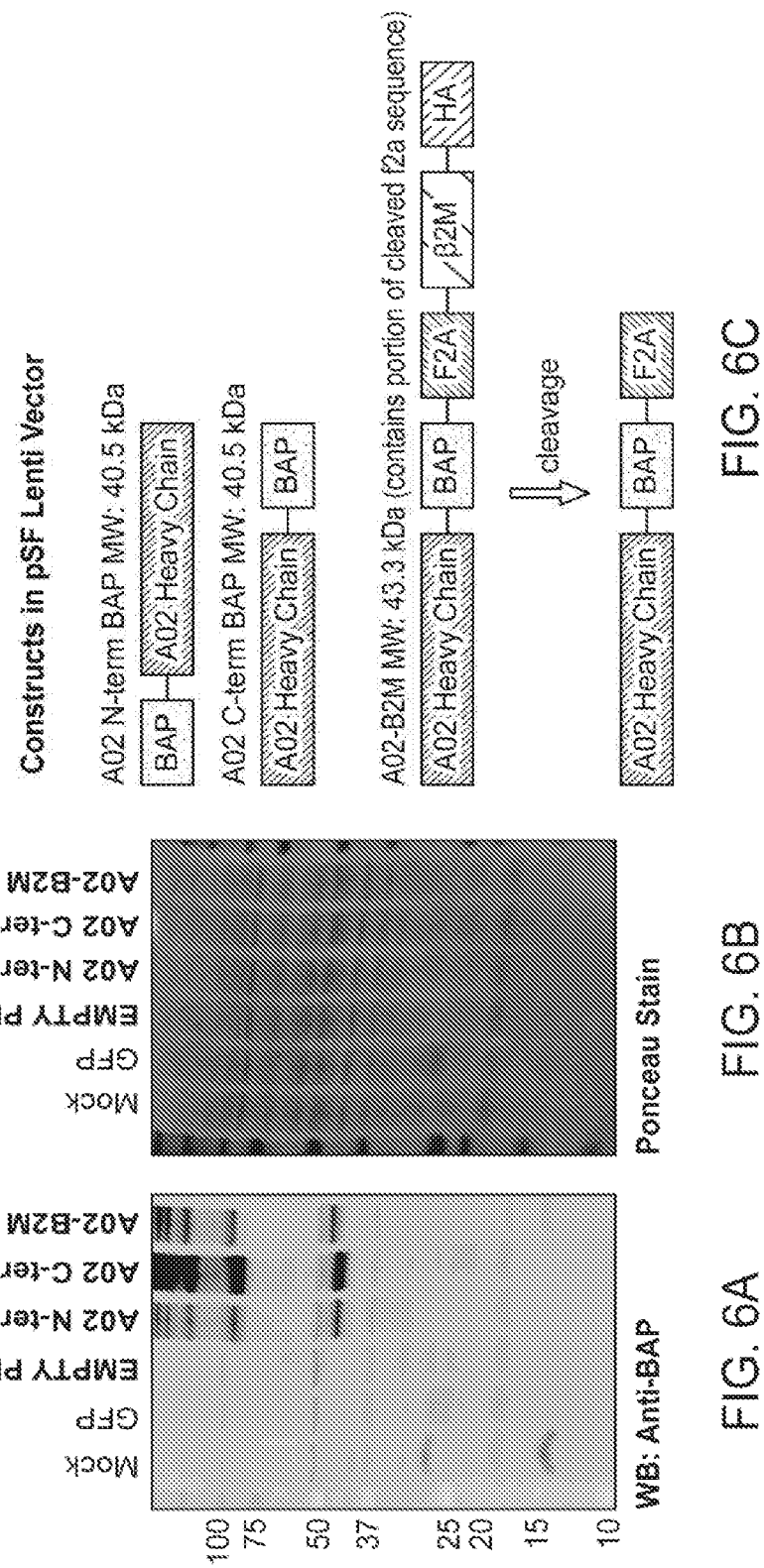

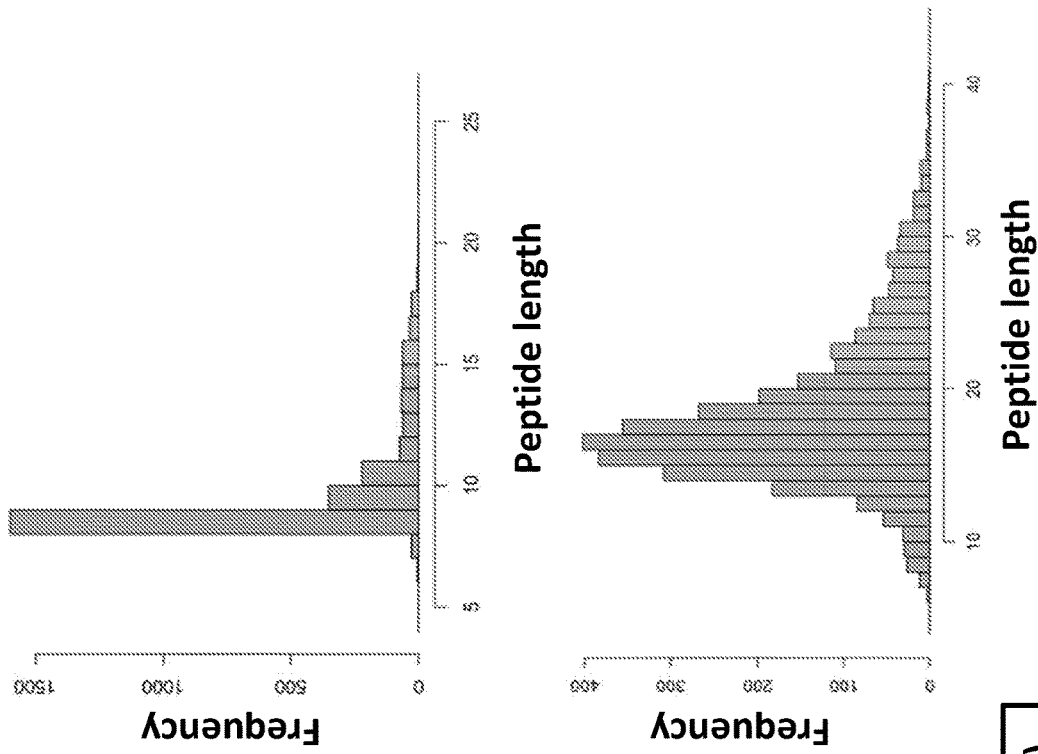
FIG. 10B
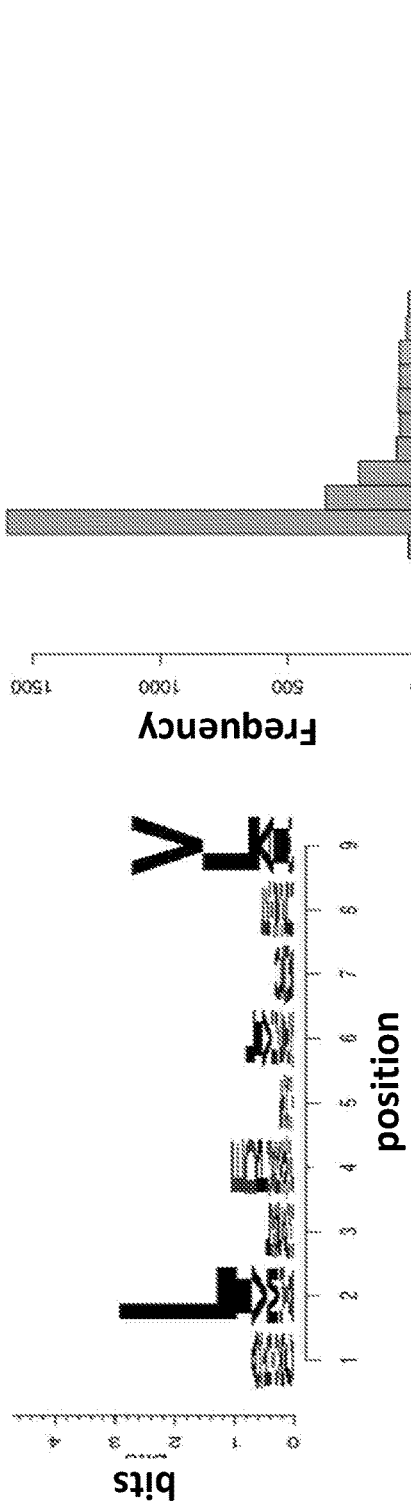
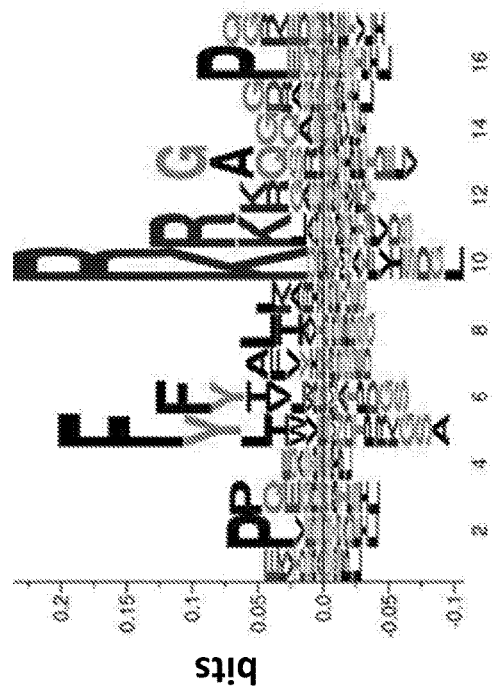
Only "high quality" peptides used (>70% SPI)
FIG. 10A

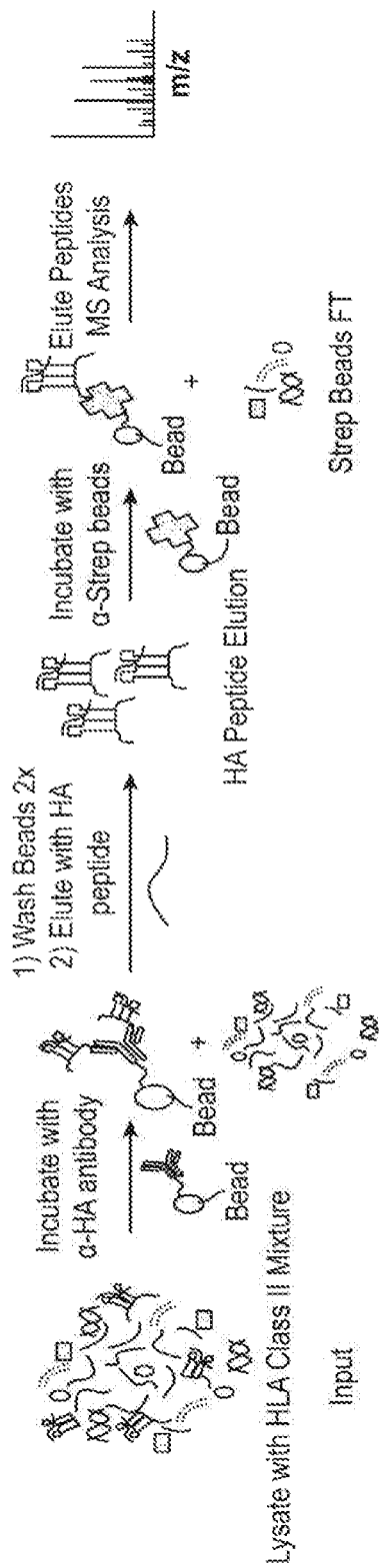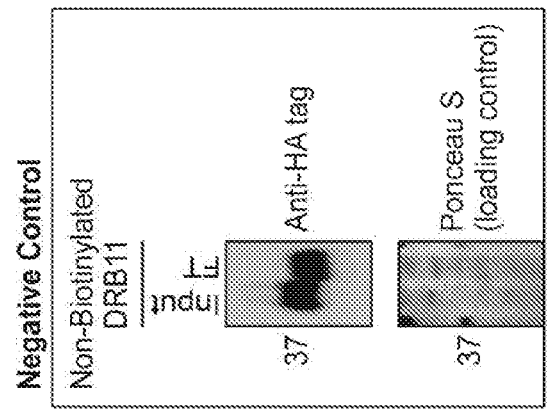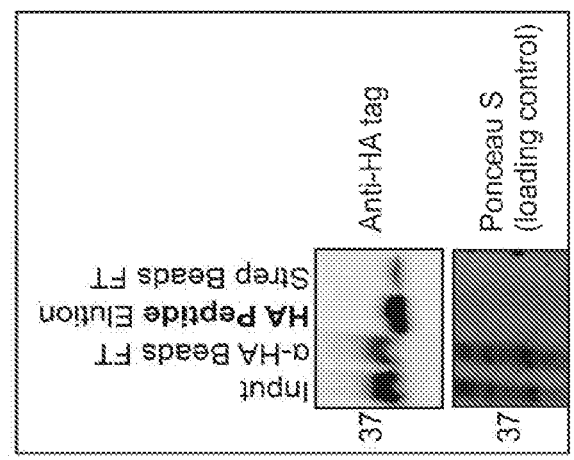
FIG. 12A
FIG. 12B
FIG. 12C

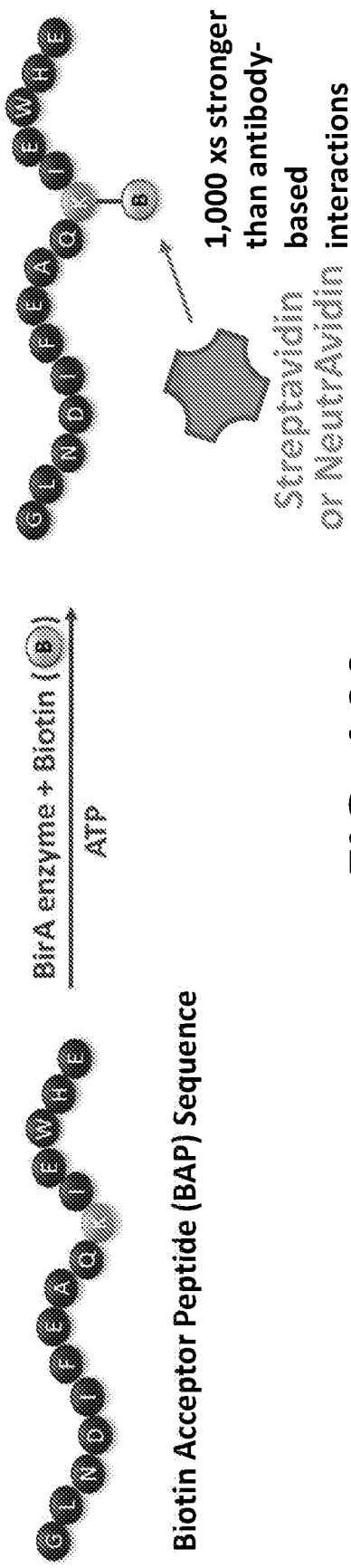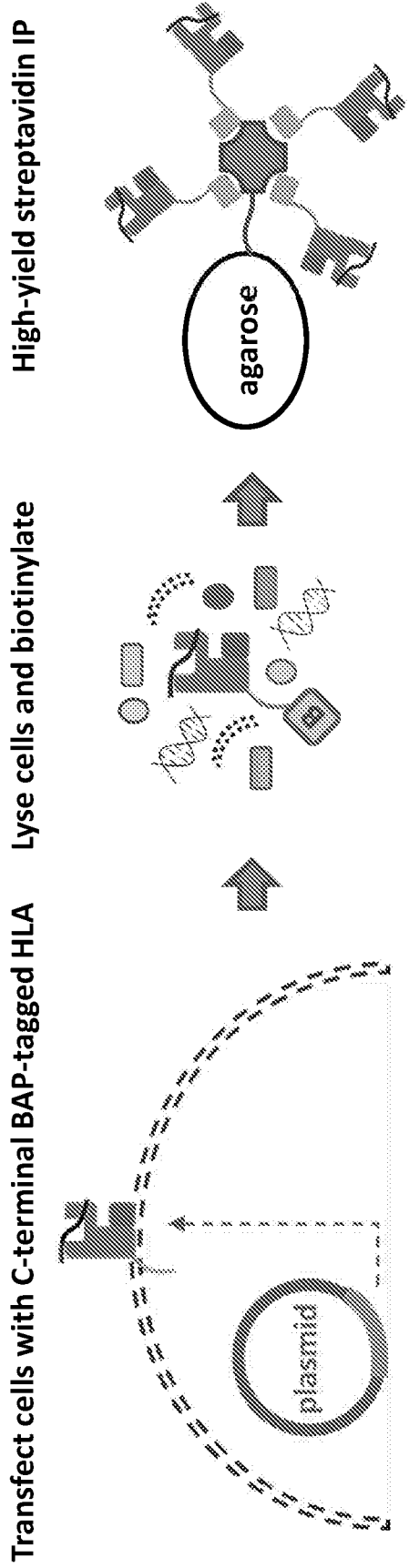
FIG. 14A
FIG. 14B

FIG. 19

HLA-BASED METHODS AND COMPOSITIONS AND USES THEREOF

CROSS-REFERENCE

This application is an U.S. National Stage entry of International Application No. PCT/US2018/017849, filed Feb. 2, 2018, which claims the benefit of priority from U.S. Provisional Application No. 62/457,978, filed Feb. 12, 2017, and U.S. Provisional Application No. 62/461,162, filed Feb. 20, 2017, each of which is incorporated herein by reference in their entirety.

SEQUENCE LISTING

The instant application contains a Sequence Listing which has been submitted electronically in ASCII format and is hereby incorporated by reference in its entirety. Said ASCII copy was initially filed concurrently with the national stage application on Aug. 9, 2019, was named 50401-704.601_SL.txt and was 6,897 bytes in size; and is recreated on Jul. 7, 2021, named 50401-704.831_SL.txt and is 10,756 bytes in size.

BACKGROUND

The major histocompatibility complex (MHC) is a gene complex encoding human leukocyte antigen (HLA) genes. HLA genes are expressed as protein heterodimers that are displayed on the surface of human cells to circulating T cells. HLA genes are highly polymorphic, allowing them to fine-tune the adaptive immune system. Adaptive immune responses rely, in part, on the ability of T cells to identify and eliminate cells that display disease-associated peptide antigens bound to human leukocyte antigen (HLA) heterodimers.

In humans, endogenous and exogenous proteins can be processed into peptides by the proteasome and by cytosolic and endosomal/lysosomal proteases and peptidases and presented by two classes of cell surface proteins encoded by MHC. These cell surface proteins are referred to as human leukocyte antigens (HLA class I and class II), and the group of peptides that bind them and elicit immune responses are termed HLA epitopes. HLA epitopes are a key component that enables the immune system to detect danger signals, such as pathogen infection and transformation of self. Circulating CD8+ T cells recognize class I MHC (HLA-A, HLA-B, and HLA-C) epitopes derived from endogenous processing pathways and displayed on almost all nucleated cells. CD4+ T cells recognize class II MHC (HLA-DR, HLA-DQ, and HLA-DP) epitopes displayed on antigen presenting cells (APCs), such as dendritic cells and macrophages. HLA class II-peptide presentation activates helper T cells, subsequently promoting B cell differentiation and antibody production as well as CTL responses. Activated helper T cells also secrete cytokines and chemokines that activate and induce differentiation of other T cells.

The genes coding for HLA heterodimers are highly polymorphic, with more than 12,000 class I and 4,000 class II allele variants identified across the human population. From maternal and paternal HLA haplotypes, an individual can inherit different alleles for each of the class I and class II HLA loci. Class I HLA molecules are heterodimers made up of a heavy α-chain, encoded by class I HLA genes, and the β-2-microglobulin (B2M). Class II HLA molecules are α- and β-chain heterodimers, both encoded by the class II HLA genes. Because of the α- and β-chain pairing combinations, the population of HLA heterodimers is highly complex. In addition, each HLA heterodimer is estimated to bind thousands of peptides with allele-specific binding preferences. In fact, each HLA allele is estimated to bind and present ~1,000-10,000 unique peptides to T cells; ≤0.1% of ~10 million potential 9mer peptides from human protein-coding genes. Given such diversity in HLA binding, accurate prediction of whether a peptide is likely to bind to a specific HLA allele is highly challenging. Less is known about allele-specific peptide-binding characteristics of HLA class II molecules because of the heterogeneity of a and R chain pairing, complexity of data limiting the ability to confidently assign core binding epitopes, and the lack of immunoprecipitation grade, allele-specific antibodies required for high-resolution biochemical analyses. Furthermore, analyzing peptide epitopes derived from a given HLA allele raises ambiguity when multiple HLA alleles are presented on a cell surface.

Understanding the binding preferences of every HLA heterodimer is a key to successfully predicting which neoantigens are likely to elicit tumor-specific T cell responses. Clearly, there is a need for methods of identifying and isolating specific class I and class II HLA-associated peptides (e.g., neoantigen peptides). Such methodology and isolated molecules are useful, e.g., for the research of HLA-associated peptides, as well as for the development of therapeutics, including but not limited to, immune based therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

The methods and compositions described herein find uses in a wide range of applications. For example, the methods and compositions described herein be used to identify immunogenic antigen peptides and can be used to develop drugs, such as personalized medicine drugs.

Provided herein is a method of characterizing HLA-peptide complexes comprising: providing a population of cells, wherein one or more cells of the population of cells comprise a polynucleic acid comprising a sequence encoding an affinity acceptor tagged class I or class II HLA allele, wherein the sequence encoding an affinity acceptor tagged HLA comprises a sequence encoding a recombinant class I or class II HLA allele operatively linked to a sequence encoding an affinity acceptor peptide; expressing the affinity acceptor tagged HLA in at least one cell of the one or more cells of the population of cells, thereby forming affinity acceptor tagged HLA-peptide complexes in the at least one cell; enriching for the affinity acceptor tagged HLA-peptide complexes; and characterizing HLA-peptide complexes. In some embodiments, the encoded affinity acceptor tagged class I or class II HLA allele is a soluble affinity acceptor tagged class I or class II HLA allele.

In some embodiments, the characterizing comprises characterizing a peptide bound to the affinity acceptor tagged HLA-peptide complex from the enriching. In some embodiments, the method comprises carrying out the steps of the method for two or more class I and/or class II HLA alleles. In some embodiments, the two or more class I and/or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles. In some embodiments, the affinity acceptor tagged HLA-peptide complexes comprise a transmembrane domain. In some embodiments, the affinity acceptor tagged HLA-peptide complexes comprise an intracellular domain. In some embodiments, the affinity acceptor tagged HLA-peptide complexes are not secreted. In some embodiments, the affinity acceptor tagged HLA-peptide complexes incorporate into a cell membrane when expressed. In some embodiments, the affinity acceptor tagged HLA-peptide complexes are soluble affinity acceptor tagged HLA-peptide complexes. In some embodiments, the affinity acceptor tagged HLA-peptide complexes are not soluble affinity acceptor tagged HLA-peptide complexes. In some embodiments, the method further comprises generating an HLA-allele specific peptide database. In some embodiments, the recombinant class I or class II HLA allele is a single recombinant class I or class II HLA allele.

In some embodiments, the method comprises: providing a population of cells each comprising one or more cells comprising an affinity acceptor tagged HLA, wherein the affinity acceptor tagged HLA comprises a different recombinant polypeptide encoded by a different HLA allele operatively linked to an affinity acceptor peptide; enriching for affinity acceptor tagged HLA-peptide complexes; and characterizing a peptide or a portion thereof bound to the affinity acceptor tagged HLA-peptide complex from the enriching.

In some embodiments, the method comprises introducing one or more peptides to the population of cells. In some embodiments, the introducing comprises contacting the population of cells with the one or more peptides or expressing the one or more peptides in the population of cells. In some embodiments, the introducing comprises contacting the population of cells with one or more nucleic acids encoding the one or more peptides. In some embodiments, the one or more nucleic acids encoding the one or more peptides is DNA. In some embodiments, the one or more nucleic acids encoding the one or more peptides is RNA, optionally wherein the RNA is mRNA. In some embodiments, the enriching does not comprise use of a tetramer reagent.

In some embodiments, the characterizing comprises determining the sequence of a peptide or a portion thereof bound to the affinity acceptor tagged HLA-peptide complex from the enriching, optionally determining whether a peptide or a portion thereof is modified. In some embodiments, the determining comprises biochemical analysis, mass spectrometry analysis, MS analysis, MS/MS analysis, LC-MS/MS analysis, or a combination thereof. In some embodiments, the characterizing comprises evaluating a binding affinity or stability of a peptide or a portion thereof bound to the affinity acceptor tagged HLA-peptide complex from the enriching. In some embodiments, the characterizing comprises determining whether a peptide or a portion thereof bound to the affinity acceptor tagged HLA-peptide complex from the enriching contains one or more mutations. In some embodiments, the characterizing comprises evaluating associations of peptides with HLA molecules in the affinity acceptor tagged HLA-peptide complexes.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes.

In some embodiments, the library comprises a library of peptides associated with a disease or condition. In some embodiments, the library comprises a library of peptides derived from a polypeptide drug, such as a biologic (e.g., an antibody drug).

In some embodiments, the disease or condition is cancer, an infection with an infectious agent, or an autoimmune reaction. In some embodiments, the method comprises introducing the infectious agent or portions thereof into one or more cells of the population of cells. In some embodiments, the method comprises introducing a polypeptide drug, such as a biologic (e.g., an antibody drug) or portions thereof into one or more cells of the population of cells. In some embodiments, the method comprises characterizing one or more peptides from the HLA-peptide complexes, optionally wherein the peptides are from one or more target proteins of the infectious agent or the polypeptide drug. In some embodiments, the method comprises characterizing one or more regions of the peptides from the one or more target proteins of the infectious agent or the polypeptide drug.

In some embodiments, the method comprises identifying peptides from the HLA-peptide complexes derived from an infectious agent. In some embodiments, the population of cells is from a biological sample from a subject with a disease or condition. In some embodiments, the population of cells is a cell line. In some embodiments, the population of cells is a population of primary cells. In some embodiments, the recombinant class I or class II HLA allele is matched to a subject with a disease or condition.

In some embodiments, the peptide from the affinity acceptor tagged HLA-peptide complex is capable of activating a T cell from a subject when presented by an antigen presenting cell. In some embodiments, the characterizing comprises comparing HLA-peptide complexes from cancer cells to HLA-peptide complexes from non-cancer cells. In some embodiments, the population of cells comprises a plurality of populations of cells, each population of cells expressing a different recombinant class I or class II HLA allele. In some embodiments, each population of cells of the plurality is in a same or a separate container.

In some embodiments, the method further comprises isolating peptides from the affinity acceptor tagged HLA-peptide complexes before the characterizing. In some embodiments, an HLA-peptide complex is isolated using an anti-HLA antibody. In some cases, an HLA-peptide complex with or without an affinity tag is isolated using an anti-HLA antibody. In some cases, a soluble HLA (sHLA) with or without an affinity tag is isolated from media of a cell culture. In some cases, a soluble HLA (sHLA) with or without an affinity tag is isolated using an anti-HLA antibody. For example, an HLA, such as a soluble HLA (sHLA) with or without an affinity tag, can be isolated using a bead or column containing an anti-HLA antibody. In some embodiments, the peptides are isolated using anti-HLA antibodies. In some cases, a soluble HLA (sHLA) with or without an affinity tag is isolated using an anti-HLA antibody. In some cases, a soluble HLA (sHLA) with or without an affinity tag is isolated using a column containing an anti-HLA antibody. In some embodiments, the method further comprises removing one or more amino acids from a terminus of a peptide bound to an affinity acceptor tagged HLA-peptide complex.

In some embodiments, the population of cells is a population of low cell surface HLA class I or class II expressing cells. In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles. In some embodiments, the population of cells is a knock-out of all HLA class II alleles. In some embodiments, the population of cells is a knock-out of all HLA class I alleles and a knock-out of all HLA class II alleles. In some embodiments, the sequence encoding the recombinant class I or class II HLA allele encodes a class I HLA. In some embodiments, the class I HLA is selected from the group consisting of HLA-A, HLA-B, HLA-C, HLA-E, HLA-F, and HLA-G. In some embodiments, the sequence encoding the recombinant class I or class II HLA allele encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof. In some embodiments, each sequence encodes at least two different class I and/or class II HLA alleles.

In some embodiments, the at least two different class I and/or class II HLA alleles are each operatively linked to a sequence encoding an affinity acceptor peptide. In some embodiments, the at least two different class I and/or class II HLA alleles are each operatively linked to a sequence encoding a different affinity acceptor peptide. In some embodiments, the at least two different class I and/or class II HLA alleles are each operatively linked to a sequence encoding an affinity acceptor peptide. In some embodiments, one or more of the at least two different class I and/or class II HLA alleles is operatively linked to a sequence encoding a first affinity acceptor peptide and one or more of the at least two different class I and/or class II HLA alleles is operatively linked to a sequence encoding a second affinity acceptor peptide. In some embodiments, the at least two different class I and/or class II HLA alleles are each operatively linked to a sequence encoding a different affinity acceptor peptide. In some embodiments, each of the at least two different class I and/or class II HLA alleles are each operatively linked to a sequence encoding a different affinity acceptor peptide. In some embodiments, the at least two different class I and/or class II HLA alleles are each operatively linked to a sequence encoding an affinity tag. In some embodiments, the method comprises administering at least a second polynucleic acid comprising a sequence encoding a different recombinant HLA allele operatively linked to the same or a different affinity acceptor peptide.

In some embodiments, the sequence encoding the affinity acceptor peptide is operatively linked to a sequence that encodes an extracellular portion of the recombinant class I or class II HLA allele. In some embodiments, the encoded affinity acceptor peptide is expressed extracellularly. In some embodiments, the encoded affinity acceptor peptide is located on an extracellular site of the recombinant class I or class II HLA allele. In some embodiments, the sequence encoding the affinity acceptor peptide is operatively linked to the N-terminus of the sequence encoding the recombinant class I or class II HLA allele. In some embodiments, the sequence encoding the affinity acceptor peptide is operatively linked to a sequence that encodes an intracellular portion of the recombinant class I or class II HLA allele. In some embodiments, the encoded affinity acceptor peptide is expressed intracellularly. In some embodiments, the sequence encoding the affinity acceptor peptide is operatively linked to the C-terminus of the sequence encoding the recombinant class I or class II HLA allele. In some embodiments, the sequence encoding the affinity acceptor peptide is operatively linked to an internal sequence of the sequence encoding the recombinant class I or class II HLA allele, such as a flexible loop sequence. In some embodiments, the sequence encoding the affinity acceptor peptide is operatively linked to the sequence encoding the recombinant class I or class II HLA allele by a linker. In some embodiments, enriching comprises enriching for intact cells expressing the affinity acceptor tagged HLA-peptide complexes. In some embodiments, the method does not comprise lysing the cells before enriching. In some embodiments, the method further comprises lysing the one or more cells before enriching. In some embodiments, enriching comprises contacting an affinity acceptor peptide binding molecule to the affinity acceptor tagged HLA-peptide complexes, wherein the affinity acceptor peptide binding molecule binds specifically to the affinity acceptor peptide.

In some embodiments, the affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, sortase tag, a tag the forms a covalent peptide bond to a bead, or a combination thereof, optionally, wherein the affinity acceptor peptide comprises two or more repeats of a tag sequence.

In some embodiments, the affinity acceptor peptide binding molecule is biotin or an antibody specific to the affinity acceptor peptide. In some embodiments, the enriching comprises contacting an affinity molecule to the affinity acceptor tagged HLA-peptide complexes, wherein the affinity molecule binds specifically to the affinity acceptor peptide binding molecule.

In some embodiments, the affinity molecule comprises a molecule that binds to biotin. For example, the affinity molecule can comprise streptavidin, NeutrAvidin, including protein homologs from other organisms and derivatives thereof.

In some embodiments, enriching comprises immunoprecipitating affinity acceptor tagged HLA-peptide complexes. In some embodiments, the affinity acceptor peptide binding molecule is attached to a solid surface. In some embodiments, the affinity molecule is attached to a solid surface.

In some embodiments, the solid surface is a bead. In some embodiments, enriching comprises immunoprecipitating affinity acceptor tagged HLA-peptide complexes with an affinity acceptor peptide binding molecule that binds specifically to the affinity acceptor peptide.

In some embodiments, the affinity acceptor peptide binding molecule does not specifically interact with the amino acid sequence of the encoded recombinant class I or class II HLA. In some embodiments, enriching comprises contacting an affinity molecule specific to an extracellular portion of the recombinant class I or class II HLA allele. In some embodiments, enriching comprises contacting an affinity molecule specific to an N-terminal portion of the recombinant class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the recombinant class I or class II HLA comprises a sequence encoding a HLA class I α-chain. In some embodiments, the method further comprises expressing a sequence encoding β2 microglobulin in the one or more cells. In some embodiments, the sequence encoding β2 microglobulin is connected to the sequence encoding the HLA class I α-chain. In some embodiments, the sequence encoding β2 microglobulin is connected to the sequence encoding the HLA class I α-chain by a linker. In some embodiments, the sequence encoding β2 microglobulin is connected to a sequence encoding a second affinity acceptor peptide. In some embodiments, the sequence encoding the recombinant class I or class II HLA comprises a sequence encoding a HLA class II α-chain. In some embodiments, the method further comprises expressing a sequence encoding a HLA class II β-chain in the one or more cells. In some embodiments, the sequence encoding the HLA class II β-chain is connected to the sequence encoding the HLA class II α-chain. In some embodiments, the sequence encoding the HLA class II β-chain is connected to the sequence encoding the HLA class II α-chain by a linker. In some embodiments, the sequence encoding the HLA class II β-chain is connected to a sequence encoding a second affinity acceptor peptide.

In some embodiments, the second affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP) tag, glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof, optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the determining comprises performing biochemical analysis or mass spectrometry, such as tandem mass spectrometry. In some embodiments, the determining comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides. In some embodiments, the peptide database is a no-enzyme specificity peptide database, such as a without modification database or a with modification database. In some embodiments, the method further comprises searching the peptide database using a reversed-database search strategy. In some embodiments, the population of cells is a cell line. In some embodiments, the population of cells is a human cell line. In some embodiments, the population of cells is a mouse cell line. In some embodiments, the population of cells is a CHO cell line. In some embodiments, the population of cells is a cell line selected from HEK293T, expi293, HeLa, A375, 721.221, JEG-3, K562, Jurkat, Hep G2, SH-SY5Y, CACO-2, U937, U-2 OS, ExpiCHO, CHO and THP1.

In some embodiments, the population of cells is treated with one or more cytokines, checkpoint inhibitors, epigenetically-active drugs, IFN-γ, agents that alter antigen processing (such as peptidase inhibitors, proteasome inhibitors, and TAP inhibitors), or a combination thereof. In some embodiments, the population of cells is treated with one or more reagents that modulate a metabolic pathway or a metabolic status of the cells. In some embodiments, the population of cells is treated with one or more reagents that modulate the cellular proteome of the cells. In some embodiments, the population of cells is treated with one or more reagents that modulate or regulate cellular expression or transcription (e.g. AIRE or a CREB binding protein or modulators thereof) of the cells. In some embodiments, the population of cells is treated with one or more reagents that modulate or regulate a transcription factor of the cells. In some embodiments, the population of cells is treated with one or more reagents that modulate or regulate cellular expression or transcription of an HLA of the cells. In some embodiments, the population of cells is treated with one or more reagents that modulate or regulate cellular expression or transcription of the proteome of the cells.

In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells. In some embodiments, the population of cells is contacted with an agent prior to isolating said HLA-peptide complexes from the one or more cells. In some embodiments, said agent is an inflammatory cytokine, a chemical agent, an adjuvant, a therapeutic agent or radiation.

In some embodiments, the HLA allele is a mutated HLA allele. In some embodiments, the sequence encoding the HLA allele comprises a barcode sequence. In some embodiments, the method further comprises assaying for expression of the affinity acceptor tagged class I or class II HLA allele. In some embodiments, the assaying comprises assaying comprises sequencing an affinity acceptor tagged class I or class II HLA allele, detecting affinity acceptor tagged class I or class II HLA allele RNA, detecting affinity acceptor tagged class I or class II HLA allele protein, or a combination thereof. In some embodiments, assaying for expression can comprise a Western blot assay, fluorescent activated cell sorting (FACS), mass spectrometry (MS), a microarray hybridization assay, an RNA-seq assay, a polymerase chain reaction assay, a LAMP assay, a ligase chain reaction assay, a Southern blot assay, a Northern blot assay, or an enzyme-linked immunosorbent assay (ELISA).

In some embodiments, the method comprises carrying out the steps of the method for different HLA alleles. In some embodiments, each different HLA allele comprises a unique barcode sequence. In some embodiments, each polynucleic acid encoding a different HLA allele comprises a unique barcode sequence.

Provided herein is a HLA-allele specific binding peptide sequence database obtained by carrying out a method described herein. Provided herein is a combination of two or more HLA-allele specific binding peptide sequence databases obtained by carrying out a method described herein repeatedly, each time using a different HLA-allele. Provided herein is a method for generating a prediction algorithm for identifying HLA-allele specific binding peptides, comprising training a machine with a peptide sequence database described herein or a combination described herein.

In some embodiments, the machine combines one or more linear models, support vector machines, decision trees and neural networks. In some embodiments, a variable used to train the machine comprises one or more variables selected from the group consisting of peptide sequence, amino acid physical properties, peptide physical properties, expression level of the source protein of a peptide within a cell, protein stability, protein translation rate, ubiquitination sites, protein degradation rate, translational efficiencies from ribosomal profiling, protein cleavability, protein localization, motifs of host protein that facilitate TAP transport, host protein is subject to autophagy, motifs that favor ribosomal stalling, and protein features that favor NMD.

In some embodiments, the motifs that favor ribosomal stalling comprise polyproline or polylysine stretches. In some embodiments, the protein features that favor NMD are selected from the group consisting of a long 3' UTR, a stop codon greater than 50 nucleic acids upstream of last exon: exon junction, and peptide cleavability.

Provided herein is a method for identifying HLA-allele specific binding peptides comprising analyzing the sequence of a peptide with a machine which has been trained with a peptide sequence database obtained by carrying out a method described herein for the HLA-allele. In some embodiments, the method comprises determining the expression level of the source protein of the peptide within a cell; and wherein the source protein expression is a predictive variable used by the machine. In some embodiments, the expression level is determined by measuring the amount of source protein or the amount of RNA encoding said source protein.

Provided herein is a composition comprising a recombinant polynucleic acid comprising two or more sequences each encoding an affinity acceptor tagged HLA, wherein the sequences encoding the affinity acceptor tagged HLAs comprise a sequence encoding a different recombinant HLA class I α-chain allele, a sequence encoding an affinity acceptor peptide, and optionally, a sequence encoding β2 microglobulin; wherein the sequences of (a) and (b), and optionally (c), are operatively linked.

Provided herein is a composition comprising a recombinant polynucleic acid comprising two or more sequences each comprising a sequence encoding an affinity acceptor tagged HLA, wherein the sequences encoding the affinity acceptor tagged HLAs comprise a sequence encoding a recombinant HLA class II α-chain allele, a sequence encoding an affinity acceptor peptide, and optionally, a sequence encoding a HLA class II β-chain; wherein the sequences of (a) and (b), and optionally (c), are operatively linked. In some embodiments, the recombinant polynucleic acid is isolated. In some embodiments, the class I HLA is selected from the group consisting of HLA-A, HLA-B, HLA-C, HLA-E, HLA-F, and HLA-G. In some embodiments, the class II HLA is selected from the group consisting of HLA-DR, HLA-DQ, and HLA-DP.

In some embodiments, the sequence encoding the affinity acceptor peptide is operatively linked to a sequence that encodes for an extracellular portion of the recombinant HLA allele. In some embodiments, the sequence encoding the affinity acceptor molecule is operatively linked to the N-terminus of the sequence encoding the recombinant HLA allele. In some embodiments, the sequence encoding the affinity acceptor peptide is operatively linked to a sequence encoding an intracellular portion of the recombinant HLA allele. In some embodiments, the sequence encoding the affinity acceptor peptide is operatively linked to the C-terminus of the sequence encoding the recombinant HLA allele. In some embodiments, the sequence encoding the affinity acceptor peptide is operatively linked to the sequence encoding the recombinant HLA allele by a linker.

In some embodiments, the two or more sequences encoding an affinity acceptor tagged HLA are expressed from the same polynucleotide. In some embodiments, the two or more sequences encoding an affinity acceptor tagged HLA are expressed from different polynucleotides. In some embodiments, the encoded affinity acceptor peptide binds specifically to an affinity acceptor peptide binding molecule. In some embodiments, the two or more sequences encoding an affinity acceptor tagged HLA comprise two or more affinity acceptor peptides. In some embodiments, the two or more sequences encoding an affinity acceptor tagged HLA comprise three or more sequences encoding an affinity acceptor tagged HLA, wherein at least two of the three or more sequences encoding an affinity acceptor tagged HLA comprises the same affinity acceptor peptide. In some embodiments, the two or more affinity acceptor peptides are unique for each of the two or more sequences encoding an affinity acceptor tagged HLA.

In some embodiments, the encoded affinity acceptor peptide is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof; optionally, wherein the first or second affinity acceptor peptide comprises two or more repeats of a tag sequence.

In some embodiments, the affinity acceptor peptide binding molecule is biotin or an antibody specific to the affinity acceptor peptide. In some embodiments, the affinity acceptor peptide binding molecule binds specifically to an affinity molecule. In some embodiments, the affinity molecule is streptavidin, NeutrAvidin, or a derivative thereof. In some embodiments, the affinity acceptor peptide binding molecule does not specifically interact with an amino acid sequence of the recombinant class I or class II HLA. In some embodiments, for two or more of the recombinant polynucleic acids: the sequence encoding the affinity acceptor tagged HLA is stably integrated into the genome of a cell. In some embodiments, the sequence encoding β2 microglobulin or the sequence encoding the HLA class II β-chain is connected to a sequence encoding a second affinity acceptor peptide. In some embodiments, the second affinity acceptor peptide comprises an HA tag. In some embodiments, the sequence encoding β2 microglobulin or the sequence encoding the HLA class II β-chain is connected to the sequence encoding the recombinant HLA and the affinity acceptor peptide by a linker.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A In some embodiments, the IRES element is selected from common cellular or viral IRES sequences.

Provided herein is a composition comprising two or more isolated polypeptide molecules encoded by the polynucleic acid of a composition described herein. Provided herein is a composition comprising a population of cells comprising two or more polypeptide molecules encoded by the polynucleic acid of a composition described herein. Provided herein is a composition comprising a population of cells comprising a composition described herein. Provided herein is a composition comprising a population of cells comprising one or more cells comprising a composition described herein.

In some embodiments, the population of cells express one or more endogenous class I or class II HLA alleles. In some embodiments, the population of cells are engineered to lack one or more endogenous HLA class I alleles. In some embodiments, the population of cells are engineered to lack endogenous HLA class I alleles. In some embodiments, the population of cells are engineered to lack one or more endogenous HLA class II alleles. In some embodiments, the population of cells are engineered to lack endogenous HLA class II alleles. In some embodiments, the population of cells are engineered to lack one or more endogenous HLA class I alleles and one or more endogenous HLA class II alleles. In some embodiments, the population of cells is a population of low cell surface HLA class I or class II expressing cells. In some embodiments, the composition is formulated using peptides or polynucleic acids encoding peptides specific to an HLA type of a patient. Provided herein is a method of making a cell comprising transducing or transfecting two or more cells with the two or more polynucleic acids of a composition described herein.

Provided herein is a peptide identified according to a method described herein. Provided herein is a method of inducing an anti-tumor response in a mammal comprising administering to the mammal an effective amount of a polynucleic acid comprising a sequence of a peptide described herein. Provided herein is a method of inducing an anti-tumor response in a mammal comprising administering to the mammal an effective amount of a peptide comprising the sequence of a peptide described herein. Provided herein is a method of inducing an anti-tumor response in a mammal comprising administering to the mammal a cell comprising a peptide comprising the sequence of a peptide described herein. Provided herein is a method of inducing an anti-tumor response in a mammal comprising administering to the mammal a cell comprising an effective amount of a polynucleic acid comprising a sequence encoding a peptide comprising the sequence of a peptide described herein. In some embodiments, the cell presents the peptide as an HLA-peptide complex.

Provided herein is a method of for inducing an immune response in a mammal comprising administering to the mammal an effective amount of a polynucleic acid comprising a sequence encoding a peptide described herein. Provided herein is a method for inducing an immune response in a mammal comprising administering to the mammal an effective amount of a peptide comprising the sequence of a peptide described herein. Provided herein is a method for inducing an immune response in a mammal comprising administering to the mammal an effective amount of a cell comprising a peptide comprising the sequence of a peptide described herein. Provided herein is a method for inducing an immune response in a mammal comprising administering to the mammal an effective amount of a cell comprising a polynucleic acid comprising a sequence encoding a peptide comprising the sequence of a peptide described herein.

In some embodiments, the immune response is a T cell immune response. In some embodiments, the immune response is a CD8 T cell response. In some embodiments, the immune response is a CD4 T cell response. In some embodiments, the immune response is humoral immune response.

Provided herein is a method for treating a mammal having a disease comprising administering to the mammal an effective amount of a polynucleic acid comprising a sequence encoding a peptide described herein. Provided herein is a method for treating a mammal having a disease comprising administering to the mammal an effective amount of a peptide comprising the sequence of a peptide described herein. Provided herein is a method for treating a mammal having a disease comprising administering to the mammal an effective amount of a cell comprising a peptide comprising the sequence of a peptide described herein. Provided herein is a method for treating a mammal having a disease comprising administering to the mammal an effective amount of a cell comprising a polynucleic acid comprising a sequence encoding a peptide comprising the sequence of a peptide described herein. In some embodiments, the disease is cancer. In some embodiments, the disease is infection by an infectious agent. In some embodiments, the infectious agent is a pathogen, optionally a virus or bacteria, or a parasite.

In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof.

In some embodiments, the bacteria is selected from the group consisting of: *Klebsiella* spp., *Tropheryma whipplei*, *Mycobacterium leprae*, *Mycobacterium lepromatosis*, and *Mycobacterium tuberculosis*, typhoid, pneumococcal, meningococcal, *haemophilus* B, anthrax, tetanus toxoid, meningococcal group B, bcg, cholera, and any combination thereof.

In some embodiments, the parasite is a helminth or a protozoan. In some embodiments, the parasite is selected from the group consisting of: *Leishmania* spp., *Plasmodium* spp., *Trypanosoma cruzi*, *Ascaris lumbricoides*, *Trichuris trichiura*, *Necator americanus*, *Schistosoma* spp., and any combination thereof.

Provided herein is a method of enriching for immunogenic peptides comprising: providing a population of cells comprising one or more cells expressing an affinity acceptor tagged HLA, wherein the affinity acceptor tagged HLA comprises an affinity acceptor peptide operatively linked to a recombinant HLA encoded by a recombinant HLA allele; and enriching for HLA-peptide complexes comprising the affinity acceptor tagged HLA. In some embodiments, the method further comprises determining the sequence of immunogenic peptides isolated from the HLA-peptide complexes. In some embodiments, the determining comprises using LC-MS/MS.

Provided herein is a method of treating a disease or disorder in a subject, the method comprising administering to the subject an effective amount of a polynucleic acid comprising a sequence encoding a peptide described herein. Provided herein is a method of treating a disease or disorder in a subject, the method comprising administering to the subject an effective amount of a peptide comprising the sequence of a peptide described herein. Provided herein is a method of treating a disease or disorder in a subject, the method comprising administering to the subject an effective amount of a cell comprising a peptide comprising the sequence of a peptide described herein. Provided herein is a method of treating a disease or disorder in a subject, the method comprising administering to the subject a cell comprising an effective amount of a polynucleic acid comprising a sequence encoding a peptide comprising the sequence of a peptide described herein.

Provided herein is a method of developing an therapeutic for a subject with a disease or condition comprising providing a population of cells derived from a subject with a disease or condition, expressing in one or more cells of the population of cells an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching and characterizing the affinity acceptor tagged HLA-peptide complexes; and, optionally, developing an therapeutic based on the characterization.

Provided herein is a method of identifying at least one subject specific immunogenic antigen and preparing a subject-specific immunogenic composition that includes the at least one subject specific immunogenic antigen, wherein the subject has a disease and the at least one subject specific immunogenic antigen is specific to the subject and the subject's disease, said method comprising: providing a population of cells derived from a subject with a disease or condition, expressing in one or more cells of the population of cells from the subject, an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching affinity acceptor tagged HLA-peptide complexes from the one or more cells; identifying an immunogenic peptide from the enriched affinity acceptor tagged HLA-peptide complexes that is specific to the subject and the subject's disease; and formulating a subject-specific immunogenic composition based one or more of the subject specific immunogenic peptides identified.

In some embodiments, the therapeutic or subject specific immunogenic composition comprises a peptide from the enriched affinity acceptor tagged HLA-peptide complexes or a or a polynucleotide encoding the polypeptide from the enriched affinity acceptor tagged HLA-peptide complexes. In some embodiments, the therapeutic or subject specific immunogenic composition comprises a T cell expressing a T cell receptor (TCR) that specifically binds to the polypeptide from the enriched affinity acceptor tagged HLA-peptide complexes. In some embodiments, the subject specific immunogenic composition comprises a chimeric antigen receptor (CAR) T cell expressing a receptor that specifically binds to the polypeptide from the enriched affinity acceptor tagged HLA-peptide complexes.

In some embodiments, the method further comprises administering another therapeutic agent, optionally, an immune checkpoint inhibitor to the subject. In some embodiments, the method further comprises administering an adjuvant, optionally, poly-ICLC to the subject.

In some embodiments, the disease or disorder is cancer. In some embodiments, the disease or disorder is an autoimmune disease. In some embodiments, the disease or disorder is an infection. In some embodiments, the infection is an infection by an infectious agent. In some embodiments, the infectious agent is a pathogen, a virus, bacteria, or a parasite.

In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof.

In some embodiments, the bacteria is selected from the group consisting of: *Klebsiella* spp., *Tropheryma whipplei*, *Mycobacterium leprae, Mycobacterium lepromatosis*, and *Mycobacterium tuberculosis*, typhoid, pneumococcal, meningococcal, *haemophilus* B, anthrax, tetanus toxoid, meningococcal group B, bcg, cholera, and combinations thereof.

In some embodiments, the parasite is a helminth or a protozoan. In some embodiments, the parasite is selected from the group consisting of: *Leishmania* spp., *Plasmodium* spp., *Trypanosoma cruzi, Ascaris lumbricoides, Trichuris trichiura, Necator americanus, Schistosoma* spp., and any combination thereof.

Provided herein is a method of developing a therapeutic for a subject with a disease or condition comprising: providing a population of cells, wherein one or more cells of the population of cells comprise a polynucleic acid comprising a sequence encoding at least two affinity acceptor tagged class I or class II HLA alleles, wherein the sequence encoding the at least two affinity acceptor tagged class I or class II HLAs comprises a first recombinant sequence comprising a sequence encoding a first class I or class II HLA allele operatively linked to a sequence encoding a first affinity acceptor peptide; and a second recombinant sequence comprising a sequence encoding a second class I or class II HLA allele operatively linked to a sequence encoding a second affinity acceptor peptide; expressing the at least two affinity acceptor tagged HLAs in at least one cell of the one or more cells of the population of cells, thereby forming affinity acceptor tagged HLA-peptide complexes in the at least one cell; enriching for the affinity acceptor tagged HLA-peptide complexes; and identifying a peptide from the enriched affinity acceptor tagged HLA-peptide complexes; and formulating an immunogenic composition based one or more of the peptides identified, wherein the first and the second recombinant class I or class II HLA alleles are matched to an HLA haplotype of a subject. In some embodiments, the subject has a disease or condition.

In some embodiments, the first recombinant class I or class II HLA allele is different than the second recombinant class I or class II HLA allele. In some embodiments, the first affinity acceptor peptide is the same as the second affinity acceptor peptide. In some embodiments, the method comprises characterizing a peptide bound to the first and/or second affinity acceptor tagged HLA-peptide complexes from the enriching. In some embodiments, the at least two affinity acceptor tagged class I or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles. In some embodiments, the first and/or the second affinity acceptor tagged HLA-peptide complexes comprise a transmembrane domain. In some embodiments, the first and/or the second affinity acceptor tagged HLA-peptide complexes comprise an intracellular domain. In some embodiments, the first and/or the second affinity acceptor tagged HLA-peptide complexes are not excreted. In some embodiments, the first and/or the second affinity acceptor tagged HLA-peptide complexes incorporate into a cell membrane when expressed. In some embodiments, the first and/or the second affinity acceptor tagged HLA-peptide complexes are not soluble affinity acceptor tagged HLA-peptide complexes.

In some embodiments, the method further comprises generating an HLA-allele specific peptide database. In some embodiments, the method comprises introducing one or more exogenous peptides to the population of cells. In some embodiments, the introducing comprises contacting the population of cells with the one or more exogenous peptides or expressing the one or more exogenous peptides in the population of cells. In some embodiments, the introducing comprises contacting the population of cells with one or more nucleic acids encoding the one or more exogenous peptides.

In some embodiments, the one or more nucleic acids encoding the one or more peptides is DNA. In some embodiments, the one or more nucleic acids encoding the one or more peptides is RNA, optionally wherein the RNA is mRNA.

In some embodiments, the enriching does not comprise use of a tetramer reagent. In some embodiments, the method comprises determining the sequence of a peptide or a portion thereof bound to the first and/or the second affinity acceptor tagged HLA-peptide complex from the enriching. In some embodiments, the determining comprises biochemical analysis, mass spectrometry analysis, MS analysis, MS/MS analysis, LC-MS/MS analysis, or a combination thereof.

In some embodiments, the method comprises evaluating a binding affinity or stability of a peptide or a portion thereof bound to the first and/or the second affinity acceptor tagged HLA-peptide complex from the enriching. In some embodiments, the method comprises determining whether a peptide or a portion thereof bound to the first and/or the second affinity acceptor tagged HLA-peptide complex from the enriching contains one or more mutations. In some embodiments, the method comprises evaluating associations of peptides with HLA molecules in the first and/or the second affinity acceptor tagged HLA-peptide complex.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition.

In some embodiments, the disease or condition is cancer or an infection with an infectious agent. In some embodiments, the method comprises introducing the infectious agent or portions thereof into one or more cells of the population of cells. In some embodiments, the method comprises characterizing one or more peptides from the first and/or the second HLA-peptide complexes, optionally wherein the peptides are from one or more target proteins of the infectious agent. In some embodiments, the method comprises characterizing one or more regions of the peptides from the one or more target proteins of the infectious agent. In some embodiments, the method comprises identifying peptides from the first and/or the second HLA-peptide complexes derived from an infectious agent.

In some embodiments, the population of cells is from a biological sample from a subject with a disease or condition. In some embodiments, the population of cells is a cell line. In some embodiments, the population of cells is a population of primary cells. In some embodiments, the peptide from the first and/or the second affinity acceptor tagged HLA-peptide complex is capable of activating a T cell from a subject when presented by an antigen presenting cell. In some embodiments, the method comprises comparing HLA-peptide complexes from diseased cells to HLA-peptide complexes from non-diseased cells. In some embodiments, the method further comprises isolating peptides from the first and/or the second affinity acceptor tagged HLA-peptide complexes before the identifying. In some embodiments, the population of cells is a population of low cell surface HLA class I or class II expressing cells.

In some embodiments, the population of cells expresses one or more endogenous HLA alleles. In some embodiments, the population of cells expresses the endogenous HLA alleles normally expressed by the population of cells. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles. In some embodiments, the population of cells is a knock-out of all HLA class II alleles. In some embodiments, the population of cells is a knock-out of all HLA class I alleles and a knock-out of all HLA class II alleles. In some embodiments, the sequence encoding the at least two affinity acceptor tagged class I or class II HLA alleles encodes a class I HLA. In some embodiments, the class I HLA is selected from the group consisting of HLA-A, HLA-B, HLA-C, HLA-E, HLA-F, and HLA-G. In some embodiments, the first recombinant class I or class II HLA allele is a first class I HLA allele and the second recombinant class I or class II HLA allele is a second class I HLA allele. In some embodiments, the sequence encoding the at least two affinity acceptor tagged class I or class II HLA alleles encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof. In some embodiments, the first recombinant class I or class II HLA allele is a first class II HLA allele and the second recombinant class I or class II HLA allele is a second class II HLA allele.

In some embodiments, the first sequence and the second sequence are each operatively linked. In some embodiments, the first sequence and the second sequence are comprised on different polynucleotide molecules. In some embodiments, the sequence encoding the first and/or second affinity acceptor peptide is operatively linked to a sequence that encodes an extracellular portion of the first and/or second class I or class II HLA allele. In some embodiments, the first and/or second encoded affinity acceptor peptide is expressed extracellularly. In some embodiments, the sequence encoding the first and/or second affinity acceptor peptide is operatively linked to the N-terminus of the sequence encoding the first and/or second class I or class II HLA allele. In some embodiments, the sequence encoding the first and/or second affinity acceptor peptide is operatively linked to a sequence that encodes an intracellular portion of the first and/or second class I or class II HLA allele. In some embodiments, the encoded first and/or second affinity acceptor peptide is expressed intracellularly. In some embodiments, the sequence encoding the first and/or second affinity acceptor peptide is operatively linked to the C-terminus of the sequence encoding the first and/or second class I or class II HLA allele. In some embodiments, the sequence encoding the first and/or second affinity acceptor peptide is operatively linked to the sequence encoding the first and/or second class I or class II HLA allele by a linker.

In some embodiments, enriching comprises enriching for intact cells expressing the first and/or second affinity acceptor tagged HLA-peptide complexes. In some embodiments, the method does not comprise lysing the cells before enriching. In some embodiments, the method further comprises lysing the one or more cells before enriching. In some embodiments, enriching comprises contacting an affinity acceptor peptide binding molecule to the first and/or second affinity acceptor tagged HLA-peptide complexes, wherein the affinity acceptor peptide binding molecule binds specifically to the first and/or second affinity acceptor peptide.

In some embodiments, the first and/or second affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof; optionally, wherein the first and/or second affinity acceptor peptide comprises two or more repeats of a tag sequence.

In some embodiments, the affinity acceptor peptide binding molecule is biotin or an antibody specific to the first and/or second affinity acceptor peptide. In some embodiments, the enriching comprises contacting an affinity molecule to the first and/or second affinity acceptor tagged HLA-peptide complexes, wherein the affinity molecule binds specifically to the affinity acceptor peptide binding molecule. In some embodiments, the affinity molecule is streptavidin, NeutrAvidin, or a derivative thereof. In some embodiments, enriching comprises immunoprecipitating the first and/or second affinity acceptor tagged HLA-peptide complexes.

In some embodiments, the affinity acceptor peptide binding molecule is attached to a solid surface. In some embodiments, the affinity molecule is attached to a solid surface. In some embodiments, the solid surface is a bead.

In some embodiments, enriching comprises immunoprecipitating the first and/or second affinity acceptor tagged HLA-peptide complexes with an affinity acceptor peptide binding molecule that binds specifically to the first and/or second affinity acceptor peptide. In some embodiments, the affinity acceptor peptide binding molecule does not specifically interact with the amino acid sequence of the encoded first and/or second class I or class II HLA. In some embodiments, enriching comprises contacting an affinity molecule specific to an extracellular portion of the first and/or second class I or class II HLA allele. In some embodiments, enriching comprises contacting an affinity molecule specific to an N-terminal portion of the first and/or second class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the first and/or second class I or class II HLA comprises a sequence encoding a HLA class I α-chain. In some embodiments, the first recombinant class I or class II HLA allele is a first HLA class I α-chain and the second recombinant class I or class II HLA allele is a second HLA class I α-chain.

In some embodiments, the method further comprises expressing a sequence encoding β2 microglobulin in the one or more cells. In some embodiments, the sequence encoding β2 microglobulin is connected to the sequence encoding the first and/or second class I or class II HLA. In some embodiments, the sequence encoding β2 microglobulin is connected to the sequence encoding the first and/or second class I or class II HLA by a linker. In some embodiments, the sequence encoding β2 microglobulin is connected to a sequence encoding a third affinity acceptor peptide.

In some embodiments, the third affinity acceptor peptide is different than the first and/or second affinity acceptor peptide. In some embodiments, the sequence encoding the first and/or second class I or class II HLA comprises a sequence encoding a HLA class II α-chain and/or a HLA class II β-chain. In some embodiments, the sequence encoding the first and/or second class I or class II HLA comprises a sequence encoding a first HLA class II α-chain and a second HLA class II α-chain. In some embodiments, the method further comprises expressing a sequence encoding a HLA class II β-chain in the one or more cells. In some embodiments, the sequence encoding a first HLA class II α-chain and a second HLA class II α-chain HLA is connected to the sequence encoding the HLA class II β-chain. In some embodiments, the sequence encoding the first and/or second class I or class II HLA comprises a sequence encoding a first HLA class II β-chain and a second HLA class II β-chain.

In some embodiments, the method further comprises expressing a sequence encoding a HLA class II α-chain in the one or more cells. In some embodiments, the sequence encoding a first HLA class II β-chain and a second HLA class II β-chain is connected to the sequence encoding the HLA class II α-chain by a linker. In some embodiments, the sequence encoding the HLA class II β-chain or the HLA class II α-chain is connected to a sequence encoding a third affinity acceptor peptide. In some embodiments, the third affinity acceptor peptide is different than the first and/or second affinity acceptor peptide.

In some embodiments, the third affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof, optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the method comprises performing biochemical analysis or mass spectrometry, such as tandem mass spectrometry. In some embodiments, the method comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides.

In some embodiments, the population of cells is a cell line selected from HEK293T, expi293, HeLa, A375, 721.221, JEG-3, K562, Jurkat, Hep G2, SH-SY5Y, CACO-2, U937, U-2 OS, ExpiCHO, CHO and THP1. In some embodiments, the cell line is treated with one or more cytokines, checkpoint inhibitors, epigenetically-active drugs, IFN-γ, or a combination thereof. In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells.

In some embodiments, the population of cells is contacted with an agent prior to isolating the first and/or second HLA-peptide complexes from the one or more cells. In some embodiments, the agent is an inflammatory cytokine, a chemical agent, an adjuvant, a therapeutic agent or radiation.

In some embodiments, the first and or second HLA allele is a mutated HLA allele. In some embodiments, the sequence encoding the first and or second HLA allele comprises a barcode sequence. In some embodiments, the method further comprises assaying for expression of the first and/or second affinity acceptor tagged class I or class II HLA allele.

In some embodiments, the assaying comprises sequencing the first and/or second affinity acceptor tagged class I or class II HLA allele, detecting RNA encoding the first and/or second affinity acceptor tagged class I or class II HLA allele RNA, detecting the first and/or second affinity acceptor tagged class I or class II HLA allele protein, or a combination thereof. In some embodiments, the first and second affinity acceptor tagged class I or class II HLA allele comprises a unique barcode sequence. In some embodiments, the first sequence and the second sequence comprise a unique barcode sequence.

BRIEF DESCRIPTION OF THE DRAWINGS

The features of the present disclosure are set forth with particularity in the appended claims. The patent or application file contains at least one drawing executed in color. Copies of this patent or patent application with color drawings will be provided by the office upon request and payment of necessary fees. A better understanding of the features and advantages of the present disclosure will be obtained by reference to the following detailed description that sets forth illustrative embodiments, in which the principles of the disclosure are utilized, and the accompanying drawings of which:

FIG. 2 is a representative schematic of constructs designed for HLA class I and II expression in cultured cell lines. HLA-A*02:01 constructs represent HLA class I design that implement biotin acceptor peptides (BAP) for biotinylation and immunopurification. HLA-DRB1*11:01 constructs represent HLA class II design that implement biotin acceptor peptides (BAP) for biotinylation and immunopurification.

FIG. 6A is a Western blot (anti-biotinylation) comparing mock, GFP and empty plasmid transfections with HLA-A*02:01 constructs for biotinylation-based immunoprecipitation demonstrating expression of class I HLA alleles in HEK293T cells.

FIG. 6B is a Ponceau stained gel used as a loading control for the Western blot analysis.

FIG. 6C is a schematic representation of class I HLA constructs used to generate engineered HEK293T cells imaged in FIG. 6A and FIG. 6B.

FIG. 10A is an exemplary schematic of the characteristics of class I and class II HLA-associated peptides discovered using the Universal IP pipeline. An exemplary sequence logo representation of class I HLA-A*02:01-associated peptides and class II HLA-DRβ*11:01-associated peptides isolated and sequenced using the Universal IP platform is shown.

FIG. 10B is a bar graph showing HLA-associated peptide length distributions comparing class I (red; HLA-A*02:01) and class II (blue; HLA-DRβ*11:01) HLA-associated peptides identified using the Universal IP pipeline. The length distributions of both class I and class II HLA-associated peptides identified using the Universal IP follow the expected trends.

FIG. 12A is a schematic representation of a serial Universal IP strategy that can be used for deconvolution of class II HLA α-chain and β-chain pairing depicted in FIG. 11B and unambiguous peptide-binding assignments to specific class II HLA complexes and demonstrates validation of serial universal IP of class II HLA complexes containing multiple affinity tags. Cells expressing dual-affinity tagged class II HLA constructs are lysed, biotinylated, and incubated with beads coupled to anti-HA antibodies. Class II HLA complexes with HA-tagged subunits are isolated, washed, and eluted using an HA peptide (e.g., YPYDVPDYA (SEQ ID NO: 1)). The elution is then incubated with beads coupled to either NeutrAvidin or streptavidin to isolate the HA-tagged and biotin-tagged class II HLA complexes. Peptides bound to dual-tagged class II HLA complexes are then eluted and sequenced by LC-MS/MS.

FIG. 12B is a Western blot validation of the serial Universal IP strategy in HEK293T expressing dual-tagged HLA-DRB*11:01 constructs. An anti-HA antibody was used to follow the serial enrichment process. A loading control (Ponceau S stained gel) is shown.

FIG. 12C represents the results from an exemplary negative control experiment where cells expressing dual-affinity tagged class II HLA construct HLA-DRB*11:01 were lysed and incubated with beads coupled to anti-HA antibodies without biotinylation. A Western blot and loading control (Ponceau S stained gel) are shown to demonstrate the specificity of the serial Universal IP pipeline. No enrichment was observed when the biotinylation step was removed from the serial Universal IP protocol.

FIG. 14A is a schematic representation of a mono-allelic HLA-peptidome profiling approach that implements a biotin affinity tag. An exemplary embodiment of the present disclosure makes use of the biotin acceptor peptide (BAP) (SEQ ID NO: 8) that is biotinylated on a lysine (K) residue by a BirA enzyme. The BAP peptide sequence (SEQ ID NO: 8) contains a lysine residue that is biotinylated upon the addition of BirA enzyme, biotin, and ATP. The biotinylated product displays high affinity for streptavidin/NeutrAvidin. Streptavidin/NeutrAvidin beads can be used to enrich for the biotinylated BAP peptide sequence.

FIG. 14B is a schematic representation of biotin-based immunopurification of genetically engineered HLA molecules. A specific HLA allele with a BAP sequence at either the N- or C-terminus of the HLA protein is introduced into a cell, e.g., by transfection or transduction of a plasmid. Note that the plasmid contains a DNA barcode that allows for a PCR-based method to monitor the cell line for each allele. Barcode lengths can be at least 5 base pairs, at least 10 base pairs, at least 15 base pairs, at least 20 base pairs or more. Cells expressing the HLA-BAP proteins are lysed and biotinylated. HLA-BAP-peptide complexes are immunopurified from the complex lysate mixture, which can be subjected to LC-MS/MS analysis for peptide identification.

FIG. 19 shows a schematic showing different experimental approaches of different HLA-ligand profiling. Biochemical peptide:MHC (p:MHC) binding assay is slow and low-throughput and has no insights on processing. Multi-allelic mass spectrometry is high-throughput and has ability to learn processing rules; however, it requires in silico imputation to assign peptides to alleles. Mono-allelic mass spectrometry provides a rapid, unbiased, and clean approach for defining peptide-binding motifs across diverse MHC alleles. Mono-allelic mass spectrometry can rapidly and systematically fill allege coverage gaps and makes it possible to leverage allele-specific peptide length preferences.

DETAILED DESCRIPTION

Figure 1A:
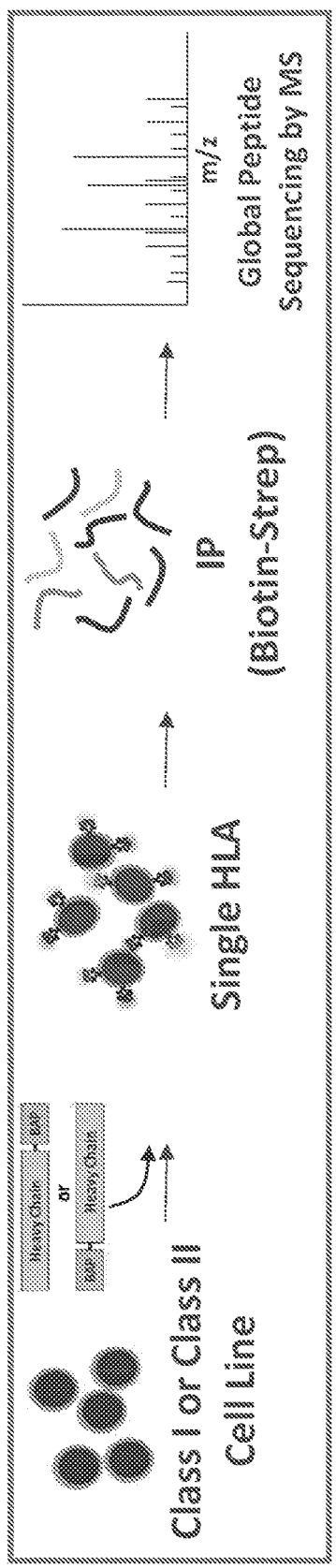
FIG. 1A is a representative schematic of a universal immunopurification and data generation pipeline. Class I and/or class II HLA molecules are introduced into any cell, including a cell not expressing class I or class II HLA) so that specific class I or class II HLA allele(s) are expressed in the cell. Populations of genetically engineered HLA expressing cells are harvested, lysed, and their HLA-peptide complexes are tagged (e.g., biotinylated) and immunopurified (e.g., using the biotin-streptavidin interaction). HLA-associated peptides specific to a single HLA can be eluted from their tagged (e.g., biotinylated) complexes and evaluated (e.g., sequenced using high resolution LC-MS/MS).

The following description and examples illustrate embodiments of the disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, exemplary materials and methods are described

Definitions

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The terms "one or more" or "at least one," such as one or more or at least one member(s) of a group of members, is clear per se, by means of further exemplification, the term encompasses inter alia a reference to any one of said members, or to any two or more of said members, such as, e.g., any ≥3, ≥4, ≥5, 6 or ≥7 etc. of said members, and up to all said members.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−20% or less, +/−10% or less, +/−5% or less, or +/−1% or less of and from the specified value, insofar such variations are appropriate to perform in the present disclosure. It is to be understood that the value to which the modifier "about" or "approximately" refers is itself also specifically disclosed.

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

A "receptor" is to be understood as meaning a biological molecule or a molecule grouping capable of binding a ligand. A receptor can serve to transmit information in a cell, a cell formation or an organism. The receptor comprises at least one receptor unit and can contain two or more receptor units, where each receptor unit can consist of a protein molecule, e.g., a glycoprotein molecule. The receptor has a structure that complements the structure of a ligand and can complex the ligand as a binding partner. Signaling information can be transmitted by conformational changes of the receptor following binding with the ligand on the surface of a cell. According to the present disclosure, a receptor can refer to proteins of MHC classes I and II capable of forming a receptor/ligand complex with a ligand, e.g., a peptide or peptide fragment of suitable length.

A "barcode" sequence can be a nucleic acid sequence that can encode an item of information about a sequence, such the identity of a sequence to which the barcode is attached or the identity of a sample from which a sequence is derived.

By "ligand" is meant a molecule which is capable of forming a complex with a receptor. According to the present disclosure, a ligand is to be understood as meaning, for example, a peptide or peptide fragment which has a suitable length and suitable binding motives in its amino acid sequence, so that the peptide or peptide fragment is capable of forming a complex with proteins of MHC class I or MHC class II.

An "antigen" is a molecule capable of stimulating an immune response, and can be produced by cancer cells or infectious agents or an autoimmune disease. Antigens recognized by T cells, whether helper T lymphocytes (T helper ($T_H$) cells) or cytotoxic T lymphocytes (CTLs), are not recognized as intact proteins, but rather as small peptides that associate with class I or class II MHC proteins on the surface of cells. During the course of a naturally occurring immune response, antigens that are recognized in association with class II MHC molecules on antigen presenting cells (APCs) are acquired from outside the cell, internalized, and processed into small peptides that associate with the class II MHC molecules. APCs can also cross-present peptide antigens by processing exogenous antigens and presenting the processed antigens on class I MHC molecules. Antigens that give rise to proteins that are recognized in association with class I MHC molecules are generally proteins that are produced within the cells, and these antigens are processed and associate with class I MHC molecules. It is now understood that the peptides that associate with given class I or class II MHC molecules are characterized as having a common binding motif, and the binding motifs for a large number of different class I and II MHC molecules have been determined. Synthetic peptides, that correspond to the amino acid sequence of a given antigen and that contain a binding motif for a given class I or II MHC molecule, can also be synthesized. These peptides can then be added to appropriate APCs, and the APCs can be used to stimulate a T helper cell or CTL response either in vitro or in vivo. The binding motifs, methods for synthesizing the peptides, and methods for stimulating a T helper cell or CTL response are all known and readily available to one of ordinary skill in the art.

The term "peptide" is used interchangeably with "mutant peptide" and "neoantigenic peptide" in the present specification. Similarly, the term "polypeptide" is used interchangeably with "mutant polypeptide" and "neoantigenic polypeptide" in the present specification. By "neoantigen" or "neoepitope" is meant a class of tumor antigens or tumor epitopes which arises from tumor-specific mutations in expressed protein. The present disclosure further includes peptides that comprise tumor specific mutations, peptides that comprise known tumor specific mutations, and mutant polypeptides or fragments thereof identified by the method of the present disclosure. These peptides and polypeptides are referred to herein as "neoantigenic peptides" or "neoantigenic polypeptides." The polypeptides or peptides can be a variety of lengths, either in their neutral (uncharged) forms or in forms which are salts, and either free of modifications such as glycosylation, side chain oxidation, phosphorylation, or any post-translational modification or containing these modifications, subject to the condition that the modification not destroy the biological activity of the polypeptides as herein described. In some embodiments, the neoantigenic peptides of the present disclosure can include: for MHC Class I, 22 residues or less in length, e.g., from about 8 to about 22 residues, from about 8 to about 15 residues, or 9 or 10 residues; for MHC Class II, 40 residues or less in length, e.g., from about 8 to about 40 residues in length, from about 8 to about 24 residues in length, from about 12 to about 19 residues, or from about 14 to about 18 residues. In some embodiments, a neoantigenic peptide or neoantigenic polypeptide comprises a neoepitope.

The term "epitope" includes any protein determinant capable of specific binding to an antibody, antibody peptide, and/or antibody-like molecule (including but not limited to a T cell receptor) as defined herein. Epitopic determinants typically consist of chemically active surface groups of molecules such as amino acids or sugar side chains and generally have specific three dimensional structural characteristics as well as specific charge characteristics.

By "T-cell epitope" is meant a peptide sequence which can be bound by the MHC molecules of class I or II in the form of a peptide-presenting MHC molecule or MHC complex and then, in this form, be recognized and bound by cytotoxic T-lymphocytes or T-helper cells, respectively.

The term "antibody" as used herein includes IgG (including IgG1, IgG2, IgG3, and IgG4), IgA (including IgA1 and IgA2), IgD, IgE, or IgM, and IgY, and is meant to include whole antibodies, including single-chain whole antibodies, and antigen-binding (Fab) fragments thereof. Antigen-binding antibody fragments include, but are not limited to, Fab, Fab' and F(ab')$_2$, Fd (consisting of VH and CHI), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CHI, CH2, and CH3 domains. Also included are any combinations of variable region(s) and hinge region, CHI, CH2, and CH3 domains. Antibodies can be monoclonal, polyclonal, chimeric, humanized, and human monoclonal and polyclonal antibodies which, e.g., specifically bind an HLA-associated polypeptide or an HLA-peptide complex. A person of skill in the art will recognize that a variety of immunoaffinity techniques are suitable to enrich soluble proteins, such as soluble HLA-peptide complexes or membrane bound HLA-associated polypeptides, e.g., which have been proteolytically cleaved from the membrane. These include techniques in which (1) one or more antibodies capable of specifically binding to the soluble protein are immobilized to a fixed or mobile substrate—(e.g., plastic wells or resin, latex or paramagnetic beads), and (2) a solution containing the soluble protein from a biological sample is passed over the antibody coated substrate, allowing the soluble protein to bind to the antibodies. The substrate with the antibody and bound soluble protein is separated from the solution, and optionally the antibody and soluble protein are disassociated, for example by varying the pH and/or the ionic strength and/or ionic composition of the solution bathing the antibodies. Alternatively, immunoprecipitation techniques in which the antibody and soluble protein are combined and allowed to form macromolecular aggregates can be used. The macromolecular aggregates can be separated from the solution by size exclusion techniques or by centrifugation.

The term "immunopurification (IP)" (or immunoaffinity purification or immunoprecipitation) is a process well known in the art and is widely used for the isolation of a desired antigen from a sample. In general, the process involves contacting a sample containing a desired antigen with an affinity matrix comprising an antibody to the antigen covalently attached to a solid phase. The antigen in the sample becomes bound to the affinity matrix through an immunochemical bond. The affinity matrix is then washed to remove any unbound species. The antigen is removed from the affinity matrix by altering the chemical composition of a solution in contact with the affinity matrix. The immunopurification can be conducted on a column containing the affinity matrix, in which case the solution is an eluent. Alternatively the immunopurification can be in a batch process, in which case the affinity matrix is maintained as a suspension in the solution. An important step in the process is the removal of antigen from the matrix. This is commonly achieved by increasing the ionic strength of the solution in contact with the affinity matrix, for example, by the addition of an inorganic salt. An alteration of pH can also be effective to dissociate the immunochemical bond between antigen and the affinity matrix.

By "agent" is meant any small molecule chemical compound, antibody, nucleic acid molecule, or polypeptide, or fragments thereof.

By "alteration" or "change" is meant an increase or decrease. An alteration can be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism. As used herein, the term "sample" includes a biologic sample such as any tissue, cell, fluid, or other material derived from an organism. By "specifically binds" is meant a compound (e.g., peptide) that recognizes and binds a molecule (e.g., polypeptide), but which does not substantially recognize and bind other molecules in a sample, for example, a biological sample.

By "capture reagent" is meant a reagent that specifically binds a molecule (e.g., a nucleic acid molecule or polypeptide) to select or isolate the molecule (e.g., a nucleic acid molecule or polypeptide).

As used herein, the terms "determining", "assessing", "assaying", "measuring", "detecting" and their grammatical equivalents refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "fragment" is meant a portion of a protein or nucleic acid that is substantially identical to a reference protein or nucleic acid. In some embodiments, the portion retains at least 50%, 75%, or 80%, or 90%, 95%, or even 99% of the biological activity of the reference protein or nucleic acid described herein.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

By an "isolated" polypeptide (e.g., a peptide from a HLA-peptide complex) or polypeptide complex (e.g., a HLA-peptide complex) is meant a polypeptide or polypeptide complex of the present disclosure that has been separated from components that naturally accompany it. Typically, the polypeptide or polypeptide complex is isolated when it is at least 60%, by weight, free from the proteins and naturally-occurring organic molecules with which it is naturally associated. The preparation can be at least 75%, at least 90%, or at least 99%, by weight, a polypeptide or polypeptide complex of the present disclosure. An isolated polypeptide or polypeptide complex of the present disclosure can be obtained, for example, by extraction from a natural source, by expression of a recombinant nucleic acid encoding such a polypeptide or one or more components of a polypeptide complex, or by chemically synthesizing the polypeptide or one or more components of the polypeptide complex. Purity can be measured by any appropriate method, for example, column chromatography, polyacrylamide gel electrophoresis, or by HPLC analysis.

The term "vectors" refers to a nucleic acid molecule capable of transporting or mediating expression of a heterologous nucleic acid. A plasmid is a species of the genus encompassed by the term "vector." A vector typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

By "molecular profile" is meant a characterization of the expression or expression level of two or more markers (e.g., polypeptides or polynucleotides).

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence. Still other amino acid sequences that can be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180.

The term "neoplasia" refers to any disease that is caused by or results in inappropriately high levels of cell division, inappropriately low levels of apoptosis, or both. Glioblastoma is one non-limiting example of a neoplasia or cancer. The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

The term "vaccine" is to be understood as meaning a composition for generating immunity for the prophylaxis and/or treatment of diseases (e.g., neoplasia/tumor/infectious agents/autoimmune diseases). Accordingly, vaccines are medicaments which comprise antigens and are intended to be used in humans or animals for generating specific defense and protective substance by vaccination. A "vaccine composition" can include a pharmaceutically acceptable excipient, carrier or diluent. Aspects of the present disclosure relate to use of the technology in preparing an antigen-based vaccine. In these embodiments, vaccine is meant to refer one or more disease-specific antigenic peptides (or corresponding nucleic acids encoding them). In some embodiments, the antigen-based vaccine contains at least two, at least three, at least four, at least five, at least six, at least seven, at least eight, at least nine, at least 10, at least 11, at least 12, at least 13,at least 14, at least 15, at least 16, at least 17, at least 18, at least 19, at least 20, at least 21, at least 22, at least 23, at least 24, at least 25, at least 26, at least 27, at least 28, at least 29, at least 30, or more antigenic peptides. In some embodiments, the antigen-based vaccine contains from 2 to 100, 2 to 75, 2 to 50, 2 to 25, 2 to 20, 2 to 19, 2 to 18, 2 to 17, 2 to 16, 2 to 15, 2 to 14, 2 to 13, 2 to 12, 2 to 10, 2 to 9, 2 to 8, 2 to 7, 2 to 6, 2 to 5, 2 to 4, 3 to 100, 3 to 75, 3 to 50, 3 to 25, 3 to 20, 3 to 19, 3 to 18, 3 to 17, 3 to 16, 3 to 15, 3 to 14, 3 to 13, 3 to 12, 3 to 10, 3 to 9, 3 to 8, 3 to 7, 3 to 6, 3 to 5, 4 to 100, 4 to 75, 4 to 50, 4 to 25, 4 to 20, 4 to 19, 4 to 18, 4 to 17, 4 to 16, 4 to 15, 4 to 14, 4 to 13, 4 to 12, 4to 10, 4 to 9, 4 to 8, 4 to 7, 4 to 6, 5 to 100, 5 to 75, 5 to 50, 5 to 25, 5 to 20, 5 to 19, 5 to 18, 5 to 17, 5 to 16, 5 to 15, 5 to 14, 5 to 13, 5 to 12, 5 to 10, 5 to 9, 5 to 8, or 5 to 7 antigenic peptides. In some embodiments, the antigen-based vaccine contains 2, 3, 4, 5, 6, 7, 8, 9, 10, 11, 12, 13, 14, 15, 16, 17, 18, 19, or 20 antigenic peptides. In some cases, the antigenic peptides are neoantigenic peptides. In some cases, the antigenic peptides comprise one or more neoepitopes.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent. A "pharmaceutically acceptable salt" of pooled disease specific antigens as recited herein can be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluene sulfonic, methane sulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled disease specific antigens provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having substantial identity to an endogenous sequence are typically capable of hybridizing with at least one strand of a double-stranded nucleic acid molecule. By "hybridize" is meant pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152:507). For example, stringent salt concentration can ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions can ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an exemplary embodiment, hybridization can occur at 30° C. in 750 mM NaCl, 75 mM trisodium citrate, and 1% SDS. In another exemplary embodiment, hybridization can occur at 37° C. in 500 mM NaCl, 50 mM trisodium citrate, 1% SDS, 35% formamide, and 100 µg/ml denatured salmon sperm DNA (ssDNA). In another exemplary embodiment, hybridization can occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or at least about 68° C. In exemplary embodiments, wash steps can occur at 25° C. in 30 mM NaCl, 3 mM trisodium citrate, and 0.1% SDS. In other exemplary embodiments, wash steps can occur at 42° C. in 15 mM NaCl, 1.5 mM trisodium citrate, and 0.1% SDS. In another exemplary embodiment, wash steps can occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95%, 96%, 97%, 98%, or even 99% or more identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program can be used, with a probability score between e-3 and e-m° indicating a closely related sequence. By "reference" is meant a standard of comparison.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which refers to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "prevent", "preventing", "prevention" and their grammatical equivalents as used herein, means avoiding or delaying the onset of symptoms associated with a disease or condition in a subject that has not developed such symptoms at the time the administering of an agent or compound commences.

The term "therapeutic effect" refers to some extent of relief of one or more of the symptoms of a disorder (e.g., a neoplasia, tumor, or infection by an infectious agent or an autoimmune disease) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., $ED_{50}$) of the pharmaceutical composition required. For example, the physician or veterinarian can start doses of the compounds of the present disclosure employed in a pharmaceutical composition at levels lower than that required in order to achieve the desired therapeutic effect and gradually increase the dosage until the desired effect is achieved. Disease, condition, and disorder are used interchangeably herein.

In some embodiments, the nucleic acid sequence encoding the HLA allele further comprises a peptide tag, an affinity tag, an epitope tag, or an affinity acceptor tag which can be used to immunopurify the HLA-protein. Those of ordinary skill in the art will recognize that the terms "peptide tag," "affinity tag," "epitope tag," or "affinity acceptor tag" are used interchangeably herein. As used herein, the term "affinity acceptor tag" refers to an amino acid sequence that permits the tagged protein to be readily detected or purified, for example, by affinity purification. An affinity acceptor tag is generally (but need not be) placed at or near the N- or C-terminus of a HLA allele. Various peptide tags are well known in the art. Non-limiting examples include polyhistidine tag (e.g., 4 to 15 consecutive His residues (SEQ ID NO: 2), such as 8 consecutive His residues); poly-histidine-glycine tag; HA tag (e.g., Field et al., Mol. Cell. Biol., 8:2159, 1988); c-myc tag (e.g., Evans et al., Mol. Cell. Biol., 5:3610, 1985); Herpes simplex virus glycoprotein D (gD) tag (e.g., Paborsky et al., Protein Engineering, 3:547, 1990); FLAG tag (e.g., Hopp et al., BioTechnology, 6:1204, 1988; U.S. Pat. Nos. 4,703,004 and 4,851,341); KT3 epitope tag (e.g., Martine et al., Science, 255:192, 1992); tubulin epitope tag (e.g., Skinner, Biol. Chem., 266:15173, 1991); T7 gene 10 protein peptide tag (e.g., Lutz-Freyemuth et al., Proc. Natl. Acad. Sci. USA, 87:6393, 1990); streptavidin tag (StrepTag™ or StrepTagII™; see, e.g., Schmidt et al., J. Mol. Biol., 255(5):753-766, 1996 or U.S. Pat. No. 5,506,121; also commercially available from Sigma-Genosys); or a VSV-G epitope tag derived from the Vesicular Stomatis viral glycoprotein; or a V5 tag derived from a small epitope (Pk) found on the P and V proteins of the paramyxovirus of simian virus 5 (SV5). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG. In some embodiments, the matrix of IgG Sepharose 6 Fast Flow chromatography resin is covalently coupled to human IgG. This resin allows high flow rates, for rapid and convenient purification of a protein tagged with protein A. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

As used herein, the term "affinity molecule" refers to a molecule or a ligand that binds with chemical specificity to an affinity acceptor peptide. Chemical specificity is the ability of a protein's binding site to bind specific ligands. The fewer ligands a protein can bind, the greater its specificity. Specificity describes the strength of binding between a given protein and ligand. This relationship can be described by a dissociation constant ($K_D$), which characterizes the balance between bound and unbound states for the protein-ligand system.

The term "affinity acceptor tagged HLA-peptide complex" refers to a complex comprising an HLA class I or class II-associated peptide or a portion thereof specifically bound to a single allelic recombinant class I or class II HLA peptide comprising an affinity acceptor peptide.

The terms "specific binding" or "specifically binding" when used in reference to the interaction of an affinity molecule and an affinity acceptor tag or an epitope and an HLA peptide means that the interaction is dependent upon the presence of a particular structure (i.e., the antigenic determinant or epitope) on the protein; in other words, the affinity molecule is recognizing and binding to a specific affinity acceptor peptide structure rather than to proteins in general.

As used herein, the term "affinity" refers to a measure of the strength of binding between two members of a binding pair, for example, an "affinity acceptor tag" and an "affinity molecule" and an HLA-binding peptide and a class I or II HLA. $K_D$ is the dissociation constant and has units of molarity. The affinity constant is the inverse of the dissociation constant. An affinity constant is sometimes used as a generic term to describe this chemical entity. It is a direct measure of the energy of binding. Affinity can be determined experimentally, for example by surface plasmon resonance (SPR) using commercially available Biacore SPR units. Affinity can also be expressed as the inhibitory concentration 50 ($IC_{50}$), that concentration at which 50% of the peptide is displaced. Likewise, $\ln(IC_{50})$ refers to the natural log of the $IC_{50}$. $K_{off}$ refers to the off-rate constant, for example, for dissociation of an affinity molecule from the affinity acceptor tagged HLA-peptide complex.

In some embodiments, an affinity acceptor tagged HLA-peptide complex comprises biotin acceptor peptide (BAP) and are immunopurified from complex cellular mixtures using streptavidin/NeutrAvidin beads. The biotin-avidin/streptavidin binding is the strongest non-covalent interaction known in nature. This property is exploited as a biological tool for a wide range of applications, such as immunopurification of a protein to which biotin is covalently attached. In an exemplary embodiment, the nucleic acid sequence encoding the HLA allele implements biotin acceptor peptide (BAP) as an affinity acceptor tag for immunopurification. BAP can be specifically biotinylated in vivo or in vitro at a single lysine residue within the tag (e.g., U.S. Pat. Nos. 5,723,584; 5,874,239; and 5,932,433; and U.K Pat. No. GB2370039). BAP is typically 15 amino acids long and contains a single lysine as a biotin acceptor residue. In some embodiments, BAP is placed at or near the N- or C-terminus of a single allele HLA peptide. In some embodiments, BAP is placed in between a heavy chain domain and β2 microglobulin domain of a class I HLA peptide. In some embodiments, BAP is placed in between β-chain domain and α-chain domain of a class II HLA peptide. In some embodiments, BAP is placed in loop regions between α1, α2, and α3 domains of the heavy chain of class I HLA, or between α1 and α2 and β1 and β2 domains of the α-chain and β-chain, respectively of class II HLA. Exemplary constructs designed for HLA class I and II expression implementing BAP for biotinylation and immunopurification are described in FIG. 2.

As used herein, the term "biotin" refers to the compound biotin itself and analogues, derivatives and variants thereof. Thus, the term "biotin" includes biotin (cis-hexahydro-2-oxo-1H-thieno [3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-E-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, desthiobiotin, and the like. The term "biotin" also comprises biotin variants that can specifically bind to one or more of a Rhizavidin, avidin, streptavidin, tamavidin moiety, or other avidin-like peptides.

HLA Ligand Profiling Approaches

Figure 17:
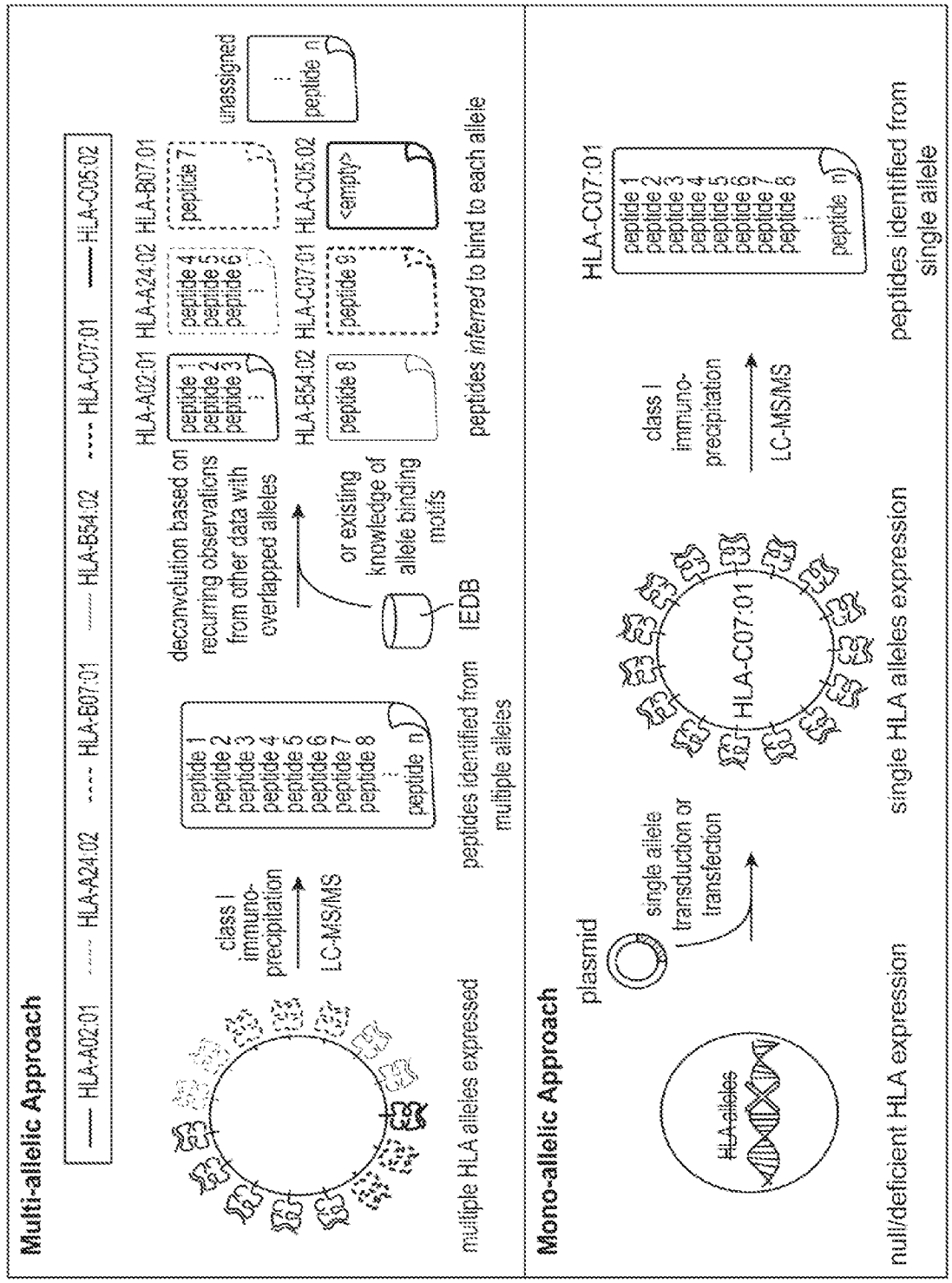
FIG. 17 is schematics of multi-allelic and mono-allelic approaches in HLA ligand profiling. In a multi-allelic approach, the HLA ligands are co-immunoprecipitated with HLA heterodimers directly from patient material or cell lines (top). Because these cells naturally expressed multiple HLA alleles, peptides identified from such multi-allelic approaches must be deconvoluted to assign binding to a specific HLA heterodimer if the HLA types are known. In a mono-allelic approach, the HLA-ligands are co-immunoprecipitated with HLA heterodimers from cell lines genetically modified for expression of only a single HLA allele (bottom). Thus, peptides identified from mono-allelic approaches do not require deconvolution for HLA heterodimer binding assignments.
Figure 19:
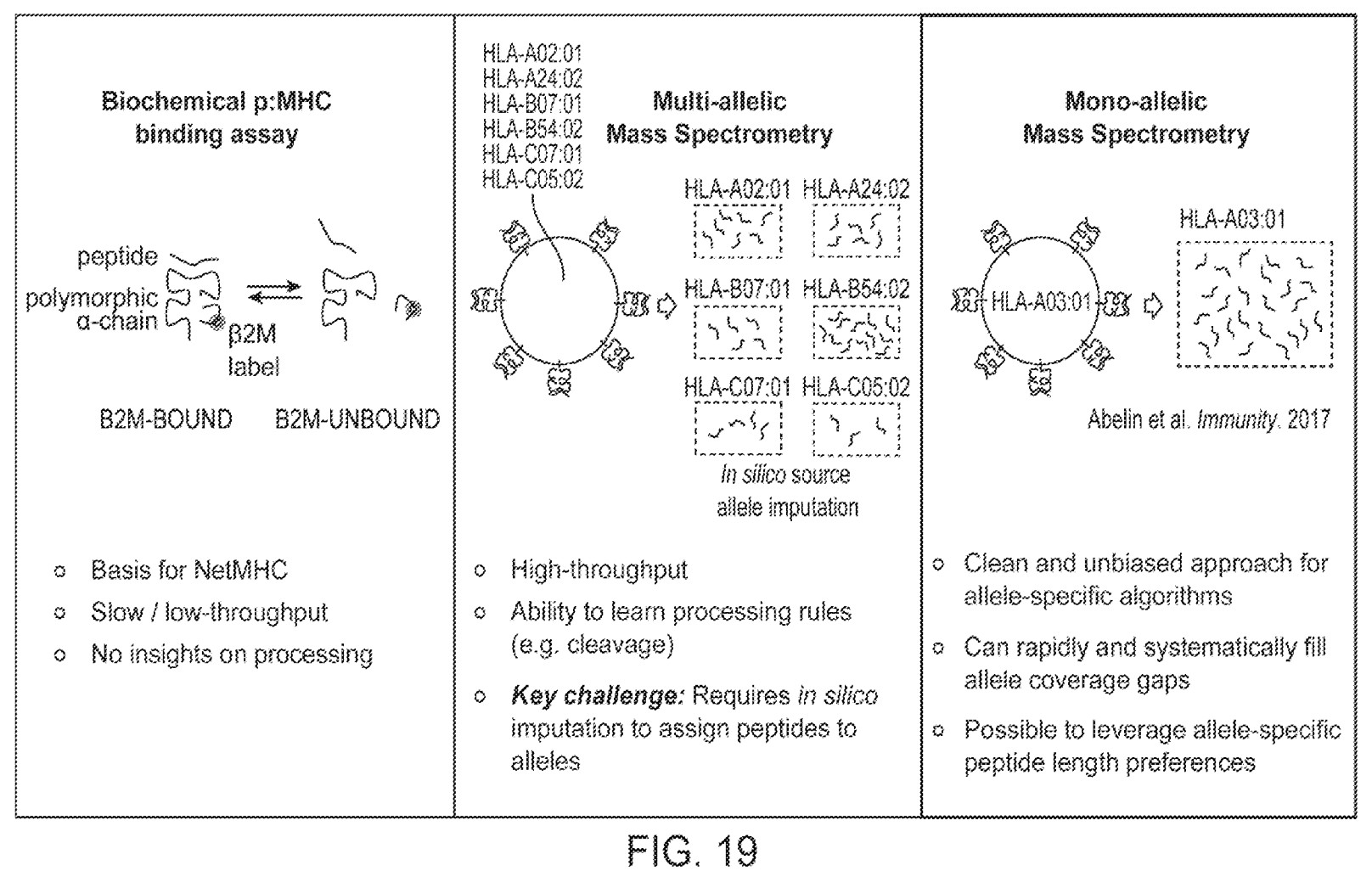

Biochemical peptide-MHC binding assay for HLA-epitope discovery was the basis for NetMHC, the allele-specific predictor using artificial neural networks; however, biochemical p:MHC binding assay slow is a low-throughput method (FIG. 19). Endogenously processed and presented HLA-ligands profiled from cell lines and patient-derived materials are commonly multi-allelic, meaning that LC-MS/MS data generated from these samples contain a mixed population of ligands that can bind to one of the multiple simultaneously expressed HLA alleles, as shown in FIG. 17 and FIG. 19. Multi-allelic datasets require deconvolution to ascertain which peptides bind to the different HLA heterodimers presented by an individual. Thus, ligands from multi-allelic datasets have to be assigned to their corresponding HLA heterodimers using either (1) binding predictors trained with preexisting data or (2) deconvolution algorithms that leverage overlap across HLA alleles represented in large ligand datasets. It is important to note that only LC-MS/MS datasets with available HLA typing information can be confidently deconvoluted. In fact, nearly 40% of the naturally processed ligands bound to HLA class I complexes reported from multi-allelic studies in the Immune Epitope Database (IEDB) lack HLA allele-specific assignments either due to the lack of HLA typing information or inability to deconvolute, making it challenging to use this subset of data for allele-specific epitope prediction. In addition, it is difficult to identify peptides bound to rare class I HLA heterodimers and many class II HLA heterodimers because there is not enough annotated data for deconvolution. The multi-allelic data generation approach also limits the discovery of novel binding motifs as it deconvolution relies on preexisting knowledge. Though there are caveats to utilizing multi-allelic datasets for allele-specific epitope predictions, they are immensely valuable for determining patterns of ligand presentation that require co-expression of multiple alleles and for validating epitope prediction algorithms.

An orthogonal approach to multi-allelic data generation and subsequent deconvolution is the creation of mono-allelic datasets from which peptide populations presented by a single HLA allele are identified (FIG. 17 and FIG. 19). One method for generating mono-allelic data utilizes cell lines that are deficient in HLA expression. These cells can be transfected or transduced with single HLA alleles, so ligands can be profiled by LC-MS/MS to generate allele-specific ligand libraries. Peptides bound to soluble HLA (sHLA) molecules can also be isolated from cell media and profiled by LC-MS/MS to produce mono-allelic data. A major advantage of mono-allelic datasets is that they require no deconvolution and enable confident peptide-HLA allele assignments without preexisting data. Mono-allelic approaches also rapidly provide data for HLA alleles that have not been characterized previously—a task that multi-allelic data can do only if enough overlap is present amongst large datasets. Additionally, novel peptide-binding motifs can easily be discovered using mono-allelic systems as no previous knowledge is required for confident HLA-binding assignments. Mono-allelic data can even be leveraged to assign ligands from multi-allelic datasets when deconvolution methods fail to do so.

The limiting factor of currently available mono-allelic approach is that it requires an HLA deficient cell line. A key innovative feature of the present disclosure is that an HLA deficient cell line is not required for mono-allelic data generation. The affinity-tagged constructs as provided herein can be put into any cell line presenting endogenous HLA-peptide complexes to isolate the allele of interest using the affinity tag. Another advantage of the present disclosure is that the same reagents can be used for any class I or class II allele in the library provided that it has the same affinity tag, making presently disclosed method scalable (automated). In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition. In some embodiments, the disease or condition is cancer. In some embodiments, the population of cells is from a biological sample from a subject with a disease or condition.

In some embodiments, the method further comprises isolating the peptides from the affinity acceptor tagged HLA-peptide complexes before the characterizing. In some embodiments, the peptides are isolated using anti-HLA antibodies. In some cases, soluble HLA (sHLA) with affinity tags are isolated using anti-HLA antibodies. In some cases, soluble HLA (sHLA) with affinity tags are isolated using a column containing an anti-HLA antibody.

Methods and Compositions

Provided herein is a method of characterizing HLA-peptide complexes comprising: providing a population of cells, wherein one or more cells of the population of cells comprise a polynucleic acid comprising a sequence encoding an affinity acceptor tagged class I or class II HLA allele, wherein the sequence encoding an affinity acceptor tagged HLA comprises a sequence encoding a recombinant class I or class II HLA allele operatively linked to a sequence encoding an affinity acceptor peptide; expressing the affinity acceptor tagged HLA in at least one cell of the one or more cells of the population of cells, thereby forming affinity acceptor tagged HLA-peptide complexes in the at least one cell; enriching for the affinity acceptor tagged HLA-peptide complexes; and characterizing HLA-peptide complexes.

In some embodiments, the characterizing comprises characterizing a peptide from the affinity acceptor tagged HLA-peptide complex. In some embodiments, the method comprises carrying out the steps of the method for different class I and/or class II HLA alleles. In some embodiments, the method comprises using more than one class I and/or class II HLA allele. In some embodiments, the population of cells are derived from a subject (e.g., a patient having a disease). In some embodiments, the population of cells are class I and/or class II negative cell lines. In some embodiments, the method further comprises generating an HLA-allele specific peptide database.

Provided herein is a method of generating an HLA-allele specific peptide database comprising: providing a first and a second population of cells each comprising one or more cells comprising an affinity acceptor tagged HLA, wherein the sequence affinity acceptor tagged HLA comprises a different recombinant polypeptide encoded by a different HLA allele operatively linked to an affinity acceptor peptide; enriching for affinity acceptor tagged HLA-peptide complexes; characterizing a peptide or a portion thereof bound to an affinity acceptor tagged HLA-peptide complex from the enriching; and generating an HLA-allele specific peptide database.

In some embodiments, the enriching does not comprise use of a tetramer reagent.

In some embodiments, the characterizing comprises determining the sequence of a peptide or a portion thereof bound to an affinity acceptor tagged HLA-peptide complex from the enriching.

In some embodiments, the characterizing comprises determining whether the peptide or a portion thereof is modified (e.g., post-translational modification). In some embodiments, the determining comprises biochemical analysis. In some embodiments, the determining comprises mass spectrometry analysis. In some embodiments, the mass spectrometry is MS analysis, MS/MS analysis, LC-MS/MS analysis, or a combination thereof. In some embodiments, MS analysis is used to determine a mass of an intact peptide. For example, the determining can comprise determining a mass of an intact peptide (e.g., MS analysis). In some embodiments, MS/MS analysis is used to determine a mass of peptide fragments. For example, the determining can comprise determining a mass of peptide fragments, which can be used to determine an amino acid sequence of a peptide or portion thereof (e.g., MS/MS analysis). In some embodiments, the mass of peptide fragments is used to determine a sequence of amino acids within the peptide. In some embodiments, LC-MS/MS analysis used to separate complex peptide mixtures. For example, the determining can comprise separating complex peptide mixtures, such as by liquid chromatography, and determining a mass of an intact peptide, a mass of peptide fragments, or a combination thereof (e.g., LC-MS/MS analysis). This data can be used, e.g., for peptide sequencing.

In some embodiments, the characterizing comprises evaluating a binding affinity or stability of a peptide or a portion thereof bound to an affinity acceptor tagged HLA-peptide complex from the enriching. In some embodiments, the characterizing comprises determining whether a peptide or a portion thereof bound to an affinity acceptor tagged HLA-peptide complex from the enriching contains one or more mutations. In some embodiments, the characterizing comprises determining whether the peptide or a portion thereof is modified (e.g., post-translational modification). In some embodiments, the characterizing comprises evaluating associations of peptides of affinity acceptor tagged HLA-peptide complexes with HLA alleles.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition. In some embodiments, the disease or condition is cancer. In some embodiments, the population of cells is from a biological sample from a subject with a disease or condition.

In some embodiments, the population of cells is a cell line. In some embodiments, the population of cells is a population of primary cells.

In some embodiments, the recombinant class I or class II HLA allele is matched to a subject with a disease or condition. In some embodiments, an antigen presenting cell comprising the peptide or a mutant thereof bound to an affinity acceptor tagged HLA-peptide complex has reactivity to a T cell expressing a T cell receptor from a subject. In some embodiments, the characterizing comprises comparing HLA-peptide complexes from cancer cells to HLA-peptide complexes from non-cancer cells.

In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles. In some embodiments, the population of cells is a knock-out of all HLA class II alleles. In some embodiments, the population of cells is a knock-out of all HLA class I alleles and a knock-out of all HLA class II alleles. In some embodiments, knock-out of an HLA class I or class II allele comprises elimination of the function of the HLA class I or class II allele. In some embodiments, knock-out of the HLA class I or class II allele is achieved through gene editing. In some embodiments, gene editing is performed by administering to an individual in need thereof a nuclease, wherein the nuclease targets the HLA class I allele or class II allele to be knocked-out. In some embodiments, the nuclease is a CRISPR associated protein (e.g. Cas proteins, e.g., Cas9), a Zinc finger nuclease (ZFN), a Transcription Activator-Like Effector Nuclease (TALEN), or a meganuclease. In some embodiments, gene editing is achieved by administering to an individual in need thereof a CRISPR-Cas9 system. In some embodiments, any suitable nuclease that induces a nick or double-stranded break into a desired recognition site is used. In some embodiments, a naturally-occurring or native nuclease is used. In some embodiments, a modified or engineered nuclease is used.

In some embodiments, the population of cells is a knock-down of one or more HLA class I alleles. In some embodiments, the population of cells is a knock-down of one or more HLA class II alleles. In some embodiments, the population of cells is a knock-down of all HLA class I alleles. In some embodiments, the population of cells is a knock-down of all HLA class II alleles. In some embodiments, the population of cells is a knock-down of all HLA class I alleles and a knock-out of all HLA class II alleles. In some embodiments, knock-down of an HLA class I or class II allele comprises a reduction in the expression of the HLA class I or class II allele. In some embodiments, knock-down of the HLA class I allele or class II allele is achieved by administering to an individual in need thereof a therapeutically effective amount of a small double-stranded interfering RNA (siRNA), a microRNA (miRNA), a short hairpin RNA (shRNA), wherein the siRNA, miRNA, shRNA targets the HLA class I allele or class II allele to be knocked-down. In some embodiments, the expression of the HLA class I or class II allele is reduced by about 99%, about 95%, about 90%, about 85%, about 80%, about 75%, about 70%, about 65%, about 60%, about 55%, about 50%, about 45%, about 40%, about 35%, about 30%, about 25%, or about 20% compared to when the HLA class I allele or class II allele has not been knocked-down.

In some embodiments, the population of cells comprises cells that have been enriched or sorted for cell surface expression of an HLA class I allele, an HLA class II allele, or a combination thereof, such as by fluorescence activated cell sorting (FACS). In some embodiments, fluorescence activated cell sorting (FACS) is used to sort the population of cells. In some embodiments, fluorescence activated cell sorting (FACS) is used to sort the population of cells for cell surface expression of an HLA class I allele, an HLA class II allele, or a combination thereof. In some embodiments, FACS is used to enrich or sort for low cell surface HLA class I or class II expressing cells.

In some embodiments, the population of cells comprises a plurality of populations of cells, each expressing a different recombinant class I or class II HLA allele. In some embodiments, each population of cells of the plurality is in a separate container.

Figure 13:
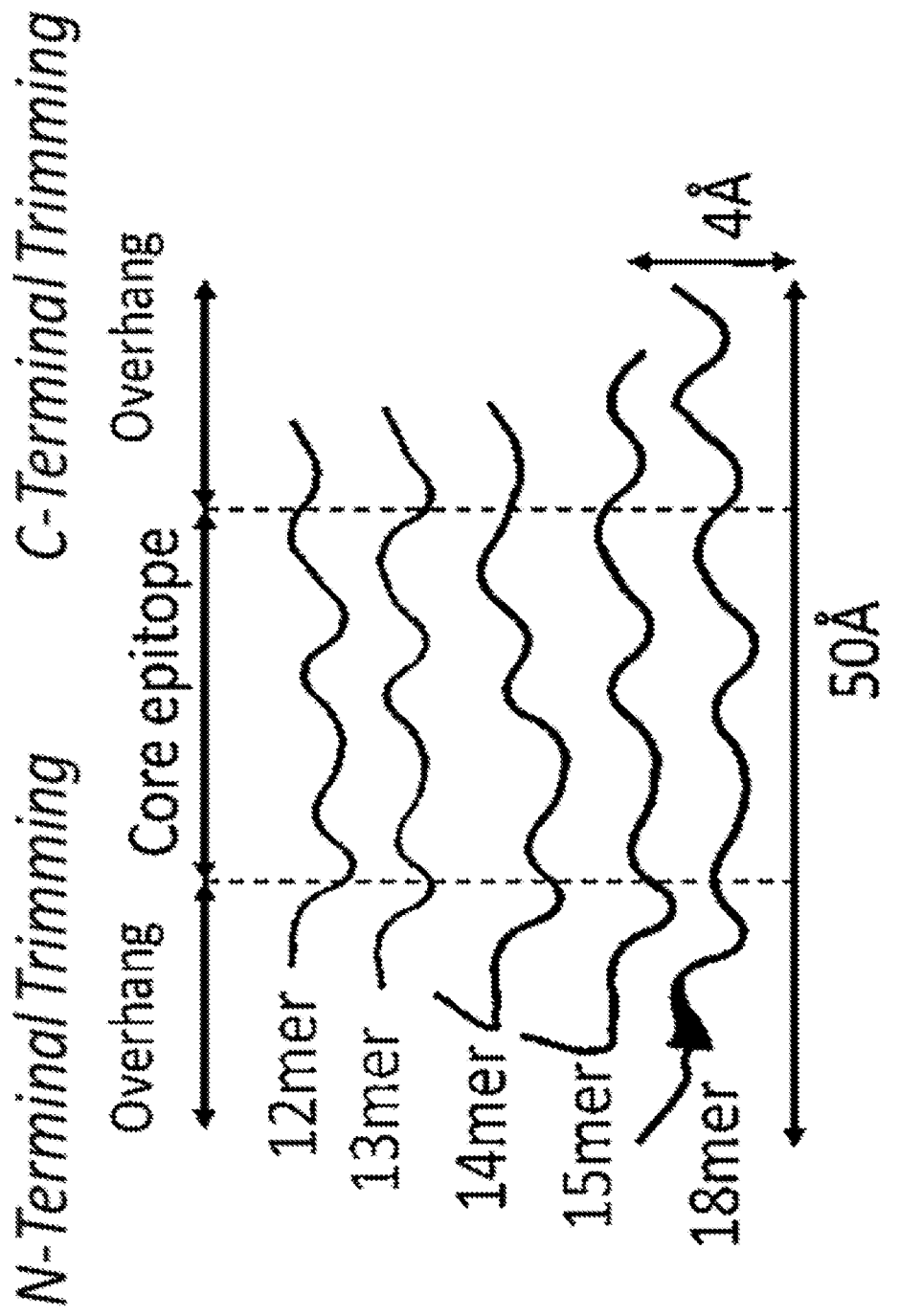
FIG. 13 is a schematic representation of an overview HLA class II trimming experiments that enable identification of core binding epitopes. HLA class II molecules bind nested sets of peptides, usually 12-18 amino acids in length, generated from the same source protein. Longer peptides overhang from the N- and C-terminal sides of HLA class II molecules, while the core epitope interacts most strongly with peptide-binding groove. Peptides bound to HLA class II molecules are trimmed using peptidases specific for N- and C-terminal ends. After trimming, core peptide epitopes are sequenced using LC-MS/MS.

In some embodiments, the method further comprises isolating peptides from the affinity acceptor tagged HLA-peptide complexes before the characterizing. In some embodiments, the method further comprises trimming a terminus of the peptide bound to the HLA-peptide complexes (FIG. 13).

In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the sequence encoding a recombinant class I or class II HLA allele encodes a class I HLA. In some embodiments, the sequence encoding a recombinant class I or class II HLA allele encodes a class II HLA. In some embodiments, the class I HLA is selected from the group consisting of HLA-A, HLA-B, HLA-C. In some embodiments, the class I HLA is a non-classical class-I-b group. In some embodiments, the class I HLA is selected from the group consisting of HLA-E, HLA-F, and HLA-G. In some embodiments, the class I HLA is a non-classical class-I-b group selected from the group consisting of HLA-E, HLA-F, and HLA-G. In some embodiments, the class II HLA comprises a HLA class II α-chain, a HLA class II β-chain, or a combination thereof.

In some embodiments, each sequence encoding a different class I and/or class II HLA allele is operatively linked to a sequence encoding a different affinity acceptor peptide. In some embodiments, the sequence encoding an affinity acceptor peptide is operatively linked to a sequence encoding a recombinant class I or class II HLA allele that encodes for an extracellular portion of the recombinant class I or class II HLA allele. In some embodiments, the encoded affinity acceptor peptide is expressed extracellularly. In some embodiments, the sequence encoding an affinity acceptor peptide is operatively linked to the N-terminus of the sequence encoding a recombinant class I or class II HLA allele. In some embodiments, the sequence encoding an affinity acceptor peptide is operatively linked to a sequence encoding a recombinant class I or class II HLA allele that encodes for an intracellular portion of the recombinant class I or class II HLA allele. In some embodiments, the encoded affinity acceptor peptide is expressed intracellularly. In some embodiments, the sequence encoding an affinity acceptor peptide is operatively linked to the C-terminus of the sequence encoding a recombinant class I or class II HLA allele.

In some embodiments, the sequence encoding an affinity acceptor peptide is operatively linked to the sequence encoding a recombinant class I or class II HLA allele by a linker.

In some embodiments, the enriching comprises enriching for intact cells expressing the affinity acceptor tagged HLA-peptide complexes.

In some embodiments, the method does not comprise lysing the one or more cells before the enriching. In some embodiments, the method further comprises lysing the one or more cells before the enriching.

In some embodiments, the enriching comprises contacting an affinity acceptor peptide binding molecule to the affinity acceptor tagged HLA-peptide complexes, wherein the affinity acceptor peptide binding molecule binds specifically to the affinity acceptor peptide. In some embodiments, the affinity acceptor peptide can comprise a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof, optionally, wherein the affinity acceptor peptide comprises two or more repeats of a tag sequence. In some embodiments, the affinity acceptor peptide binding molecule is biotin or an antibody specific to the affinity acceptor peptide.

In some embodiments, the enriching comprises contacting an affinity molecule to the affinity acceptor tagged HLA-peptide complexes, wherein the affinity molecule binds specifically to the affinity acceptor peptide binding molecule. In some embodiments, the affinity molecule is streptavidin, NeutrAvidin, or a derivative thereof. In some embodiments, the enriching comprises immunoprecipitating affinity acceptor tagged HLA-peptide complexes. In some embodiments, the affinity acceptor peptide binding molecule is attached to a solid surface. In some embodiments, the affinity molecule is attached to a solid surface. In some embodiments, the solid surface is a bead.

In some embodiments, the enriching comprises immunoprecipitating affinity acceptor tagged HLA-peptide complexes with an affinity acceptor peptide binding molecule that binds specifically to the affinity acceptor peptide. In some embodiments, the affinity acceptor peptide binding molecule does not specifically interact with the amino acid sequence of the encoded recombinant class I or class II HLA. In some embodiments, the enriching comprises contacting an affinity molecule specific to an extracellular portion of the HLA-peptide complexes. In some embodiments, the enriching comprises contacting an affinity molecule specific to an N-terminal portion of the HLA-peptide complexes.

In some embodiments, the providing comprises contacting the population of cells with the polynucleic acid comprising a sequence encoding an affinity acceptor tagged HLA. In some embodiments, the contacting comprises transfecting or transducing. In some embodiments, the providing comprises contacting the population of cells with a vector or plasmid comprising the polynucleic acid comprising a sequence encoding an affinity acceptor tagged HLA. In some embodiments, the vector is a viral vector.

Any suitable biochemical assay can be used to determine an HLA expressed in a cell (e.g., an engineered cell line). Exemplary methods to determine the identity of an HLA allele expressed in a cell (e.g., an engineered cell line) include Western blot analysis, e.g., to determine the class of an HLA allele (class I or class II), sequence analysis, e.g., sequencing individual alleles (e.g., using different primers for identification of different alleles of similar sequence). In some embodiments, a polynucleic acid encoding a HLA allele comprises a barcode sequence. The barcode sequence can be used to identify an HLA allele expressed in a cell. In some embodiments, the barcode sequence is unique to a single HLA. In some embodiments, the barcode sequence is unique to a single HLA class I or class II allele.

In some embodiments, the polynucleic acid comprising a sequence encoding an affinity acceptor tagged HLA is stably integrated into the genome of the population of cells. In some embodiments, sequence encoding a recombinant class I or class II HLA comprises a sequence encoding a HLA class I α-chain. In some embodiments, the method further comprises expressing a sequence encoding β2 microglobulin in the one or more cells. In some embodiments, the sequence encoding β2 microglobulin is connected to the sequence encoding a HLA class I α-chain. In some embodiments, the sequence encoding β2 microglobulin is connected to the sequence encoding a HLA class I α-chain by a linker. In some embodiments, the sequence encoding β2 microglobulin is connected to a sequence encoding a second affinity acceptor peptide.

In some embodiments, the sequence encoding a recombinant class I or class II HLA comprises a sequence encoding a HLA class II α-chain. In some embodiments, the method further comprises expressing a sequence encoding a HLA class II β-chain in the one or more cells. In some embodiments, the sequence encoding a HLA class II β-chain is connected to the sequence encoding a HLA class II α-chain. In some embodiments, the sequence encoding a HLA class II β-chain is connected to the sequence encoding a HLA class II α-chain by a linker. In some embodiments, the sequence encoding a HLA class II β-chain is connected to a sequence encoding a second affinity acceptor peptide.

In some embodiments, the second affinity acceptor peptide is different than the first affinity acceptor peptide and can comprise a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the determining comprises performing mass spectrometry, such as tandem mass spectrometry. In some embodiments, the determining comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides.

In some embodiments, the population of cells is a cell line is selected from HEK293T, expi293, HeLa, A375, 721.221, JEG-3, K562, Jurkat, Hep G2, SH-SY5Y, CACO-2, U937, U-2 OS, ExpiCHO, CHO and THP1. In some embodiments, the cell line is treated with one or more cytokines, checkpoint inhibitors, epigenetically-active drugs, IFN-γ, an agent that alters antigen processing (e.g., peptidase inhibitors, proteasome inhibitor, TAP inhibitor, etc.), or a combination thereof. In some embodiments, the peptide database is a no-enzyme specificity peptide database, such as a without modification database or a with modification (e.g., phosphorylation or cysteinylation) database. In some embodiments, the peptide database is a polypeptide database. In some embodiments, the polypeptide database is a protein database. In some embodiments, the method further comprises searching the peptide database using a reversed-database search strategy. In some embodiments, the method further comprises searching a protein database using a reversed-database search strategy. In some embodiments, a de novo search is performed, e.g., to discover new peptides that are not included in a normal peptide or protein database.

In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells or cells infected by an infectious agent or a portion thereof.

In some embodiments, the population of cells is contacted with an agent prior to isolating said HLA-peptide complexes from the one or more cells. In some embodiments, said agent is an inflammatory cytokine, a chemical agent, an adjuvant, a therapeutic agent or radiation.

In some embodiments, the HLA allele is a mutated HLA allele.

In some embodiments, the method comprises carrying out the steps of the method for different HLA alleles.

Provided herein is a HLA-allele specific binding peptide sequence database obtained by carrying out the methods described herein. Provided herein is a combination of two or more HLA-allele specific binding peptide sequence databases obtained by carrying out the methods described herein repeatedly, each time using a different HLA-allele. Provided herein is a method for generating a prediction algorithm for identifying HLA-allele specific binding peptides, comprising training a machine with a peptide sequence database of described herein. In some embodiments, the machine combines one or more linear models, support vector machines, decision trees and neural networks.

Generating a prediction algorithm by training a machine is a well-known technique. The most important in the training of the machine is the quality of the database used for the training. Typically, the machine combines one or more linear models, support vector machines, decision trees and/or a neural network.

In some embodiments, a variable used to train the machine or algorithm comprises one or more variables selected from the group consisting of peptide sequence, amino acid physical properties, peptide physical properties, expression level of the source protein of a peptide within a cell, protein stability, protein translation rate, ubiquitination sites, protein degradation rate, translational efficiencies from ribosomal profiling, protein cleavability, protein localization, motifs of host protein that facilitate TAP transport, host protein is subject to autophagy, motifs that favor ribosomal stalling (e.g., polyproline or polylysine stretches), protein features that favor NMD (e.g., long 3' UTR, stop codon>50 nt upstream of last exon:exon junction and peptide cleavability).

Provided herein is a method for identifying HLA-allele specific binding peptides comprising analyzing the sequence of a peptide with a machine which has been trained with a peptide sequence database obtained by carrying out a method described herein for the HLA-allele. In some embodiments, the method comprises determining the expression level of the source protein of the peptide within a cell; and wherein the source protein expression is a predictive variable used by the machine. In some embodiments, the expression level is determined by measuring the amount of source protein or the amount of RNA encoding said source protein.

Provided herein is a composition comprising a first and a second recombinant polynucleic acid each comprising a sequence encoding an affinity acceptor tagged HLA, wherein the sequence encoding an affinity acceptor tagged HLA comprises (a) a sequence encoding a different recombinant HLA class I α-chain allele, (b) a sequence encoding an affinity acceptor peptide, and optionally, (c) a sequence encoding β2 microglobulin; wherein the sequences of (a) and (b), and optionally (c), are operatively linked.

Provided herein is a composition comprising a first and a second recombinant polynucleic acid each comprising a sequence encoding an affinity acceptor tagged HLA, wherein the sequence encoding an affinity acceptor tagged HLA comprises (a) a sequence encoding a recombinant HLA class II α-chain allele, (b) a sequence encoding an affinity acceptor peptide, and optionally, (c) a sequence encoding a HLA class II β-chain; wherein the sequences of (a) and (b), and optionally (c), are operatively linked.

In some embodiments, the first and second recombinant polynucleic acids are isolated.

In some embodiments, the sequence encodes a recombinant class I or class II HLA allele. In some embodiments, the class I HLA is selected from the group consisting of HLA-A, HLA-B, HLA-C. In some embodiments, the class I HLA is a non-classical class-I-b group. In some embodiments, the class I HLA is selected from the group consisting of HLA-E, HLA-F, and HLA-G. In some embodiments, the class I HLA is a non-classical class-I-b group selected from the group consisting of HLA-E, HLA-F, and HLA-G.

In some embodiments, for both the first and the second recombinant polynucleic acids: the sequence encoding an affinity acceptor peptide is operatively linked to a sequence of the sequence encoding a different recombinant HLA allele that encodes for an extracellular portion of the different recombinant HLA allele. In some embodiments, for both the first and the second recombinant polynucleic acids: the sequence encoding an affinity acceptor molecule is operatively linked to the N-terminus of the sequence encoding a different recombinant HLA allele. In some embodiments, for both the first and the second recombinant polynucleic acids: the sequence encoding an affinity acceptor peptide is operatively linked to a sequence of the sequence encoding a different recombinant HLA allele that encodes for an intracellular portion of the different recombinant HLA allele. In some embodiments, for both the first and the second recombinant polynucleic acids: the sequence encoding an affinity acceptor peptide is operatively linked to the C-terminus of the sequence encoding a different recombinant HLA allele. In some embodiments, for both the first and the second recombinant polynucleic acids: the sequence encoding an affinity acceptor peptide is operatively linked to the sequence encoding a different recombinant HLA allele by a linker. In some embodiments, the encoded affinity acceptor peptide binds specifically to an affinity acceptor peptide binding molecule. In some embodiments, the affinity acceptor peptide of the first and the second recombinant polynucleic acids is different.

In some embodiments, the encoded affinity acceptor peptide can comprise a biotin acceptor peptide (BAP), polyhistidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, cholinebinding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof; optionally, wherein the affinity acceptor peptide comprises two or more repeats of a tag sequence. In some embodiments, the affinity acceptor peptide binding molecule is biotin or an antibody specific to the affinity acceptor peptide. In some embodiments, the affinity acceptor peptide binding molecule binds specifically to an affinity molecule. In some embodiments, the affinity molecule is streptavidin, NeutrAvidin, or a derivative thereof. In some embodiments, the affinity acceptor peptide binding molecule does not specifically interact with an amino acid sequence of the encoded recombinant class I or class II HLA. In some embodiments, for both the first and the second recombinant polynucleic acids: the sequence encoding an affinity acceptor tagged HLA is stably integrated into the genome of a cell. In some embodiments, the sequence encoding β2 microglobulin or the sequence encoding a HLA class II β-chain is connected to a sequence encoding a second affinity acceptor peptide.

In some embodiments, the second affinity acceptor peptide comprises an HA tag. In some embodiments, the second affinity acceptor peptide can comprise a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof, optionally, wherein the second affinity acceptor peptide comprises two or more repeats of a tag sequence.

In some embodiments, for both the first and the second recombinant polynucleic acids: the sequence encoding β2 microglobulin or the sequence encoding a HLA class II β-chain is connected to the sequence encoding a different recombinant HLA and the affinity acceptor peptide by a linker. In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

Provided herein is a composition comprising a first and a second isolated polypeptide molecule encoded by the first and the second polynucleic acids, respectively of a composition described herein. Provided herein is a composition comprising a first and a second cell comprising a first and a second polypeptide molecule encoded by the first and the second polynucleic acids, respectively of a composition described herein. Provided herein is a composition comprising a first and a second cell comprising the first and the second polynucleic acids, respectively of a composition described herein. Provided herein is a composition comprising a first and a second population of cells comprising one or more cells comprising the first and the second polynucleic acids, respectively of a composition described herein.

In some embodiments, the first and the second population of cells express one or more endogenous class I or class II HLA alleles. In some embodiments, the first and the second population of cells are engineered to lack one or more endogenous HLA class I alleles. In some embodiments, the first and the second population of cells are engineered to lack endogenous HLA class I alleles. In some embodiments, the first and the second population of cells are engineered to lack one or more endogenous HLA class II alleles. In some embodiments, the first and the second population of cells are engineered to lack endogenous HLA class II alleles. In some embodiments, the first and the second population of cells are engineered to lack endogenous HLA class I alleles and endogenous HLA class II alleles.

Provided herein is a method of making a cell comprising transducing or transfecting a first and a second cell with the first and the second polynucleic acids, respectively of a composition described herein.

Provided herein is a peptide identified according to a method described herein.

Provided herein is a method of enriching for immunogenic peptides comprising: providing a population of cells comprising one or more cells expressing an affinity acceptor tagged HLA, wherein the affinity acceptor tagged HLA comprises an affinity acceptor peptide operatively linked to a recombinant HLA encoded by a recombinant HLA allele; and enriching for HLA-peptide complexes comprising the affinity acceptor tagged HLA. In some embodiments, the method further comprises determining the sequence of immunogenic peptides isolated from the HLA-peptide complexes. In some embodiments, the determining comprises using LC-MS/MS.

Human Leukocyte Antigen (HLA) System

The immune system can be classified into two functional subsystems: the innate and the adaptive immune system. The innate immune system is the first line of defense against infections, and most potential pathogens are rapidly neutralized by this system before they can cause, for example, a noticeable infection. The adaptive immune system reacts to molecular structures, referred to as antigens, of the intruding organism. Unlike the innate immune system, the adaptive immune system is highly specific to a pathogen. Adaptive immunity can also provide long-lasting protection; for example, someone who recovers from measles is now protected against measles for their lifetime. There are two types of adaptive immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in T cells, of the body. Cytotoxic T cells recognize these antigens and kill the cells that harbor the antigens.

The term "major histocompatibility complex (MHC)", "MHC molecules", or "MHC proteins" refers to proteins capable of binding peptides resulting from the proteolytic cleavage of protein antigens and representing potential T-cell epitopes, transporting them to the cell surface and presenting them there to specific cells, e.g., in cytotoxic T-lymphocytes or T-helper cells. The human MHC is also called the HLA complex. Thus, the term "human leukocyte antigen (HLA) system", "HLA molecules" or "HLA proteins" refers to a gene complex encoding the MHC proteins in humans. The term MHC is referred as the "H-2" complex in murine species. Those of ordinary skill in the art will recognize that the terms "major histocompatibility complex (MHC)", "MHC molecules", "MHC proteins" and "human leukocyte antigen (HLA) system", "HLA molecules", "HLA proteins" are used interchangeably herein.

HLA proteins are classified into two types, referred to as HLA class I and HLA class II. The structures of the proteins of the two HLA classes are very similar; however, they have very different functions. Class I HLA proteins are present on the surface of almost all cells of the body, including most tumor cells. Class I HLA proteins are loaded with antigens that usually originate from endogenous proteins or from pathogens present inside cells, and are then presented to naïve or cytotoxic T-lymphocytes (CTLs). HLA class II proteins are present on antigen presenting cells (APCs), including but not limited to dendritic cells, B cells, and macrophages. They mainly present peptides, which are processed from external antigen sources, i.e. outside of the cells, to helper T cells. Most of the peptides bound by the HLA class I proteins originate from cytoplasmic proteins produced in the healthy host cells of an organism itself, and do not normally stimulate an immune reaction.

Class I HLA molecules consist of a heavy chain and a light chain and are capable of binding a peptide of about 7 to 13 amino acids (e.g., about 8 to 11 amino acids, or 9 or 10 amino acids), if this peptide has suitable binding motifs, and presenting it to cytotoxic T-lymphocytes. The peptides bound by class I HLA molecules originate from an endogenous protein antigen. The heavy chain of the HLA molecules of class I can be an HLA-A, HLA-B or HLA-C monomer, and the light chain is β-2-microglobulin. Class I HLA occurs as an α chain composed of three domains—α1, α2, and α3. This chain is often referred to as the class I heavy chain, and is referred to herein as the class I alpha-chain. The α1 rests upon a unit of the non-HLA molecule β2 microglobulin (encoded on human chromosome 15). The α3 domain is transmembrane, anchoring the HLA class I molecule to the cell membrane. The peptide being presented is held by the floor of the peptide-binding groove, in the central region of the α1/α2 heterodimer (a molecule composed of two nonidentical subunits). Class I HLA-A, HLA-B or HLA-C are highly polymorphic. Class Ib HLA exhibits limited polymorphism, expression patterns and presented antigens. This group is subdivided into a group encoded within HLA loci, e.g., HLA-E, HLA-F, HLA-G, as well as those not, e.g., stress ligands such as ULBPs, Rae1 and H60. The antigen/ligand for many of these molecules remain unknown, but they can interact with each of CD8+ T cells, NKT cells, and NK cells.

In some embodiments, the present disclosure utilizes a non-classical class I HLA-E allele. HLA-E is one of non-classical class I molecule recognized by natural killer (NK) cells and CD8+ T cells. HLA-E is expressed in almost all tissues including lung, liver, skin and placental cells. HLA-E expression is also detected in solid tumors (e.g., osteosarcoma and melanoma). HLA-E binds to TCR expressed on CD8+ T cells, resulting in the T cell activation. HLA-E is also known to bind CD94/NKG2 receptor expressed on NK cells and CD8+ T cells. CD94 can pair with several different isoforms of NKG2 to form receptors with potential to either inhibit (NKG2A, NKG2B) or promote (NKG2C) cellular activation. HLA-E can bind to a peptide derived from amino acid residues 3-11 of the leader sequences of most HLA-A, -B, -C, and -G molecules, but cannot bind its own leader peptide. HLA-E has also been shown to present peptides derived from endogenous proteins similar to HLA-A, -B, and -C alleles. Under physiological conditions, the engagement of CD94/NKG2A with HLA-E, loaded with peptides from the HLA class I leader sequences, usually induces inhibitory signals. Cytomegalovirus (CMV) utilizes the mechanism for escape from NK cell immune surveillance via expression of the UL40 glycoprotein, mimicking the HLA-A leader. However, it is also reported that CD8+ T cells can recognize HLA-E loaded with the UL40 peptide derived from CMV Toledo strain and play a role in defense against CMV. A number of studies revealed several important functions of HLA-E in infectious disease and cancer.

The peptide antigens attach themselves to the molecules of HLA class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

Figure 1B:
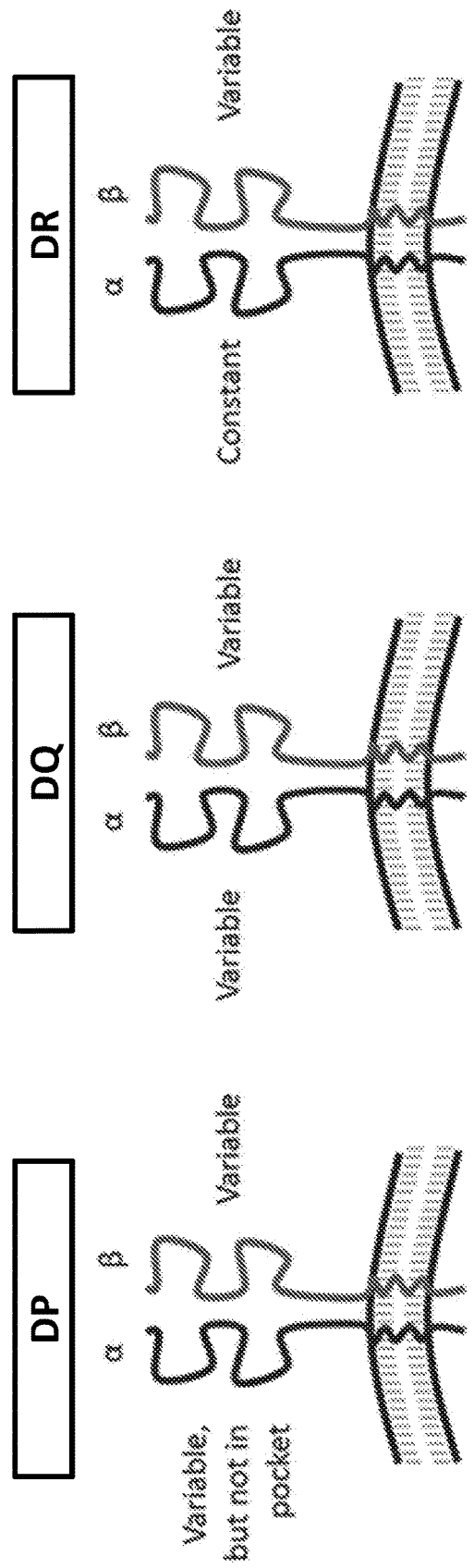
FIG. 1B is a schematic of structures of HLA class II molecules -DP, -DQ, and -DR. HLA-DR molecules are heterodimers containing a constant α-chain and a variable β-chain. HLA-DQ and HLA-DP molecules are heterodimers containing variable α-chains and variable β-chains.

Class II HLA molecules have two chains, α and R, each having two domains—α1 and α2 and β1 and β2—each chain having a transmembrane domain, α2 and β2, respectively, anchoring the HLA class II molecule to the cell membrane. The peptide-binding groove is formed of the heterodimer of α1 and β1. The peptide bound by the HLA molecules of class II usually originates from an extracellular of exogenous protein antigen. The α-chain and the R-chain are in HLA-DR, HLA-DQ and HLA-DP monomers (FIG. 1B). Class II HLA molecules have six isotypes. Classic molecules present peptides to CD4+ lymphocytes. Nonclassic molecules, accessories, with intracellular functions, are not exposed on cell membranes, but in internal membranes in lysosomes, normally loading the antigenic peptides onto classic HLA class II molecules.

In HLA class II, phagocytes such as macrophages and immature dendritic cells take up entities by phagocytosis into phagosomes—though B cells exhibit the more general endocytosis into endosomes—which fuse with lysosomes whose acidic enzymes cleave the uptaken protein into many different peptides. Authophagy is another source of HLA class II peptides. Via physicochemical dynamics in molecular interaction with the HLA class II variants borne by the host, encoded in the host's genome, a particular peptide exhibits immunodominance and loads onto HLA class II molecules. These are trafficked to and externalized on the cell surface. The most studied subclass II HLA genes are: HLA-DPA1, HLA-DPB1, HLA-DQA1, HLA-DQB1, HLA-DRA, and HLA-DRB1.

Presentation of peptides by HLA class II molecules to CD4+ helper T cells is required for immune responses to foreign antigens (Roche and Furuta, 2015). Once activated, CD4+ T cells promote B cell differentiation and antibody production, as well as CD8+ T cell (CTL) responses. CD4+ T cells also secrete cytokines and chemokines that activate and induce differentiation of other immune cells. HLA class II molecules are heterodimers of α and R chains that interact to form a peptide-binding groove that is more open than class I peptide-binding grooves (Unanue et al., 2016). Peptides bound to HLA class II molecules are believed to have a 9-amino acid binding core with flanking residues on either N- or C-terminal side that overhang from the groove (Jardetzky et al., 1996; Stem et al., 1994). These peptides are usually 12-16 amino acids in length and often contain 3-4 anchor residues at positions P1, P4, P6/7 and P9 of the binding register (Rossjohn et al., 2015).

HLA alleles are expressed in codominant fashion, meaning that the alleles (variants) inherited from both parents are expressed equally. For example, each person carries 2 alleles of each of the 3 class I genes, (HLA-A, HLA-B and HLA-C), and so can express six different types of class II HLA. In the class II HLA locus, each person inherits a pair of HLA-DP genes (DPA1 and DPB1, which encode a and 3 chains), a couple of genes HLA-DQ (DQA1 and DQB1, for a and 3 chains), one gene HLA-DRα (DRA1), and one or more genes HLA-DRβ (DRB1 and DRB3, -4 or -5). That means that one heterozygous individual can inherit six or eight functioning class II HLA alleles, three or more from each parent. Thus, the HLA genes are highly polymorphic; many different alleles exist in the different individuals inside a population. Genes encoding HLA proteins have many possible variations, allowing each person's immune system to react to a wide range of foreign invaders. Some HLA genes have hundreds of identified versions (alleles), each of which is given a particular number. In some embodiments, the class I HLA alleles are HLA-A*02:01, HLA-B*14:02, HLA-A*23:01, HLA-E*01:01 (non-classical). In some embodiments, class II HLA alleles are HLA-DRB*01:01, HLA-DRB*01:02, HLA-DRB*11:01, HLA-DRB*15:01, and HLA-DRB*07:01.

Subject specific HLA alleles or HLA genotype of a subject can be determined by any method known in the art. In exemplary embodiments, HLA genotypes are determined by any method described in International Patent Application number PCT/US2014/068746, published Jun. 11, 2015 as WO2015085147. Briefly, the methods include determining polymorphic gene types that can comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

As described herein, there is a large body of evidence in both animals and humans that mutated epitopes are effective in inducing an immune response and that cases of spontaneous tumor regression or long term survival correlate with CD8+ T-cell responses to mutated epitopes (Buckwalter and Srivastava PK. "It is the antigen(s), stupid" and other lessons from over a decade of vaccitherapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al. The response of autologous T cells to a human melanoma is dominated by mutated neoantigens. Proc Natl Acad Sci USA. 102:16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.

The term "T cell" includes CD4+ T cells and CD8+ T cells. The term T cell also includes both T helper 1 type T cells and T helper 2 type T cells. T cells as used herein are generally classified by function and cell surface antigens (cluster differentiation antigens, or CDs), which also facilitate T cell receptor binding to antigen, into two major classes: helper T ($T_H$) cells and cytotoxic T-lymphocytes (CTLs).

Mature helper T ($T_H$) cells express the surface protein CD4 and are referred as CD4+ T cells. Following T cell development, matured, naïve T cells leave the thymus and begin to spread throughout the body, including the lymph nodes. Naïve T cells are those T cells that have never been exposed to the antigen that they are programmed to respond to. Like all T cells, they express the T cell receptor-CD3 complex. The T cell receptor (TCR) consists of both constant and variable regions. The variable region determines what antigen the T cell can respond to. CD4+ T cells have TCRs with an affinity for Class II MHC, and CD4 is involved in determining MHC affinity during maturation in the thymus. Class II MHC proteins are generally only found on the surface of specialized antigen-presenting cells (APCs). Specialized antigen presenting cells (APCs) are primarily dendritic cells, macrophages and B cells, although dendritic cells are the only cell group that expresses MHC Class II constitutively (at all times). Some APCs also bind native (or unprocessed) antigens to their surface, such as follicular dendritic cells, but unprocessed antigens do not interact with T cells and are not involved in their activation. The peptide antigens that bind to MHC class I proteins are typically shorter than peptide antigens that bind to MHC class II proteins.

Cytotoxic T-lymphocytes (CTLs), also known as cytotoxic T cells, cytolytic T cells, CD8+ T cells, or killer T cells, refer to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells. Cytotoxic T-lymphocytes have both T-cell receptors (TCR) and CD8 molecules on their surface. T cell receptors are capable of recognizing and binding peptides complexed with the molecules of HLA class I. Each cytotoxic T-lymphocyte expresses a unique T-cell receptor which is capable of binding specific MHC/peptide complexes. Most cytotoxic T cells express T-cell receptors (TCRs) that can recognize a specific antigen. In order for the TCR to bind to the class I MHC molecule, the former must be accompanied by a glycoprotein called CD8, which binds to the constant portion of the class I MHC molecule. Therefore, these T cells are called CD8+ T cells. The affinity between CD8 and the MHC molecule keeps the T cell and the target cell bound closely together during antigen-specific activation. CD8+ T cells are recognized as T cells once they become activated and are generally classified as having a pre-defined cytotoxic role within the immune system. However, CD8+ T cells also have the ability to make some cytokines.

"T cell receptors (TCR)" are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable regions of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

The term "HLA peptidome" refers to a pool of peptides which specifically interacts with a particular HLA class and can encompass thousands of different sequences. HLA peptidomes include a diversity of peptides, derived from both normal and abnormal proteins expressed in the cells. Thus, the HLA peptidomes can be studied to identify cancer specific peptides, for development of tumor immunotherapeutics and as a source of information about protein synthesis and degradation schemes within the cancer cells. In some embodiments, HLA peptidome is a pool of soluble HLA molecules (sHLA). In some embodiments, HLA peptidome is a pool of membranal HLA (mHLA).

The term "antigen presenting cell" or "APC" includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). An "antigen presenting cell" or "APC" is a cell that expresses the Major Histocompatibility complex (MHC) molecules and can display foreign antigen complexed with MHC on its surface.

Universal IP Pipeline: Universal Mono-Allelic HLA-Peptide Complex Identification Platform Adaptive immune responses rely, in part, on the ability of cytotoxic CD8+ T cells to identify and eliminate cells that display disease-associated antigens bound to human leukocyte antigen (HLA) class I molecules. HLA class I proteins (HLA-A, B and C) are expressed on the surface of almost all nucleated cells in the human body and are required for presentation of short peptides for detection by CD8$^+$ T cell receptors. The HLA-bound peptides arise from endogenous or foreign proteins that are cleaved by the proteasome and ER peptidases prior to loading and display by HLA class I proteins. The HLA genes are the most polymorphic genes across the human population, with more than 10,000 HLA class I allele variants identified to date (Robinson et al., 2015). Each HLA allele is estimated to bind and present ~1,000-10,000 unique peptides to T cells; ≤0.1% of ~10 million potential 9mer peptides from human protein-coding genes (Bassani-Stemberg et al., 2015; Hunt et al., 1992; Rammensee et al., 1995, 1999; Rock et al.; Vita et al., 2015; Walz et al., 2015).

Unlike class I, HLA class II proteins (HLA-DR, DQ and DP) are only expressed on the surface of antigen presenting cells (APCs) and epithelial, vascular and connective tissues cells in response to inflammatory signals. Presentation of peptides, most often derived from exogenous proteins, by HLA class II molecules to CD4+ T cells is required for immune responses to foreign antigens (Roche and Furuta, 2015). Once activated, CD4+ T cells promote B cell differentiation and antibody production, as well as CD8+ T cell responses. CD4+ T cells also secrete cytokines and chemokines that activate and induce differentiation of other immune cells. HLA class II molecules are heterodimers of a and R chains that interact to form a peptide-binding groove that is more open than class I peptide-binding grooves (Unanue et al., 2016). Peptides bound to HLA class II molecules are believed to have a 9-amino acid binding core with flanking residues on either N- or C-terminal side that overhang from the groove (Jardetzky et al., 1996; Stem et al., 1994). These peptides are usually 12-16 amino acids in length and often contain 3-4 anchor residues at positions P1, P4, P6/7 and P9 of the binding register (Rossjohn et al., 2015). Less is known about allele-specific peptide-binding characteristics of HLA class II molecules because of the heterogeneity of a and R chain pairing, complexity of data limiting the ability to confidently assign core binding epitopes, and the lack of immunoprecipitation grade, allele-specific antibodies required for high-resolution biochemical analyses.

Peptide-binding rules have been studied extensively for a subset of HLA alleles (Vita et al., 2015) and encoded in advanced neural network-based algorithms that predict binding (Hoof et al., 2009; Lundegaard et al., 2008). However, several factors limit the power to predict peptides presented on HLA alleles. First, the provenance of peptide data upon which these algorithms are trained is diverse, ranging from peptide library screens to Edman degradation and mass spectrometry-based sequencing of endogenously processed and presented peptides (Boen et al., 2000; Rammensee et al., 1995, 1999; Vita et al., 2015). Mass spectrometry-based peptide identifications make up around 30% of the total identification in IEDB. Mass spectrometry has become a desired method of HLA-associated peptide sequencing because of pioneering work by Donald F. Hunt and colleagues (Cobbold et al., 2013; Hunt et al., 1992; Meadows et al., 1997; Mohammed et al., 2008; Zarling et al., 2000, 2006), as well as improvements to instrumentation demonstrated by many groups over the past two decades (Bassani-Stemberg et al., 2015; Caron et al., 2015; Mommen et al., 2014). Second, many existing prediction algorithms have focused on predicting binding but may not fully take into account endogenous processes that generate and transport peptides prior to binding (Larsen et al., 2007). Third, the number of binding peptides for many HLA alleles is too small to develop a reliable predictor. Until now, however, the generation of high-quality resource datasets has been hampered by inefficient protocols that necessitate prohibitively large amounts of input cellular material and a lack of database search tools for HLA-peptide sequencing (Caron et al., 2015; Hoof et al., 2009; Lundegaard et al., 2008; Vita et al., 2015).

Disclosed herein is a unique biochemical enrichment strategy for peptide-HLA class I and II complexes from live cells and cellular lysate. HLA molecules containing an N-terminal or C-terminal tag sequence (e.g., BAP or HA) can be labeled on the cell surface or in cell lysate. For example, HLA molecules containing an N-terminal or C-terminal biotin acceptor peptide (BAP) sequence can be enzymatically labeled with biotin on the cell surface or in cell lysate. For example, HLA molecules containing an N-terminal or C-terminal HA sequence can be enriched from complex cellular mixtures using an HA-specific antibody. In an exemplary embodiment, biotin labeled HLA-peptide complexes are enriched from complex cellular mixtures using streptavidin/NeutrAvidin beads and the enriched HLA-peptide complexes are analyzed or characterized. In an exemplary embodiment, HA labeled HLA-peptide complexes are enriched from complex cellular mixtures using an HA-specific antibody and the enriched HLA-peptide complexes are analyzed or characterized. For example, associated peptides can be eluted and sequenced by LC-MS/MS. Importantly, the presently disclosed methods provide a universal platform for analyzing and characterizing HLA-peptide complexes. For example, the presently disclosed methods provide a universal platform for the identification of endogenously presented peptides from cell line expressing all possible class I or II constructs.

Disclosed herein are single HLA class I and class II allele-expressing cell lines enabling unambiguous peptide:allele assignments (Shimizu and DeMars, 1989; Shimizu et al., 1986). This is an improvement upon current HLA-bound peptide detection methods as most MS-based studies involve eluting and sequencing a messy admixture of ligands bound to multiple HLA-A, B, and C molecules, which require affinity predictions and sometimes deconvolution for allele assignments (Bassani-Stemberg and Gfeller, 2016). Studies with soluble HLA transfected cell lines have been able to derive peptide-binding epitopes for a single HLA allele, but the most comprehensive experiments to date have identified only <200 unique peptides and have required several orders of magnitude more starting cellular material (Hawkins et al., 2008). By removing the uncertainty of peptide:HLA assignments, presently disclosed methods facilitate deeper and more precise evaluations of HLA-peptide ligandomes and rules related to peptide antigen processing and presenting using less cellular material than previous efforts.

The methods and compositions described herein include, for example, chemically labeled variable β-chain (biotinylation) to differentiate between class II HLA heterodimers presented by cells, which allow for improved epitope mapping. HLA class I and class II constructs that contain a tag, such as a biotin acceptor peptide sequence (BAP), at the N- or C-terminus, can be used in the methods described herein. N- and C-terminal affinity tagging enables HLA-allele selective immunopurification from cells expressing endogenous HLA. N-terminal affinity tagging enables HLA-allele selective immunopurification of complexes presented on the cell surface. For example, after transfection or transduction, N-terminal biotinylation enables differentiation between HLA complexes presented on the cell surface vs. all HLA-peptide complexes in cellular lysates. For example, biotinylation of HLA-peptide complexes on intact cell surfaces (no lysis) enables unbiased mass spectrometry (MS) sequencing methods of endogenously processed and presented peptides. The enrichment methods disclosed herein, such as immunoprecipitation enrichment methods, enable high throughput analysis of cell samples.

Provided herein is a method of characterizing HLA-peptide complexes comprising: providing a population of cells, wherein one or more cells of the population of cells comprise a polynucleic acid comprising a sequence encoding an affinity acceptor tagged class I or class II HLA allele, wherein the sequence encoding an affinity acceptor tagged HLA comprises a sequence encoding a recombinant class I or class II HLA allele operatively linked to a sequence encoding an affinity acceptor peptide; expressing the affinity acceptor tagged HLA in at least one cell of the one or more cells of the population of cells, thereby forming affinity acceptor tagged HLA-peptide complexes in the at least one cell; enriching for the affinity acceptor tagged HLA-peptide complexes; and characterizing HLA-peptide complexes.

In some embodiments, the characterizing comprises characterizing a peptide bound to the affinity acceptor tagged HLA-peptide complex from the enriching.

In some embodiments, the method comprises carrying out the steps of the method for two or more class I and/or class II HLA alleles. In some embodiments, the two or more class I and/or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles.

In some embodiments, the affinity acceptor tagged HLA-peptide complexes comprise a transmembrane domain. In some embodiments, the affinity acceptor tagged HLA-peptide complexes comprise an intracellular domain. In some embodiments, the affinity acceptor tagged HLA-peptide complexes are not excreted. In some embodiments, the affinity acceptor tagged HLA-peptide complexes incorporate into a cell membrane when expressed. In some embodiments, the affinity acceptor tagged HLA-peptide complexes are not soluble affinity acceptor tagged HLA-peptide complexes.

In some embodiments, the method further comprises generating an HLA-allele specific peptide database.

In some embodiments, the recombinant class I or class II HLA allele is a single recombinant class I or class II HLA allele.

In some embodiments, method comprises: providing a population of cells each comprising one or more cells comprising an affinity acceptor tagged HLA, wherein the affinity acceptor tagged HLA comprises a different recombinant polypeptide encoded by a different HLA allele operatively linked to an affinity acceptor peptide; enriching for affinity acceptor tagged HLA-peptide complexes; and characterizing a peptide or a portion thereof bound to the affinity acceptor tagged HLA-peptide complex from the enriching.

In some embodiments, the method comprises introducing one or more peptides to the population of cells.

In some embodiments, the introducing comprises contacting the population of cells with the one or more peptides or expressing the one or more peptides in the population of cells. In some embodiments, the introducing comprises contacting the population of cells with one or more nucleic acids encoding the one or more peptides. In some embodiments, the one or more nucleic acids encoding the one or more peptides is DNA. In some embodiments, the one or more nucleic acids encoding the one or more peptides is RNA, optionally wherein the RNA is mRNA.

In some embodiments, the enriching does not comprise use of a tetramer reagent.

In some embodiments, the characterizing comprises determining the sequence of a peptide or a portion thereof bound to the affinity acceptor tagged HLA-peptide complex from the enriching, optionally determining whether a peptide or a portion thereof is modified. In some embodiments, the determining comprises biochemical analysis, mass spectrometry analysis, MS analysis, MS/MS analysis, LC-MS/MS analysis, or a combination thereof. In some embodiments, the characterizing comprises evaluating a binding affinity or stability of a peptide or a portion thereof bound to the affinity acceptor tagged HLA-peptide complex from the enriching. In some embodiments, the characterizing comprises determining whether a peptide or a portion thereof bound to the affinity acceptor tagged HLA-peptide complex from the enriching contains one or more mutations. In some embodiments, the characterizing comprises evaluating associations of peptides with HLA molecules in the affinity acceptor tagged HLA-peptide complexes.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition. In some embodiments, the disease or condition is cancer, an infection with an infectious agent, or an autoimmune reaction. In some embodiments, the method comprises introducing the infectious agent or portions thereof into one or more cells of the population of cells. In some embodiments, the method comprises characterizing one or more peptides from the HLA-peptide complexes, optionally wherein the peptides are from one or more target proteins of the infectious agent. In some embodiments, the method comprises characterizing one or more regions of the peptides from the one or more target proteins of the infectious agent. In some embodiments, the method comprises identifying peptides from the HLA-peptide complexes derived from an infectious agent.

In some embodiments, the population of cells is from a biological sample from a subject with a disease or condition. In some embodiments, the population of cells is a cell line. In some embodiments, the population of cells is a population of primary cells. In some embodiments, the recombinant class I or class II HLA allele is matched to a subject with a disease or condition.

In some embodiments, the method comprises screening for drug (e.g., biologics) hypersensitivity. In some embodiments, the method comprises assessing whether an administered biologic (e.g., a protein, peptide or antibody drug), a fragment of administered biologics, or a processed biologic fragment are presented to T cells. These epitopes can cause adverse effect in the subject, and thus how administered biologics are processed in the subject should be monitored. For example, an HIV drug (e.g., Abacavir) can bind to HLA molecules and change peptide-binding motifs for certain HLA alleles (e.g., HLA-B5701).

In some embodiments, the peptide from the affinity acceptor tagged HLA-peptide complex is capable of activating a T cell from a subject when presented by an antigen presenting cell. In some embodiments, the characterizing comprises comparing HLA-peptide complexes from cancer cells to HLA-peptide complexes from non-cancer cells.

In some embodiments, the population of cells comprises a plurality of populations of cells, each population of cells expressing a different recombinant class I or class II HLA allele. In some embodiments, each population of cells of the plurality is in a same or a separate container.

In some embodiments, the method further comprises isolating peptides from the affinity acceptor tagged HLA-peptide complexes before the characterizing. In some embodiments, the method further comprises removing one or more amino acids from a terminus of a peptide bound to an affinity acceptor tagged HLA-peptide complex.

In some embodiments, the population of cells is a population of low cell surface HLA class I or class II expressing cells. In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles.

In some embodiments, the population of cells is a knock-out of one or more HLA class II alleles. In some embodiments, the population of cells is a knock-out of all HLA class I alleles. In some embodiments, the population of cells is a knock-out of all HLA class II alleles In some embodiments, the population of cells is a knock-out of all HLA class I alleles and a knock-out of all HLA class II alleles. In some embodiments, the sequence encoding the recombinant class I or class II HLA allele encodes a class I HLA. In some embodiments, the class I HLA is selected from the group consisting of HLA-A, HLA-B, HLA-C, HLA-E, HLA-F, and HLA-G. In some embodiments, the sequence encoding the recombinant class I or class II HLA allele encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof.

In some embodiments, each sequence encodes at least two different class I and/or class II HLA alleles. In some embodiments, the at least two different class I and/or class II HLA alleles are each operatively linked to a sequence encoding a different affinity acceptor peptide. In some embodiments, the at least two different class I and/or class II HLA alleles are each operatively linked to a sequence encoding the affinity acceptor peptide.

In some embodiments, the method comprises administering at least a second polynucleic acid comprising a sequence encoding a different recombinant HLA allele operatively linked to the same or a different affinity acceptor peptide.

In some embodiments, the sequence encoding the affinity acceptor peptide is operatively linked to a sequence that encodes an extracellular portion of the recombinant class I or class II HLA allele.

In some embodiments, the encoded affinity acceptor peptide is expressed extracellularly. In some embodiments, the sequence encoding the affinity acceptor peptide is operatively linked to the N-terminus of the sequence encoding the recombinant class I or class II HLA allele. In some embodiments, the sequence encoding the affinity acceptor peptide is operatively linked to a sequence that encodes an intracellular portion of the recombinant class I or class II HLA allele. In some embodiments, the encoded affinity acceptor peptide is expressed intracellularly. In some embodiments, the sequence encoding the affinity acceptor peptide is operatively linked to the C-terminus of the sequence encoding the recombinant class I or class II HLA allele. In some embodiments, the sequence encoding the affinity acceptor peptide is operatively linked to the sequence encoding the recombinant class I or class II HLA allele by a linker.

In some embodiments, enriching comprises enriching for intact cells expressing the affinity acceptor tagged HLA-peptide complexes. In some embodiments, the method does not comprise lysing the cells before enriching. In some embodiments, the method further comprises lysing the one or more cells before enriching. In some embodiments, enriching comprises contacting an affinity acceptor peptide binding molecule to the affinity acceptor tagged HLA-peptide complexes, wherein the affinity acceptor peptide binding molecule binds specifically to the affinity acceptor peptide.

In some embodiments, the affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof; optionally, wherein the affinity acceptor peptide comprises two or more repeats of a tag sequence. In some embodiments, the affinity acceptor peptide binding molecule is biotin or an antibody specific to the affinity acceptor peptide. In some embodiments, the enriching comprises contacting an affinity molecule to the affinity acceptor tagged HLA-peptide complexes, wherein the affinity molecule binds specifically to the affinity acceptor peptide binding molecule. In some embodiments, the affinity molecule is streptavidin, NeutrAvidin, or a derivative thereof. In some embodiments, enriching comprises immunoprecipitating affinity acceptor tagged HLA-peptide complexes. In some embodiments, the affinity acceptor peptide binding molecule is attached to a solid surface. In some embodiments, the affinity molecule is attached to a solid surface. In some embodiments, the solid surface is a bead. In some embodiments, enriching comprises immunoprecipitating affinity acceptor tagged HLA-peptide complexes with an affinity acceptor peptide binding molecule that binds specifically to the affinity acceptor peptide. In some embodiments, the affinity acceptor peptide binding molecule does not specifically interact with the amino acid sequence of the encoded recombinant class I or class II HLA. In some embodiments, enriching comprises contacting an affinity molecule specific to an extracellular portion of the recombinant class I or class II HLA allele. In some embodiments, enriching comprises contacting an affinity molecule specific to an N-terminal portion of the recombinant class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the recombinant class I or class II HLA comprises a sequence encoding a HLA class I α-chain. In some embodiments, the method further comprises expressing a sequence encoding β2 microglobulin in the one or more cells. In some embodiments, the sequence encoding β2 microglobulin is connected to the sequence encoding the HLA class I α-chain. In some embodiments, the sequence encoding β2 microglobulin is connected to the sequence encoding the HLA class I α-chain by a linker. In some embodiments, the sequence encoding β2 microglobulin is connected to a sequence encoding a second affinity acceptor peptide. In some embodiments, the sequence encoding the recombinant class I or class II HLA comprises a sequence encoding a HLA class II α-chain. In some embodiments, the method further comprises expressing a sequence encoding a HLA class II β-chain in the one or more cells In some embodiments, the sequence encoding the HLA class II β-chain is connected to the sequence encoding the HLA class II α-chain. In some embodiments, the sequence encoding the HLA class II β-chain is connected to the sequence encoding the HLA class II α-chain by a linker.

In some embodiments, the sequence encoding the HLA class II β-chain is connected to a sequence encoding a second affinity acceptor peptide. In some embodiments, the second affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof; optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the determining comprises performing biochemical analysis or mass spectrometry, such as tandem mass spectrometry. In some embodiments, the determining comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides.

In some embodiments, the population of cells is a cell line selected from HEK293T, expi293, HeLa, A375, 721.221, JEG-3, K562, Jurkat, Hep G2, SH-SY5Y, CACO-2, U937, U-2 OS, ExpiCHO, CHO and THP1. In some embodiments, the cell line is treated with one or more cytokines, checkpoint inhibitors, epigenetically-active drugs, IFN-γ, agents that alter antigen processing (such as peptidase inhibitors, proteasome inhibitors, and TAP inhibitors), or a combination thereof.

In some embodiments, the peptide database is a no-enzyme specificity peptide database, such as a without modification database or a with modification database. In some embodiments, the method further comprises searching the peptide database using a reversed-database search strategy.

In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells. In some embodiments, the population of cells is contacted with an agent prior to isolating said HLA-peptide complexes from the one or more cells. In some embodiments, said agent is an inflammatory cytokine, a chemical agent, an adjuvant, a therapeutic agent or radiation.

In some embodiments, the HLA allele is a mutated HLA allele.

In some embodiments, the sequence encoding the HLA allele comprises a barcode sequence. In some embodiments, the method further comprises assaying for expression of the affinity acceptor tagged class I or class II HLA allele. In some embodiments, the assaying comprises assaying comprises sequencing an affinity acceptor tagged class I or class II HLA allele, detecting affinity acceptor tagged class I or class II HLA allele RNA, detecting affinity acceptor tagged class I or class II HLA allele protein, or a combination thereof.

In some embodiments, the method comprises carrying out the steps of the method for different HLA alleles. In some embodiments, each different HLA allele comprises a unique barcode sequence. In some embodiments, each polynucleic acid encoding a different HLA allele comprises a unique barcode sequence.

Provided herein is a HLA-allele specific binding peptide sequence database obtained by carrying out a method described herein. Provided herein is a combination of two or more HLA-allele specific binding peptide sequence databases obtained by carrying out a method described herein repeatedly, each time using a different HLA-allele. Provided herein is a method for generating a prediction algorithm for identifying HLA-allele specific binding peptides, comprising training a machine with a peptide sequence database described herein or a combination described herein. In some embodiments, the machine combines one or more linear models, support vector machines, decision trees and neural networks. In some embodiments, a variable used to train the machine comprises one or more variables selected from the group consisting of peptide sequence, amino acid physical properties, peptide physical properties, expression level of the source protein of a peptide within a cell, protein stability, protein translation rate, ubiquitination sites, protein degradation rate, translational efficiencies from ribosomal profiling, protein cleavability, protein localization, motifs of host protein that facilitate TAP transport, host protein is subject to autophagy, motifs that favor ribosomal stalling, and protein features that favor NMD. In some embodiments, the motifs that favor ribosomal stalling comprises polyproline or polylysine stretches. In some embodiments, the protein features that favor NMD are selected from the group consisting of a long 3' UTR, a stop codon greater than 50 nt upstream of last exon:exon junction, and peptide cleavability. Provided herein is a method for identifying HLA-allele specific binding peptides comprising analyzing the sequence of a peptide with a machine which has been trained with a peptide sequence database obtained by carrying out a method described herein for the HLA-allele. In some embodiments, the method comprises determining the expression level of the source protein of the peptide within a cell; and wherein the source protein expression is a predictive variable used by the machine. In some embodiments, the expression level is determined by measuring the amount of source protein or the amount of RNA encoding said source protein.

Provided herein is a composition comprising a recombinant polynucleic acid comprising two or more sequences each encoding an affinity acceptor tagged HLA, wherein the sequences encoding the affinity acceptor tagged HLAs comprise (a) a sequence encoding a different recombinant HLA class I α-chain allele, (b) a sequence encoding an affinity acceptor peptide, and optionally, (c) a sequence encoding β2 microglobulin; wherein the sequences of (a) and (b), and optionally (c), are operatively linked.

Provided herein is a composition comprising a recombinant polynucleic acid comprising two or more sequences each comprising a sequence encoding an affinity acceptor tagged HLA, wherein the sequences encoding the affinity acceptor tagged HLAs comprise (a) a sequence encoding a recombinant HLA class II α-chain allele, (b) a sequence encoding an affinity acceptor peptide, and optionally, (c) a sequence encoding a HLA class II β-chain; wherein the sequences of (a) and (b), and optionally (c), are operatively linked. In some embodiments, the recombinant polynucleic acid is isolated. In some embodiments, the class I HLA is selected from the group consisting of HLA-A, HLA-B, HLA-C, HLA-E, HLA-F, and HLA-G. In some embodiments, the class II HLA is selected from the group consisting of HLA-DR, HLA-DQ, and HLA-DP.

In some embodiments, the sequence encoding the affinity acceptor peptide is operatively linked to a sequence that encodes for an extracellular portion of the recombinant HLA allele. In some embodiments, the sequence encoding the affinity acceptor molecule is operatively linked to the N-terminus of the sequence encoding the recombinant HLA allele. In some embodiments, the sequence encoding the affinity acceptor peptide is operatively linked to a sequence encoding an intracellular portion of the recombinant HLA allele. In some embodiments, the sequence encoding the affinity acceptor peptide is operatively linked to the C-terminus of the sequence encoding the recombinant HLA allele.

In some embodiments, the sequence encoding the affinity acceptor peptide is operatively linked to the sequence encoding the recombinant HLA allele by a linker.

In some embodiments, the two or more sequences encoding an affinity acceptor tagged HLA are expressed from the same polynucleotide. In some embodiments, the two or more sequences encoding an affinity acceptor tagged HLA are expressed from different polynucleotides.

In some embodiments, the encoded affinity acceptor peptide binds specifically to an affinity acceptor peptide binding molecule.

In some embodiments, the two or more sequences encoding an affinity acceptor tagged HLA comprise two or more affinity acceptor peptides. In some embodiments, the two or more sequences encoding an affinity acceptor tagged HLA comprise three or more sequences encoding an affinity acceptor tagged HLA, wherein at least two of the three or more sequences encoding an affinity acceptor tagged HLA comprises the same affinity acceptor peptide. In some embodiments, the two or more affinity acceptor peptides are unique for each of the two or more sequences encoding an affinity acceptor tagged HLA. In some embodiments, the encoded affinity acceptor peptide is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof, optionally, wherein the first or second affinity acceptor peptide comprises two or more repeats of a tag sequence. In some embodiments, the affinity acceptor peptide binding molecule is biotin or an antibody specific to the affinity acceptor peptide. In some embodiments, the affinity acceptor peptide binding molecule binds specifically to an affinity molecule. In some embodiments, the affinity molecule is streptavidin, NeutrAvidin, or a derivative thereof. In some embodiments, the affinity acceptor peptide binding molecule does not specifically interact with an amino acid sequence of the recombinant class I or class II HLA.

In some embodiments, for two or more of the recombinant polynucleic acids: the sequence encoding the affinity acceptor tagged HLA is stably integrated into the genome of a cell.

In some embodiments, the sequence encoding β2 microglobulin or the sequence encoding the HLA class II β-chain is connected to a sequence encoding a second affinity acceptor peptide. In some embodiments, the second affinity acceptor peptide comprises an HA tag. In some embodiments, the sequence encoding β2 microglobulin or the sequence encoding the HLA class II β-chain is connected to the sequence encoding the recombinant HLA and the affinity acceptor peptide by a linker. In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A In some embodiments, the IRES element is selected from common cellular or viral IRES sequences.

Provided herein is a composition comprising two or more isolated polypeptide molecules encoded by the polynucleic acid of a composition described herein. Provided herein is a composition comprising a population of cells comprising two or more polypeptide molecules encoded by the polynucleic acid of a composition described herein. Provided herein is a composition comprising a population of cells comprising a composition described herein. Provided herein is a composition comprising a population of cells comprising one or more cells comprising a composition described herein.

In some embodiments, the population of cells express one or more endogenous class I or class II HLA alleles. In some embodiments, the population of cells are engineered to lack one or more endogenous HLA class I alleles. In some embodiments, the population of cells are engineered to lack endogenous HLA class I alleles. In some embodiments, the population of cells are engineered to lack one or more endogenous HLA class II alleles. In some embodiments, the population of cells are engineered to lack endogenous HLA class II alleles. In some embodiments, the population of cells are engineered to lack one or more endogenous HLA class I alleles and one or more endogenous HLA class II alleles. In some embodiments, the population of cells is a population of low cell surface HLA class I or class II expressing cells. In some embodiments, the composition is formulated using peptides or polynucleic acids encoding peptides specific to an HLA type of a patient.

Provided herein is a method of making a cell comprising transducing or transfecting two or more cells with the two or more polynucleic acids of a composition described herein. Provided herein is a peptide identified according to a method described herein.

Provided herein is a method of inducing an anti-tumor response in a mammal comprising administering to the mammal an effective amount of a polynucleic acid comprising a sequence of a peptide described herein. Provided herein is a method of inducing an anti-tumor response in a mammal comprising administering to the mammal an effective amount of a peptide comprising the sequence of a peptide described herein. Provided herein is a method of inducing an anti-tumor response in a mammal comprising administering to the mammal a cell comprising a peptide comprising the sequence of a peptide described herein.

Provided herein is a method of inducing an anti-tumor response in a mammal comprising administering to the mammal a cell comprising an effective amount of a polynucleic acid comprising a sequence encoding a peptide comprising the sequence of a peptide described herein. In some embodiments, the cell presents the peptide as an HLA-peptide complex. Provided herein is a method of for inducing an immune response in a mammal comprising administering to the mammal an effective amount of a polynucleic acid comprising a sequence encoding a peptide described herein. Provided herein is a method for inducing an immune response in a mammal comprising administering to the mammal an effective amount of a peptide comprising the sequence of a peptide described herein. Provided herein is a method for inducing an immune response in a mammal comprising administering to the mammal an effective amount of a cell comprising a peptide comprising the sequence of a peptide described herein. Provided herein is a method for inducing an immune response in a mammal comprising administering to the mammal an effective amount of a cell comprising a polynucleic acid comprising a sequence encoding a peptide comprising the sequence of a peptide described herein.

In some embodiments, the immune response is a T cell immune response. In some embodiments, the immune response is a CD8 T cell response. In some embodiments, the immune response is a CD4 T cell response. In some embodiments, the immune response is humoral immune response.

Provided herein is a method for treating a mammal having a disease comprising administering to the mammal an effective amount of a polynucleic acid comprising a sequence encoding a peptide described herein Provided herein is a method for treating a mammal having a disease comprising administering to the mammal an effective amount of a peptide comprising the sequence of a peptide described herein. Provided herein is a method for treating a mammal having a disease comprising administering to the mammal an effective amount of a cell comprising a peptide comprising the sequence of a peptide described herein. Provided herein is a method for treating a mammal having a disease comprising administering to the mammal an effective amount of a cell comprising a polynucleic acid comprising a sequence encoding a peptide comprising the sequence of a peptide described herein.

In some embodiments, the disease is cancer. In some embodiments, the disease is infection by an infectious agent. In some embodiments, the infectious agent is a pathogen, optionally a virus or bacteria, or a parasite. In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof. In some embodiments, the bacteria is selected from the group consisting of: *Klebsiella* spp., *Tropheryma whipplei, Mycobacterium leprae, Mycobacterium lepromatosis*, and *Mycobacterium tuberculosis*, typhoid, pneumococcal, meningococcal, haemophilus B, anthrax, tetanus toxoid, meningococcal group B, bcg, cholera, and any combination thereof. In some embodiments, the parasite is a helminth or a protozoan. In some embodiments, the parasite is selected from the group consisting of: *Leishmania* spp., *Plasmodium* spp., *Trypanosoma cruzi, Ascaris lumbricoides, Trichuris trichiura, Necator americanus, Schistosoma* spp., and any combination thereof.

Provided herein is a method of enriching for immunogenic peptides comprising: providing a population of cells comprising one or more cells expressing an affinity acceptor tagged HLA, wherein the affinity acceptor tagged HLA comprises an affinity acceptor peptide operatively linked to a recombinant HLA encoded by a recombinant HLA allele; and enriching for HLA-peptide complexes comprising the affinity acceptor tagged HLA. In some embodiments, the method further comprises determining the sequence of immunogenic peptides isolated from the HLA-peptide complexes. In some embodiments, the determining comprises using LC-MS/MS.

Provided herein is a method of treating a disease or disorder in a subject, the method comprising administering to the subject an effective amount of a polynucleic acid comprising a sequence encoding a peptide described herein. Provided herein is a method of treating a disease or disorder in a subject, the method comprising administering to the subject an effective amount of a peptide comprising the sequence of a peptide described herein. Provided herein is a method of treating a disease or disorder in a subject, the method comprising administering to the subject an effective amount of a cell comprising a peptide comprising the sequence of a peptide described herein. Provided herein is a method of treating a disease or disorder in a subject, the method comprising administering to the subject a cell comprising an effective amount of a polynucleic acid comprising a sequence encoding a peptide comprising the sequence of a peptide described herein.

Enrichment of HLA-Peptide Complexes

The genes encoding HLA class I and class II glycoproteins are amongst the most polymorphic coding sequences in the human genome. However, there are relatively constant or invariable regions for each of the HLA class I heavy chains and HLA class II a and R chains which can be targeted by antibodies to selectively capture any HLA class I heavy chain or HLA class II a or β chain. However, since the α and β chains are normally associated with each other in vivo, immunopurification of the α-chain of an intact soluble HLA can co-precipitate the β-chain and vice versa. Anti-HLA class II antibodies for the purpose of enriching for HLA-associated polypeptides can recognize conserved epitopes presented on either the α or β chain.

The enrichment method employing HLA allele specific antibodies or utilizing non-HLA specific reagents is well-known in the art. For example, HLA-C polypeptides are typically expressed by individuals at lower levels than HLA-A and HLA-B. Accordingly, in order to enhance the detection of HLA-C using antibodies, it can be advantageous to provide a specific immunopurification of HLA-C using an HLA-C specific antibody, in addition to other purification methods. Numerous examples of monoclonal or polyclonal antibodies which bind specifically to individual HLA chains are commercially available.

Provided herein is a universal immunopurification (IP) pipeline for enriching one or more single allele HLA polypeptide complexes. Illustrative of such a method for enriching for an HLA-associated polypeptide is a method which comprises an immunopurification step. Universal IP pipeline comprises universal IP constructs consisting of a DNA construct coding for affinity-tagged HLA class I or class II alleles that are expressed off an expression vector via cellular transfection or transduction. Non-limiting example of an expression vector is a lentiviral vector.

Cells transfected or transduced with universal IP constructs were either expanded or selected and then expanded prior to LC-MS/MS sequence analyses. Suitable cell populations for transfection or transduction include, e.g., class I deficient cells lines in which a single HLA class I allele is expressed, class II deficient cell lines in which a single pair of HLA class II alleles are expressed, or class I and class II deficient cell lines in which a single HLA class I and/or single pair of class II alleles are expressed. As an exemplary embodiment, the class I deficient B cell line is B721.221. In some embodiments, the cells are A375, or HEK293T, HeLa, or expi293. However, it is clear to a skilled person that other cell populations can be generated which are class I and/or class II deficient. Methods for generating class I and/or class II deficient cells as well as class I and/or class II deficient cell lines are known in the art, and an exemplary method for deleting/inactivating endogenous class I or class II genes includes CRISPR-Cas9 mediated genome editing in, for example, THP-1 cells. In some embodiments, the populations of cells are professional antigen presenting cells, such as macrophages, B cells, and dendritic cells. The cells can be B cells or dendritic cells. In some embodiments, the cells are tumor cells or cells from a tumor cell line. In some embodiments, the cells are cells isolated from a patient. In some embodiments, the cells contain an infectious agent or a portion thereof.

In some embodiments, universal IP constructs comprise class I or class II HLA constructs comprising an affinity acceptor tag and affinity molecule. In some embodiments, universal IP constructs comprise at least one specifically binding affinity acceptor tag and affinity molecule. In some embodiments, an affinity acceptor tag is poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, a VSV-G epitope tag derived from the Vescular Stomatis viral glycoprotein, or a V5 tag derived from a small epitope (Pk) found on the P and V proteins of the paramyxovirus of simian virus 5 (SV5). In some embodiments, the affinity acceptor tag can include multiple repeats of the tag sequence (e.g. 3× poly histidine tag, 3× FLAG tag). In some embodiments, the affinity acceptor tag can include multiple repeats of the tag sequence (e.g. 3× poly histidine tag, 3× FLAG tag). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG. In some embodiments, affinity acceptor tags include the biotin acceptor peptide (BAP) or Human influenza hemagglutinin (HA) peptide sequence. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

The affinity tags can be placed on either the N-terminus or C-terminus of the HLA allele. A cleavage sequence, such as F2A, or an internal ribosome entry site (IRES) can be placed between the α-chain and β2-microglobulin (class I) or between the α-chain and β-chain (class II). In some embodiments, a single class I HLA allele is HLA-A*02:01, HLA-A*23:01 and HLA-B*14:02, or HLA-E*01:01, and class II HLA allele is HLA-DRB*01:01, HLA-DRB*01:02 and HLA-DRB*11:01, HLA-DRB*15:01, or HLA-DRB*07:01. In some embodiments, the cleavage sequence is a T2A, P2A, E2A, or F2A sequence. For example, the cleavage sequence can be E G R G S L L T C G D V E E N P G P (T2A) (SEQ ID NO: 3), A T N F S L L K Q A G D V E E N P G P (P2A) (SEQ ID NO: 4), Q C T N Y A L L K L A G D V E S N P G P (E2A) (SEQ ID NO: 5), or V K Q T L N F D L L K L A G D V E S N P G P (F2A)(SEQ ID NO: 6).

In some embodiments, HLA-peptide complex immunopurification is biotin-based. In some embodiments, HLA-peptide complex immunopurification is streptavidin or NeutrAvidin based. In some embodiments, HLA-peptide complexes can also be enriched from a biological sample by chromatography techniques, such as HPLC. In some embodiments, the depletion of high abundance serum proteins can be used to enrich for HLA-peptide complexes. In some embodiments, methods for removing abundant serum proteins include dye ligands (for albumin), protein A and G (for γ-globulins) or specific antibodies which bind with high affinity and selectively deplete these species from the sample (Govorukhina, Reijmers et al. 2006). Such strategies would increase the number of HLA-derived peptide sequences identified in a single mass spectrometry analysis.

The degree of enrichment desirable to optimize the resolution of particular HLA sequences from a biological sample will depend on the initial concentration of the HLA sequence in the biological sample, and the concentration and nature of other non-HLA proteins in the sample.

To enrich HLA-peptide complexes within a biological sample, classical protein purification techniques can be used alone or in combination with the universal IP pipeline methods provided herein. Classical protein separation (purification) techniques are based on; size differences (ultrafiltration, gel filtration, or size exclusion chromatography); charge differences (pi) (anion/cation exchange chromatography, or hydrophobic interaction chromatography); and combinations of size and charge differences (1D or 2D electrophoresis). Immunopurification options include the use of monoclonal or polyclonal antibodies that specifically bind HLA proteins. Other protein affinity purification options involve the use of proteins that are known to bind HLA, these include; CD8, which binds to the α3 domain of all HLA class I proteins; CD4 which binds to all HLA class II proteins; autologous T-cell receptors; and antigenic peptides which bind HLA with high affinity (computer modelling algorithms can be used to predict peptide/HLA binding characteristics). Any of these high HLA affinity protein options can be immobilized onto an insoluble solid support to prepare an affinity matrix which can be used to capture the HLA from a liquid biological sample. Appropriate elution conditions will result in the concentration and purification (isolation) of the sample's HLA content.

In some embodiments, the enriching comprises enriching for intact cells expressing the affinity acceptor tagged HLA-peptide complexes. In some embodiments, the method does not comprise lysing the cells before the enriching. In some embodiments, the method further comprises lysing the one or more cells before the enriching. In some embodiments, the enriching comprises contacting an affinity acceptor peptide binding molecule to the affinity acceptor tagged HLA-peptide complexes, wherein the affinity acceptor peptide binding molecule binds specifically to the affinity acceptor peptide. In some instances, the enriching does not comprise use of a tetramer reagent.

Disease Specific Antigens

In some embodiments, the size of at least one antigenic peptide molecule can comprise, but is not limited to, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein.

In some embodiments, the antigenic peptide molecules are equal to or less than 50 amino acids. In some embodiments, the antigenic peptide molecules are equal to about 20 to about 30 amino acids. A longer peptide can be designed in several ways. For example, when the HLA-binding regions are predicted or known, a longer peptide can consist of either: individual binding peptides with an extension of 0-10 amino acids toward the N- and C-terminus of each corresponding gene product. A longer peptide can also consist of a concatenation of some or all of the binding peptides with extended sequences for each. In another case, when sequencing reveals a long (>10 residues) epitope sequence present in the diseased tissue (e.g. due to a frameshift, read-through or intron inclusion that leads to a novel peptide sequence), a longer peptide can consist of the entire stretch of novel disease-specific amino acids. In both cases, use of a longer peptide requires endogenous processing by professional antigen presenting cells such as dendritic cells and can lead to more effective antigen presentation and induction of T cell responses. In some embodiments, the extended sequence is altered to improve the biochemical properties of the polypeptide (properties such as solubility or stability) or to improve the likelihood for efficient proteasomal processing of the peptide.

The antigenic peptides and polypeptides can bind an HLA protein. In some embodiments, the antigenic peptides can bind an HLA protein with greater affinity than a corresponding native/wild-type peptide. The antigenic peptide can have an IC50 of about less than 1000 nM, about less than 500 nM, about less than 250 nM, about less than 200 nM, about less than 150 nM, about less than 100 nM, or about less than 50 nM. In some embodiments, the antigenic peptides do not induce an autoimmune response and/or invoke immunological tolerance when administered to a subject.

The present disclosure also provides compositions comprising a plurality of antigenic peptides. Reference to antigenic peptides includes any suitable delivery modality that can result in introduction of the peptide into a subject's cell (e.g., nucleic acid). In some embodiments, the composition comprises at least 3 or more antigenic peptides. In some embodiments the composition contains at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 distinct peptides. In some embodiments the composition contains at least 20 distinct peptides. In some embodiments the composition contains at most 20 distinct peptides. According to the present disclosure, 2 or more of the distinct peptides can be derived from the same polypeptide. For example, if an antigenic mutation encodes a polypeptide, two or more of the antigenic peptides can be derived from the polypeptide. In one embodiment, the two or more antigenic peptides derived from the polypeptide can comprise a tiled array that spans the polypeptide (e.g., the antigenic peptides can comprise a series of overlapping antigenic peptides that spans a portion, or all, of the polypeptide). Antigenic peptides can be derived from any protein coding gene. The antigenic peptides can be derived from mutations in human cancer or from an infectious agent or an autoimmune disease.

The antigenic peptides, polypeptides, and analogs can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in Remington's Pharmaceutical Sciences, 20th ed., Mack Publishing Co., Easton, PA (2000). For example, antigenic peptides and polypeptides having the desired activity can be modified as necessary to provide certain desired attributes, e.g. improved pharmacological characteristics, while increasing or at least retaining substantially all of the biological activity of the unmodified peptide to bind the desired MHC molecule and activate the appropriate T cell. For instance, the antigenic peptide and polypeptides can be subject to various changes, such as substitutions, either conservative or non-conservative, where such changes might provide for certain advantages in their use, such as improved MHC binding. Such conservative substitutions can encompass replacing an amino acid residue with another amino acid residue that is biologically and/or chemically similar, e.g., one hydrophobic residue for another, or one polar residue for another. The effect of single amino acid substitutions can also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

The antigenic peptide can also be modified by extending or decreasing the compound's amino acid sequence, e.g., by the addition or deletion of amino acids. The antigenic peptides, polypeptides, or analogs can also be modified by altering the order or composition of certain residues. It will be appreciated by the skilled artisan that certain amino acid residues essential for biological activity, e.g., those at critical contact sites or conserved residues, may generally not be altered without an adverse effect on biological activity. The non-critical amino acids need not be limited to those naturally occurring in proteins, such as L-a-amino acids, or their D-isomers, but can include non-natural amino acids as well, such as β-γ-δ-amino acids, as well as many derivatives of L-a-amino acids.

An antigen peptide can be optimized by using a series of peptides with single amino acid substitutions to determine the effect of electrostatic charge, hydrophobicity, etc. on MHC binding. For instance, a series of positively charged (e.g., Lys or Arg) or negatively charged (e.g., Glu) amino acid substitutions can be made along the length of the peptide revealing different patterns of sensitivity towards various MHC molecules and T cell receptors. In addition, multiple substitutions using small, relatively neutral moieties such as Ala, Gly, Pro, or similar residues can be employed. The substitutions can be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor can also be achieved by such substitutions, compared to the affinity of the parent peptide. In any event, such substitutions should employ amino acid residues or other molecular fragments chosen to avoid, for example, steric and charge interference which might disrupt binding. Amino acid substitutions are typically of single residues. Substitutions, deletions, insertions or any combination thereof can be combined to arrive at a final peptide.

An antigenic peptide can be modified to provide desired attributes. For instance, the ability of the peptides to induce CTL activity can be enhanced by linkage to a sequence which contains at least one epitope that is capable of inducing a T helper cell response. In some embodiments, immunogenic peptides/T helper conjugates are linked by a spacer molecule. In some embodiments, a spacer comprises relatively small, neutral molecules, such as amino acids or amino acid mimetics, which are substantially uncharged under physiological conditions. Spacers can be selected from, e.g., Ala, Gly, or other neutral spacers of nonpolar amino acids or neutral polar amino acids. It will be understood that the optionally present spacer need not be comprised of the same residues and thus can be a hetero- or homo-oligomer. The antigenic peptide can be linked to the T helper peptide either directly or via a spacer either at the amino or carboxy terminus of the peptide. The amino terminus of either the antigenic peptide or the T helper peptide can be acylated. Exemplary T helper peptides include tetanus toxoid 830-843, influenza 307-319, malaria circumsporozoite 382-398 and 378-389.

Mono-Allelic HLA Cell Lines

A mono-allelic cell line expressing either a single class I HLA allele, a single pair of class II HLA alleles, or a single class I HLA allele and a single pair of class II HLA alleles can be generated by transducing or transfecting a suitable cell population with a polynucleic acid, e.g., a vector, coding a single HLA allele. Suitable cell populations include, e.g., class I deficient cells lines in which a single HLA class I allele is expressed, class II deficient cell lines in which a single pair of HLA class II alleles are expressed, or class I and class II deficient cell lines in which a single HLA class I and/or single pair of class II alleles are expressed. As an exemplary embodiment, the class I deficient B cell line is B721.221. However, it is clear to a skilled person that other cell populations can be generated which are class I and/or class II deficient. An exemplary method for deleting/inactivating endogenous class I or class II genes includes CRISPR-Cas9 mediated genome editing in, for example, THP-1 cells. In some embodiments, the populations of cells are professional antigen presenting cells, such as macrophages, B cells, and dendritic cells. The cells can be B cells or dendritic cells. In some embodiments, the cells are tumor cells or cells from a tumor cell line. In some embodiments, the cells are cells isolated from a patient. In some embodiments, the cells contain an infectious agent or a portion thereof. In some embodiments, the population of cells comprises at least $10^7$ cells. In some embodiments, the population of cells are further modified, such as by increasing or decreasing the expression and/or activity of at least one gene. In some embodiments, the gene encodes a member of the immunoproteasome. The immunoproteasome is known to be involved in the processing of HLA class I binding peptides and includes the LMP2 ($\beta$1i), MECL-1 ($\beta$2i), and LMP7 ($\beta$5i) subunits. The immunoproteasome can also be induced by interferon-gamma. Accordingly, in some embodiments, the population of cells can be contacted with one or more cytokines, growth factors, or other proteins. The cells can be stimulated with inflammatory cytokines such as interferon-gamma, IL-10, IL-6, and/or TNF-$\alpha$. The population of cells can also be subjected to various environmental conditions, such as stress (heat stress, oxygen deprivation, glucose starvation, DNA damaging agents, etc.). In some embodiments, the cells are contacted with one or more of a chemotherapy drug, radiation, targeted therapies, immunotherapy. The methods disclosed herein can therefore be used to study the effect of various genes or conditions on HLA peptide processing and presentation. In some embodiments, the conditions used are selected so as to match the condition of the patient for which the population of HLA-peptides is to be identified.

Figure 3:
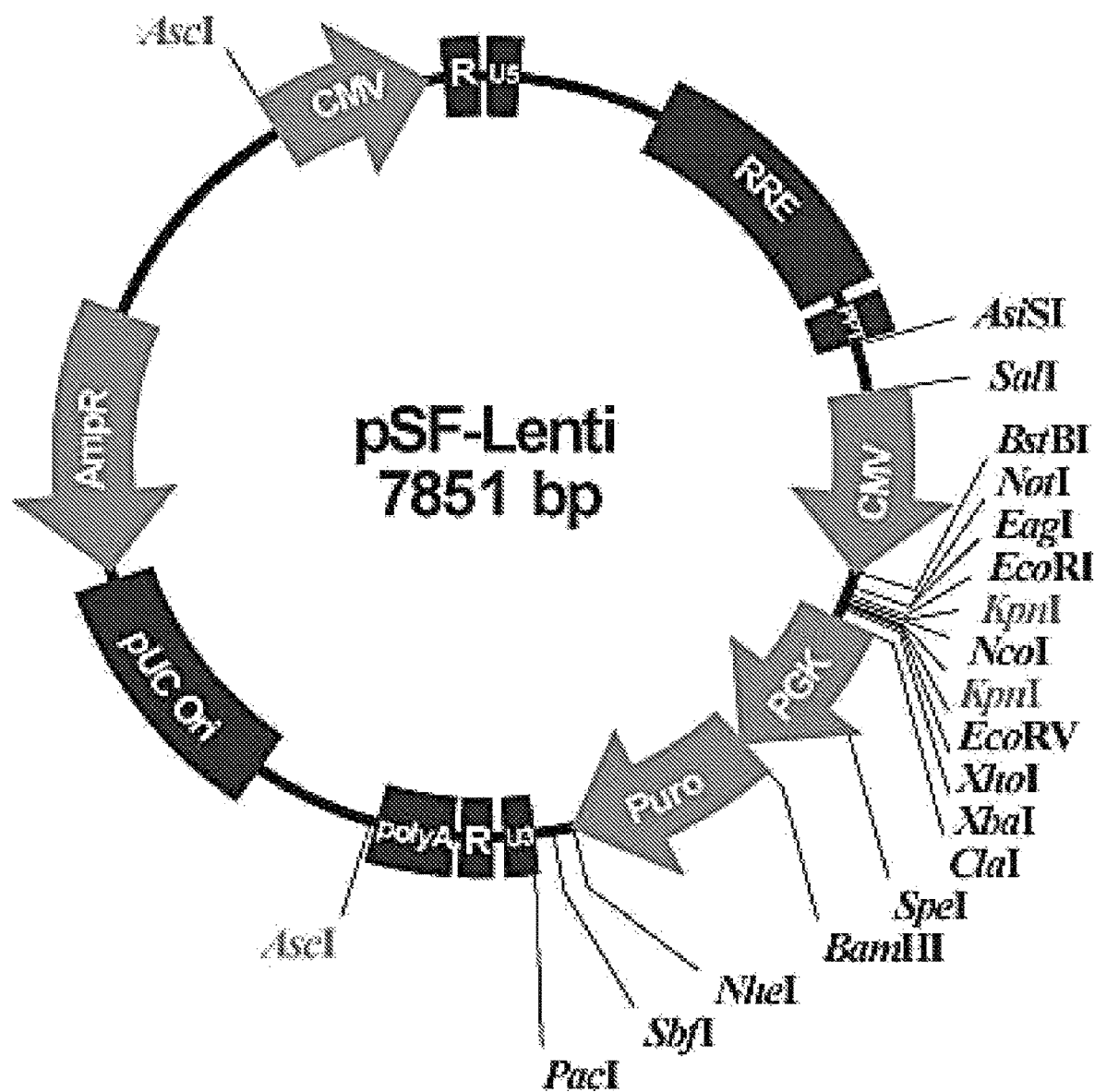
FIG. 3 is a schematic of an exemplary lentiviral vector that can be used to generate stable cell lines expressing HLA class I and class II constructs.

A single HLA-allele of the present disclosure can be encoded and expressed using a viral based system (e.g., an adenovirus system, an adeno associated virus (AAV) vector, a poxvirus, or a lentivirus). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference). Among vectors that can be used in the practice of the present disclosure, integration in the host genome of a cell is possible with retrovirus gene transfer methods, often resulting in long term expression of the inserted transgene. In an exemplary embodiment, the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors can be used in the practice of the present disclosure). Moreover, lentiviral vectors are able to transduce or infect non-dividing cells and typically produce high viral titers. An exemplary lentiviral vector that can be used to generate stable cell lines transduced to express HLA class I and class II is shown in FIG. 3.

Selection of a retroviral gene transfer system can depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that can be used in the practice of the present disclosure include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Also, useful in the practice of the present disclosure is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience DOI: 10.1002/jgm.845). The vectors can have cytomegalovirus (CMV) promoter driving expression of the target gene. Accordingly, the present disclosure contemplates amongst vector(s) useful in the practice of the present disclosure: viral vectors, including retroviral vectors and lentiviral vectors.

Any HLA allele can be expressed in the cell population. In an exemplary embodiment, the HLA allele is a class I HLA allele. In some embodiments, the class I HLA allele is an HLA-A allele or an HLA-B allele. In some embodiments, the HLA allele is a class II HLA allele. Sequences of class I and class II HLA alleles can be found in the IPD-IMGT/HLA Database. Exemplary HLA alleles include, but are not limited to, HLA-A*02:01, HLA-B*14:02, HLA-A*23:01, HLA-E*01:01, HLA-DRB*01:01, HLA-DRB*01:02, HLA-DRB*11:01, HLA-DRB*15:01, and HLA-DRB*07:01.

In some embodiments, the HLA allele is selected so as to correspond to a genotype of interest. In some embodiments, the HLA allele is a mutated HLA allele, which can be non-naturally occurring allele or a naturally occurring allele in an afflicted patient. The methods disclosed herein have the further advantage of identifying HLA binding peptides for HLA alleles associated with various disorders as well as alleles which are present at low frequency. Accordingly, in some embodiments, method the HLA allele is present at a frequency of less than 1% within a population, such as within the Caucasian population.

In some embodiments, the nucleic acid sequence encoding the HLA allele further comprises an affinity acceptor tag which can be used to immunopurify the HLA-protein. Suitable tags are well-known in the art. In some embodiments, an affinity acceptor tag is poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, a VSV-G epitope tag derived from the Vescular Stomatis viral glycoprotein, or a V5 tag derived from a small epitope (Pk) found on the P and V proteins of the paramyxovirus of simian virus 5 (SV5). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG. In some embodiments, affinity acceptor tags include the biotin acceptor peptide (BAP) or Human influenza hemagglutinin (HA) peptide sequence. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

The methods provided herein comprise isolating HLA-peptide complexes from the cells transfected or transduced with universal IP HLA constructs. In some embodiments, the complexes can be isolated using standard immunoprecipitation techniques known in the art with commercially available antibodies. The cells can be first lysed. HLA class I-peptide complexes can be isolated using HLA class I specific antibodies such as the W6/32 antibody, while HLA class II-peptide complexes can be isolated using HLA class II specific antibodies such as the M5/114.15.2 monoclonal antibody. In some embodiments, the single (or pair of) HLA alleles are expressed as a fusion protein with a peptide tag and the HLA-peptide complexes are isolated using binding molecules that recognize the peptide tags.

The methods further comprise isolating peptides from said HLA-peptide complexes and sequencing the peptides. The peptides are isolated from the complex by any method known to one of skill in the art, such as acid elution. While any sequencing method can be used, methods employing mass spectrometry, such as liquid chromatography-mass spectrometry (LC-MS or LC-MS/MS, or alternatively HPLC-MS or HPLC-MS/MS) are utilized in some embodiments. These sequencing methods are well-known to a skilled person and are reviewed in Medzihradszky K F and Chalkley RJ. Mass Spectrom Rev. 2015 Jan-Feb; 34(1):43-63.

In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles or an engineered population of cells lacking endogenous HLA class I alleles and endogenous HLA class II alleles. In some embodiments, the population of cells comprises cells that have been enriched or sorted, such as by fluorescence activated cell sorting (FACS). In some embodiments, fluorescence activated cell sorting (FACS) is used to sort the population of cells. In some embodiments, the population of cells is previously FACS sorted for cell surface expression of either class I or class II HLA or both class I and class II HLA. For example, FACS can be used to sort the population of cells for cell surface expression of an HLA class I allele, an HLA class II allele, or a combination thereof.

Libraries of Affinity Acceptor Tagged HLA Constructs

The term "library" as used herein refers to a collection of nucleic acid molecules (circular or linear). In one embodiment, a library can comprise a plurality (i.e., two or more) of nucleic acid molecules, which can be from a common source organism, organ, tissue, or cell. In some embodiments, a library is representative of all or a portion or a significant portion of the nucleic acid content of an organism (a "genomic" library), or a set of nucleic acid molecules representative of all or a portion or a significant portion of the expressed nucleic acid molecules (a cDNA library or segments derived therefrom) in a cell, tissue, organ or organism. A library can also comprise random sequences made by de novo synthesis, mutagenesis of one or more sequences and the like. Such libraries can be contained in one or more vectors. A library of affinity acceptor tagged HLA constructs as provided herein comprises a DNA sequence encoding elements of a HLA allele, an affinity acceptor peptide, or a linker. Appropriate molecular biological techniques can be found in Sambrook et al. (Molecular Cloning; A Laboratory Manual, New York: Cold Spring Harbor Laboratory Press, 1989). Several methods for facilitating the cloning of nucleic acid segments have been described, e.g., as in the following references: Ferguson, J., et al., Gene 16:191 (1981) and Hashimoto-Gotoh, T., et al., Gene 41:125 (1986). Other terms used in the fields of recombinant nucleic acid technology and molecular and cell biology as used herein will be generally understood by one of ordinary skill in the applicable arts.

The various elements or domains of a recombinant HLA allele can be arranged in any order between the N-terminal and C-terminal ends of the recombinant HLA allele. An element or domain that is closer to the N-terminus of a recombinant polypeptide encoded from a recombinant HLA allele than another element or domain is said to be "N-terminal" of the other element or domain. Similarly, an element or domain that is closer to the C-terminus of a recombinant polypeptide encoded from a recombinant HLA allele than another element or domain is said to be "C-terminal" of the other element or domain. Unless expressly stated otherwise, different elements or domains of a recombinant polypeptide encoded from a recombinant HLA allele need not be adjacent (that is, without one or more intervening elements or domains). In some embodiments, different elements or domains of a recombinant polypeptide encoded from a recombinant HLA allele can be adjacent.

A recombinant polypeptide encoded from a recombinant HLA allele can include one or more optional elements, such as one or more linker(s), peptide tags (such as, epitope tags), or protease-recognition site(s). In some embodiments, a peptide tag is an affinity acceptor peptide. A linker is a relatively short series of amino acids that separates other elements or domains of the recombinant protein. In some embodiments, a linker is from 1 to 100 amino acids in length; for example, from 5 to 75, from 10 to 60, from 15 to 50, from 15 to 40, or from 1 to 50 amino acids in length.

Methods of expressing proteins in heterologous expression systems are well known in the art. Typically, a nucleic acid molecule encoding all or part of a protein of interest (such as a recombinant HLA class I or class II affinity acceptor tagged peptide) is obtained using methods such as those described herein. The protein-encoding nucleic acid sequence is cloned into an expression vector that is suitable for the particular host cell of interest using standard recombinant DNA procedures. Expression vectors include (among other elements) regulatory sequences (e.g., promoters) that can be operably linked to the desired protein-encoding nucleic acid molecule to cause the expression of such nucleic acid molecule in the host cell. Together, the regulatory sequences and the protein-encoding nucleic acid sequence are an "expression cassette." Expression vectors can also include an origin of replication, marker genes that provide phenotypic selection in transformed cells, one or more other promoters, and a polylinker region containing several restriction sites for insertion of heterologous nucleic acid sequences.

Expression vectors useful for expression of heterologous protein(s) in a multitude of host cells are well known in the art, and some specific examples are provided herein. The host cell is transfected with (or infected with a virus containing) the expression vector using any method suitable for the particular host cell. Such transfection methods are also well known in the art and non-limiting exemplar methods are described herein. The transfected or transduced host cell is capable of expressing the protein encoded by the corresponding nucleic acid sequence in the expression cassette.

In some embodiments, class I or class II HLA constructs comprising an affinity acceptor tag and affinity molecule at N-terminus or C-terminus. In some embodiments, class I or class II HLA constructs comprise at least one specifically binding affinity acceptor tag and affinity molecule. In some embodiments, an affinity acceptor tag is poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, a VSV-G epitope tag derived from the Vescular *Stomatis* viral glycoprotein, or a V5 tag derived from a small epitope (Pk) found on the P and V proteins of the paramyxovirus of simian virus 5 (SV5). In some embodiments, the affinity acceptor tag can include multiple repeats of the tag sequence (e.g. 3× poly histidine tag, 3× FLAG tag). In some embodiments, the affinity acceptor tag can include multiple repeats of the tag sequence (e.g. 3× poly histidine tag, 3× FLAG tag). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG.

In some embodiments, affinity acceptor tags include the biotin acceptor peptide (BAP) or Human influenza hemagglutinin (HA) peptide sequence. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

The affinity tags can be placed on either the N-terminus or C-terminus of the HLA allele. In some embodiments, the affinity tag placed at C-terminus of the HLA allele to enable HLA-peptide localization to cell surface vs. ER. In some embodiments, the affinity tag placed at N-terminus of the HLA allele to enable single-HLA isolations from cell lines expressing multiple endogenous HLA alleles. In yet another embodiment, the affinity tag is added to variable β-chains to immunopurify specific class II HLA heterodimers.

In some embodiments, a cleavage sequence, such as F2A, or an internal ribosome entry site (IRES) can be placed between the α-chain and β2-microglobulin (class I) or between the α-chain and β-chain (class II). In some embodiments, a single class I HLA allele is HLA-A*02:01, HLA-A*23:01 and HLA-B*14:02, or HLA-E*01:01, and class II HLA allele is HLA-DRB*01:01, HLA-DRB*01:02 and HLA-DRB*11:01, HLA-DRB*15:01, or HLA-DRB*07:01.

Figures 7A, 7B, 7C:
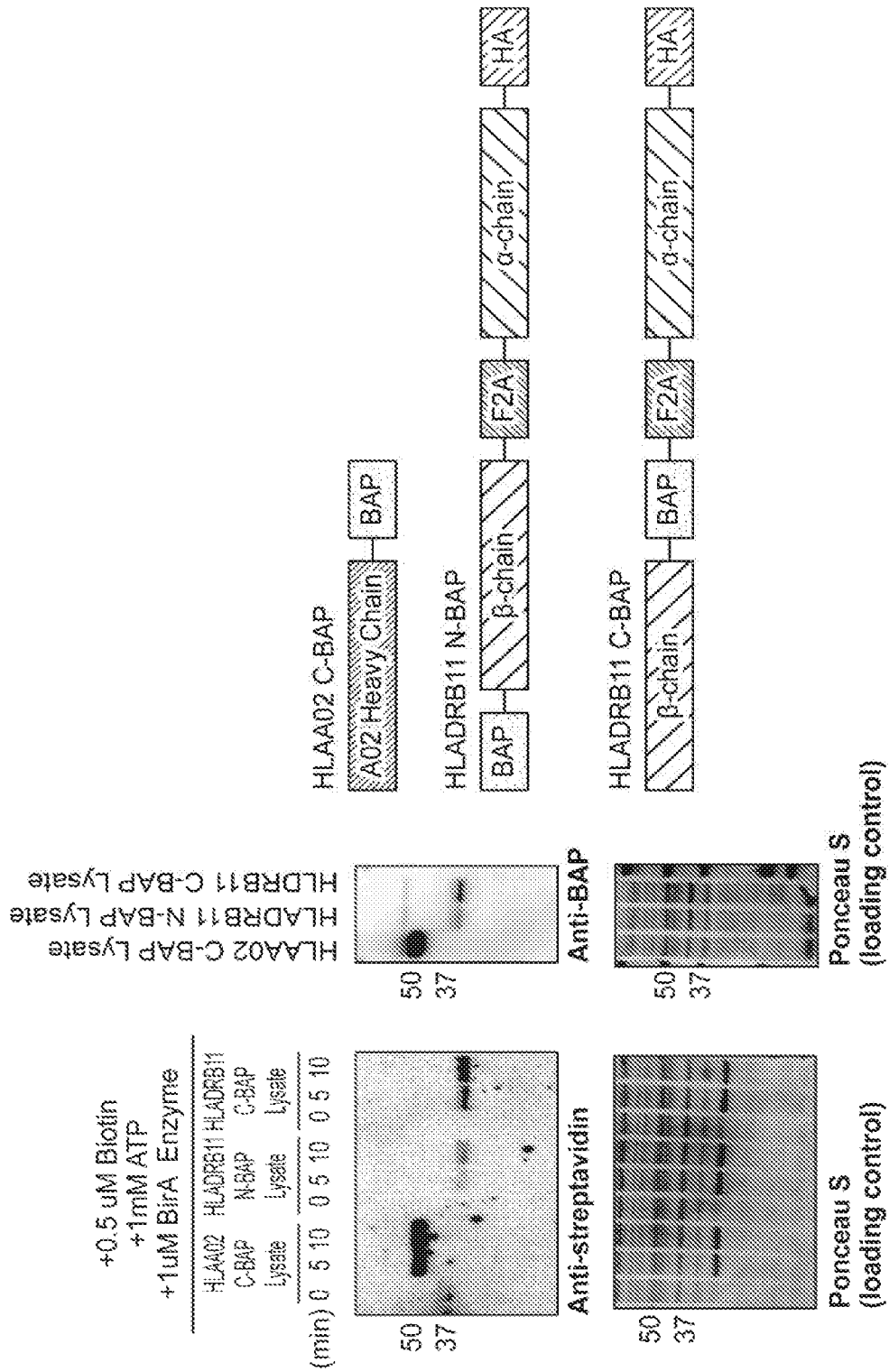
FIG. 7A is Western blot (top) and loading control (bottom) images of a biotinylation time course experiment demonstrating that C- and N-terminally labeled HLA-BAP biotinylation is complete in 10 minutes for both class I and class II HLA-BAP expressing cells. The results show transfection and biotinylation optimization of class I and class II HLA-BAP alleles expressed by HEK293T cells.
FIG. 7B is a Western blot against the anti-BAP (top) and loading control (bottom) from cells expressing both N- and C-terminal BAP-labeled class I and class II HLA constructs.
FIG. 7C is a schematic representation of both N- and C-terminal BAP-labeled class I (HLA-A*02:01) and class II HLA-DRβ*11:01) constructs used for transfection and biotinylation optimization.

Non-limiting exemplary affinity acceptor tagged HLA constructs are depicted in FIG. 2, FIG. 6C, and FIG. 7C.

Therapeutic Methods

Figures 18A, 18B:
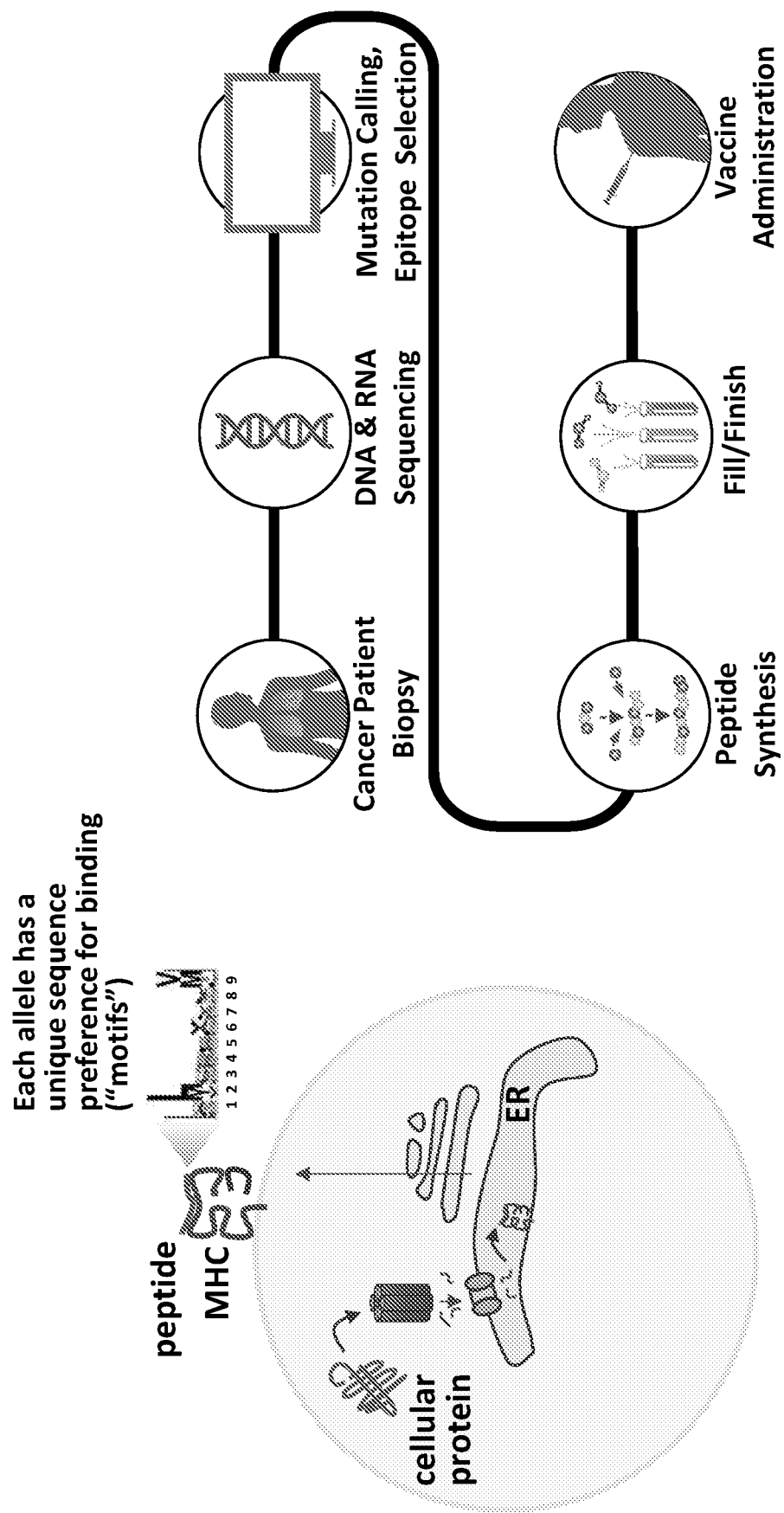
FIG. 18A is a diagram showing mutated neoantigenic peptide presented on MHC.
FIG. 18B is a schematic method of developing personalized neoantigen-targeting therapy as described herein.

Personalized immunotherapy using tumor-specific peptides has been described (Ott et al., Hematol. Oncol. Clin. N. Am. 28 (2014) 559-569). Efficiently choosing which particular peptides to utilize as an immunogen requires the ability to predict which tumor-specific peptides would efficiently bind to the HLA alleles present in a patient. One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized antigens, and producing neoantigens for use in a vaccine or immunogenic composition. These problems can be addressed by: identifying mutations in neoplasias/tumors which are present at the DNA level in tumor but not in matched germline samples from a high proportion of subjects having cancer; analyzing the identified mutations with one or more peptide-MHC binding prediction algorithms to generate a plurality of neoantigen T cell epitopes that are expressed within the neoplasia/tumor and that bind to a high proportion of patient HLA alleles; and synthesizing the plurality of neoantigenic peptides selected from the sets of all neoantigen peptides and predicted binding peptides for use in a cancer vaccine or immunogenic composition suitable for treating a high proportion of subjects having cancer (FIG. 18A and FIG. 18B).

For example, translating peptide sequencing information into a therapeutic vaccine can include prediction of mutated peptides that can bind to HLA molecules of a high proportion of individuals. Efficiently choosing which particular mutations to utilize as immunogen requires the ability to predict which mutated peptides would efficiently bind to a high proportion of patient's HLA alleles. Recently, neural network based learning approaches with validated binding and non-binding peptides have advanced the accuracy of prediction algorithms for the major HLA-A and -B alleles. However, even using advanced neural network-based algorithms to encode HLA-peptide binding rules, several factors limit the power to predict peptides presented on HLA alleles.

For example, translating peptide sequencing information into a therapeutic vaccine can include formulating the drug as a multi-epitope vaccine of long peptides. Targeting as many mutated epitopes as practically possible takes advantage of the enormous capacity of the immune system, prevents the opportunity for immunological escape by down-modulation of an immune targeted gene product, and compensates for the known inaccuracy of epitope prediction approaches. Synthetic peptides provide a useful means to prepare multiple immunogens efficiently and to rapidly translate identification of mutant epitopes to an effective vaccine. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

For example, translating peptide sequencing information into a therapeutic vaccine can include a combination with a strong vaccine adjuvant. Effective vaccines can require a strong adjuvant to initiate an immune response. For example, poly-ICLC, an agonist of TLR3 and the RNA helicase-domains of MDA5 and RIG3, has shown several desirable properties for a vaccine adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NYESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile.

In some embodiments, immunogenic peptides can be identified from cells from a subject with a disease or condition. In some embodiments, immunogenic peptides can be specific to a subject with a disease or condition. In some embodiments, immunogenic peptides can bind to an HLA that is matched to an HLA haplotype of a subject with a disease or condition.

In some embodiments, a library of peptides can be expressed in the cells. In some embodiments, the cells comprise the peptides to be identified or characterized. In some embodiments, the peptides to be identified or characterized are endogenous peptides. In some embodiments, the peptides are exogenous peptides. For example, the peptides to be identified or characterized can be expressed from a plurality of sequences encoding a library of peptides.

Prior to disclosure of the instant specification, the majority of LC-MS/MS studies of the HLA peptidome have used cells expressing multiple HLA molecules, which requires peptides to be assigned to 1 of up to 6 class I alleles using pre-existing bioinformatics predictors or "deconvolution" (Bassani-Stemberg and Gfeller, 2016). Thus, peptides that do not closely match known motifs could not confidently be reported as binders to a given HLA allele.

Provided herein are methods of prediction of peptides, such as mutated peptides, that can bind to HLA molecules of individuals. In some embodiments, the application provides methods of identifying from a given set of antigen comprising peptides the most suitable peptides for preparing an immunogenic composition for a subject, said method comprising selecting from set given set of peptides the plurality of peptides capable of binding an HLA protein of the subject, wherein said ability to bind an HLA protein is determined by analyzing the sequence of peptides with a machine which has been trained with peptide sequence databases corresponding to the specific HLA-binding peptides for each of the HLA-alleles of said subject. Provided herein are methods of identifying from a given set of antigen comprising peptides the most suitable peptides for preparing an immunogenic composition for a subject, said method comprising selecting from set given set of peptides the plurality of peptides determined as capable of binding an HLA protein of the subject, ability to bind an HLA protein is determined by analyzing the sequence of peptides with a machine which has been trained with a peptide sequence database obtained by carrying out the methods described herein above. Thus, in some embodiments, the present disclosure provides methods of identifying a plurality of subject-specific peptides for preparing a subject-specific immunogenic composition, wherein the subject has a tumor and the subject-specific peptides are specific to the subject and the subject's tumor, said method comprising: sequencing of a sample of the subject's tumor and a non-tumor sample of the subject; determining based on the nucleic acid sequencing: non-silent mutations present in the genome of cancer cells of the subject but not in normal tissue from the subject, and the HLA genotype of the subject; and selecting from the identified non-silent mutations the plurality of subject-specific peptides, each having a different tumor epitope that is an epitope specific to the tumor of the subject and each being identified as capable of binding an HLA protein of the subject, as determined by analyzing the sequence of peptides derived from the non-silent mutations in the methods for predicting HLA binding described herein.

In some embodiments, disclosed herein, is a method of characterizing HLA-peptide complexes specific to an individual.

In some embodiments, a method of characterizing HLA-peptide complexes specific to an individual is used to develop an immunotherapeutic in an individual in need thereof, such as a subject with a condition or disease.

Provided herein is a method of providing an anti-tumor immunity in a mammal comprising administering to the mammal a polynucleic acid comprising a sequence encoding a peptide identified according to a method described Provided herein is a method of providing an anti-tumor immunity in a mammal comprising administering to the mammal an effective amount of a peptide with a sequence of a peptide identified according to a method described herein. Provided herein is a method of providing an anti-tumor immunity in a mammal comprising administering to the mammal a cell comprising a peptide comprising the sequence of a peptide identified according to a method described herein. Provided herein is a method of providing an anti-tumor immunity in a mammal comprising administering to the mammal a cell comprising a polynucleic acid comprising a sequence encoding a peptide comprising the sequence of peptide identified according to a method described herein. In some embodiments, the cell presents the peptide as an HLA-peptide complex.

Provided herein is a method of treating a disease or disorder in a subject, the method comprising administering to the subject a polynucleic acid comprising a sequence encoding a peptide identified according to a method described herein. Provided herein is a method of treating a disease or disorder in a subject, the method comprising administering to the subject an effective amount of a peptide comprising the sequence of a peptide identified according to a method described herein. Provided herein is a method of treating a disease or disorder in a subject, the method comprising administering to the subject a cell comprising a peptide comprising the sequence of a peptide identified according to a method described herein. Provided herein is a method of treating a disease or disorder in a subject, the method comprising administering to the subject a cell comprising a polynucleic acid comprising a sequence encoding a peptide comprising the sequence of a peptide identified according to a method described herein. In some embodiments, wherein the disease or disorder is cancer. In some embodiments, the method further comprises administering an immune checkpoint inhibitor to the subject.

Disclosed herein, in some embodiments, are methods of developing an immunotherapeutic for an individual in need thereof by characterizing HLA-peptide complexes comprising: a) providing a population of cells derived from the individual in need thereof wherein one or more cells of the population of cells comprise a polynucleic acid comprising a sequence encoding an affinity acceptor tagged class I or class II HLA allele, wherein the sequence encoding an affinity acceptor tagged HLA comprises: i) a sequence encoding a recombinant class I or class II HLA allele operatively linked to ii) a sequence encoding an affinity acceptor peptide; b) expressing the affinity acceptor tagged HLA in at least one cell of the one or more cells of the population of cells, thereby forming affinity acceptor tagged HLA-peptide complexes in the at least one cell; c) enriching for the affinity acceptor tagged HLA-peptide complexes; characterizing HLA-peptide complexes specific to the individual in need thereof, and d) developing the immunotherapeutic based on an HLA-peptide complex specific to the individual in need thereof, wherein the individual has a disease or condition.

In some embodiments, the immunotherapeutic is a nucleic acid or a peptide therapeutic.

In some embodiments, the method comprises introducing one or more peptides to the population of cells. In some embodiments, the method comprises contacting the population of cells with the one or more peptides or expressing the one or more peptides in the population of cells. In some embodiments, the introducing comprises contacting the population of cells with one or more nucleic acids encoding the one or more peptides.

In some embodiments, the method comprises introducing one or more HLAs specific for the patient. In some embodiments, the method comprises introducing all HLAs specific for the patient. In some embodiments, patient specific HLAs can be introduced as single allele. In some embodiments, multiple patient specific HLAs can be introduced. In some embodiments, the method comprises developing a immunotherapeutic based on peptides identified in connection with the patient-specific HLAs]. In some embodiments, the population of cells is derived from the individual in need thereof.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with the disease or condition. In some embodiments, the disease or condition is cancer or an infection with an infectious agent or an autoimmune disease. In some embodiments, the method comprises introducing the infectious agent or portions thereof into one or more cells of the population of cells. In some embodiments, the method comprises characterizing one or more peptides from the HLA-peptide complexes specific to the individual in need thereof, optionally wherein the peptides are from one or more target proteins of the infectious agent or the autoimmune disease. In some embodiments, the method comprises characterizing one or more regions of the peptides from the one or more target proteins of the infectious agent or autoimmune disease. In some embodiments, the method comprises identifying peptides from the HLA-peptide complexes derived from an infectious agent or an autoimmune disease.

In some embodiments, the infectious agent is a pathogen. In some embodiments, the pathogen is a virus, bacteria, or a parasite.

In some embodiments, the virus is selected from the group consisting of BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and combinations thereof.

In some embodiments, the bacteria is selected from the group consisting of: *Klebsiella* spp., *Tropheryma whipplei*, *Mycobacterium leprae, Mycobacterium lepromatosis*, and *Mycobacterium tuberculosis*. In some embodiments, the bacteria is selected from the group consisting of: typhoid, pneumococcal, meningococcal, *haemophilus* B, anthrax, tetanus toxoid, meningococcal group B, bcg, cholera, and combinations thereof.

In some embodiments, the parasite is a helminth or a protozoan. In some embodiments, the parasite is selected from the group consisting of: *Leishmania* spp. (e.g. *L. major, L. infantum, L. braziliensis, L. donovani, L. chagasi, L. mexicana*), *Plasmodium* spp. (e.g. *P. falciparum, P. vivax, P. ovale, P. malariae*), *Trypanosoma cruzi, Ascaris lumbricoides, Trichuris trichiura, Necator americanus*, and *Schistosoma* spp. (*S. mansoni, S. haematobium, S. japonicum*).

In some embodiments, the immunotherapeutic is an engineered receptor. In some embodiments, the engineered receptor is a chimeric antigen receptor (CAR), a T-cell receptor (TCR), or a B-cell receptor (BCR), an adoptive T cell therapy (ACT), or a derivative thereof. In other aspects, the engineered receptor is a chimeric antigen receptor (CAR). In some aspects, the CAR is a first generation CAR. In other aspects, the CAR is a second generation CAR. In still other aspects, the CAR is a third generation CAR.

In some aspects, the CAR comprises an extracellular portion, a transmembrane portion, and an intracellular portion. In some aspects, the intracellular portion comprises at least one T cell co-stimulatory domain. In some aspects, the T cell co-stimulatory domain is selected from the group consisting of CD27, CD28, TNFRS9 (4-1BB), TNFRSF4 (OX40), TNFRSF8 (CD30), CD40LG (CD40L), ICOS, ITGB2 (LFA-1), CD2, CD7, KLRC2 (NKG2C), TNFRS18 (GITR), TNFRSF14 (HVEM), or any combination thereof. In some aspects, the engineered receptor binds a target. In some aspects, the binding is specific to a peptide identified from the method of characterizing HLA-peptide complexes specific to an individual suffering from a disease or condition.

In some aspects, the immunotherapeutic is a cell as described in detail herein. In some aspects, the immunotherapeutic is a cell comprising a receptor that specifically binds a peptide identified from the method characterizing HLA-peptide complexes specific to an individual suffering from a disease or condition. In some aspects, the immunotherapeutic is a cell used in combination with the peptides/nucleic acids of this invention. In some embodiments, the cell is a patient cell. In some embodiments, the cell is a T cell. In some embodiments, the cell is tumor infiltrating lymphocyte.

In some aspects, a subject with a condition or disease is treated based on a T cell receptor repertoire of the subject. In some embodiments, an antigen vaccine is selected based on a T cell receptor repertoire of the subject. In some embodiments, a subject is treated with T cells expressing TCRs specific to an antigen or peptide identified using the methods described herein. In some embodiments, a subject is treated with an antigen or peptide identified using the methods described herein specific to TCRs, e.g., subject specific TCRs. In some embodiments, a subject is treated with an antigen or peptide identified using the methods described herein specific to T cells expressing TCRs, e.g., subject specific TCRs. In some embodiments, a subject is treated with an antigen or peptide identified using the methods described herein specific to subject specific TCRs.

In some embodiments, an immunogenic antigen composition or vaccine is selected based on TCRs identified in a subject. In one embodiment identification of a T cell repertoire and testing in functional assays is used to determine an immunogenic composition or vaccine to be administered to a subject with ta condition or disease. In some embodiments, the immunogenic composition is an antigen vaccine. In some embodiments, the antigen vaccine comprises subject specific antigen peptides. In some embodiments, antigen peptides to be included in an antigen vaccine are selected based on a quantification of subject specific TCRs that bind to the antigens. In some embodiments, antigen peptides are selected based on a binding affinity of the peptide to a TCR. In some embodiments, the selecting is based on a combination of both the quantity and the binding affinity. For example, a TCR that binds strongly to an antigen in a functional assay, but that is not highly represented in a TCR repertoire can be a good candidate for an antigen vaccine because T cells expressing the TCR would be advantageously amplified.

In some embodiments, antigens are selected for administering to a subject based on binding to TCRs. In some embodiments, T cells, such as T cells from a subject with a disease or condition, can be expanded. Expanded T cells that express TCRs specific to an immunogenic antigen peptide identified using the method described herein, can be administered back to a subject. In some embodiments, suitable cells, e.g., PBMCs, are transduced or transfected with polynucleotides for expression of TCRs specific to an immunogenic antigen peptide identified using the method described herein and administered to a subject. T cells expressing TCRs specific to an immunogenic antigen peptide identified using the method described herein can be expanded and administered back to a subject. In some embodiments, T cells that express TCRs specific to an immunogenic antigen peptide identified using the method described herein that result in cytolytic activity when incubated with autologous diseased tissue can be expanded and administered to a subject. In some embodiments, T cells used in functional assays result in binding to an immunogenic antigen peptide identified using the method described herein can be expanded and administered to a subject. In some embodiments, TCRs that have been determined to bind to subject specific immunogenic antigen peptides identified using the method described herein can be expressed in T cells and administered to a subject.

The methods described herein can involve adoptive transfer of immune system cells, such as T cells, specific for selected antigens, such as tumor or pathogen associated antigens. Various strategies can be employed to genetically modify T cells by altering the specificity of the T cell receptor (TCR) for example by introducing new TCR u and R chains with specificity to an immunogenic antigen peptide identified using the method described herein (see, e.g., U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

Chimeric antigen receptors (CARs) can be used to generate immunoresponsive cells, such as T cells, specific for selected targets, such a immunogenic antigen peptides identified using the method described herein, with a wide variety of receptor chimera constructs (see, e.g., U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs can be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ζ or FcRy or scFv-FcRy (see, e.g., U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain, e.g., scFv-CD28/OX40/4-lBB-CD3 (see, e.g., U.S. Pat. Nos. 8,911,993; 8,916,381; 8,975,071; 9,101,584; 9,102,760; 9,102,761). Third-generation CARs include a combination of costimulatory endodomains, such a CD3C-chain, CD97, GDI la-CD18, CD2, ICOS, CD27, CD154, CDS, OX40, 4-1BB, or CD28 signaling domains, e.g., scFv-CD28-4-lBB-CD3C or scFv-CD28-OX40-CD3Q (see, e.g., U.S. Pat. Nos. 8,906,682; 8,399,645; 5,686,281; PCT Publication No. WO2014134165; PCT Publication No. WO2012079000). In some embodiments, costimulation can be coordinated by expressing CARs in antigen-specific T cells, chosen so as to be activated and expanded following, for example, interaction with antigen on professional antigen-presenting cells, with costimulation. Additional engineered receptors can be provided on the immunoresponsive cells, e.g., to improve targeting of a T-cell attack and/or minimize side effects.

Alternative techniques can be used to transform target immunoresponsive cells, such as protoplast fusion, lipofection, transfection or electroporation. A wide variety of vectors can be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), can be used to introduce CARs, for example using 2nd generation antigen-specific CARs signaling through CD3 and either CD28 or CD137. Viral vectors can for example include vectors based on HIV, SV40, EBV, HSV or BPV Cells that are targeted for transformation can for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells can be differentiated. T cells expressing a desired CAR can for example be selected through co-culture with γ-irradiated activating and propagating cells (APC), which co-express the cancer antigen and co-stimulatory molecules. The engineered CAR T-cells can be expanded, for example by co-culture on APC in presence of soluble factors, such as IL-2 and IL-21. This expansion can for example be carried out so as to provide memory CAR T cells (which for example be assayed by non-enzymatic digital array and/or multi-panel flow cytometry). In this way, CAR T cells can be provided that have specific cytotoxic activity against antigen-bearing tumors (optionally in conjunction with production of desired chemokines such as interferon-γ). CAR T cells of this kind can for example be used in animal models, for example to threat tumor xenografts.

Approaches such as the foregoing can be adapted to provide methods of treating and/or increasing survival of a subject having a disease, such as a neoplasia or pathogenic infection, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction). Dosing in CAR T cell therapies can for example involve administration of from $10^6$ to $10^9$ cells/kg, with or without a course of lymphodepletion, for example with cyclophosphamide.

To guard against possible adverse reactions, engineered immunoresponsive cells can be equipped with a transgenic safety switch, in the form of a transgene that renders the cells vulnerable to exposure to a specific signal. For example, the herpes simplex viral thymidine kinase (TK) gene can be used in this way, for example by introduction into allogeneic T lymphocytes used as donor lymphocyte infusions following stem cell transplantation. In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see, e.g., U.S. Patent Publication No. 20130071414; PCT Patent Publication WO2011146862; PCT Patent Publication WO201401 1987; PCT Patent Publication WO2013040371). In a further refinement of adoptive therapies, genome editing can be used to tailor immunoresponsive cells to alternative implementations, for example providing edited CAR T cells.

Cell therapy methods can also involve the ex-vivo activation and expansion of T-cells. In some embodiments, T cells can be activated before administering them to a subject in need thereof. Examples of these type of treatments include the use tumor infiltrating lymphocyte (TIL) cells (see U.S. Pat. No. 5,126,132), cytotoxic T-cells (see U.S. Pat. Nos. 6,255,073; and 5,846,827), expanded tumor draining lymph node cells (see U.S. Pat. No. 6,251,385), and various other lymphocyte preparations (see U.S. Pat. Nos. 6,194,207; 5,443,983; 6,040,177; and 5,766,920).

An ex vivo activated T-cell population can be in a state that maximally orchestrates an immune response to cancer, infectious diseases, or other disease states, e.g., an autoimmune disease state. For activation, at least two signals can be delivered to the T cells. The first signal is normally delivered through the T-cell receptor (TCR) on the T-cell surface. The TCR first signal is normally triggered upon interaction of the TCR with peptide antigens expressed in conjunction with an MHC complex on the surface of an antigen-presenting cell (APC). The second signal is normally delivered through co-stimulatory receptors on the surface of T-cells. Co-stimulatory receptors are generally triggered by corresponding ligands or cytokines expressed on the surface of APCs.

It is contemplated that the T cells specific to immunogenic antigen peptides identified using the method described herein can be obtained and used in methods of treating or preventing disease. In this regard, the disclosure provides a method of treating or preventing a disease or condition in a subject, comprising administering to the subject a cell population comprising cells specific to immunogenic antigen peptides identified using the method described herein in an amount effective to treat or prevent the disease in the subject. In some embodiments, a method of treating or preventing a disease in a subject, comprises administering a cell population enriched for disease-reactive T cells to a subject in an amount effective to treat or prevent cancer in the mammal. The cells can be cells that are allogeneic or autologous to the subject.

The disclosure further provides a method of inducing a disease specific immune response in a subject, vaccinating against a disease, treating and/or alleviating a symptom of a disease in a subject by administering the subject an antigenic peptide or vaccine.

The peptide or composition of the disclosure can be administered in an amount sufficient to induce a CTL response. An antigenic peptide or vaccine composition can be administered alone or in combination with other therapeutic agents. Exemplary therapeutic agents include, but are not limited to, a chemotherapeutic or biotherapeutic agent, radiation, or immunotherapy. Any suitable therapeutic treatment for a particular disease can be administered. Examples of chemotherapeutic and biotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. In addition, the subject can be further administered an anti-immunosuppressive or immunostimulatory agent. For example, the subject can be further administered an anti-CTLA antibody or anti-PD-1 or anti-PD-Ll.

The amount of each peptide to be included in a vaccine composition and the dosing regimen can be determined by one skilled in the art. For example, a peptide or its variant can be prepared for intravenous (i.v.) injection, sub-cutaneous (s.c.) injection, intradermal (i.d.) injection, intraperitoneal (i.p.) injection, intramuscular (i.m.) injection. Exemplary methods of peptide injection include s.c, i.d., i.p., i.m., and i.v. Exemplary methods of DNA injection include i.d., i.m., s.c, i.p. and i.v. Other methods of administration of the vaccine composition are known to those skilled in the art.

A pharmaceutical composition can be compiled such that the selection, number and/or amount of peptides present in the composition is/are disease and/or patient-specific. For example, the exact selection of peptides can be guided by expression patterns of the parent proteins in a given tissue to avoid side effects. The selection can be dependent on the specific type of disease, the status of the disease, earlier treatment regimens, the immune status of the patient, and the HLA-haplotype of the patient. Furthermore, the vaccine according to the present disclosure can contain individualized components, according to personal needs of the particular patient. Examples include varying the amounts of peptides according to the expression of the related antigen in the particular patient, unwanted side-effects due to personal allergies or other treatments, and adjustments for secondary treatments following a first round or scheme of treatment.

Production of Disease Specific Antigens

The present disclosure is based, at least in part, on the ability to present the immune system of the patient with one or more disease-specific antigens. One of skill in the art from this disclosure and the knowledge in the art will appreciate that there are a variety of ways in which to produce such disease specific antigens. In general, such disease specific antigens can be produced either in vitro or in vivo. Disease specific antigens can be produced in vitro as peptides or polypeptides, which can then be formulated into a vaccine or immunogenic composition and administered to a subject. As described in further detail herein, such in vitro production can occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, disease specific antigens can be produced in vivo by introducing molecules (e.g., DNA, RNA, viral expression systems, and the like) that encode disease specific antigens into a subject, whereupon the encoded disease specific antigens are expressed. The methods of in vitro and in vivo production of antigens is also further described herein as it relates to pharmaceutical compositions and methods of delivery of the therapy.

In some embodiments, the present disclosure includes modified antigenic peptides. A modification can include a covalent chemical modification that does not alter the primary amino acid sequence of the antigenic peptide itself. Modifications can produce peptides with desired properties, for example, prolonging the in vivo half-life, increasing the stability, reducing the clearance, altering the immunogenicity or allergenicity, enabling the raising of particular antibodies, cellular targeting, antigen uptake, antigen processing, MHC affinity, MHC stability, or antigen presentation. Changes to an antigenic peptide that can be carried out include, but are not limited to, conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.

Issues associated with short plasma half-life or susceptibility to protease degradation can be overcome by various modifications, including conjugating or linking the polypeptide sequence to any of a variety of non-proteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography can be used to separate conjugates, and a fraction is then identified which contains the conjugate having, for example, the desired number of PEGs attached, purified free from unmodified protein sequences and from conjugates having other numbers of PEGs attached.

PEG can be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which can be bound to the free amino group includes N-hydroxysuccinylimide polyethylene glycol which can be prepared by activating succinic acid ester of polyethylene glycol with N-hydroxy succinylimide. Another activated polyethylene glycol which can be bound to a free amino group is 2,4-bis(O-methoxypolyethyleneglycol)-6-chloro-s-triazine which can be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH>7), and longer reaction time tend to increase the number of PEGs attached. Various means known in the art can be used to terminate the reaction. In some embodiments the reaction is terminated by acidifying the reaction mixture and freezing at, e.g., −20° C.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix's XTEN technology; Mountain View, CA). This obviates the need for an additional conjugation step during the manufacturing process. Moreover, established molecular biology techniques enable control of the side chain composition of the polypeptide chains, allowing optimization of immunogenicity and manufacturing properties.

Glycosylation can affect the physical properties of proteins and can also be important in protein stability, secretion, and subcellular localization. Proper glycosylation can be important for biological activity. In fact, some genes from eukaryotic organisms, when expressed in bacteria (e.g., *E. coli*) which lack cellular processes for glycosylating proteins, yield proteins that are recovered with little or no activity by virtue of their lack of glycosylation. Addition of glycosylation sites can be accomplished by altering the amino acid sequence. The alteration to the polypeptide can be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type can be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. Embodiments of the present disclosure comprise the generation and use of N-glycosylation variants.

The polypeptide sequences of the present disclosure can optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates can be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Additional suitable components and molecules for conjugation include, for example, molecules for targeting to the lymphatic system, thyroglobulin; albumins such as human serum albumin (HAS); tetanus toxoid; Diphtheria toxoid; polyamino acids such as poly(D-lysine:D-glutamic acid); VP6 polypeptides of rotaviruses; influenza virus hemagglutinin, influenza virus nucleoprotein; Keyhole Limpet Hemocyanin (KLH); and hepatitis B virus core protein and surface antigen; or any combination of the foregoing.

Fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression can be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells. Furthermore, albumin itself can be modified to extend its circulating half-life. Fusion of the modified albumin to one or more polypeptides can be attained by the genetic manipulation techniques described above or by chemical conjugation; the resulting fusion molecule has a half-life that exceeds that of fusions with non-modified albumin. (See WO2011/051489). Several albumin-binding strategies have been developed as alternatives for direct fusion, including albumin binding through a conjugated fatty acid chain (acylation). Because serum albumin is a transport protein for fatty acids, these natural ligands with albumin—binding activity have been used for half-life extension of small protein therapeutics. For example, insulin detemir (LEVEMIR), an approved product for diabetes, comprises a myristyl chain conjugated to a genetically-modified insulin, resulting in a long-acting insulin analog.

Another type of modification is to conjugate (e.g., link) one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification can result in a polypeptide sequence that retains activity with an additional or complementary function or activity of the second molecule. For example, a polypeptide sequence can be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A polypeptide can also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes. Purification methods such as cation exchange chromatography can be used to separate conjugates by charge difference, which effectively separates conjugates into their various molecular weights. The content of the fractions obtained by cation exchange chromatography can be identified by molecular weight using conventional methods, for example, mass spectroscopy, SDS-PAGE, or other known methods for separating molecular entities by molecular weight.

In some embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

The present disclosure contemplates the use of other modifications, currently known or developed in the future, of the polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

In Vitro Peptide/Polypeptide Synthesis

Proteins or peptides can be made by any technique known to those of skill in the art, including the expression of proteins, polypeptides or peptides through standard molecular biological techniques, the isolation of proteins or peptides from natural sources, in vitro translation, or the chemical synthesis of proteins or peptides.

Peptides can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963). In some embodiments, antigenic peptides are prepared by (1) parallel solid-phase synthesis on multi-channel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Alternatively, a nucleic acid (e.g., a polynucleotide) encoding an antigenic peptide of the present disclosure can be used to produce the antigenic peptide in vitro. The polynucleotide can be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it can contain introns so long as it codes for the peptide. In one embodiment in vitro translation is used to produce the peptide. Many exemplary systems exist that one skilled in the art could utilize (e.g., Retic Lysate IVT Kit, Life Technologies, Waltham, MA). An expression vector capable of expressing a polypeptide can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA can be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

Expression vectors comprising the isolated polynucleotides, as well as host cells containing the expression vectors, are also contemplated. The antigenic peptides can be provided in the form of RNA or cDNA molecules encoding the desired antigenic peptides. One or more antigenic peptides of the disclosure can be encoded by a single expression vector.

In some embodiments, the polynucleotides can comprise the coding sequence for the disease specific antigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In some embodiments, the polynucleotides can comprise the coding sequence for the disease specific antigenic peptide fused in the same reading frame to a marker sequence that allows, for example, for purification of the encoded polypeptide, which can then be incorporated into a personalized disease vaccine or immunogenic composition. For example, the marker sequence can be a hexa-histidine tag (SEQ ID NO: 7) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In some embodiments, the polynucleotides can comprise the coding sequence for one or more of the disease specific antigenic peptides fused in the same reading frame to create a single concatamerized antigenic peptide construct capable of producing multiple antigenic peptides.

In some embodiments, isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a disease specific antigenic peptide of the present disclosure, can be provided.

The isolated disease specific antigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors can be used to amplify and express DNA encoding the disease specific antigenic peptides. Recombinant expression vectors are replicable DNA constructs which have synthetic or cDNA-derived DNA fragments encoding a disease specific antigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 7), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography. For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In Vivo Peptide/Polypeptide Synthesis

The present disclosure also contemplates the use of nucleic acid molecules as vehicles for delivering antigenic peptides/polypeptides to the subject in need thereof, in vivo, in the form of, e.g., DNA/RNA vaccines (see, e.g., WO2012/159643, and WO2012/159754, hereby incorporated by reference in their entirety).

In some embodiments, antigens can be administered to a patient in need thereof by use of a plasmid. These are plasmids which usually consist of a strong viral promoter to drive the in vivo transcription and translation of the gene (or complementary DNA) of interest (Mor, et al., (1995). The Journal of Immunology 155 (4): 2039-2046). Intron A can sometimes be included to improve mRNA stability and hence increase protein expression (Leitner, et al. (1997).The Journal of Immunology 159 (12): 6112-6119). Plasmids also include a strong polyadenylation/transcriptional termination signal, such as bovine growth hormone or rabbit beta-globulin polyadenylation sequences (Alarcon et al., (1999). Adv. Parasitol. Advances in Parasitology 42: 343-410; Robinson et al., (2000). Adv. Virus Res. Advances in Virus Research 55: 1-74; Bohm et al., (1996). Journal of Immunological Methods 193 (1): 29-40.). Multicistronic vectors are sometimes constructed to express more than one immunogen, or to express an immunogen and an immunostimulatory protein (Lewis et al., (1999). Advances in Virus Research (Academic Press) 54: 129-88)

Plasmids can be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (IM) in skeletal muscle, or intradermally (ID), with DNA being delivered to the extracellular spaces. This can be assisted by electroporation by temporarily damaging muscle fibers with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410; Lewis et al., (1999). Advances in Virus Research (Academic Press) 54: 129-88).

Alternative delivery methods can include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated *Shigella* or *Listeria* vectors for oral administration to the intestinal mucosa, and recombinant adenovirus vectors. DNA or RNA can also be delivered to cells following mild mechanical disruption of the cell membrane, temporarily permeabilizing the cells. Such a mild mechanical disruption of the membrane can be accomplished by gently forcing cells through a small aperture (Ex vivo Cytosolic Delivery of Functional Macromolecules to Immune Cells, Sharei et al, PLOS ONE|DOI: 10.1371/journal.pone.0118803 Apr. 13, 2015).

In some embodiments, a disease specific vaccine or immunogenic composition can include separate DNA plasmids encoding, for example, one or more antigenic peptides/polypeptides as identified in according to the disclosure. As discussed herein, the exact choice of expression vectors can depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection.

One or more antigenic peptides of the present disclosure can be encoded and expressed in vivo using a viral based system (e.g., an adenovirus system, an adeno associated virus (AAV) vector, a poxvirus, or a lentivirus). In one embodiment, the disease vaccine or immunogenic composition can include a viral based vector for use in a human patient in need thereof, such as, for example, an adenovirus (see, e.g., Baden et al. First-in-human evaluation of the safety and immunogenicity of a recombinant adenovirus serotype 26 HIV-1 Env vaccine (IPCAVD 001). J Infect Dis. 2013 Jan 15; 207(2):240-7, hereby incorporated by reference in its entirety). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference).

The peptides and polypeptides of the disclosure can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the disclosure. Upon introduction into an acutely or chronically infected host or into a noninfected host, the vector expresses the immunogenic peptide, and thereby elicits a host CTL response.

Among vectors that can be used in the practice of the disclosure, integration in the host genome of a cell is possible with retrovirus gene transfer methods, often resulting in long term expression of the inserted transgene. In some embodiments, the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors can be used in the practice of the disclosure). Moreover, lentiviral vectors are able to transduce or infect non-dividing cells and typically produce high viral titers. Selection of a retroviral gene transfer system can therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that can be used in the practice of the disclosure include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700).

Also useful in the practice of the disclosure is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience. The vectors can have cytomegalovirus (CMV) promoter driving expression of the target gene. Accordingly, the disclosure contemplates amongst vector(s) useful in the practice of the disclosure: viral vectors, including retroviral vectors and lentiviral vectors.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for delivery to the Brain, see, e.g., US Patent Publication Nos. US20110293571; US20040013648, US20070025970, US20090111106 and U.S. Pat. No. 7,259,015. In another embodiment lentiviral vectors are used to deliver vectors to the brain of those being treated for a disease. As to lentivirus vector systems useful in the practice of the disclosure, mention is made of U.S. Pat. Nos. 6,428,953, 6,165,782, 6,013,516, 5,994,136, 6,312,682, and 7,198,784, and documents cited therein. In an embodiment herein the delivery is via an lentivirus. Zou et al. administered about 10 µL of a recombinant lentivirus having a titer of $1\times10^9$ transducing units (TU)/ml by an intrathecal catheter. These sort of dosages can be adapted or extrapolated to use of a retroviral or lentiviral vector in the present disclosure. For transduction in tissues such as the brain, it is necessary to use very small volumes, so the viral preparation is concentrated by ultracentrifugation. Other methods of concentration such as ultrafiltration or binding to and elution from a matrix can be used. In other embodiments the amount of lentivirus administered can be $1\times10^5$ or about $1\times10^5$ plaque forming units (PFU), $5\times10^5$ or about $5\times10^5$ PFU, $1\times10^6$ or about $1\times10^6$ PFU, $5\times10^6$ or about $5\times10^6$ PFU, $1\times10^7$ or about $1\times1^{07}$ PFU, $5\times10^7$ or about $5\times10^7$ PFU, $1\times10^8$ or about $1\times10^8$ PFU, $5\times10^8$ or about $5\times10^8$ PFU, $1\times10^9$ or about $1\times10^9$ PFU, $5\times10^9$ or about $5\times10^9$ PFU, $1\times10^{10}$ or about $1\times10^{10}$ PFU or $5\times10^{10}$ or about $5\times10^{10}$ PFU as total single dosage for an average human of 75 kg or adjusted for the weight and size and species of the subject. One of skill in the art can determine suitable dosage. Suitable dosages for a virus can be determined empirically.

Also useful in the practice of the disclosure is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference). As to adenovirus vectors useful in the practice of the disclosure, mention is made of U.S. Pat. No. 6,955,808. The adenovirus vector used can be selected from the group consisting of the Ad5, Ad35, Ad11, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558. Adenovirus vectors that are E1-defective or deleted, E3-defective or deleted, and/or E4-defective or deleted can also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region can have enhanced the immunogenicity by disrupting the mechanism whereby adenovirus down-regulates MHC class I molecules. Adenoviruses having E4 mutations can have reduced immunogenicity of the adenovirus vector because of suppression of late gene expression. Such vectors can be particularly useful when repeated re-vaccination utilizing the same vector is desired. Adenovirus vectors that are deleted or mutated in E1, E3, E4, E1 and E3, and E1 and E4 can be used in accordance with the present disclosure. Furthermore, "gutless" adenovirus vectors, in which all viral genes are deleted, can also be used in accordance with the present disclosure. Such vectors require a helper virus for their replication and require a special human 293 cell line expressing both Ela and Cre, a condition that does not exist in natural environment. Such "gutless" vectors are non-immunogenic and thus the vectors can be inoculated multiple times for re-vaccination. The "gutless" adenovirus vectors can be used for insertion of heterologous inserts/genes such as the transgenes of the present disclosure, and can even be used for co-delivery of a large number of heterologous inserts/genes. In some embodiments, the delivery is via an adenovirus, which can be at a single booster dose. In some embodiments, the adenovirus is delivered via multiple doses. In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. For brain expression, the following promoters can be used: SynapsinI for all neurons, CaMKIIalpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA). With regard to AAV vectors useful in the practice of the disclosure, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein. As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. In some embodiments the delivery is via an AAV. The dosage can be adjusted to balance the therapeutic benefit against any side effects.

In some embodiments, effectively activating a cellular immune response for a disease vaccine or immunogenic composition can be achieved by expressing the relevant antigens in a vaccine or immunogenic composition in a non-pathogenic microorganism. Well-known examples of such microorganisms are *Mycobacterium bovis* BCG, *Salmonella* and Pseudomona (See, U.S. Pat. No. 6,991,797, hereby incorporated by reference in its entirety).

In some embodiments, a Poxvirus is used in the disease vaccine or immunogenic composition. These include orthopoxvirus, avipox, vaccinia, MVA, NYVAC, canarypox, ALVAC, fowlpox, TROVAC, etc. (see e.g., Verardi et al., Hum Vaccin Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels. Information concerning poxviruses that can be used in the practice of the disclosure, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants can be found in scientific and patent literature.

In some embodiments, the vaccinia virus is used in the disease vaccine or immunogenic composition to express a antigen. (Rolph et al., Recombinant viruses as vaccines and immunological tools. Curr Opin Immunol 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In some embodiments, ALVAC is used as a vector in a disease vaccine or immunogenic composition. ALVAC is a canarypox virus that can be modified to express foreign transgenes and has been used as a method for vaccination against both prokaryotic and eukaryotic antigens (Horig H, Lee DS, Conkright W, et al. Phase I clinical trial of a recombinant canarypoxvirus (ALVAC) vaccine expressing human carcinoembryonic antigen and the B7.1 co-stimulatory molecule. Cancer Immunol Immunother 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin Cancer Res 2000; 6:2219-28; Musey L, Ding Y, Elizaga M, et al. HIV-1 vaccination administered intramuscularly can induce both systemic and mucosal T cell immunity in HIV-1-uninfected individuals. J Immunol 2003; 171:1094-101; Paoletti E. Applications of pox virus vectors to vaccination: an update. Proc Natl Acad Sci USA 1996; 93:11349-53; U.S. Pat. No. 7,255,862). In a phase I clinical trial, an ALVAC virus expressing the tumor antigen CEA showed an excellent safety profile and resulted in increased CEA-specific T-cell responses in selected patients; objective clinical responses, however, were not observed (Marshall J L, Hawkins MJ, Tsang K Y, et al. Phase I study in cancer patients of a replication-defective avipox recombinant vaccine that expresses human carcinoembryonic antigen. J Clin Oncol 1999; 17:332-7).

In some embodiments, a Modified Vaccinia Ankara (MVA) virus can be used as a viral vector for an antigen vaccine or immunogenic composition. MVA is a member of the Orthopoxvirus family and has been generated by about 570 serial passages on chicken embryo fibroblasts of the Ankara strain of Vaccinia virus (CVA) (for review see Mayr, A., et al., Infection 3, 6-14, 1975). As a consequence of these passages, the resulting MVA virus contains 31 kilobases less genomic information compared to CVA, and is highly host-cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol Immunother. January 2012; 61(1): 19-29). Methods to make and use recombinant MVA has been described (e.g., see U.S. Pat. Nos. 8,309,098 and 5,185,146 hereby incorporated in its entirety).

In some embodiments, recombinant viral particles of the vaccine or immunogenic composition are administered to patients in need thereof.

Provided herein is a method of developing an therapeutic for a subject with a disease or condition comprising providing a population of cells derived from a subject with a disease or condition, expressing in one or more cells of the population of cells an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching and characterizing the affinity acceptor tagged HLA-peptide complexes; and, optionally developing an therapeutic based on the characterization.

Provided herein is a method of identifying at least one subject specific immunogenic antigen and preparing a subject-specific immunogenic composition that includes the at least one subject specific immunogenic antigen, wherein the subject has a disease and the at least one subject specific immunogenic antigen is specific to the subject and the subject's disease, said method comprising: providing a population of cells derived from a subject with a disease or condition, expressing in one or more cells of the population of cells from the subject, an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching affinity acceptor tagged HLA-peptide complexes from the one or more cells; identifying an immunogenic peptide from the enriched affinity acceptor tagged HLA-peptide complexes that is specific to the subject and the subject's disease; and formulating a subject-specific immunogenic composition based one or more of the subject specific immunogenic peptides identified.

In some embodiments, the therapeutic or subject specific immunogenic composition comprises a peptide from the enriched affinity acceptor tagged HLA-peptide complexes or a or a polynucleotide encoding the polypeptide from the enriched affinity acceptor tagged HLA-peptide complexes.

In some embodiments, the therapeutic or subject specific immunogenic composition comprises a T cell expressing a T cell receptor (TCR) that specifically binds to the polypeptide from the enriched affinity acceptor tagged HLA-peptide complexes. In some embodiments, the subject specific immunogenic composition comprises a chimeric antigen receptor (CAR) T cell expressing a receptor that specifically binds to the polypeptide from the enriched affinity acceptor tagged HLA-peptide complexes. In some embodiments, the method further comprises administering another therapeutic agent, optionally, an immune checkpoint inhibitor to the subject. In some embodiments, the method further comprises administering an adjuvant, optionally, poly-ICLC to the subject.

In some embodiments, the disease or disorder is cancer. In some embodiments, the disease or disorder is an autoimmune disease. In some embodiments, the disease or disorder is an infection. In some embodiments, the infection is an infection by an infectious agent. In some embodiments, the infectious agent is a pathogen, a virus, bacteria, or a parasite. In some embodiments, the virus is selected from the group consisting of BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof. In some embodiments, the bacteria is selected from the group consisting of: *Klebsiella* spp., *Tropheryma whipplei, Mycobacterium leprae, Mycobacterium lepromatosis*, and *Mycobacterium tuberculosis*, typhoid, pneumococcal, meningococcal, *haemophilus* B, anthrax, tetanus toxoid, meningococcal group B, bcg, cholera, and combinations thereof. In some embodiments, the parasite is a helminth or a protozoan. In some embodiments, the parasite is selected from the group consisting of: *Leishmania* spp., *Plasmodium* spp., *Trypanosoma cruzi, Ascaris lumbricoides, Trichuris trichiura, Necator americanus, Schistosoma* spp., and any combination thereof.

Provided herein is a method of developing a therapeutic for a subject with a disease or condition comprising: providing a population of cells, wherein one or more cells of the population of cells comprise a polynucleic acid comprising a sequence encoding at least two affinity acceptor tagged class I or class II HLA alleles, wherein the sequence encoding the at least two affinity acceptor tagged class I or class II HLAs comprises a first recombinant sequence comprising a sequence encoding a first class I or class II HLA allele operatively linked to a sequence encoding a first affinity acceptor peptide; and a second recombinant sequence comprising a sequence encoding a second class I or class II HLA allele operatively linked to a sequence encoding a second affinity acceptor peptide; expressing the at least two affinity acceptor tagged HLAs in at least one cell of the one or more cells of the population of cells, thereby forming affinity acceptor tagged HLA-peptide complexes in the at least one cell; enriching for the affinity acceptor tagged HLA-peptide complexes; and identifying a peptide from the enriched affinity acceptor tagged HLA-peptide complexes; and formulating an immunogenic composition based one or more of the peptides identified, wherein the first and the second recombinant class I or class II HLA alleles are matched to an HLA haplotype of a subject.

In some embodiments, the subject has a disease or condition. In some embodiments, the first recombinant class I or class II HLA allele is different than the second recombinant class I or class II HLA allele. In some embodiments, the first affinity acceptor peptide is the same as the second affinity acceptor peptide. In some embodiments, the method comprises characterizing a peptide bound to the first and/or second affinity acceptor tagged HLA-peptide complexes from the enriching. In some embodiments, the at least two affinity acceptor tagged class I or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles. In some embodiments, the first and/or the second affinity acceptor tagged HLA-peptide complexes comprise a transmembrane domain. In some embodiments, the first and/or the second affinity acceptor tagged HLA-peptide complexes comprise an intracellular domain. In some embodiments, the first and/or the second affinity acceptor tagged HLA-peptide complexes are not excreted. In some embodiments, the first and/or the second affinity acceptor tagged HLA-peptide complexes incorporate into a cell membrane when expressed. In some embodiments, the first and/or the second affinity acceptor tagged HLA-peptide complexes are not soluble affinity acceptor tagged HLA-peptide complexes. In some embodiments, the method further comprises generating an HLA-allele specific peptide database. In some embodiments, the method comprises introducing one or more exogenous peptides to the population of cells. In some embodiments, the introducing comprises contacting the population of cells with the one or more exogenous peptides or expressing the one or more exogenous peptides in the population of cells. In some embodiments, the introducing comprises contacting the population of cells with one or more nucleic acids encoding the one or more exogenous peptides. In some embodiments, the one or more nucleic acids encoding the one or more peptides is DNA. In some embodiments, the one or more nucleic acids encoding the one or more peptides is RNA, optionally wherein the RNA is mRNA. In some embodiments, the enriching does not comprise use of a tetramer reagent. In some embodiments, the method comprises determining the sequence of a peptide or a portion thereof bound to the first and/or the second affinity acceptor tagged HLA-peptide complex from the enriching. In some embodiments, the determining comprises biochemical analysis, mass spectrometry analysis, MS analysis, MS/MS analysis, LC-MS/MS analysis, or a combination thereof. In some embodiments, the method comprises evaluating a binding affinity or stability of a peptide or a portion thereof bound to the first and/or the second affinity acceptor tagged HLA-peptide complex from the enriching.

In some embodiments, the method comprises determining whether a peptide or a portion thereof bound to the first and/or the second affinity acceptor tagged HLA-peptide complex from the enriching contains one or more mutations. In some embodiments, the method comprises evaluating associations of peptides with HLA molecules in the first and/or the second affinity acceptor tagged HLA-peptide complex.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition. In some embodiments, the disease or condition is cancer or an infection with an infectious agent.

In some embodiments, the method comprises introducing the infectious agent or portions thereof into one or more cells of the population of cells. In some embodiments, the method comprises characterizing one or more peptides from the first and/or the second HLA-peptide complexes, optionally wherein the peptides are from one or more target proteins of the infectious agent. In some embodiments, the method comprises characterizing one or more regions of the peptides from the one or more target proteins of the infectious agent. In some embodiments, the method comprises identifying peptides from the first and/or the second HLA-peptide complexes derived from an infectious agent.

In some embodiments, the population of cells is from a biological sample from a subject with a disease or condition. In some embodiments, the population of cells is a cell line. In some embodiments, the population of cells is a population of primary cells.

In some embodiments, the peptide from the first and/or the second affinity acceptor tagged HLA-peptide complex is capable of activating a T cell from a subject when presented by an antigen presenting cell. In some embodiments, the method comprises comparing HLA-peptide complexes from diseased cells to HLA-peptide complexes from non-diseased cells.

In some embodiments, the method further comprises isolating peptides from the first and/or the second affinity acceptor tagged HLA-peptide complexes before the identifying.

In some embodiments, the population of cells is a population of low cell surface HLA class I or class II expressing cells. In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles.

In some embodiments, the population of cells is a knock-out of all HLA class II alleles. In some embodiments, the population of cells is a knock-out of all HLA class I alleles and a knock-out of all HLA class II alleles.

In some embodiments, the sequence encoding the at least two affinity acceptor tagged class I or class II HLA alleles encodes a class I HLA. In some embodiments, the class I HLA is selected from the group consisting of HLA-A, HLA-B, HLA-C, HLA-E, HLA-F, and HLA-G. In some embodiments, the first recombinant class I or class II HLA allele is a first class I HLA allele and the second recombinant class I or class II HLA allele is a second class I HLA allele. In some embodiments, the sequence encoding the at least two affinity acceptor tagged class I or class II HLA alleles encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof. In some embodiments, the first recombinant class I or class II HLA allele is a first class II HLA allele and the second recombinant class I or class II HLA allele is a second class II HLA allele.

In some embodiments, the first sequence and the second sequence are each operatively linked. In some embodiments, the first sequence and the second sequence are comprised on different polynucleotide molecules.

In some embodiments, the sequence encoding the first and/or second affinity acceptor peptide is operatively linked to a sequence that encodes an extracellular portion of the first and/or second class I or class II HLA allele. In some embodiments, the first and/or second encoded affinity acceptor peptide is expressed extracellularly. In some embodiments, the sequence encoding the first and/or second affinity acceptor peptide is operatively linked to the N-terminus of the sequence encoding the first and/or second class I or class II HLA allele.

In some embodiments, the sequence encoding the first and/or second affinity acceptor peptide is operatively linked to a sequence that encodes an intracellular portion of the first and/or second class I or class II HLA allele. In some embodiments, the encoded first and/or second affinity acceptor peptide is expressed intracellularly. In some embodiments, the sequence encoding the first and/or second affinity acceptor peptide is operatively linked to the C-terminus of the sequence encoding the first and/or second class I or class II HLA allele. In some embodiments, the sequence encoding the first and/or second affinity acceptor peptide is operatively linked to the sequence encoding the first and/or second class I or class II HLA allele by a linker.

In some embodiments, enriching comprises enriching for intact cells expressing the first and/or second affinity acceptor tagged HLA-peptide complexes. In some embodiments, the method does not comprise lysing the cells before enriching. In some embodiments, the method further comprises lysing the one or more cells before enriching.

In some embodiments, enriching comprises contacting an affinity acceptor peptide binding molecule to the first and/or second affinity acceptor tagged HLA-peptide complexes, wherein the affinity acceptor peptide binding molecule binds specifically to the first and/or second affinity acceptor peptide. In some embodiments, the first and/or second affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof; optionally, wherein the first and/or second affinity acceptor peptide comprises two or more repeats of a tag sequence. In some embodiments, the affinity acceptor peptide binding molecule is biotin or an antibody specific to the first and/or second affinity acceptor peptide.

In some embodiments, the enriching comprises contacting an affinity molecule to the first and/or second affinity acceptor tagged HLA-peptide complexes, wherein the affinity molecule binds specifically to the affinity acceptor peptide binding molecule. In some embodiments, the affinity molecule is streptavidin, NeutrAvidin, or a derivative thereof. In some embodiments, enriching comprises immunoprecipitating the first and/or second affinity acceptor tagged HLA-peptide complexes. In some embodiments, the affinity acceptor peptide binding molecule is attached to a solid surface. In some embodiments, the affinity molecule is attached to a solid surface. In some embodiments, the solid surface is a bead.

In some embodiments, enriching comprises immunoprecipitating the first and/or second affinity acceptor tagged HLA-peptide complexes with an affinity acceptor peptide binding molecule that binds specifically to the first and/or second affinity acceptor peptide. In some embodiments, the affinity acceptor peptide binding molecule does not specifically interact with the amino acid sequence of the encoded first and/or second class I or class II HLA. In some embodiments, enriching comprises contacting an affinity molecule specific to an extracellular portion of the first and/or second class I or class II HLA allele. In some embodiments, enriching comprises contacting an affinity molecule specific to an N-terminal portion of the first and/or second class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the first and/or second class I or class II HLA comprises a sequence encoding a HLA class I α-chain. In some embodiments, the first recombinant class I or class II HLA allele is a first HLA class I α-chain and the second recombinant class I or class II HLA allele is a second HLA class I α-chain. In some embodiments, the method further comprises expressing a sequence encoding β2 microglobulin in the one or more cells. In some embodiments, the sequence encoding β2 microglobulin is connected to the sequence encoding the first and/or second class I or class II HLA. In some embodiments, the sequence encoding β2 microglobulin is connected to the sequence encoding the first and/or second class I or class II HLA by a linker. In some embodiments, the sequence encoding β2 microglobulin is connected to a sequence encoding a third affinity acceptor peptide. In some embodiments, the third affinity acceptor peptide is different than the first and/or second affinity acceptor peptide.

In some embodiments, the sequence encoding the first and/or second class I or class II HLA comprises a sequence encoding a HLA class II α-chain and/or a HLA class II β-chain. In some embodiments, the sequence encoding the first and/or second class I or class II HLA comprises a sequence encoding a first HLA class II α-chain and a second HLA class II α-chain. In some embodiments, the method further comprises expressing a sequence encoding a HLA class II β-chain in the one or more cells. In some embodiments, the sequence encoding a first HLA class II α-chain and a second HLA class II α-chain HLA is connected to the sequence encoding the HLA class II β-chain. In some embodiments, the sequence encoding the first and/or second class I or class II HLA comprises a sequence encoding a first HLA class II β-chain and a second HLA class II β-chain. In some embodiments, the method further comprises expressing a sequence encoding a HLA class II α-chain in the one or more cells. In some embodiments, the sequence encoding a first HLA class II β-chain and a second HLA class II β-chain is connected to the sequence encoding the HLA class II α-chain by a linker. In some embodiments, the sequence encoding the HLA class II β-chain or the HLA class II α-chain is connected to a sequence encoding a third affinity acceptor peptide. In some embodiments, the third affinity acceptor peptide is different than the first and/or second affinity acceptor peptide.

In some embodiments, the third affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof, optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the method comprises performing biochemical analysis or mass spectrometry, such as tandem mass spectrometry.

In some embodiments, the method comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides.

In some embodiments, the population of cells is a cell line selected from HEK293T, expi293, HeLa, A375, 721.221, JEG-3, K562, Jurkat, Hep G2, SH-SY5Y, CACO-2, U937, U-2 OS, ExpiCHO, CHO and THP1.

In some embodiments, the cell line is treated with one or more cytokines, checkpoint inhibitors, epigenetically-active drugs, IFN-γ, or a combination thereof.

In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells.

In some embodiments, the population of cells is contacted with an agent prior to isolating the first and/or second HLA-peptide complexes from the one or more cells. In some embodiments, the agent is an inflammatory cytokine, a chemical agent, an adjuvant, a therapeutic agent or radiation.

In some embodiments, the first and or second HLA allele is a mutated HLA allele. In some embodiments, the sequence encoding the first and or second HLA allele comprises a barcode sequence. In some embodiments, the method further comprises assaying for expression of the first and/or second affinity acceptor tagged class I or class II HLA allele. In some embodiments, the assaying comprises sequencing the first and/or second affinity acceptor tagged class I or class II HLA allele, detecting RNA encoding the first and/or second affinity acceptor tagged class I or class II HLA allele RNA, detecting the first and/or second affinity acceptor tagged class I or class II HLA allele protein, or a combination thereof. In some embodiments, the first and second affinity acceptor tagged class I or class II HLA allele comprises a unique barcode sequence. In some embodiments, the first sequence and the second sequence comprise a unique barcode sequence.

EXAMPLES

The examples provided below are for illustrative purposes only and do not to limit the scope of the claims provided herein.

Figure 4A:
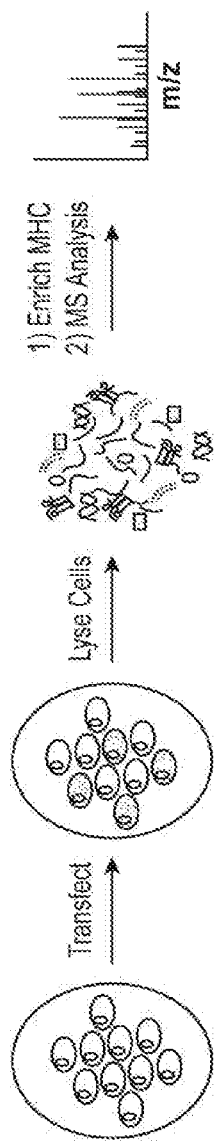
FIG. 4A is a representative schematic of a transfection-based introduction of class I or class II HLA constructs for universal IP and HLA-associated peptide sequencing by LC-MS/MS.
Figure 4B:
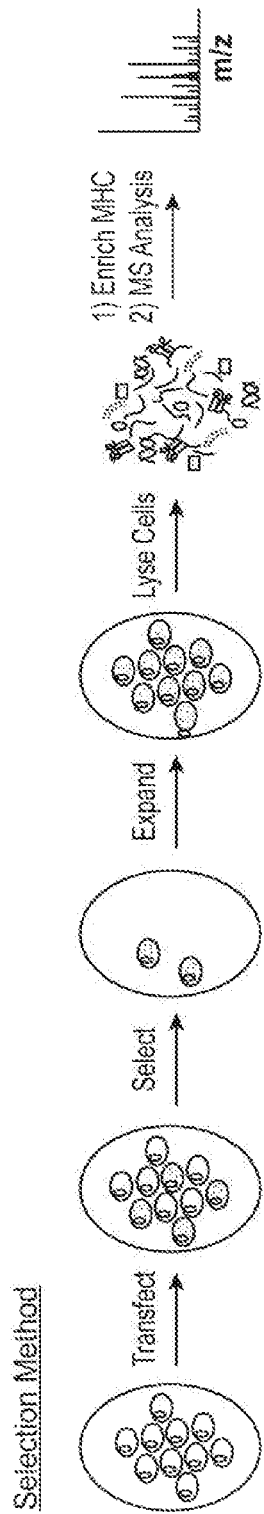
FIG. 4B is a representative schematic of a transfection-based introduction of class I or class II HLA constructs followed by a selection process, e.g., inclusion of an antibiotic resistance gene. The selected cells can then be submitted for universal IP and HLA-associated peptide sequencing by LC-MS/MS.
Figure 5:
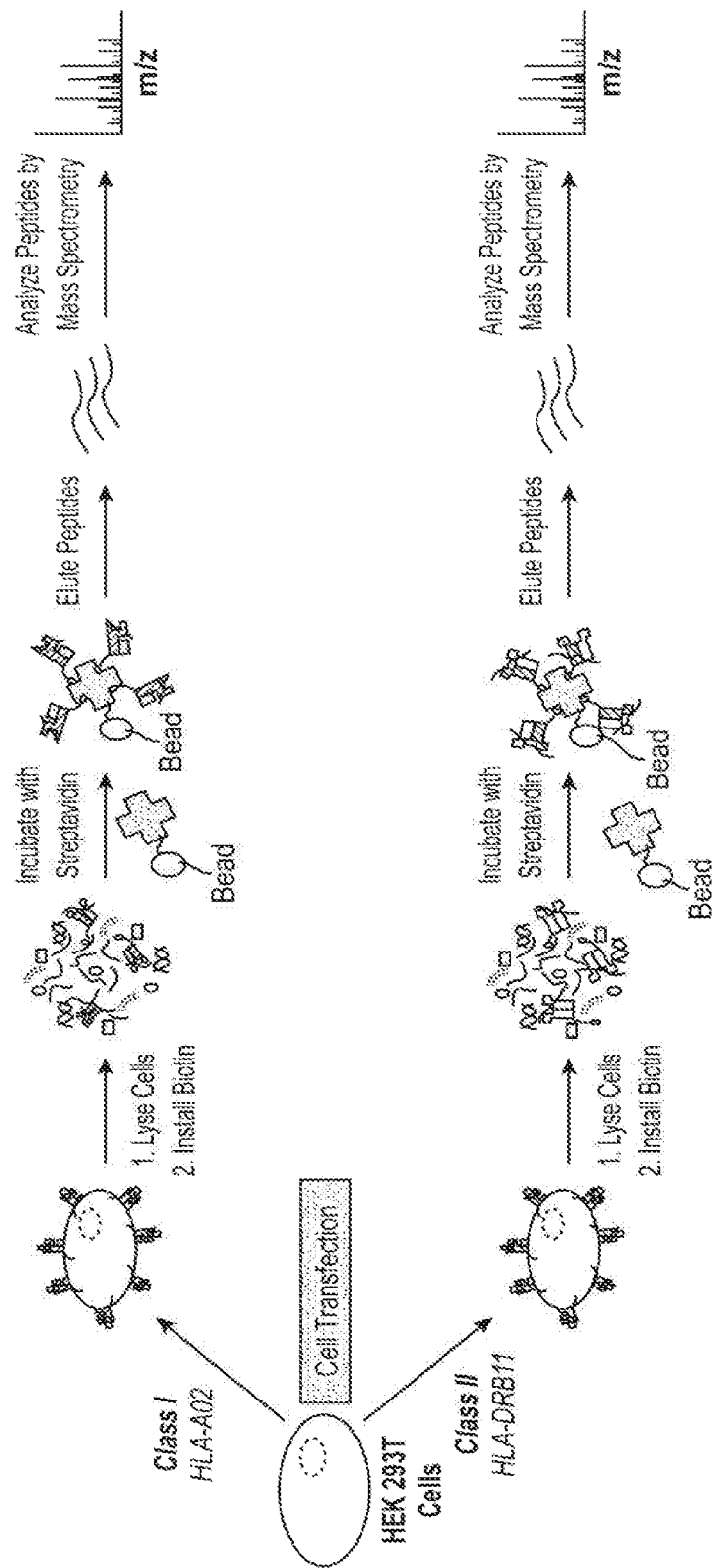
FIG. 5 is a schematic of universal immunopurification for class I and class II HLA. Cells, such as HEK293T (human embryonic kidney), are either transfected or transduced to express a single class I or class II HLA allele with an affinity tag for immunopurification. HLA-tagged expressing cells are harvested, lysed, and their HLA-peptide complexes are biotinylated and immunopurified using the biotin-streptavidin interaction. HLA-associated peptides specific to a single HLA are eluted from their biotinylated complexes and analyzed (e.g., sequenced using high resolution LC-MS/MS).

Example 1. Universal IP Pipeline: Universal Single-Allelic HLA-Peptide Complex Identification Platform Universal immunopurification (IP) constructs disclosed herein consist of a DNA construct coding for affinity-tagged HLA class I or class II alleles that are expressed off a mammalian expression vector via cellular transfection or transduction (FIG. 1A and FIG. 1B). Non-limiting exemplary class I and class II HLA constructs are shown in FIG. 2. Non-limiting exemplary affinity tags include the biotin acceptor peptide (BAP) or Human influenza hemagglutinin (HA) peptide sequence. The affinity tags can be placed on either the N-terminus or C-terminus of the HLA allele. A cleavage sequence, such as F2A shown in FIG. 2, or an internal ribosome entry site (IRES) can be placed between the α-chain and β2-microglobulin (class I) or between the α-chain and β-chain (class II). Non-limiting exemplary vectors include a lentiviral vector as shown in FIG. 3. Antibody resistance genes, such as puromycin resistance (Puro), are incorporated into the constructs to allow for selection after transfection or transduction. Cells transfected or transduced with Universal IP constructs are either expanded (FIG. 4A) or selected and then expanded (FIG. 4B) prior to LC-MS/MS analyses. Schematics of universal immunopurification platform for class I and class II HLA are shown in FIG. 5.

Example 2. Cell Culture and HLA-Peptide Immunopurification and Sequencing

Mono-allelic HLA cells were generated by transducing B721.221, A375, JEG-3, K562, Jurkat, or HEK293T, HeLa, or expi293 cells with a retroviral vector coding a single class I HLA allele (e.g., HLA-A*02:01, HLA-A*23:01 and HLA-B*14:02, or HLA-E*01:01) or class II HLA allele (e.g., HLA-DRB*01:01, HLA-DRB*01:02 and HLA-DRB*11:01, or HLA-DRB*15:01, or HLA-DRB*07:01) as described previously (Reche et al., 2006). The class I or II HLA-types of cell lines were confirmed by standard molecular typing. The cells were cultured and HLA-peptide immunopurification was performed.

Proof of concept transduction of class I HLA alleles (FIG. 6C) into HEK293T cells is shown in FIGS. 6A-6C. Mock, GFP, and empty plasmid transductions with HLA-A*02:01 constructs for biotinylation-based universal immunopurification was performed and biotinylation was confirmed in a Western blot (FIG. 6A). A Ponceau stained gel was used as a loading control for the Western blot analysis (FIG. 6B). Transfection and biotinylation optimization of class I and class II HLA-BAP alleles (FIG. 7C) expressed by HEK293T cells are shown in FIGS. 7A-7C. A biotinylation time course experiment showed that C- and N-terminally labeled HLA-BAP biotinylation was complete in 10 minutes for both class I and class II HLA-BAP expressing cells (FIG. 7A and FIG. 7B)

Figures 8A, 8B, 8C, 8D:
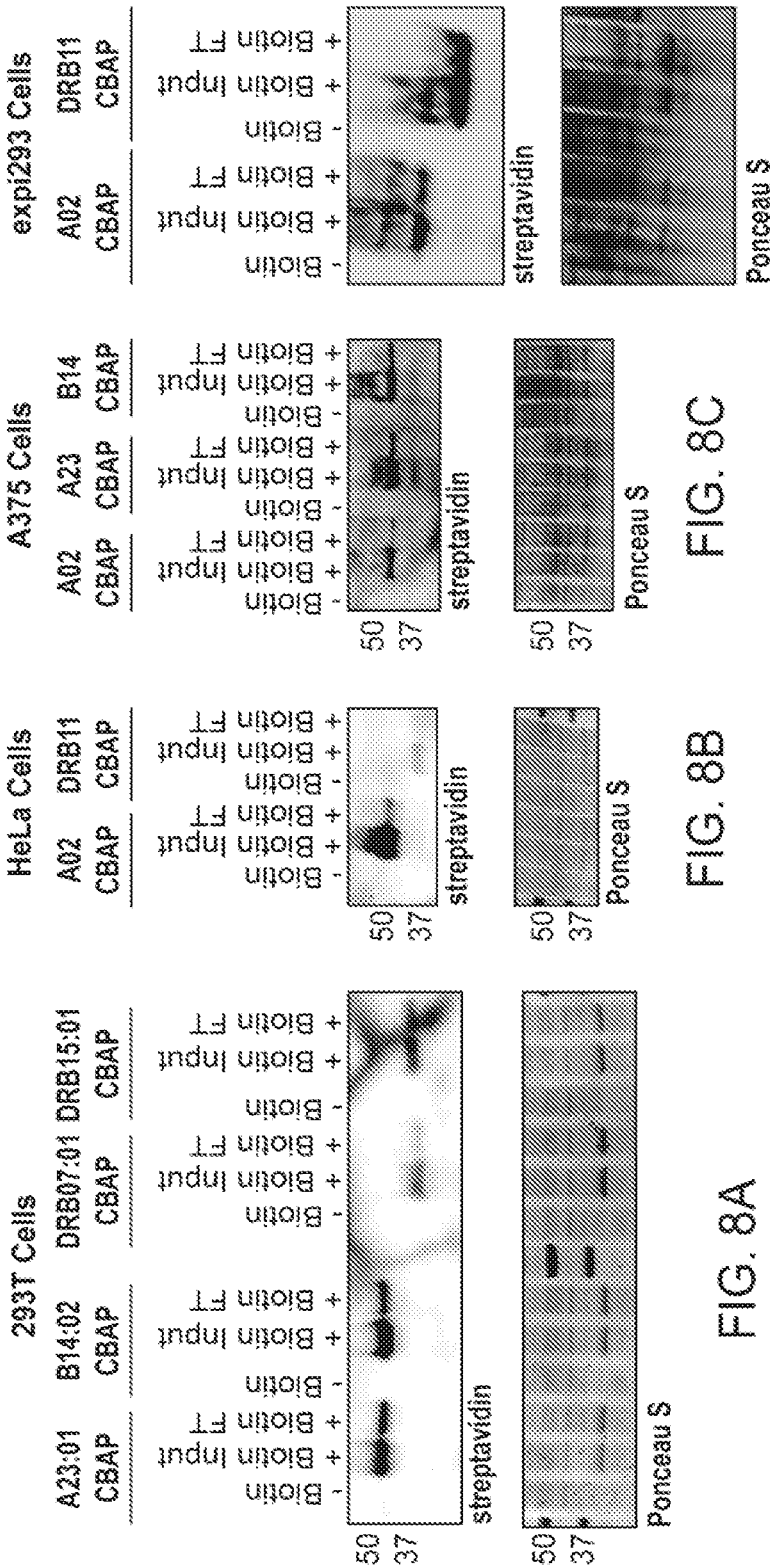
FIG. 8A is a Western blot image (anti-streptavidin for BAP label and anti-HA for HA label) and loading controls (Ponceau S) showing the expression of biotinylated class I and class II HLA constructs used for HLA immunoprecipitation in HEK293T cells. Lysates were analyzed before addition of biotin (-Biotin), after the addition of biotin (+Biotin Input), and after biotinylation and subsequent pulldown with streptavidin beads (+Biotin FT). The reduction in signal in the +Biotin FT lane demonstrates that biotinylated MHC is being removed from the lysate and binding to the streptavidin beads.
FIG. 8B is a Western blot image (anti-streptavidin for BAP label and anti-HA for HA label) and loading controls (Ponceau S) showing the expression of biotinylated class I and class II HLA constructs used for HLA immunoprecipitation in HeLa (human cervical cancer) cells. Lysates were analyzed before addition of biotin (-Biotin), after the addition of biotin (+Biotin Input), and after biotinylation and subsequent pulldown with streptavidin beads (+Biotin FT). The reduction in signal in the +Biotin FT lane demonstrates that biotinylated MHC is being removed from the lysate and binding to the streptavidin beads.
FIG. 8C is a Western blot image (anti-streptavidin for BAP label and anti-HA for HA label) and loading controls (Ponceau S) showing the expression of biotinylated class I and class II HLA constructs used for HLA immunoprecipitation in A375 (human malignant melanoma) cells. Lysates were analyzed before addition of biotin (-Biotin), after the addition of biotin (+Biotin Input), and after biotinylation and subsequent pulldown with streptavidin beads (+Biotin FT). The reduction in signal in the +Biotin FT lane demonstrates that biotinylated MHC is being removed from the lysate and binding to the streptavidin beads.
FIG. 8D is a Western blot image (anti-streptavidin for BAP label and anti-HA for HA label) and loading controls (Ponceau S) showing the expression of biotinylated class I and class II HLA constructs used for HLA immunoprecipitation in Expi293 cells (human embryonic kidney genetically engineered for high density culture and protein expression). Lysates were analyzed before addition of biotin (-Biotin), after the addition of biotin (+Biotin Input), and after biotinylation and subsequent pulldown with streptavidin beads (+Biotin FT). The reduction in signal in the +Biotin FT lane demonstrates that biotinylated MHC is being removed from the lysate and binding to the streptavidin beads.

The presently disclosed universal IP pipeline was tested in multiple cell types (FIGS. 8A-8D). The universal IP constructs for both class I and class II HLA were transfected into HEK293T (human embryonic kidney) (FIG. 8A), HeLa (human cervical cancer) (FIG. 8B), A375 (human malignant melanoma) (FIG. 8C), and Expi293 (human embryonic kidney genetically engineered for high density culture and protein expression) cells (FIG. 8D). Western blots were performed using anti-streptavidin for BAP label and anti-HA for HA label, and a Ponceau stained gel was used as a loading control for the Western blots. The Western blots confirmed the expressions of both class I and class II constructs in all cell types tested (FIGS. 8A-8D).

The following describes materials and methods used in this Example.

Universal IP of Class I and Class II HLA Alleles (Biotin)

Cells were transfected or transduced to express Universal IP constructs following standard methods. After transduction, the cells are resuspended in the media and transferred to a 50 ml falcon tubes. The tubes were spun at 1500 rpm for 5 minutes and the media was removed. The cells were then resuspended in 1.5 ml of cold PBS and transferred to a 1.5 mL Eppendorf tube. The tubes were then centrifuged (550×g at 4° C.) for 5 minutes. The PBS was removed and the cells were then resuspended in 1.2 ml lysis buffer. The cells were resuspended in the buffer followed by the addition of benzonase. The tubes were incubated on ice with occasional mixing. After 15 minutes incubating on ice, the tubes were centrifuged (15,000×g at 4° C.) for 20 minutes. The supernatants (500 µL) were transferred to another 1.5 mL tube (pre-washed) for biotinylation. Biotinylation of cellular lysates was achieved by addition of biotin, ATP, and BirA to each sample. The sample was then incubated at room temperature for 10 minutes and then placed on ice prior to immunoprecipitation.

Immunoprecipitation with NeutrAvidin or streptavidin beads was conducted by addition of pre-washed streptavidin or NeutrAvidin agarose resin slurry to the biotinylated lysate. The sample is then placed on a tube rotisserie, and incubated for 30 minutes at 4° C. After the 30-minute incubation, the beads are pelleted by centrifugation (1500×g, 1 min, 4° C.) and the supernatant is removed and discarded. The beads were then resuspended in 1 ml of Wash buffer. The beads were then pelleted by centrifugation (1,500×g, 1 min, 4° C.) and the wash buffer was removed and discarded. This step was repeated to give a total of four washes in wash buffer. The pelleted beads were resuspended in 1 ml of Tris buffer, pelleted by centrifugation (1,500×g, 1 min, 4° C.), and the Tris buffer was removed. This step was repeated to give a total of four washes in Tris buffer. A final wash was performed in MS grade water by resuspending beads in 1 ml of Mass Spec grade water and centrifuging (1,500×g, 1 min, 4° C.) to pellet the beads. The supernatant was removed and the beads were either stored at −80° C. or immediately subjected to HLA-peptide elution and desalting.

Serial Universal IP of Class H HLA Alleles (HA and Biotin Tagging)

Cells were transfected or transduced to express Universal IP constructs following standard protocols. After transduction, the cells are resuspended in the media and transferred to a 50 ml falcon tubes. The tubes were spun at 1500 rpm for 5 min and the media was removed. The cells were then resuspended in 1.5 ml of cold PBS and transferred to a 1.5 ml Eppendorf tube. The tubes were then centrifuged (550×g at 4° C.) for 5 minutes. The PBS was removed and the cells were then resuspended in 1.2 ml lysis buffer. The cells were resuspended in the buffer followed by the addition of benzonase. The tubes were incubated on ice with occasional mixing. After 15 minutes incubating on ice, the tubes were centrifuged (15,000×g at 4° C.) for 20 minutes. The supernatants were transferred to another 1.5 ml tube (pre-washed) for biotinylation. Biotinylation of cellular lysates was achieved by addition of biotin, ATP, and BirA to each sample. The sample was then incubated at room temperature for 10 minutes and then placed on ice prior to immunoprecipitation.

Immunoprecipitation of HA-tagged class II alleles was carried out by addition of pre-washed protein G agarose resin that was pre-bound with anti-HA antibody. The sample was then incubated for 60 minutes at 4° C. on a tube rotisserie. After the 60 min incubation, the beads are pelleted by centrifugation (1500×g, 1 min, 4° C.) and the supernatant was removed and discarded. The beads were washed two times with lysis buffer and resuspended in lysis buffer containing free HA peptide and incubated for 15 minutes at 4° C. on a tube rotisserie. The beads were then pelleted by centrifugation (1500×g, 1 min, 4° C.) and the supernatant was transferred to a 1.5 ml Eppendorf containing 200 ul of pre-washed NeutrAvidin or streptavidin agarose beads. The sample was then placed on a tube rotisserie and incubated for 30 minutes at 4° C. After the 30 min incubation, the beads are pelleted by centrifugation (1500×g, 1 min, 4° C.) and the supernatant was removed and discarded. The beads were then resuspended in 1 ml of Wash buffer. The beads were then pelleted by centrifugation (1,500×g, 1 min, 4° C.) and the wash buffer was removed and discarded. This step was repeated to give a total of four washes in wash buffer. The pelleted beads were resuspended in 1 ml of Tris buffer, pelleted by centrifugation (1,500×g, 1 min, 4° C.), and the wash buffer was removed. This step was repeated to give a total of four washes in the Tris buffer. A final wash was performed in MS grade water by resuspending beads in 1 ml of Mass Spec grade water and centrifuging (1,500×g, 1 min, 4° C.) to pellet the beads. The supernatant was removed and the beads were either stored at −80° C. or immediately subjected to HLA-peptide elution and desalting.

HLA-Peptide Elution and Desalting

Peptides were eluted from HLA complexes and desalted on in-house built Empore C18 StageTips (3M, 2315) (Rappsilber et al., 2007). Sample loading, washes, and elution were performed on a tabletop centrifuge at a maximum speed of 1,500-3,000×g. StageTips were equilibrated with two washes of methanol, two washes of acetonitrile/formic acid, and two washes of formic acid. In a tube, the dried beads from HLA-associated peptide IPs were thawed at 4° C., reconstituted in ACN/formic acid mixture, and loaded onto StageTips. The beads were washed with formic acid, and peptides were further eluted using two rounds of 5 minute incubations in 10% acetic acid. The combined wash and elution volumes were combined and loaded onto StageTips. The tubes containing the IP beads were washed again with formic acid, and this volume was also loaded onto StageTips. Peptides were washed twice on StageTips or desalting cartridges with formic acid. Peptides were eluted using a step gradient of ACN and formic acid mixtures. Step elutions were combined and dried to completion.

Example 3. Class I and Class II HLA-Associated Peptide Sequencing by LC-MS/MS

All nano LC-ESI-MS/MS analyses employed the same LC separation conditions described below. Samples were chromatographically separated using a Proxeon Easy Nano LC 1000 (Thermo Scientific, San Jose, CA) fitted with a PicoFrit 75 μm inner diameter capillary with a 10 μm emitter was packed under pressure to ~20 cm with of C18 Reprosil beads (1.9 μm particle size, 200 Å pore size, Dr. Maisch GmBH) and heated at 50° C. during separation.

Samples were loaded in CAN and formic acid mixture and peptides were eluted with a linear gradient from 7-30% of Buffer B (either 0.1% FA or 0.5% AcOH and 80% or 90% ACN) over 82 min, 30-90% Buffer B over 6 min and then held at 90% Buffer B for 15 min at 200 nL/min (Buffer A, 0.1% FA and 3% ACN) to yield ~13 (FA) sec peak widths. During data-dependent acquisition, eluted peptides were introduced into either an Orbitrap Fusion Lumos Tribrid mass spectrometer (Thermo Scientific) equipped with a nanoelectrospray source at 2.2 kV. A full-scan MS was acquired at a resolution of 30,000 from 300 to 1,800 m/z. Each full scan was followed by top 10 data-dependent MS2 scans at resolution 15,000, using an isolation width of 0.7 m/z.

Figure 9A:
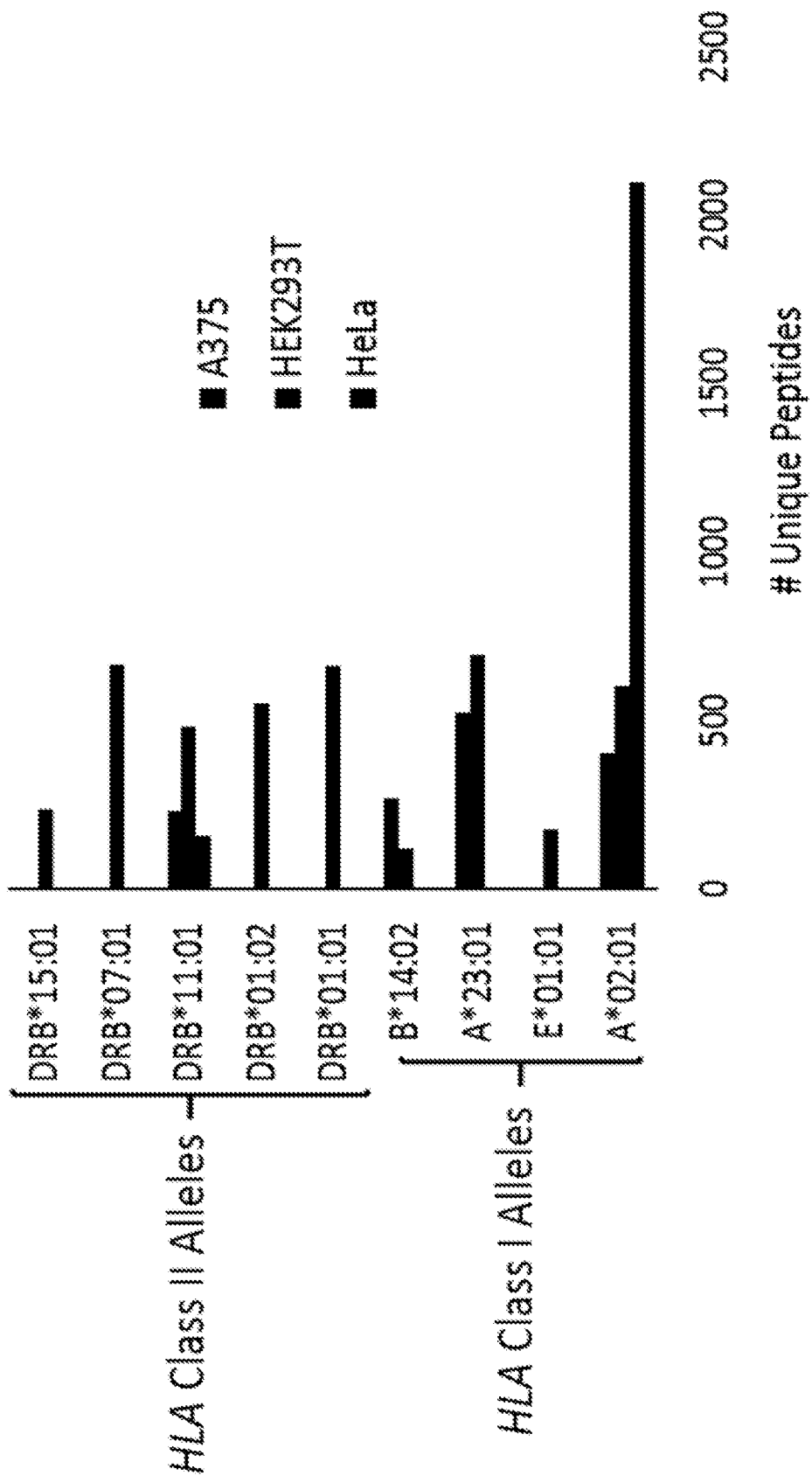
FIG. 9A is a bar graph of an exemplary LC-MS/MS analysis of HLA-associated peptides isolated using the universal HLA immunoprecipitation (Universal IP) pipeline. A bar plot representation of the total unique HLA-associated peptides identified from multiple cell types (A375; gray, HEK293T; orange, HeLa; blue) that express affinity-tagged class I and class II HLA constructs used in the Universal IP pipeline is shown.
Figure 9B:
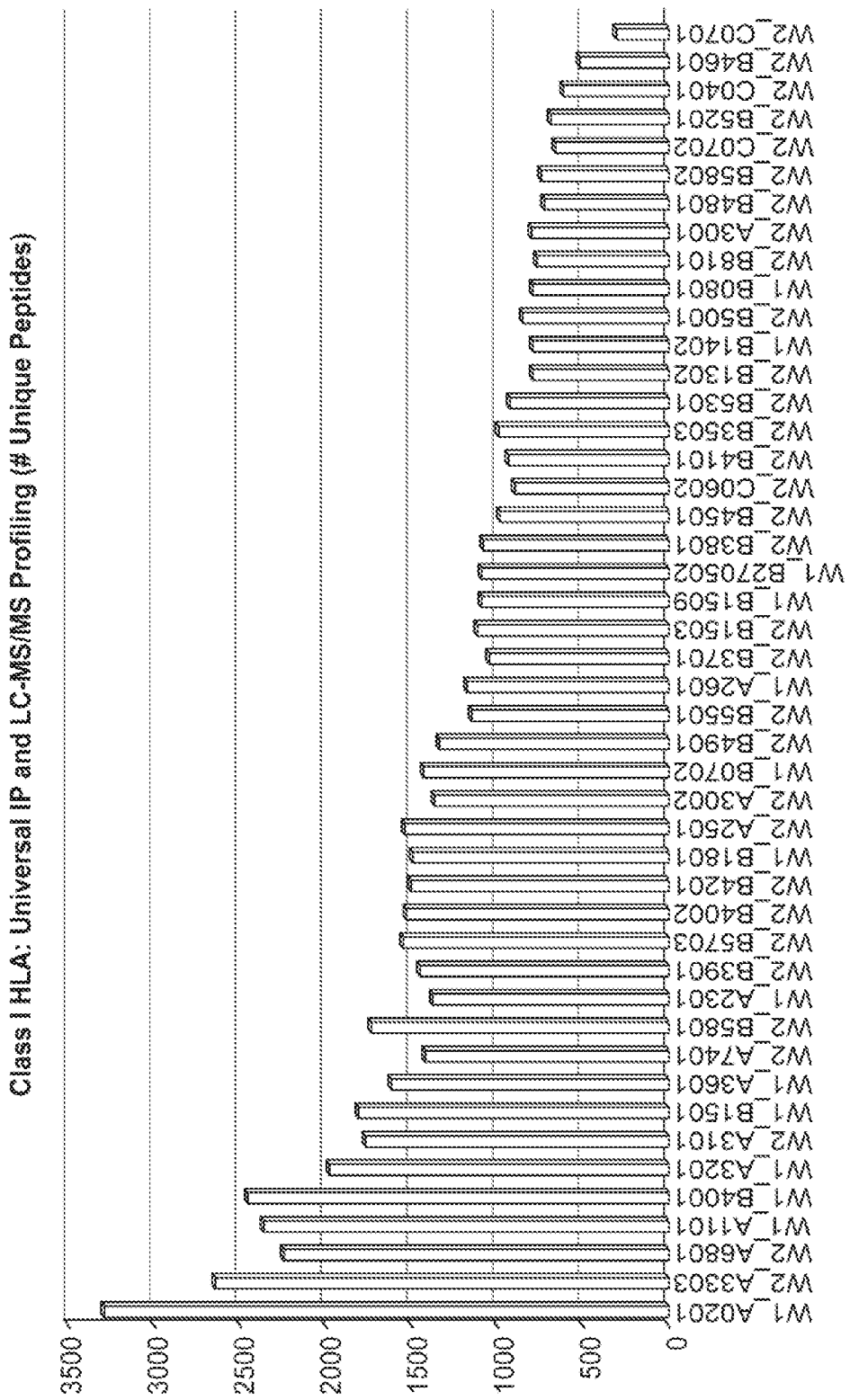
FIG. 9B is a bar plot showing representative data from class I HLA mono-allelic peptide profiling by LC-MS/MS. Each bar represents the total number of unique HLA-associated peptides identified from class I mono-allelic experiments that implemented the affinity-tagged HLA constructs.
Figure 9C:
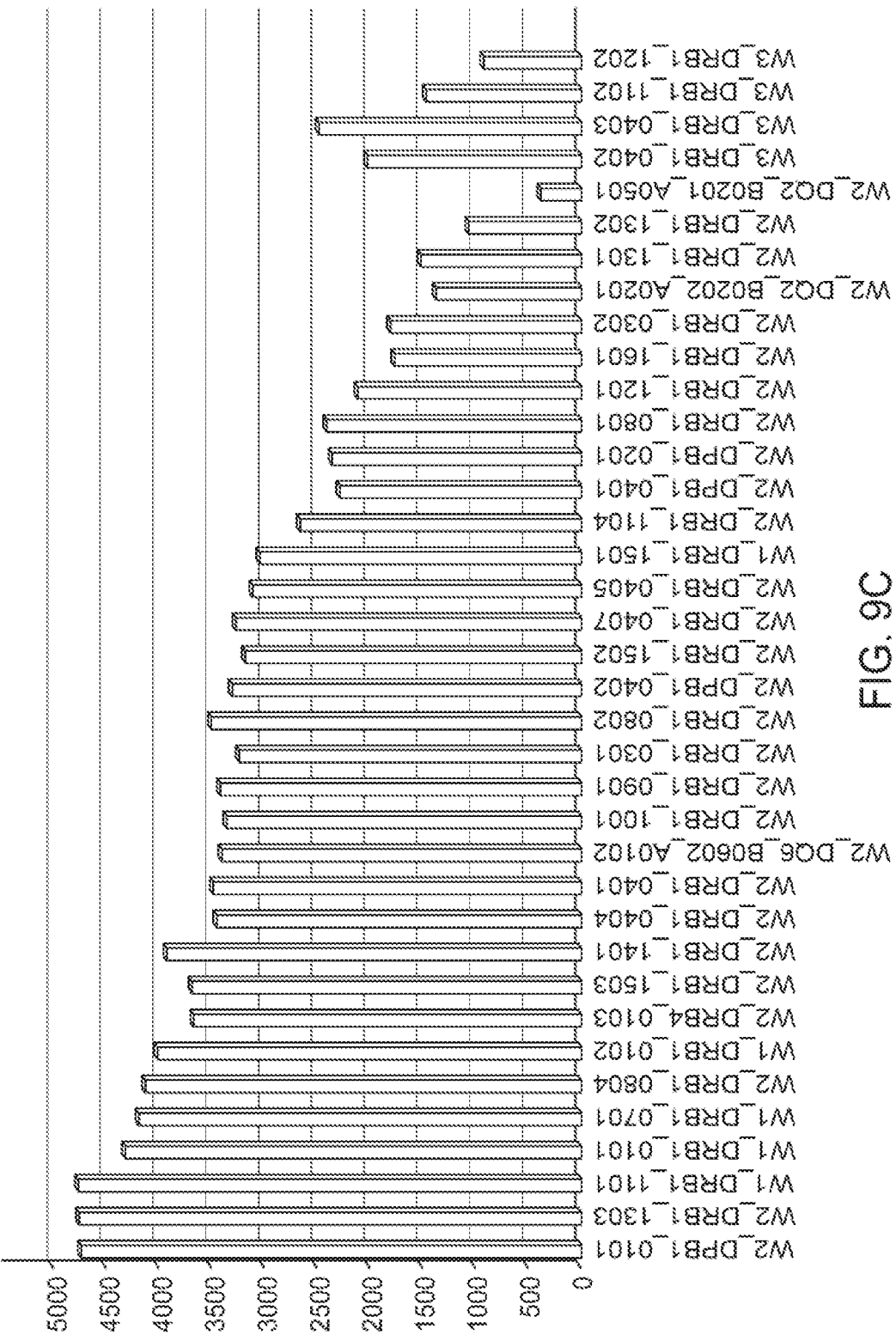
FIG. 9C is a bar plot showing representative data from class II HLA mono-allelic peptide profiling by LC-MS/MS. Each bar represents the total number of unique HLA-associated peptides identified from class II mono-allelic experiments that implemented the affinity-tagged HLA constructs.

The numbers of total unique HLA-associated peptides identified from multiple cell types expressing affinity tagged class I and class II HLA constructs used in the universal IP pipeline are shown in FIG. 9A. The number of unique peptides from class I HLA mono-allelic peptide profiling is shown in FIG. 9B. The number of unique peptides from class II HLA mono-allelic peptide profiling is shown in FIG. 9C. LC-MS/MS analysis of HLA-associated peptides revealed characteristics of class I and class II HLA-associated peptides (FIGS. 10A and 10B). Sequence logo representations of isolated and sequenced class I HLA-A*02:01-associated peptides and class II HLA-DRβ*11:01-associated peptides are shown FIG. 10A. The length distribution comparisons of both class I HLA-A*02:01-associated peptides (red) and class II HLA-DRβ*11:01-associated peptides (blue) showed that both class I and class II HLA-associated peptides followed the expected trends (FIG. 10B).

70 HLA class I alleles and 47 HLA class II alleles were assessed for mono-allelic approach as described herein. 70 unique HLA class I alleles with affinity tags (Table. 1A) and 47 unique HLA class II alleles with affinity tags (Table. 2A) were generated. Table. 1B shows the details of 96 unique experiments using the 70 unique HLA class I alleles (in some cases the same allele was placed into multiple cell lines). Table. 2B shows the details of 54 unique experiments performed using the 47 unique HLA class II alleles (in some cases the same allele was placed into multiple cell lines).

TABLE 1A

70 Unique HLA Class I alleles

| # | Unique Class I Alleles |
|---|---|
| 1 | A*0201 |
| 2 | A*0202 |
| 3 | A*0203 |
| 4 | A*0206 |
| 5 | A*0207 |
| 6 | A*1101 |
| 7 | A*2301 |
| 8 | A*2501 |
| 9 | A*2601 |
| 10 | A*3001 |
| 11 | A*3002 |
| 12 | A*3101 |
| 13 | A*3201 |
| 14 | A*3301 |
| 15 | A*3303 |
| 16 | A*3402 |
| 17 | A*3601 |
| 18 | A*6801 |
| 19 | A*7401 |
| 20 | B*0702 |
| 21 | B*0801 |
| 22 | B*1302 |
| 23 | B*1401 |
| 24 | B*1402 |
| 25 | B*1501 |
| 26 | B*1502 |
| 27 | B*1503 |
| 28 | B*1509 |
| 29 | B*1510 |
| 30 | B*1801 |
| 31 | B*270502 |
| 32 | B*3502 |
| 33 | B*3503 |
| 34 | B*3701 |
| 35 | B*3801 |
| 36 | B*3802 |
| 37 | B*3901 |
| 38 | B*3906 |
| 39 | B*4001 |
| 40 | B*4002 |
| 41 | B*4006 |
| 42 | B*4101 |
| 43 | B*4201 |
| 44 | B*4501 |
| 45 | B*4601 |
| 46 | B*4801 |
| 47 | B*4901 |
| 48 | B*5001 |
| 49 | B*5201 |
| 50 | B*5301 |
| 51 | B*5401 |
| 52 | B*5501 |
| 53 | B*5703 |
| 54 | B*5801 |
| 55 | B*5802 |
| 56 | B*8101 |
| 57 | C*0102 |
| 58 | C*0202 |
| 59 | C*0303 |
| 60 | C*0401 |
| 61 | C*0602 |
| 62 | C*0701 |
| 63 | C*0702 |
| 64 | C*0704 |
| 65 | C*1203 |
| 66 | C*1701 |
| 67 | C*1801 |
| 68 | F*0101 |
| 69 | G*0101 |
| 70 | E*0101 |

TABLE 1B

Libraries and Cell Lines for HLA class I alleles
# Unique Experiments

| # | Wave of Library | Class I Allele | Cell Line |
|---|---|---|---|
| 1 | W1 | A0201 | Hek293 |
| 2 | W1 | A0201 | HeLa |
| 3 | W1 | A0201 | A375 |
| 4 | W1 | A0201 | expi293 |
| 5 | W1 | A1101 | expi293 |
| 6 | W1 | A1101 | HeLa |
| 7 | W1 | A2301 | Hek293 |
| 8 | W1 | A2301 | A375 |
| 9 | W1 | A2301 | expi293 |
| 10 | W1 | A2601 | A375 |
| 11 | W1 | A2601 | HeLa |
| 12 | W1 | A2601 | expi293 |
| 13 | W1 | A3201 | A375 |
| 14 | W1 | A3201 | HeLa |
| 15 | W1 | A3201 | expi293 |
| 16 | W1 | A3601 | expi293 |
| 17 | W1 | B0702 | expi293 |
| 18 | W1 | B0702 | HeLa |
| 19 | W1 | B0801 | expi293 |
| 20 | W1 | B0801 | HeLa |
| 21 | W1 | B0801 | A375 |
| 22 | W1 | B1402 | Hek293 |
| 23 | W1 | B1402 | A375 |
| 24 | W1 | B1402 | expi293 |
| 25 | W1 | B1402 | HeLa |
| 26 | W1 | B1501 | expi293 |
| 27 | W1 | B1509 | HeLa |
| 28 | W1 | B1509 | expi293 |
| 29 | W1 | B1801 | HeLa |
| 30 | W1 | B1801 | expi293 |
| 31 | W1 | B270502 | HeLa |
| 32 | W1 | B270502 | expi293 |
| 33 | W1 | B4001 | HeLa |
| 34 | W1 | B4001 | expi293 |
| 35 | W2 | A2501 | expi293 |
| 36 | W2 | A3001 | expi293 |
| 37 | W2 | A3002 | expi293 |
| 38 | W2 | A3101 | expi293 |
| 39 | W2 | A3303 | expi293 |
| 40 | W2 | A6801 | expi293 |
| 41 | W2 | A7401 | expi293 |
| 42 | W2 | B1302 | expi293 |
| 43 | W2 | B1503 | expi293 |
| 44 | W2 | B3503 | expi293 |
| 45 | W2 | B3701 | expi293 |
| 46 | W2 | B3801 | expi293 |
| 47 | W2 | B3901 | expi293 |
| 48 | W2 | B4002 | expi293 |
| 49 | W2 | B4101 | expi293 |
| 50 | W2 | B4201 | expi293 |
| 51 | W2 | B4501 | expi293 |
| 52 | W2 | B4601 | expi293 |
| 53 | W2 | B4801 | expi293 |
| 54 | W2 | B4901 | expi293 |
| 55 | W2 | B5001 | expi293 |
| 56 | W2 | B5201 | expi293 |
| 57 | W2 | B5301 | expi293 |
| 58 | W2 | B5501 | expi293 |
| 59 | W2 | B5501 | A375 |
| 60 | W2 | B5703 | expi293 |
| 61 | W2 | B5801 | expi293 |
| 62 | W2 | B5801 | A375 |
| 63 | W2 | B5802 | expi293 |
| 64 | W2 | B8101 | expi293 |
| 65 | W2 | C0401 | expi293 |
| 66 | W2 | C0401 | A375 |
| 67 | W2 | C0602 | expi293 |
| 68 | W2 | C0602 | A375 |
| 69 | W2 | C0701 | expi293 |
| 70 | W2 | C0701 | A375 |
| 71 | W2 | C0702 | expi293 |
| 72 | W2 | C0702 | A375 |
| 73 | W3 | A3301 | expi293 |
| 74 | W3 | A0206 | expi293 |

TABLE 1B-continued

Libraries and Cell Lines for HLA class I alleles
Unique Experiments

| # | Wave of Library | Class I Allele | Cell Line |
|---|---|---|---|
| 75 | W3 | A0202 | expi293 |
| 76 | W3 | A3402 | expi293 |
| 77 | W3 | A0207 | expi293 |
| 78 | W3 | A0203 | expi293 |
| 79 | W3 | B3502 | expi293 |
| 80 | W3 | B1401 | expi293 |
| 81 | W3 | B3906 | expi293 |
| 82 | W3 | B1510 | expi293 |
| 83 | W3 | B4006 | expi293 |
| 84 | W3 | B1502 | expi293 |
| 85 | W3 | B3802 | expi293 |
| 86 | W3 | B5401 | expi293 |
| 87 | W3 | C0303 | expi293 |
| 88 | W3 | C0202 | expi293 |
| 89 | W3 | C1203 | expi293 |
| 90 | W3 | C0102 | expi293 |
| 91 | W3 | C1701 | expi293 |
| 92 | W3 | C0704 | expi293 |
| 93 | W3 | C1801 | expi293 |
| 94 | W2 | E0101 | expi293 |
| 95 | W3 | F0101 | expi293 |
| 96 | W3 | G0101 | expi293 |

TABLE 2A

47 Unique HLA Class II alleles

| # | Unique Class II Alleles |
|---|---|
| 1 | DPB1*0101 |
| 2 | DPB1*0101 DPA*01:03 |
| 3 | DPB1*0201 DPA*01:03 |
| 4 | DPB1*0401 DPA*01:03 |
| 5 | DPB1*0402 DPA*01:03 |
| 6 | DQ2*B0201*A0501 |
| 7 | DQ2*B0202*A0201 |
| 8 | DQ6*B0602*A0102 |
| 9 | DQ6*B1*0602 |
| 10 | DRB1*0101 |
| 11 | DRB1*0102 |
| 12 | DRB1*0301 |
| 13 | DRB1*0302 |
| 14 | DRB1*0401 |
| 15 | DRB1*0402 |
| 16 | DRB1*0403 |
| 17 | DRB1*0404 |
| 18 | DRB1*0405 |
| 19 | DRB1*0407 |
| 20 | DRB1*0701 |
| 21 | DRB1*0801 |
| 22 | DRB1*0802 |
| 23 | DRB1*0803 |
| 24 | DRB1*0804 |
| 25 | DRB1*0901 |
| 26 | DRB1*1001 |
| 27 | DRB1*1101 |
| 28 | DRB1*1102 |
| 29 | DRB1*1104 |
| 30 | DRB1*1201 |
| 31 | DRB1*1202 |
| 32 | DRB1*1301 |
| 33 | DRB1*1302 |
| 34 | DRB1*1303 |
| 35 | DRB1*1401 |
| 36 | DRB1*1501 |
| 37 | DRB1*1502 |
| 38 | DRB1*1503 |
| 39 | DRB1*1601 |
| 40 | DRB3*0101 |
| 41 | DRB3*0202 |
| 42 | DRB3*0301 |

TABLE 2A-continued

47 Unique HLA Class II alleles

| # | Unique Class II Alleles |
|---|---|
| 43 | DRB4*0103 |
| 44 | DRB5*0101 |
| 45 | HLA DM no affinity tag |
| 46 | HLA-DM with affinity tag |
| 47 | HLA-DO |

TABLE 2B

Libraries and Cell Lines for HLA class II alleles
Unique Experiments

| # | Wave of Library | Class II Allele | Cell Line |
|---|---|---|---|
| 1 | W1 | DRB1_0101 | Hek293 |
| 2 | W1 | DRB1_0101 | expi293 |
| 3 | W1 | DRB1_0102 | Hek293 |
| 4 | W1 | DRB1_0102 | expi293 |
| 5 | W1 | DRB1_0701 | Hek293 |
| 6 | W1 | DRB1_0701 | expi293 |
| 7 | W1 | DRB1_1101 | Hek293 |
| 8 | W1 | DRB1_1101 | HeLa |
| 9 | W1 | DRB1_1101 | A375 |
| 10 | W1 | DRB1_1101 | expi293 |
| 11 | W1 | DRB1_1501 | Hek293 |
| 12 | W1 | DRB1_1501 | expi293 |
| 13 | W2 | DRB1_0301 | expi293 |
| 14 | W2 | DRB1_0302 | expi293 |
| 15 | W2 | DRB1_0401 | expi293 |
| 16 | W2 | DRB1_0404 | expi293 |
| 17 | W2 | DRB1_0405 | expi293 |
| 18 | W2 | DRB1_0407 | expi293 |
| 19 | W2 | DRB1_0801 | expi293 |
| 20 | W2 | DRB1_0802 | expi293 |
| 21 | W2 | DRB1_0804 | expi293 |
| 22 | W2 | DRB1_0901 | expi293 |
| 23 | W2 | DRB1_1001 | expi293 |
| 24 | W2 | DRB1_1104 | expi293 |
| 25 | W2 | DRB1_1201 | expi293 |
| 26 | W2 | DRB1_1301 | expi293 |
| 27 | W2 | DRB1_1302 | expi293 |
| 28 | W2 | DRB1_1303 | expi293 |
| 29 | W2 | DRB1_1401 | expi293 |
| 30 | W2 | DRB1_1502 | expi293 |
| 31 | W2 | DRB1_1503 | expi293 |
| 32 | W2 | DRB1_1601 | expi293 |
| 33 | W2 | DRB4_0103 | expi293 |
| 34 | W2 | DPB1_0101 | expi293 |
| 35 | W2 | DPB1_0201 | expi293 |
| 36 | W2 | DPB1_0401 | expi293 |
| 37 | W2 | DPB1_0402 | expi293 |
| 38 | W2 | DQ2_B0201_A0501 | expi293 |
| 39 | W2 | DQ2_B0202_A0201 | expi293 |
| 40 | W2 | DQ6_B0602_A0102 | expi293 |
| 41 | W2 | HLA DM no tag | expi293 |
| 42 | W3 | DRB1*0402 | expi293 |
| 43 | W3 | DRB1*0403 | expi293 |
| 44 | W3 | DRB1*1102 | expi293 |
| 45 | W3 | DRB1*1202 | expi293 |
| 46 | W3 | DRB1*0803 | expi293 |
| 47 | W3 | DRB3*0101 | expi293 |
| 48 | W3 | DRB3*0202 | expi293 |
| 49 | W3 | DRB5*0101 | expi293 |
| 50 | W3 | DRB3*0301 | expi293 |
| Si | W3 | HLA-DO | expi293 |
| 52 | W3 | DPB1 0101 | expi293 |
| 53 | W3 | DQ6 B1 0602 | expi293 |
| 54 | W3 | HLA-DM tagged | expi293 |

Figure 11A:
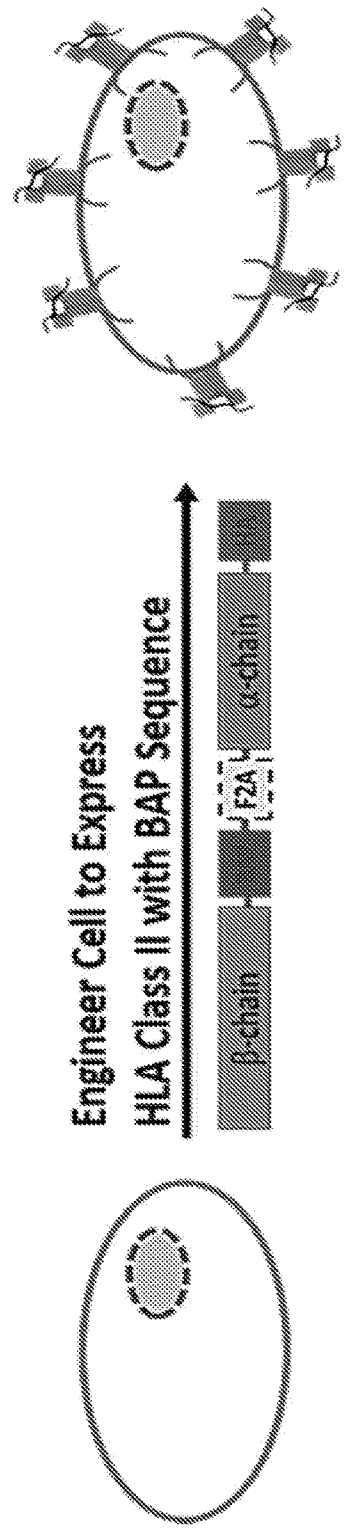
FIG. 11A is a schematic representation of class II HLA constructs that were engineered for expression by different cell types for the Universal IP pipeline.
Figure 11B:
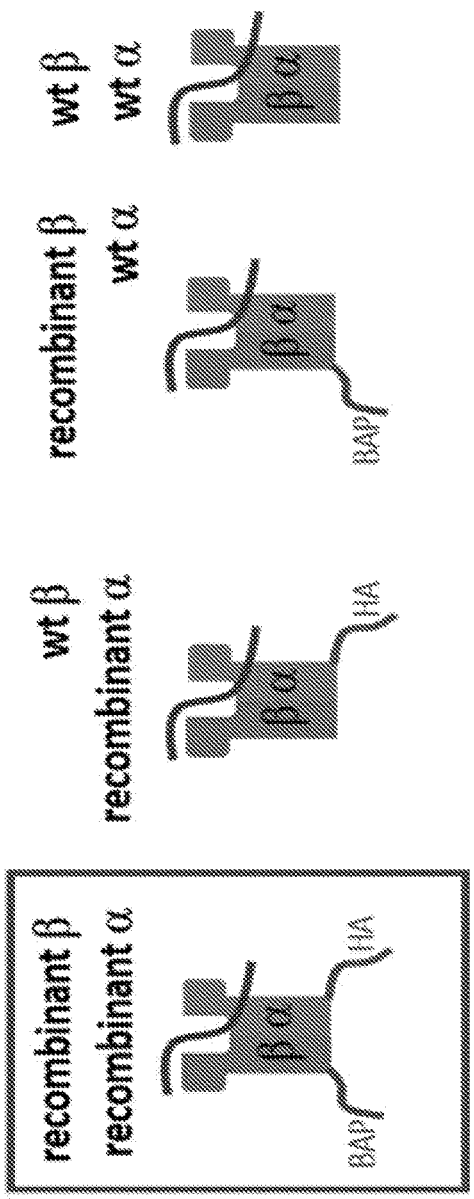
FIG. 11B is a schematic representation of the class II HLA complexes that can form upon expression of the construct shown in FIG. 11A in cell lines expressing endogenous class II HLA α-chain and β-chain subunits. Class II HLA complexes are formed by α-chain and β-chain pairing, which are each tagged with a different affinity handle.

Example 4. Tandem Universal IP of Class II HLA Complexes with Multiple Affinity Tags Class II HLA complexes are formed by α-chain and -chain pairing, each of which can be tagged with a different affinity tag. A serial IP using both affinity tags enables the deconvolution of α-chain and β-chain pairing and unambiguous peptide-binding assignments to class II HLA complexes. A schematic representation of class II HLA constructs engineered for expression by different cell types for Universal IP pipeline is shown in FIG. 11A. Schematic representations of the possible class II HLA complexes that can form upon expression of FIG. 11A constructs in cell lines expressing endogenous class II HLA α-chain and β-chain subunits are shown in FIG. 11B.

Schematics of a serial Universal IP strategy that can be used for deconvolution of α-chain and β-chain pairing and unambiguous peptide-binding assignments to specific class II HLA complexes are depicted in FIG. 12A. Cells expressing dual-affinity tagged class II HLA constructs were lysed, biotinylated, and incubated with beads coupled to anti-HA antibodies. Class II HLA complexes with HA-tagged subunits were isolated, washed, and eluted using an HA peptide (YPYDVPDYA (SEQ ID NO: 1)). The elution was then incubated with beads coupled to either NeutrAvidin or streptavidin to isolate the HA-tagged and biotin-tagged class II HLA complexes.

Peptides bound to dual-tagged class II HLA complexes are then eluted and sequenced by LC-MS/MS. A Western blot and loading control (Ponceau S stained gel) demonstrated the specificity of the serial Universal IP pipeline. A Western blot validated the serial Universal IP strategy in HEK293T expressing dual-tagged HLA-DRB*11:01 constructs (FIG. 12B). An anti-HA antibody was used to follow the serial enrichment process. A Ponceau S stained gel was used as a Western blot loading control. A Western blot of a negative control experiment where cells expressing dual-affinity tagged class II HLA construct HLA-DRB*11:01 were lysed and incubated with beads coupled to anti-HA antibodies without biotinylation is shown in FIG. 12C. As shown in FIG. 12C, no enrichment was observed when the biotinylation step was removed from the serial Universal IP protocol.

Example 5. A Mono-Allelic HLA-Peptidome Profiling Approach that Implements a Biotin Affinity Tag A schematic representation of a mono-allelic HLA-peptidome profiling approach that implements a biotin affinity tag is shown in FIG. 14A and FIG. 14B. An exemplary embodiment of the present disclosure makes use of the biotin acceptor peptide (BAP) that is biotinylated on a lysine (K) residue by a BirA enzyme. The BAP peptide sequence contains a lysine residue that is biotinylated upon the addition of BirA enzyme, biotin, and ATP. The biotinylated product displays high affinity for streptavidin/NeutrAvidin. Streptavidin/NeutrAvidin beads can be used to enrich for the biotinylated BAP peptide sequence.

Example 6. Targeted Epitope Discovery Platform

Figure 15:
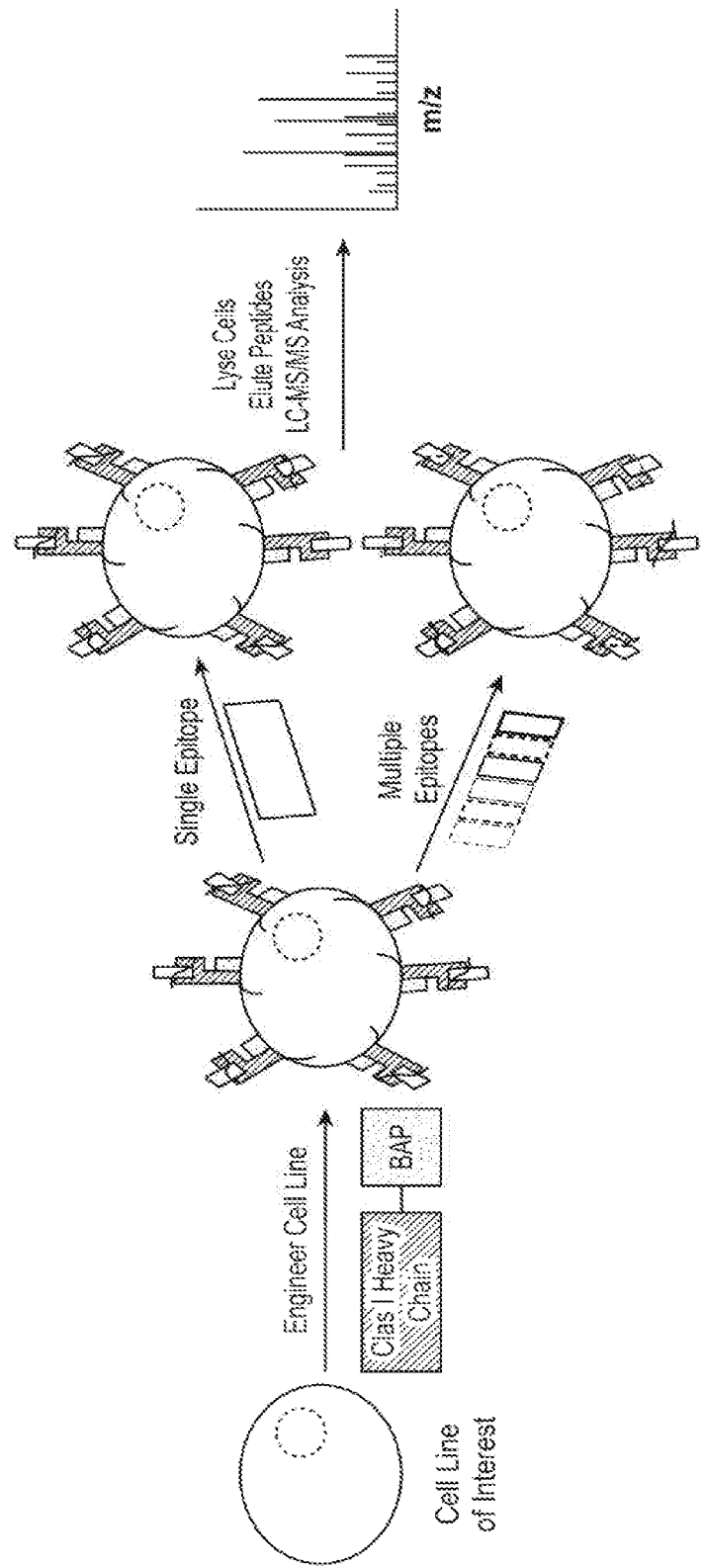
FIG. 15 is a schematic representation of an exemplary application of the Universal IP platform for targeted epitope validation and discovery. A cell line of interest is engineered to express an allele-specific HLA-tagged (e.g., BAP) construct. Cells expressing HLA-tagged (e.g., BAP) molecules are genetically engineered to express a single epitope or multiple epitopes. Epitope expressing cells are lysed and HLA-BAP-peptide complexes are immunopurified. Isolated peptide antigens can be examined by any suitable means, e.g., sequenced by LC-MS/MS, and peptide fragments generated from the introduced epitopes can be used as a high-throughput readout for HLA-allele-matched antigen processing and presentation.

A cell line of interest (e.g., 2HEK293T, expi293, HeLa, A375, 721.221, JEG-3, K562, Jurkat, Hep G2, SH-SY5Y, CACO-2, U937, U-2 OS, ExpiCHO, CHO or THP1) or primary cells (e.g., cells from a subject with a disease or condition) can be transfected/transduced with a class I or II HLA construct containing a tag (e.g., BAP sequence) on the N- or C-terminus with or without selection to enrich for HLA expressing cells (FIG. 15). The cells can then be transfected or transduced with a second plasmid that contains an epitope fragment or a chain of epitopes that can be expressed and presented on the tag-labeled HLA molecule. Alternatively, both the HLA allele plasmid and the epitope plasmid can be co-delivered into the cells followed by expansion and/or selection. These engineered cells are then lysed, biotinylated, and the HLA molecule is enriched from the lysate (e.g., using streptavidin beads). The peptides are eluted from the HLA molecule and analyzed, e.g., by LC-MS/MS. This method permits analysis of how epitopes are processed and presented by different alleles. This method can also be utilized to improve epitope delivery and design.

Example 7. Allele Multiplexing

Figure 16:
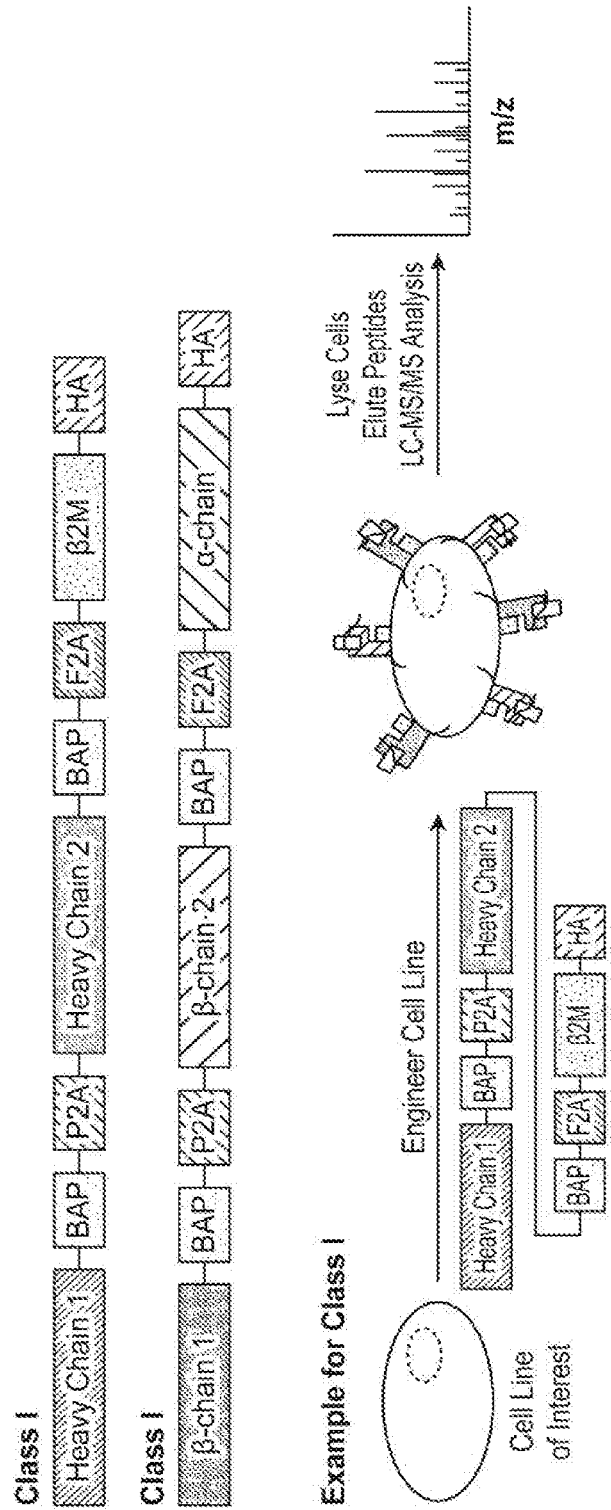
FIG. 16 is a schematic representation of HLA allele multiplexing within the Universal IP pipeline. Multiple class I and class II alleles can be expressed from a single HLA construct. For example, multiple heavy chains can be included in a class I construct and multiple β- and/or α-chains can be included in a class II construct. By multiplexing HLA alleles in a single construct, multiple HLA molecules can be delivered and expressed in a cell line of interest. Allele multiplexing enables the matching to patient HLA types and personalized peptide antigen readouts with the application of the Universal IP pipeline and subsequent complex and/or peptide analysis, e.g., LC-MS/MS readout.

A DNA construct can be designed to express multiple class I heavy chains or multiple class II (or ® chains that contain one or more tags (FIG. 16). Each HLA construct can be expressed from the same gene construct that includes a ribosomal skipping sequence (F2A, T2A, P2A, etc.) or an IRES element. A desired cell line can be transduced or transfected with this plasmid to induce expression of multiple HLA alleles that are tagged and subsequently enriched. Alternatively, a cell line can be transduced or transfected with multiple plasmids that each contain a single HLA allele. The peptides bound to the HLA alleles can then be analyzed, e.g., by LC-MS/MS. This platform permits generation of cell lines with multiple alleles. This can be used, for example, to match a patient's HLA-type. This will permit generation of peptide epitope patterns for different allele combinations.

Example 8. Improved Prediction of Processing and Allele-Specific Binding

NetMHC is an allele-specific method which trains a separate predictor for each allele's binding dataset, and NetMHCpan is pan-allele method whose inputs are vector encodings of both a peptide and a subsequence of a particular MHC molecule. The conventional wisdom is that NetMHC performs better on alleles with many assayed ligands, whereas NetMHCpan performs better for less well-characterized alleles. However, it has been shown that NetMHCpan is not accurate when no relevant data was included in the training sets.

Figures 20A, 20B:
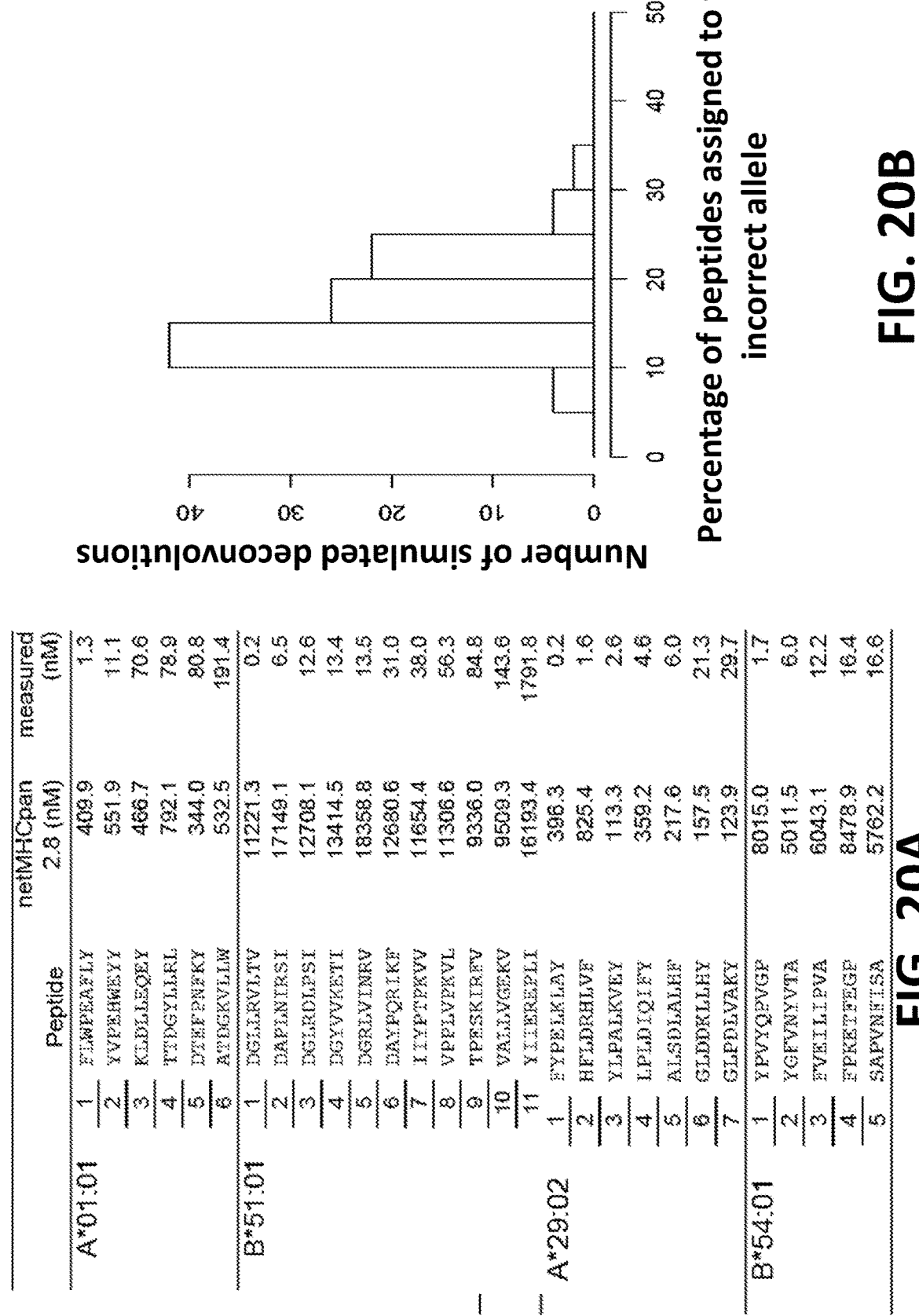
FIG. 20A shows a table of exemplary HLA binding peptides (SEQ ID NOS 9-37, respectively, in order of appearance) for A*01:01, B*51:01, A*29:02, and B*54:01 alleles uncovered using mono-allelic approach. Mono-allelic approach uncovers HLA-binding peptides that are poorly scored by NetMHCpan but biochemically validate as strong binders. As shown in the figure, the peptide sequences shown to exhibit binding to A*01:01 are FLWPEAFLY (SEQ ID NO: 38), YVPEHWEYY (SEQ ID NO: 39), KLDLLEQEY (SEQ ID NO: 40), TTDGYLLRL (SEQ ID NO: 41), DTEFPNFKY (SEQ ID NO: 42), ATDGKVLLW (SEQ ID NO: 43. The peptide sequences shown to exhibit binding to B*51:01 are DGLLRVLTV (SEQ ID NO: 44), DAPLNIRSI (SEQ ID NO: 45), DGLRDLPSI (SEQ ID NO: 46), DGYVVKETI (SEQ ID NO: 47), DGRLVINRV (SQ ID NO; 48), DAYPQRIKF (SEQ ID NO: 49), IIYPTPKVV (SEQ ID NO: 50), VPPLVPKVL (SEQ ID NO: 51), TPESKIRFV (SEQ ID NO: 52), VALLVGEKV (SEQ ID NO: 53), YIIEREPLI (SEQ ID NO: 54). The peptide sequences shown to exhibit binding to A*29:02 are FYPELKLAY (SEQ ID NO: 55), HFLDRHLVF (SEQ ID NO: 56), YLPALKVEY (SEQ ID NO: 57), LPLDIQIFY (SEQ ID NO: 58), ALSDLALHF (SEQ ID NO: 59), GLDDKLLHY (SEQ ID NO: 60), GLPDLVAKY (SEQ ID NO: 61). The peptide sequences shown to exhibit binding to B*54:01 are YPVYQPVGP (SEQ ID NO: 62), YGFVNYVTA (SEQ ID NO: 63), FVEILIPVA (SEQ ID NO: 64), FPKETFEGP (SEQ ID NO: 65), SAPVNFISA (SEQ ID NO: 66).
FIG. 20B is a bar graph showing rates of incorrect assignment in 100 simulated deconvolutions. A random six allele patient HLA genotype (2 alleles each of HLA-A, HLA-B, and HLA-C, sampling at US allele frequencies) was generated. For each allele, 500 peptides from relevant mono-allelic experiment were sampled and combined to create mock 3000 peptide multi-allelic data set. Each peptide was assigned to allele that yields the best NetMHCpan % rank score to determine percentage of peptides incorrectly assigned by NetMHCpan. This process was repeated 100 times.
Figure 21:
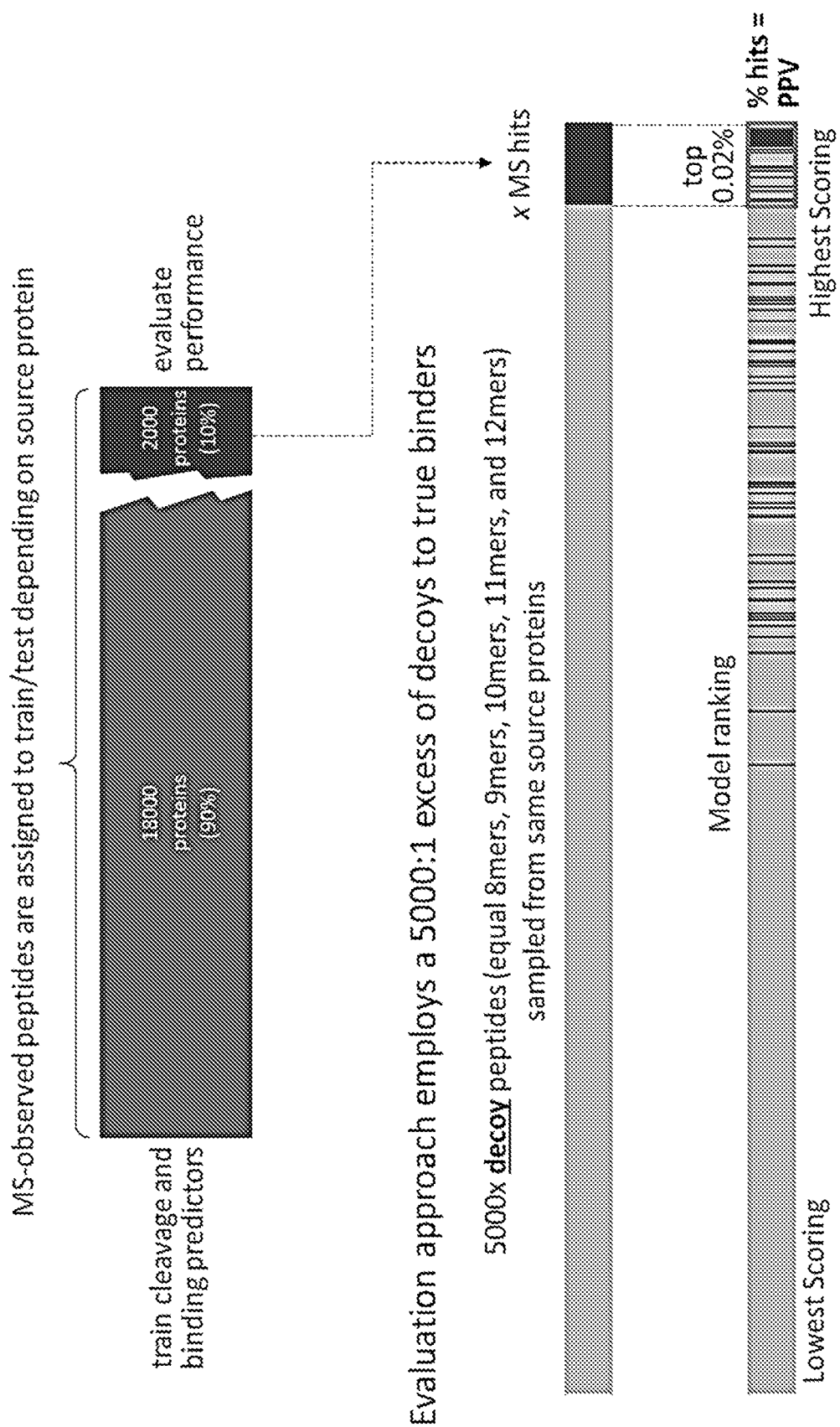
FIG. 21 is a schematic illustration of MHC presentation predictor for diverse individual MHC Class I alleles using MS data. Model training and evaluation are conducted on non-overlapping source proteins. MS-observed peptides are assigned to train/test depending on source protein. Evaluation approach employs a 5000:1 excess of decoys to true binders.
Figure 22:
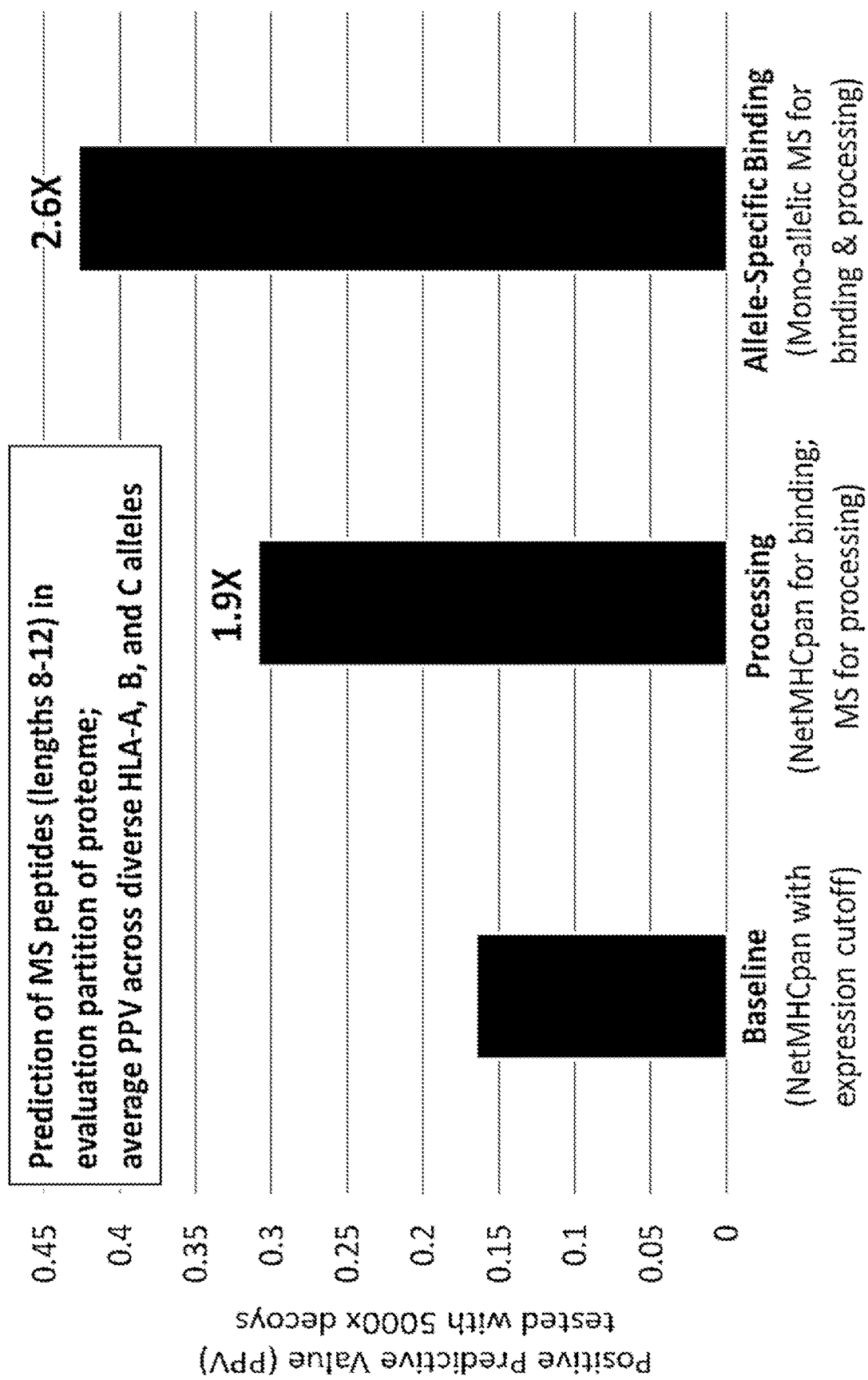
FIG. 22 is a bar graph showing significantly improved predictions both in terms of processing and allele-specific binding.

Mono-allelic approach as described herein (FIG. 21) uncovered HLA-binding peptides that were poorly scored by NetMHCpan but biochemically validated as strong binders. FIG. 20A shows exemplary HLA binding peptides for A*01: 01, B*51:01, A*29:02, and B*54:01 alleles uncovered using the presently described mono-allelic approach. FIG. 20B shows the rates of incorrect assignment in 100 simulated deconvolutions. A random six allele patient HLA genotype (2 alleles each of HLA-A, HLA-B, and HLA-C, sampling at US allele frequencies) was generated. For each allele, 500 peptides from relevant mono-allelic experiment were sampled and combined to create mock 3000 peptide multi-allelic data set. Each peptide was assigned to allele that yields the best NetMHCpan % rank score to determine percentage of peptides incorrectly assigned by NetMHCpan. This process was repeated 100 times. As shown in FIG. 22, both processing and allele-specific binding prediction were significantly improved.

Paragraphs of the Disclosure

Provided herein is a method of characterizing HLA-peptide complexes comprising: providing a population of cells, wherein one or more cells of the population of cells comprise a polynucleic acid comprising a sequence encoding an affinity acceptor tagged class I or class II HLA allele, wherein the sequence encoding an affinity acceptor tagged HLA comprises a sequence encoding a recombinant class I or class II HLA allele operatively linked to a sequence encoding an affinity acceptor peptide; expressing the affinity acceptor tagged HLA in at least one cell of the one or more cells of the population of cells, thereby forming affinity acceptor tagged HLA-peptide complexes in the at least one cell; enriching for the affinity acceptor tagged HLA-peptide complexes; and characterizing HLA-peptide complexes. In some embodiments, the encoded affinity acceptor tagged class I or class II HLA allele is a soluble affinity acceptor tagged class I or class II HLA allele.

In some embodiments, the characterizing comprises characterizing a peptide bound to the affinity acceptor tagged HLA-peptide complex from the enriching. In some embodiments, the method comprises carrying out the steps of the method for two or more class I and/or class II HLA alleles. In some embodiments, the two or more class I and/or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles. In some embodiments, the affinity acceptor tagged HLA-peptide complexes comprise a transmembrane domain. In some embodiments, the affinity acceptor tagged HLA-peptide complexes comprise an intracellular domain. In some embodiments, the affinity acceptor tagged HLA-peptide complexes are not secreted. In some embodiments, the affinity acceptor tagged HLA-peptide complexes incorporate into a cell membrane when expressed. In some embodiments, the affinity acceptor tagged HLA-peptide complexes are soluble affinity acceptor tagged HLA-peptide complexes. In some embodiments, the affinity acceptor tagged HLA-peptide complexes are not soluble affinity acceptor tagged HLA-peptide complexes. In some embodiments, the method further comprises generating an HLA-allele specific peptide database. In some embodiments, the recombinant class I or class II HLA allele is a single recombinant class I or class II HLA allele.

In some embodiments, the method comprises: providing a population of cells each comprising one or more cells comprising an affinity acceptor tagged HLA, wherein the affinity acceptor tagged HLA comprises a different recombinant polypeptide encoded by a different HLA allele operatively linked to an affinity acceptor peptide; enriching for affinity acceptor tagged HLA-peptide complexes; and characterizing a peptide or a portion thereof bound to the affinity acceptor tagged HLA-peptide complex from the enriching.

In some embodiments, the method comprises introducing one or more peptides to the population of cells. In some embodiments, the introducing comprises contacting the population of cells with the one or more peptides or expressing the one or more peptides in the population of cells. In some embodiments, the introducing comprises contacting the population of cells with one or more nucleic acids encoding the one or more peptides. In some embodiments, the one or more nucleic acids encoding the one or more peptides is DNA. In some embodiments, the one or more nucleic acids encoding the one or more peptides is RNA, optionally wherein the RNA is mRNA. In some embodiments, the enriching does not comprise use of a tetramer reagent.

In some embodiments, the characterizing comprises determining the sequence of a peptide or a portion thereof bound to the affinity acceptor tagged HLA-peptide complex from the enriching, optionally determining whether a peptide or a portion thereof is modified. In some embodiments, the determining comprises biochemical analysis, mass spectrometry analysis, MS analysis, MS/MS analysis, LC-MS/MS analysis, or a combination thereof. In some embodiments, the characterizing comprises evaluating a binding affinity or stability of a peptide or a portion thereof bound to the affinity acceptor tagged HLA-peptide complex from the enriching. In some embodiments, the characterizing comprises determining whether a peptide or a portion thereof bound to the affinity acceptor tagged HLA-peptide complex from the enriching contains one or more mutations. In some embodiments, the characterizing comprises evaluating associations of peptides with HLA molecules in the affinity acceptor tagged HLA-peptide complexes.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition. In some embodiments, the library comprises a library of peptides derived from a polypeptide drug, such as a biologic (e.g., an antibody drug).

In some embodiments, the disease or condition is cancer, an infection with an infectious agent, or an autoimmune reaction. In some embodiments, the method comprises introducing the infectious agent or portions thereof into one or more cells of the population of cells. In some embodiments, the method comprises introducing a polypeptide drug, such as a biologic (e.g., an antibody drug) or portions thereof into one or more cells of the population of cells. In some embodiments, the method comprises characterizing one or more peptides from the HLA-peptide complexes, optionally wherein the peptides are from one or more target proteins of the infectious agent or the polypeptide drug. In some embodiments, the method comprises characterizing one or more regions of the peptides from the one or more target proteins of the infectious agent or the polypeptide drug.

In some embodiments, the method comprises identifying peptides from the HLA-peptide complexes derived from an infectious agent. In some embodiments, the population of cells is from a biological sample from a subject with a disease or condition. In some embodiments, the population of cells is a cell line. In some embodiments, the population of cells is a population of primary cells. In some embodiments, the recombinant class I or class II HLA allele is matched to a subject with a disease or condition.

In some embodiments, the peptide from the affinity acceptor tagged HLA-peptide complex is capable of activating a T cell from a subject when presented by an antigen presenting cell. In some embodiments, the characterizing comprises comparing HLA-peptide complexes from cancer cells to HLA-peptide complexes from non-cancer cells. In some embodiments, the population of cells comprises a plurality of populations of cells, each population of cells expressing a different recombinant class I or class II HLA allele. In some embodiments, each population of cells of the plurality is in a same or a separate container.

In some embodiments, the method further comprises isolating peptides from the affinity acceptor tagged HLA-peptide complexes before the characterizing. In some embodiments, an HLA-peptide complex is isolated using an anti-HLA antibody. In some cases, an HLA-peptide complex with or without an affinity tag is isolated using an anti-HLA antibody. In some cases, a soluble HLA (sHLA) with or without an affinity tag is isolated from media of a cell culture. In some cases, a soluble HLA (sHLA) with or without an affinity tag is isolated using an anti-HLA antibody. For example, an HLA, such as a soluble HLA (sHLA) with or without an affinity tag, can be isolated using a bead or column containing an anti-HLA antibody. In some embodiments, the peptides are isolated using anti-HLA antibodies. In some cases, a soluble HLA (sHLA) with or without an affinity tag is isolated using an anti-HLA antibody. In some cases, a soluble HLA (sHLA) with or without an affinity tag is isolated using a column containing an anti-HLA antibody. In some embodiments, the method further comprises removing one or more amino acids from a terminus of a peptide bound to an affinity acceptor tagged HLA-peptide complex.

In some embodiments, the population of cells is a population of low cell surface HLA class I or class II expressing cells. In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles. In some embodiments, the population of cells is a knock-out of all HLA class II alleles. In some embodiments, the population of cells is a knock-out of all HLA class I alleles and a knock-out of all HLA class II alleles. In some embodiments, the sequence encoding the recombinant class I or class II HLA allele encodes a class I HLA. In some embodiments, the class I HLA is selected from the group consisting of HLA-A, HLA-B, HLA-C, HLA-E, HLA-F, and HLA-G. In some embodiments, the sequence encoding the recombinant class I or class II HLA allele encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof. In some embodiments, each sequence encodes at least two different class I and/or class II HLA alleles.

In some embodiments, the at least two different class I and/or class II HLA alleles are each operatively linked to a sequence encoding an affinity acceptor peptide. In some embodiments, the at least two different class I and/or class II HLA alleles are each operatively linked to a sequence encoding a different affinity acceptor peptide. In some embodiments, the at least two different class I and/or class II HLA alleles are each operatively linked to a sequence encoding an affinity acceptor peptide. In some embodiments, one or more of the at least two different class I and/or class II HLA alleles is operatively linked to a sequence encoding a first affinity acceptor peptide and one or more of the at least two different class I and/or class II HLA alleles is operatively linked to a sequence encoding a second affinity acceptor peptide. In some embodiments, the at least two different class I and/or class II HLA alleles are each operatively linked to a sequence encoding a different affinity acceptor peptide. In some embodiments, each of the at least two different class I and/or class II HLA alleles are each operatively linked to a sequence encoding a different affinity acceptor peptide. In some embodiments, the at least two different class I and/or class II HLA alleles are each operatively linked to a sequence encoding an affinity tag. In some embodiments, the method comprises administering at least a second polynucleic acid comprising a sequence encoding a different recombinant HLA allele operatively linked to the same or a different affinity acceptor peptide.

In some embodiments, the sequence encoding the affinity acceptor peptide is operatively linked to a sequence that encodes an extracellular portion of the recombinant class I or class II HLA allele. In some embodiments, the encoded affinity acceptor peptide is expressed extracellularly. In some embodiments, the encoded affinity acceptor peptide is located on an extracellular site of the recombinant class I or class II HLA allele. In some embodiments, the sequence encoding the affinity acceptor peptide is operatively linked to the N-terminus of the sequence encoding the recombinant class I or class II HLA allele. In some embodiments, the sequence encoding the affinity acceptor peptide is operatively linked to a sequence that encodes an intracellular portion of the recombinant class I or class II HLA allele. In some embodiments, the encoded affinity acceptor peptide is expressed intracellularly. In some embodiments, the sequence encoding the affinity acceptor peptide is operatively linked to the C-terminus of the sequence encoding the recombinant class I or class II HLA allele. In some embodiments, the sequence encoding the affinity acceptor peptide is operatively linked to an internal sequence of the sequence encoding the recombinant class I or class II HLA allele, such as a flexible loop sequence. In some embodiments, the sequence encoding the affinity acceptor peptide is operatively linked to the sequence encoding the recombinant class I or class II HLA allele by a linker. In some embodiments, enriching comprises enriching for intact cells expressing the affinity acceptor tagged HLA-peptide complexes. In some embodiments, the method does not comprise lysing the cells before enriching. In some embodiments, the method further comprises lysing the one or more cells before enriching. In some embodiments, enriching comprises contacting an affinity acceptor peptide binding molecule to the affinity acceptor tagged HLA-peptide complexes, wherein the affinity acceptor peptide binding molecule binds specifically to the affinity acceptor peptide.

In some embodiments, the affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, sortase tag, a tag the forms a covalent peptide bond to a bead, or a combination thereof, optionally, wherein the affinity acceptor peptide comprises two or more repeats of a tag sequence.

In some embodiments, the affinity acceptor peptide binding molecule is biotin or an antibody specific to the affinity acceptor peptide. In some embodiments, the enriching comprises contacting an affinity molecule to the affinity acceptor tagged HLA-peptide complexes, wherein the affinity molecule binds specifically to the affinity acceptor peptide binding molecule.

In some embodiments, the affinity molecule comprises a molecule that binds to biotin. For example, the affinity molecule can comprise streptavidin, NeutrAvidin, including protein homologs from other organisms and derivatives thereof.

In some embodiments, enriching comprises immunoprecipitating affinity acceptor tagged HLA-peptide complexes. In some embodiments, the affinity acceptor peptide binding molecule is attached to a solid surface. In some embodiments, the affinity molecule is attached to a solid surface.

In some embodiments, the solid surface is a bead. In some embodiments, enriching comprises immunoprecipitating affinity acceptor tagged HLA-peptide complexes with an affinity acceptor peptide binding molecule that binds specifically to the affinity acceptor peptide.

In some embodiments, the affinity acceptor peptide binding molecule does not specifically interact with the amino acid sequence of the encoded recombinant class I or class II HLA. In some embodiments, enriching comprises contacting an affinity molecule specific to an extracellular portion of the recombinant class I or class II HLA allele. In some embodiments, enriching comprises contacting an affinity molecule specific to an N-terminal portion of the recombinant class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the recombinant class I or class II HLA comprises a sequence encoding a HLA class I α-chain. In some embodiments, the method further comprises expressing a sequence encoding β2 microglobulin in the one or more cells. In some embodiments, the sequence encoding β2 microglobulin is connected to the sequence encoding the HLA class I α-chain. In some embodiments, the sequence encoding β2 microglobulin is connected to the sequence encoding the HLA class I α-chain by a linker. In some embodiments, the sequence encoding β2 microglobulin is connected to a sequence encoding a second affinity acceptor peptide. In some embodiments, the sequence encoding the recombinant class I or class II HLA comprises a sequence encoding a HLA class II α-chain. In some embodiments, the method further comprises expressing a sequence encoding a HLA class II β-chain in the one or more cells. In some embodiments, the sequence encoding the HLA class II β-chain is connected to the sequence encoding the HLA class II α-chain. In some embodiments, the sequence encoding the HLA class II β-chain is connected to the sequence encoding the HLA class II α-chain by a linker. In some embodiments, the sequence encoding the HLA class II β-chain is connected to a sequence encoding a second affinity acceptor peptide.

In some embodiments, the second affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof, optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the determining comprises performing biochemical analysis or mass spectrometry, such as tandem mass spectrometry. In some embodiments, the determining comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides. In some embodiments, the peptide database is a no-enzyme specificity peptide database, such as a without modification database or a with modification database. In some embodiments, the method further comprises searching the peptide database using a reversed-database search strategy.

In some embodiments, the population of cells is a cell line. In some embodiments, the population of cells is a human cell line. In some embodiments, the population of cells is a mouse cell line. In some embodiments, the population of cells is a CHO cell line. In some embodiments, the population of cells is a cell line selected from HEK293T, expi293, HeLa, A375, 721.221, JEG-3, K562, Jurkat, and THP1. In some embodiments, the population of cells is treated with one or more cytokines, checkpoint inhibitors, epigenetically-active drugs, IFN-γ, agents that alter antigen processing (such as peptidase inhibitors, proteasome inhibitors, and TAP inhibitors), or a combination thereof. In some embodiments, the population of cells is treated with one or more reagents that modulate a metabolic pathway or a metabolic status of the cells. In some embodiments, the population of cells is treated with one or more reagents that modulate the cellular proteome of the cells. In some embodiments, the population of cells is treated with one or more reagents that modulate or regulate cellular expression or transcription (e.g. AIRE or a CREB binding protein or modulators thereof) of the cells. In some embodiments, the population of cells is treated with one or more reagents that modulate or regulate a transcription factor of the cells. In some embodiments, the population of cells is treated with one or more reagents that modulate or regulate cellular expression or transcription of an HLA of the cells. In some embodiments, the population of cells is treated with one or more reagents that modulate or regulate cellular expression or transcription of the proteome of the cells.

In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells. In some embodiments, the population of cells is contacted with an agent prior to isolating said HLA-peptide complexes from the one or more cells. In some embodiments, said agent is an inflammatory cytokine, a chemical agent, an adjuvant, a therapeutic agent or radiation.

In some embodiments, the HLA allele is a mutated HLA allele. In some embodiments, the sequence encoding the HLA allele comprises a barcode sequence. In some embodiments, the method further comprises assaying for expression of the affinity acceptor tagged class I or class II HLA allele. In some embodiments, the assaying comprises assaying comprises sequencing an affinity acceptor tagged class I or class II HLA allele, detecting affinity acceptor tagged class I or class II HLA allele RNA, detecting affinity acceptor tagged class I or class II HLA allele protein, or a combination thereof. In some embodiments, assaying for expression can comprise a Western blot assay, fluorescent activated cell sorting (FACS), mass spectrometry (MS), a microarray hybridization assay, an RNA-seq assay, a polymerase chain reaction assay, a LAMP assay, a ligase chain reaction assay, a Southern blot assay, a Northern blot assay, or an enzyme-linked immunosorbent assay (ELISA).

In some embodiments, the method comprises carrying out the steps of the method for different HLA alleles. In some embodiments, each different HLA allele comprises a unique barcode sequence. In some embodiments, each polynucleic acid encoding a different HLA allele comprises a unique barcode sequence.

Provided herein is a HLA-allele specific binding peptide sequence database obtained by carrying out a method described herein. Provided herein is a combination of two or more HLA-allele specific binding peptide sequence databases obtained by carrying out a method described herein repeatedly, each time using a different HLA-allele. Provided herein is a method for generating a prediction algorithm for identifying HLA-allele specific binding peptides, comprising training a machine with a peptide sequence database described herein or a combination described herein.

In some embodiments, the machine combines one or more linear models, support vector machines, decision trees and neural networks. In some embodiments, a variable used to train the machine comprises one or more variables selected from the group consisting of peptide sequence, amino acid physical properties, peptide physical properties, expression level of the source protein of a peptide within a cell, protein stability, protein translation rate, ubiquitination sites, protein degradation rate, translational efficiencies from ribosomal profiling, protein cleavability, protein localization, motifs of host protein that facilitate TAP transport, host protein is subject to autophagy, motifs that favor ribosomal stalling, and protein features that favor NMD.

In some embodiments, the motifs that favor ribosomal stalling comprise polyproline or polylysine stretches. In some embodiments, the protein features that favor NMD are selected from the group consisting of a long 3' UTR, a stop codon greater than 50 nt upstream of last exon:exon junction, and peptide cleavability.

Provided herein is a method for identifying HLA-allele specific binding peptides comprising analyzing the sequence of a peptide with a machine which has been trained with a peptide sequence database obtained by carrying out a method described herein for the HLA-allele. In some embodiments, the method comprises determining the expression level of the source protein of the peptide within a cell; and wherein the source protein expression is a predictive variable used by the machine. In some embodiments, the expression level is determined by measuring the amount of source protein or the amount of RNA encoding said source protein.

Provided herein is a composition comprising a recombinant polynucleic acid comprising two or more sequences each encoding an affinity acceptor tagged HLA, wherein the sequences encoding the affinity acceptor tagged HLAs comprise a sequence encoding a different recombinant HLA class I α-chain allele, a sequence encoding an affinity acceptor peptide, and optionally, a sequence encoding β2 microglobulin; wherein the sequences of (a) and (b), and optionally (c), are operatively linked.

Provided herein is a composition comprising a recombinant polynucleic acid comprising two or more sequences each comprising a sequence encoding an affinity acceptor tagged HLA, wherein the sequences encoding the affinity acceptor tagged HLAs comprise a sequence encoding a recombinant HLA class II α-chain allele, a sequence encoding an affinity acceptor peptide, and optionally, a sequence encoding a HLA class II β-chain; wherein the sequences of (a) and (b), and optionally (c), are operatively linked. In some embodiments, the recombinant polynucleic acid is isolated. In some embodiments, the class I HLA is selected from the group consisting of HLA-A, HLA-B, HLA-C, HLA-E, HLA-F, and HLA-G. In some embodiments, the class II HLA is selected from the group consisting of HLA-DR, HLA-DQ, and HLA-DP.

In some embodiments, the sequence encoding the affinity acceptor peptide is operatively linked to a sequence that encodes for an extracellular portion of the recombinant HLA allele. In some embodiments, the sequence encoding the affinity acceptor molecule is operatively linked to the N-terminus of the sequence encoding the recombinant HLA allele. In some embodiments, the sequence encoding the affinity acceptor peptide is operatively linked to a sequence encoding an intracellular portion of the recombinant HLA allele. In some embodiments, the sequence encoding the affinity acceptor peptide is operatively linked to the C-terminus of the sequence encoding the recombinant HLA allele. In some embodiments, the sequence encoding the affinity acceptor peptide is operatively linked to the sequence encoding the recombinant HLA allele by a linker.

In some embodiments, the two or more sequences encoding an affinity acceptor tagged HLA are expressed from the same polynucleotide. In some embodiments, the two or more sequences encoding an affinity acceptor tagged HLA are expressed from different polynucleotides. In some embodiments, the encoded affinity acceptor peptide binds specifically to an affinity acceptor peptide binding molecule. In some embodiments, the two or more sequences encoding an affinity acceptor tagged HLA comprise two or more affinity acceptor peptides. In some embodiments, the two or more sequences encoding an affinity acceptor tagged HLA comprise three or more sequences encoding an affinity acceptor tagged HLA, wherein at least two of the three or more sequences encoding an affinity acceptor tagged HLA comprises the same affinity acceptor peptide. In some embodiments, the two or more affinity acceptor peptides are unique for each of the two or more sequences encoding an affinity acceptor tagged HLA.

In some embodiments, the encoded affinity acceptor peptide is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof; optionally, wherein the first or second affinity acceptor peptide comprises two or more repeats of a tag sequence.

In some embodiments, the affinity acceptor peptide binding molecule is biotin or an antibody specific to the affinity acceptor peptide. In some embodiments, the affinity acceptor peptide binding molecule binds specifically to an affinity molecule. In some embodiments, the affinity molecule is streptavidin, NeutrAvidin, or a derivative thereof. In some embodiments, the affinity acceptor peptide binding molecule does not specifically interact with an amino acid sequence of the recombinant class I or class II HLA. In some embodiments, for two or more of the recombinant polynucleic acids: the sequence encoding the affinity acceptor tagged HLA is stably integrated into the genome of a cell. In some embodiments, the sequence encoding $\beta 2$ microglobulin or the sequence encoding the HLA class II $\beta$-chain is connected to a sequence encoding a second affinity acceptor peptide. In some embodiments, the second affinity acceptor peptide comprises an HA tag. In some embodiments, the sequence encoding $\beta 2$ microglobulin or the sequence encoding the HLA class II $\beta$-chain is connected to the sequence encoding the recombinant HLA and the affinity acceptor peptide by a linker.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A In some embodiments, the IRES element is selected from common cellular or viral IRES sequences.

Provided herein is a composition comprising two or more isolated polypeptide molecules encoded by the polynucleic acid of a composition described herein. Provided herein is a composition comprising a population of cells comprising two or more polypeptide molecules encoded by the polynucleic acid of a composition described herein. Provided herein is a composition comprising a population of cells comprising a composition described herein. Provided herein is a composition comprising a population of cells comprising one or more cells comprising a composition described herein.

In some embodiments, the population of cells express one or more endogenous class I or class II HLA alleles. In some embodiments, the population of cells are engineered to lack one or more endogenous HLA class I alleles. In some embodiments, the population of cells are engineered to lack endogenous HLA class I alleles. In some embodiments, the population of cells are engineered to lack one or more endogenous HLA class II alleles. In some embodiments, the population of cells are engineered to lack endogenous HLA class II alleles. In some embodiments, the population of cells are engineered to lack one or more endogenous HLA class I alleles and one or more endogenous HLA class II alleles. In some embodiments, the population of cells is a population of low cell surface HLA class I or class II expressing cells. In some embodiments, the composition is formulated using peptides or polynucleic acids encoding peptides specific to an HLA type of a patient. Provided herein is a method of making a cell comprising transducing or transfecting two or more cells with the two or more polynucleic acids of a composition described herein.

Provided herein is a peptide identified according to a method described herein. Provided herein is a method of inducing an anti-tumor response in a mammal comprising administering to the mammal an effective amount of a polynucleic acid comprising a sequence of a peptide described herein. Provided herein is a method of inducing an anti-tumor response in a mammal comprising administering to the mammal an effective amount of a peptide comprising the sequence of a peptide described herein. Provided herein is a method of inducing an anti-tumor response in a mammal comprising administering to the mammal a cell comprising a peptide comprising the sequence of a peptide described herein. Provided herein is a method of inducing an anti-tumor response in a mammal comprising administering to the mammal a cell comprising an effective amount of a polynucleic acid comprising a sequence encoding a peptide comprising the sequence of a peptide described herein. In some embodiments, the cell presents the peptide as an HLA-peptide complex. Provided herein is a method of for inducing an immune response in a mammal comprising administering to the mammal an effective amount of a polynucleic acid comprising a sequence encoding a peptide described herein. Provided herein is a method for inducing an immune response in a mammal comprising administering to the mammal an effective amount of a peptide comprising the sequence of a peptide described herein. Provided herein is a method for inducing an immune response in a mammal comprising administering to the mammal an effective amount of a cell comprising a peptide comprising the sequence of a peptide described herein. Provided herein is a method for inducing an immune response in a mammal comprising administering to the mammal an effective amount of a cell comprising a polynucleic acid comprising a sequence encoding a peptide comprising the sequence of a peptide described herein.

In some embodiments, the immune response is a T cell immune response. In some embodiments, the immune response is a CD8 T cell response. In some embodiments, the immune response is a CD4 T cell response. In some embodiments, the immune response is humoral immune response.

Provided herein is a method for treating a mammal having a disease comprising administering to the mammal an effective amount of a polynucleic acid comprising a sequence encoding a peptide described herein. Provided herein is a method for treating a mammal having a disease comprising administering to the mammal an effective amount of a peptide comprising the sequence of a peptide described herein. Provided herein is a method for treating a mammal having a disease comprising administering to the mammal an effective amount of a cell comprising a peptide comprising the sequence of a peptide described herein. Provided herein is a method for treating a mammal having a disease comprising administering to the mammal an effective amount of a cell comprising a polynucleic acid comprising a sequence encoding a peptide comprising the sequence of a peptide described herein. In some embodiments, the disease is cancer. In some embodiments, the disease is infection by an infectious agent. In some embodiments, the infectious agent is a pathogen, optionally a virus or bacteria, or a parasite.

In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof.

In some embodiments, the bacteria is selected from the group consisting of: *Klebsiella* spp., *Tropheryma whipplei, Mycobacterium leprae, Mycobacterium lepromatosis*, and *Mycobacterium tuberculosis*, typhoid, pneumococcal, meningococcal, *haemophilus* B, anthrax, tetanus toxoid, meningococcal group B, bcg, cholera, and any combination thereof.

In some embodiments, the parasite is a helminth or a protozoan. In some embodiments, the parasite is selected from the group consisting of: *Leishmania* spp., *Plasmodium* spp., *Trypanosoma cruzi, Ascaris lumbricoides, Trichuris trichiura, Necator americanus, Schistosoma* spp., and any combination thereof.

Provided herein is a method of enriching for immunogenic peptides comprising: providing a population of cells comprising one or more cells expressing an affinity acceptor tagged HLA, wherein the affinity acceptor tagged HLA comprises an affinity acceptor peptide operatively linked to a recombinant HLA encoded by a recombinant HLA allele; and enriching for HLA-peptide complexes comprising the affinity acceptor tagged HLA. In some embodiments, the method further comprises determining the sequence of immunogenic peptides isolated from the HLA-peptide complexes. In some embodiments, the determining comprises using LC-MS/MS.

Provided herein is a method of treating a disease or disorder in a subject, the method comprising administering to the subject an effective amount of a polynucleic acid comprising a sequence encoding a peptide described herein. Provided herein is a method of treating a disease or disorder in a subject, the method comprising administering to the subject an effective amount of a peptide comprising the sequence of a peptide described herein. Provided herein is a method of treating a disease or disorder in a subject, the method comprising administering to the subject an effective amount of a cell comprising a peptide comprising the sequence of a peptide described herein. Provided herein is a method of treating a disease or disorder in a subject, the method comprising administering to the subject a cell comprising an effective amount of a polynucleic acid comprising a sequence encoding a peptide comprising the sequence of a peptide described herein.

Provided herein is a method of developing an therapeutic for a subject with a disease or condition comprising providing a population of cells derived from a subject with a disease or condition, expressing in one or more cells of the population of cells an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching and characterizing the affinity acceptor tagged HLA-peptide complexes; and, optionally, developing an therapeutic based on the characterization.

Provided herein is a method of identifying at least one subject specific immunogenic antigen and preparing a subject-specific immunogenic composition that includes the at least one subject specific immunogenic antigen, wherein the subject has a disease and the at least one subject specific immunogenic antigen is specific to the subject and the subject's disease, said method comprising: providing a population of cells derived from a subject with a disease or condition, expressing in one or more cells of the population of cells from the subject, an affinity acceptor tagged class I or class II HLA allele by introducing into the one or more cells a polynucleic acid encoding a sequence comprising: a sequence encoding a recombinant class I or class II HLA allele operatively linked to a sequence encoding an affinity acceptor peptide, thereby forming affinity acceptor tagged HLA-peptide complexes in the one or more cells; enriching affinity acceptor tagged HLA-peptide complexes from the one or more cells; identifying an immunogenic peptide from the enriched affinity acceptor tagged HLA-peptide complexes that is specific to the subject and the subject's disease; and formulating a subject-specific immunogenic composition based one or more of the subject specific immunogenic peptides identified.

In some embodiments, the therapeutic or subject specific immunogenic composition comprises a peptide from the enriched affinity acceptor tagged HLA-peptide complexes or a or a polynucleotide encoding the polypeptide from the enriched affinity acceptor tagged HLA-peptide complexes. In some embodiments, the therapeutic or subject specific immunogenic composition comprises a T cell expressing a T cell receptor (TCR) that specifically binds to the polypeptide from the enriched affinity acceptor tagged HLA-peptide complexes. In some embodiments, the subject specific immunogenic composition comprises a chimeric antigen receptor (CAR) T cell expressing a receptor that specifically binds to the polypeptide from the enriched affinity acceptor tagged HLA-peptide complexes.

In some embodiments, the method further comprises administering another therapeutic agent, optionally, an immune checkpoint inhibitor to the subject. In some embodiments, the method further comprises administering an adjuvant, optionally, poly-ICLC to the subject.

In some embodiments, the disease or disorder is cancer. In some embodiments, the disease or disorder is an autoimmune disease. In some embodiments, the disease or disorder is an infection. In some embodiments, the infection is an infection by an infectious agent. In some embodiments, the infectious agent is a pathogen, a virus, bacteria, or a parasite.

In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T-cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and any combination thereof.

In some embodiments, the bacteria is selected from the group consisting of: *Klebsiella* spp., *Tropheryma whipplei*, *Mycobacterium leprae*, *Mycobacterium lepromatosis*, and *Mycobacterium tuberculosis*, typhoid, pneumococcal, meningococcal, *haemophilus* B, anthrax, tetanus toxoid, meningococcal group B, bcg, cholera, and combinations thereof.

In some embodiments, the parasite is a helminth or a protozoan. In some embodiments, the parasite is selected from the group consisting of: *Leishmania* spp., *Plasmodium* spp., *Trypanosoma cruzi*, *Ascaris lumbricoides*, *Trichuris trichiura*, *Necator americanus*, *Schistosoma* spp., and any combination thereof.

Provided herein is a method of developing a therapeutic for a subject with a disease or condition comprising: providing a population of cells, wherein one or more cells of the population of cells comprise a polynucleic acid comprising a sequence encoding at least two affinity acceptor tagged class I or class II HLA alleles, wherein the sequence encoding the at least two affinity acceptor tagged class I or class II HLAs comprises a first recombinant sequence comprising a sequence encoding a first class I or class II HLA allele operatively linked to a sequence encoding a first affinity acceptor peptide; and a second recombinant sequence comprising a sequence encoding a second class I or class II HLA allele operatively linked to a sequence encoding a second affinity acceptor peptide; expressing the at least two affinity acceptor tagged HLAs in at least one cell of the one or more cells of the population of cells, thereby forming affinity acceptor tagged HLA-peptide complexes in the at least one cell; enriching for the affinity acceptor tagged HLA-peptide complexes; and identifying a peptide from the enriched affinity acceptor tagged HLA-peptide complexes; and formulating an immunogenic composition based one or more of the peptides identified, wherein the first and the second recombinant class I or class II HLA alleles are matched to an HLA haplotype of a subject. In some embodiments, the subject has a disease or condition.

In some embodiments, the first recombinant class I or class II HLA allele is different than the second recombinant class I or class II HLA allele. In some embodiments, the first affinity acceptor peptide is the same as the second affinity acceptor peptide. In some embodiments, the method comprises characterizing a peptide bound to the first and/or second affinity acceptor tagged HLA-peptide complexes from the enriching. In some embodiments, the at least two affinity acceptor tagged class I or class II HLA alleles comprise at least 3, 4, 5, 6, 7, 8, 9, 10, 11, 12, 13, 14, 15, 16, 17, 18, 19, 20, 25, 30, 35, 40, 45, or 50 class I and/or class II HLA alleles. In some embodiments, the first and/or the second affinity acceptor tagged HLA-peptide complexes comprise a transmembrane domain. In some embodiments, the first and/or the second affinity acceptor tagged HLA-peptide complexes comprise an intracellular domain. In some embodiments, the first and/or the second affinity acceptor tagged HLA-peptide complexes are not excreted. In some embodiments, the first and/or the second affinity acceptor tagged HLA-peptide complexes incorporate into a cell membrane when expressed. In some embodiments, the first and/or the second affinity acceptor tagged HLA-peptide complexes are not soluble affinity acceptor tagged HLA-peptide complexes.

In some embodiments, the method further comprises generating an HLA-allele specific peptide database. In some embodiments, the method comprises introducing one or more exogenous peptides to the population of cells. In some embodiments, the introducing comprises contacting the population of cells with the one or more exogenous peptides or expressing the one or more exogenous peptides in the population of cells. In some embodiments, the introducing comprises contacting the population of cells with one or more nucleic acids encoding the one or more exogenous peptides.

In some embodiments, the one or more nucleic acids encoding the one or more peptides is DNA. In some embodiments, the one or more nucleic acids encoding the one or more peptides is RNA, optionally wherein the RNA is mRNA.

In some embodiments, the enriching does not comprise use of a tetramer reagent. In some embodiments, the method comprises determining the sequence of a peptide or a portion thereof bound to the first and/or the second affinity acceptor tagged HLA-peptide complex from the enriching. In some embodiments, the determining comprises biochemical analysis, mass spectrometry analysis, MS analysis, MS/MS analysis, LC-MS/MS analysis, or a combination thereof.

In some embodiments, the method comprises evaluating a binding affinity or stability of a peptide or a portion thereof bound to the first and/or the second affinity acceptor tagged HLA-peptide complex from the enriching. In some embodiments, the method comprises determining whether a peptide or a portion thereof bound to the first and/or the second affinity acceptor tagged HLA-peptide complex from the enriching contains one or more mutations. In some embodiments, the method comprises evaluating associations of peptides with HLA molecules in the first and/or the second affinity acceptor tagged HLA-peptide complex.

In some embodiments, the method comprises expressing a library of peptides in the population of cells, thereby forming a library of affinity acceptor tagged HLA-peptide complexes. In some embodiments, the method comprises contacting to the population of cells a library of peptides or a library of sequences encoding peptides, thereby forming a library of affinity acceptor tagged HLA-peptide complexes. In some embodiments, the library comprises a library of peptides associated with a disease or condition.

In some embodiments, the disease or condition is cancer or an infection with an infectious agent. In some embodiments, the method comprises introducing the infectious agent or portions thereof into one or more cells of the population of cells. In some embodiments, the method comprises characterizing one or more peptides from the first and/or the second HLA-peptide complexes, optionally wherein the peptides are from one or more target proteins of the infectious agent. In some embodiments, the method comprises characterizing one or more regions of the peptides from the one or more target proteins of the infectious agent. In some embodiments, the method comprises identifying peptides from the first and/or the second HLA-peptide complexes derived from an infectious agent.

In some embodiments, the population of cells is from a biological sample from a subject with a disease or condition. In some embodiments, the population of cells is a cell line. In some embodiments, the population of cells is a population of primary cells. In some embodiments, the peptide from the first and/or the second affinity acceptor tagged HLA-peptide complex is capable of activating a T cell from a subject when presented by an antigen presenting cell. In some embodiments, the method comprises comparing HLA-peptide complexes from diseased cells to HLA-peptide complexes from non-diseased cells. In some embodiments, the method further comprises isolating peptides from the first and/or the second affinity acceptor tagged HLA-peptide complexes before the identifying. In some embodiments, the population of cells is a population of low cell surface HLA class I or class II expressing cells.

In some embodiments, the population of cells expresses one or more endogenous HLA alleles. In some embodiments, the population of cells expresses the endogenous HLA alleles normally expressed by the population of cells. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles. In some embodiments, the population of cells is an engineered population of cells lacking endogenous HLA class I alleles and endogenous HLA class II alleles. In some embodiments, the population of cells is a knock-out of one or more HLA class I alleles. In some embodiments, the population of cells is a knock-out of one or more HLA class II alleles. In some embodiments, the population of cells is a knock-out of all HLA class I alleles. In some embodiments, the population of cells is a knock-out of all HLA class II alleles. In some embodiments, the population of cells is a knock-out of all HLA class I alleles and a knock-out of all HLA class II alleles. In some embodiments, the sequence encoding the at least two affinity acceptor tagged class I or class II HLA alleles encodes a class I HLA. In some embodiments, the class I HLA is selected from the group consisting of HLA-A, HLA-B, HLA-C, HLA-E, HLA-F, and HLA-G. In some embodiments, the first recombinant class I or class II HLA allele is a first class I HLA allele and the second recombinant class I or class II HLA allele is a second class I HLA allele. In some embodiments, the sequence encoding the at least two affinity acceptor tagged class I or class II HLA alleles encodes a class II HLA. In some embodiments, the class II HLA is selected from the group consisting of HLA-DR, HLA-DQ, and HLA-DP. In some embodiments, the class II HLA comprises a HLA class II α-chain, a HLA class II β-chain, or a combination thereof. In some embodiments, the first recombinant class I or class II HLA allele is a first class II HLA allele and the second recombinant class I or class II HLA allele is a second class II HLA allele.

In some embodiments, the first sequence and the second sequence are each operatively linked. In some embodiments, the first sequence and the second sequence are comprised on different polynucleotide molecules. In some embodiments, the sequence encoding the first and/or second affinity acceptor peptide is operatively linked to a sequence that encodes an extracellular portion of the first and/or second class I or class II HLA allele. In some embodiments, the first and/or second encoded affinity acceptor peptide is expressed extracellularly. In some embodiments, the sequence encoding the first and/or second affinity acceptor peptide is operatively linked to the N-terminus of the sequence encoding the first and/or second class I or class II HLA allele. In some embodiments, the sequence encoding the first and/or second affinity acceptor peptide is operatively linked to a sequence that encodes an intracellular portion of the first and/or second class I or class II HLA allele. In some embodiments, the encoded first and/or second affinity acceptor peptide is expressed intracellularly. In some embodiments, the sequence encoding the first and/or second affinity acceptor peptide is operatively linked to the C-terminus of the sequence encoding the first and/or second class I or class II HLA allele. In some embodiments, the sequence encoding the first and/or second affinity acceptor peptide is operatively linked to the sequence encoding the first and/or second class I or class II HLA allele by a linker.

In some embodiments, enriching comprises enriching for intact cells expressing the first and/or second affinity acceptor tagged HLA-peptide complexes. In some embodiments, the method does not comprise lysing the cells before enriching. In some embodiments, the method further comprises lysing the one or more cells before enriching. In some embodiments, enriching comprises contacting an affinity acceptor peptide binding molecule to the first and/or second affinity acceptor tagged HLA-peptide complexes, wherein the affinity acceptor peptide binding molecule binds specifically to the first and/or second affinity acceptor peptide.

In some embodiments, the first and/or second affinity acceptor peptide comprises a tag sequence comprising a biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, or a combination thereof; optionally, wherein the first and/or second affinity acceptor peptide comprises two or more repeats of a tag sequence.

In some embodiments, the affinity acceptor peptide binding molecule is biotin or an antibody specific to the first and/or second affinity acceptor peptide. In some embodiments, the enriching comprises contacting an affinity molecule to the first and/or second affinity acceptor tagged HLA-peptide complexes, wherein the affinity molecule binds specifically to the affinity acceptor peptide binding molecule. In some embodiments, the affinity molecule is streptavidin, NeutrAvidin, or a derivative thereof. In some embodiments, enriching comprises immunoprecipitating the first and/or second affinity acceptor tagged HLA-peptide complexes.

In some embodiments, the affinity acceptor peptide binding molecule is attached to a solid surface. In some embodiments, the affinity molecule is attached to a solid surface. In some embodiments, the solid surface is a bead.

In some embodiments, enriching comprises immunoprecipitating the first and/or second affinity acceptor tagged HLA-peptide complexes with an affinity acceptor peptide binding molecule that binds specifically to the first and/or second affinity acceptor peptide. In some embodiments, the affinity acceptor peptide binding molecule does not specifically interact with the amino acid sequence of the encoded first and/or second class I or class II HLA. In some embodiments, enriching comprises contacting an affinity molecule specific to an extracellular portion of the first and/or second class I or class II HLA allele. In some embodiments, enriching comprises contacting an affinity molecule specific to an N-terminal portion of the first and/or second class I or class II HLA allele.

In some embodiments, providing comprises contacting the population of cells with the polynucleic acid. In some embodiments, contacting comprises transfecting or transducing. In some embodiments, providing comprises contacting the population of cells with a vector comprising the polynucleic acid. In some embodiments, the vector is a viral vector. In some embodiments, the polynucleic acid is stably integrated into the genome of the population of cells.

In some embodiments, the sequence encoding the first and/or second class I or class II HLA comprises a sequence encoding a HLA class I α-chain. In some embodiments, the first recombinant class I or class II HLA allele is a first HLA class I α-chain and the second recombinant class I or class II HLA allele is a second HLA class I α-chain.

In some embodiments, the method further comprises expressing a sequence encoding β2 microglobulin in the one or more cells. In some embodiments, the sequence encoding β2 microglobulin is connected to the sequence encoding the first and/or second class I or class II HLA. In some embodiments, the sequence encoding β2 microglobulin is connected to the sequence encoding the first and/or second class I or class II HLA by a linker. In some embodiments, the sequence encoding β2 microglobulin is connected to a sequence encoding a third affinity acceptor peptide.

In some embodiments, the third affinity acceptor peptide is different than the first and/or second affinity acceptor peptide. In some embodiments, the sequence encoding the first and/or second class I or class II HLA comprises a sequence encoding a HLA class II α-chain and/or a HLA class II β-chain. In some embodiments, the sequence encoding the first and/or second class I or class II HLA comprises a sequence encoding a first HLA class II α-chain and a second HLA class II α-chain. In some embodiments, the method further comprises expressing a sequence encoding a HLA class II β-chain in the one or more cells. In some embodiments, the sequence encoding a first HLA class II α-chain and a second HLA class II α-chain HLA is connected to the sequence encoding the HLA class II β-chain. In some embodiments, the sequence encoding the first and/or second class I or class II HLA comprises a sequence encoding a first HLA class II β-chain and a second HLA class II β-chain.

In some embodiments, the method further comprises expressing a sequence encoding a HLA class II α-chain in the one or more cells. In some embodiments, the sequence encoding a first HLA class II β-chain and a second HLA class II β-chain is connected to the sequence encoding the HLA class II α-chain by a linker. In some embodiments, the sequence encoding the HLA class II β-chain or the HLA class II α-chain is connected to a sequence encoding a third affinity acceptor peptide. In some embodiments, the third affinity acceptor peptide is different than the first and/or second affinity acceptor peptide.

In some embodiments, the third affinity acceptor peptide is different than the first affinity acceptor peptide and is selected from the group consisting of biotin acceptor peptide (BAP), poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, Si-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, VSV-G epitope tag, V5 tag, and a combination thereof; optionally, wherein the first or second affinity acceptor peptide comprises two or more repeats of a tag sequence.

In some embodiments, the linker comprises a polynucleic acid sequence encoding a cleavable linker. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences.

In some embodiments, the method comprises performing biochemical analysis or mass spectrometry, such as tandem mass spectrometry. In some embodiments, the method comprises obtaining a peptide sequence that corresponds to an MS/MS spectra of one or more peptides isolated from the enriched affinity acceptor tagged HLA-peptide complexes from a peptide database; wherein one or more sequences obtained identifies the sequence of the one or more peptides.

In some embodiments, the population of cells is a cell line selected from HEK293T, expi293, HeLa, A375, 721.221, JEG-3, K562, Jurkat, and THP1. In some embodiments, the cell line is treated with one or more cytokines, checkpoint inhibitors, epigenetically-active drugs, IFN-γ, or a combination thereof. In some embodiments, the population of cells comprises at least $10^5$ cells, at least $10^6$ cells or at least $10^7$ cells. In some embodiments, the population of cells is a population of dendritic cells, macrophages, cancer cells or B-cells. In some embodiments, the population of cells comprises tumor cells.

In some embodiments, the population of cells is contacted with an agent prior to isolating the first and/or second HLA-peptide complexes from the one or more cells. In some embodiments, the agent is an inflammatory cytokine, a chemical agent, an adjuvant, a therapeutic agent or radiation.

In some embodiments, the first and or second HLA allele is a mutated HLA allele. In some embodiments, the sequence encoding the first and or second HLA allele comprises a barcode sequence. In some embodiments, the method further comprises assaying for expression of the first and/or second affinity acceptor tagged class I or class II HLA allele.

In some embodiments, the assaying comprises sequencing the first and/or second affinity acceptor tagged class I or class II HLA allele, detecting RNA encoding the first and/or second affinity acceptor tagged class I or class II HLA allele RNA, detecting the first and/or second affinity acceptor tagged class I or class II HLA allele protein, or a combination thereof. In some embodiments, the first and second affinity acceptor tagged class I or class II HLA allele comprises a unique barcode sequence. In some embodiments, the first sequence and the second sequence comprise a unique barcode sequence.

What is claimed is:

1. A method of selecting a peptide sequence for producing a pharmaceutical composition, comprising:
 (I) selecting one or more peptide sequences using a machine, wherein selecting one or more peptide sequences using the machine comprises:
  (a) inputting into the machine amino acid sequence information of a set of candidate peptide sequences expressed by cancer cells of a single human subject, wherein the machine comprises a trained machine learning immunoprecipitated HLA-peptide presentation prediction model, wherein the trained machine learning immunoprecipitated HLA-peptide presentation prediction model generates as an output a plurality of presentation predictions based on the amino acid sequence information of the set of candidate peptide sequences, wherein each presentation prediction of the plurality of presentation predictions is indicative of a presentation likelihood that a given peptide sequence of the set of candidate peptide sequences is presented by an MHC protein encoded by an HLA allele of the single human subject, wherein the trained machine learning immunoprecipitated HLA-peptide presentation prediction model has a presentation prediction value (PPV) of at least 0.35 according to a presentation PPV determination method,
  wherein the trained machine learning immunoprecipitated HLA-peptide presentation prediction model comprises:
   (i) a plurality of parameters and
   (ii) a function representing a relation between the amino acid sequence information received as input and the presentation likelihood generated as an output based on the amino acid sequence information and the plurality of parameters; and
  (b) selecting at least one candidate peptide sequence based on the presentation likelihood; and
 (II) producing a pharmaceutical composition comprising a recombinant polypeptide or a polynucleotide encoding the recombinant polypeptide, wherein the recombinant polypeptide comprises the at least one candidate peptide sequence selected from (I)(b) of the set of candidate peptide sequences that is expressed by a cancer cell of the single human subject and is presented by the MHC protein encoded by the HLA allele of the single human subject.

2. The method of claim 1, wherein the MHC protein encoded by the HLA allele of the single human subject is an MHC class I protein.

3. The method of claim 1, wherein the plurality of parameters are based on mono-allelic training data from a set of training cells, each training cell of the set of training cells expressing a recombinant affinity acceptor peptide tagged MHC protein, the mono-allelic training data comprising:
 (1) a plurality of training peptide sequences and a plurality of MHC proteins, wherein each training peptide sequence of the plurality is associated with an identity of an MHC protein of the plurality, wherein the identity of each MHC protein of the plurality is based on an identity of the MHC protein of an immunoprecipitate from a training cell of the set of training cells, wherein the immunoprecipitate comprises an anti-affinity acceptor peptide agent that binds to the affinity acceptor peptide and a recombinant affinity acceptor peptide sequence tagged MHC protein with an affinity acceptor peptide sequence that binds to the anti-affinity acceptor peptide agent, and
 (2) an observation by mass spectrometry that one or more of the training peptide sequences of the plurality was presented by the recombinant affinity acceptor peptide tagged MHC protein of the immunoprecipitated.

4. The method of claim 3, wherein the anti-affinity acceptor peptide agent is biotin.

5. The method of claim 3, wherein the set of training cells do not express multiple endogenous MHC proteins.

6. The method of claim 5, wherein the immunoprecipitate is an immunoprecipitate from lysed training cells.

7. The method of claim 3, wherein the set of training cells are an antigen presenting cell line.

8. The method of claim 3, wherein the plurality of training peptide sequences comprises sequences of endogenous peptides of the set of training cells.

9. The method of claim 3, wherein each candidate peptide sequence of the set of candidate peptide sequences comprises a cancer specific mutation.

10. The method of claim 3, wherein the recombinant affinity acceptor peptide tagged MHC protein comprises an affinity acceptor peptide operably linked to an extracellular portion of the MHC protein.

11. The method of claim 3, wherein the affinity acceptor peptide is a Biotin Acceptor Peptide (BAP).

12. The method of claim 3, wherein the set of training cells express:
 (a) a first recombinant affinity acceptor sequence tagged MHC protein comprising a first MHC molecule and a first affinity acceptor peptide; and
 (b) a second recombinant affinity acceptor sequence tagged MHC protein comprising a second MHC molecule and a second affinity acceptor peptide,
 wherein the first MHC molecule and the second MHC molecule are non-identical; and
 wherein the first affinity acceptor peptide and the second affinity acceptor peptide are non-identical.

13. The method of claim 3, wherein the mono-allelic training data further comprises amino acid physical properties, peptide physical properties, expression level of the source protein of the peptide within a cell, protein stability, protein translation rate, ubiquitination sites, protein degradation rate, translational efficiencies from ribosomal profiling, protein cleavability, protein localization, motifs of host protein that facilitate TAP transport, host proteins subject to autophagy, motifs that favor ribosomal stalling, protein features that favor non-sense mediated degradation (NMD), or any combination thereof.

14. The method of claim 3, wherein one or more training cells of the set of training cells expressing a recombinant affinity acceptor peptide tagged MHC protein further express an endogenous MHC protein that is different from the MHC protein of the recombinant affinity acceptor peptide tagged MHC protein.

15. The method of claim 1, wherein inputting into the machine the amino acid sequence information of the set of candidate peptide sequences expressed by cancer cells of the single human subject comprises inputting into the machine an identity of one or more MHC proteins encoded by one or more HLA alleles of the single human subject.

16. The method of claim 15, wherein the set of candidate peptide sequences expressed by cancer cells of the single human subject comprises peptide sequences encoded by genomic or exomic nucleic acid sequences of the cancer cells of the single human subject that comprise mutations unique to the cancer cells of the single human subject and not present in non-cancer cells of the single human subject.

17. The method of claim 1, wherein the machine displays the plurality of presentation predictions.

18. The method of claim 1, wherein the presentation PPV determination method comprises processing amino acid information of a plurality of test peptide sequences to generate a plurality of test presentation predictions, each test presentation prediction indicative of a presentation likelihood that a test peptide sequence of the plurality of test peptide sequences is presented by an MHC protein expressed in cells,
  wherein the plurality of test peptide sequences comprises at least 5,000 test peptide sequences comprising:
    (i) at least one hit peptide sequence identified by mass spectrometry to be presented by an MHC protein expressed in cells, and
    (ii) at least 4,999 decoy peptide sequences contained within a protein encoded by a genome of a human,
  wherein the plurality of test peptide sequences comprises a ratio of 1:4,999 of the at least one hit peptide sequence to the at least 4,999 decoy peptide sequences, and wherein a top 0.2% of the plurality of test peptide sequences are predicted to be presented by the MHC protein expressed in cells by the trained machine learning immunoprecipitated HLA-peptide presentation prediction model.

19. The method of claim 18, wherein the PPV is more than 0.35 according to the presentation PPV determination method.

20. The method of claim 19, wherein the PPV is more than 0.35 at a recall rate of 10% according to the presentation PPV determination method.

21. The method of claim 19, wherein the PPV is more than 0.35 at a recall rate of 20% according to the presentation PPV determination method.

* * * * *

SEQUENCE LISTING

```
<160> NUMBER OF SEQ ID NOS: 66

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Pro Tyr Asp Val Pro Asp Tyr Ala
1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(15)
<223> OTHER INFORMATION: This sequence may encompass 4-15 residues
<220> FEATURE:
<223> OTHER INFORMATION: See specification as filed for detailed
      description of substitutions and preferred embodiments

<400> SEQUENCE: 2

His His His His His His His His His His His His His His His
1               5                   10                  15

<210> SEQ ID NO 3
<211> LENGTH: 18
<212> TYPE: PRT
<213> ORGANISM: Thosea asigna virus

<400> SEQUENCE: 3

Glu Gly Arg Gly Ser Leu Leu Thr Cys Gly Asp Val Glu Glu Asn Pro
1               5                   10                  15

Gly Pro
```

```
<210> SEQ ID NO 4
<211> LENGTH: 19
<212> TYPE: PRT
<213> ORGANISM: Teschovirus A

<400> SEQUENCE: 4

Ala Thr Asn Phe Ser Leu Leu Lys Gln Ala Gly Asp Val Glu Glu Asn
1               5                   10                  15

Pro Gly Pro

<210> SEQ ID NO 5
<211> LENGTH: 20
<212> TYPE: PRT
<213> ORGANISM: Equine rhinitis A virus

<400> SEQUENCE: 5

Gln Cys Thr Asn Tyr Ala Leu Leu Lys Leu Ala Gly Asp Val Glu Ser
1               5                   10                  15

Asn Pro Gly Pro
            20

<210> SEQ ID NO 6
<211> LENGTH: 22
<212> TYPE: PRT
<213> ORGANISM: Foot-and-mouth disease virus

<400> SEQUENCE: 6

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag"

<400> SEQUENCE: 7

His His His His His His
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Leu Asn Asp Ile Phe Glu Ala Gln Lys Ile Glu Trp His Glu
1               5                   10                  15

<210> SEQ ID NO 9
<211> LENGTH: 9
<212> TYPE: PRT
<213> ORGANISM: Homo sapiens

<400> SEQUENCE: 9

Phe Leu Trp Pro Glu Ala Phe Leu Tyr
1               5
```

```
<210> SEQ ID NO 10
<211> LENGTH: 9
<212> TYPE: PRT
<213> ORGANISM: Homo sapiens

<400> SEQUENCE: 10

Tyr Val Pro Glu His Trp Glu Tyr Tyr
1               5

<210> SEQ ID NO 11
<211> LENGTH: 9
<212> TYPE: PRT
<213> ORGANISM: Homo sapiens

<400> SEQUENCE: 11

Lys Leu Asp Leu Leu Glu Gln Glu Tyr
1               5

<210> SEQ ID NO 12
<211> LENGTH: 9
<212> TYPE: PRT
<213> ORGANISM: Homo sapiens

<400> SEQUENCE: 12

Thr Thr Asp Gly Tyr Leu Leu Arg Leu
1               5

<210> SEQ ID NO 13
<211> LENGTH: 9
<212> TYPE: PRT
<213> ORGANISM: Homo sapiens

<400> SEQUENCE: 13

Asp Thr Glu Phe Pro Asn Phe Lys Tyr
1               5

<210> SEQ ID NO 14
<211> LENGTH: 9
<212> TYPE: PRT
<213> ORGANISM: Homo sapiens

<400> SEQUENCE: 14

Ala Thr Asp Gly Lys Val Leu Leu Trp
1               5

<210> SEQ ID NO 15
<211> LENGTH: 9
<212> TYPE: PRT
<213> ORGANISM: Homo sapiens

<400> SEQUENCE: 15

Asp Gly Leu Leu Arg Val Leu Thr Val
1               5

<210> SEQ ID NO 16
<211> LENGTH: 9
<212> TYPE: PRT
<213> ORGANISM: Homo sapiens

<400> SEQUENCE: 16

Asp Ala Pro Leu Asn Ile Arg Ser Ile
1               5
```

```
<210> SEQ ID NO 17
<211> LENGTH: 9
<212> TYPE: PRT
<213> ORGANISM: Homo sapiens

<400> SEQUENCE: 17

Asp Gly Leu Arg Asp Leu Pro Ser Ile
1               5

<210> SEQ ID NO 18
<211> LENGTH: 9
<212> TYPE: PRT
<213> ORGANISM: Homo sapiens

<400> SEQUENCE: 18

Asp Gly Tyr Val Val Lys Glu Thr Ile
1               5

<210> SEQ ID NO 19
<211> LENGTH: 9
<212> TYPE: PRT
<213> ORGANISM: Homo sapiens

<400> SEQUENCE: 19

Asp Gly Arg Leu Val Ile Asn Arg Val
1               5

<210> SEQ ID NO 20
<211> LENGTH: 9
<212> TYPE: PRT
<213> ORGANISM: Homo sapiens

<400> SEQUENCE: 20

Asp Ala Tyr Pro Gln Arg Ile Lys Phe
1               5

<210> SEQ ID NO 21
<211> LENGTH: 9
<212> TYPE: PRT
<213> ORGANISM: Homo sapiens

<400> SEQUENCE: 21

Ile Ile Tyr Pro Thr Pro Lys Val Val
1               5

<210> SEQ ID NO 22
<211> LENGTH: 9
<212> TYPE: PRT
<213> ORGANISM: Homo sapiens

<400> SEQUENCE: 22

Val Pro Pro Leu Val Pro Lys Val Leu
1               5

<210> SEQ ID NO 23
<211> LENGTH: 9
<212> TYPE: PRT
<213> ORGANISM: Homo sapiens

<400> SEQUENCE: 23

Thr Pro Glu Ser Lys Ile Arg Phe Val
1               5

<210> SEQ ID NO 24
<211> LENGTH: 9
```

```
<212> TYPE: PRT
<213> ORGANISM: Homo sapiens

<400> SEQUENCE: 24

Val Ala Leu Val Gly Glu Lys Val
1               5

<210> SEQ ID NO 25
<211> LENGTH: 9
<212> TYPE: PRT
<213> ORGANISM: Homo sapiens

<400> SEQUENCE: 25

Tyr Ile Ile Glu Arg Glu Pro Leu Ile
1               5

<210> SEQ ID NO 26
<211> LENGTH: 9
<212> TYPE: PRT
<213> ORGANISM: Homo sapiens

<400> SEQUENCE: 26

Phe Tyr Pro Glu Leu Lys Leu Ala Tyr
1               5

<210> SEQ ID NO 27
<211> LENGTH: 9
<212> TYPE: PRT
<213> ORGANISM: Homo sapiens

<400> SEQUENCE: 27

His Phe Leu Asp Arg His Leu Val Phe
1               5

<210> SEQ ID NO 28
<211> LENGTH: 9
<212> TYPE: PRT
<213> ORGANISM: Homo sapiens

<400> SEQUENCE: 28

Tyr Leu Pro Ala Leu Lys Val Glu Tyr
1               5

<210> SEQ ID NO 29
<211> LENGTH: 9
<212> TYPE: PRT
<213> ORGANISM: Homo sapiens

<400> SEQUENCE: 29

Leu Pro Leu Asp Ile Gln Ile Phe Tyr
1               5

<210> SEQ ID NO 30
<211> LENGTH: 9
<212> TYPE: PRT
<213> ORGANISM: Homo sapiens

<400> SEQUENCE: 30

Ala Leu Ser Asp Leu Ala Leu His Phe
1               5

<210> SEQ ID NO 31
<211> LENGTH: 9
<212> TYPE: PRT
<213> ORGANISM: Homo sapiens
```

```
<400> SEQUENCE: 31

Gly Leu Asp Asp Lys Leu Leu His Tyr
1               5

<210> SEQ ID NO 32
<211> LENGTH: 9
<212> TYPE: PRT
<213> ORGANISM: Homo sapiens

<400> SEQUENCE: 32

Gly Leu Pro Asp Leu Val Ala Lys Tyr
1               5

<210> SEQ ID NO 33
<211> LENGTH: 9
<212> TYPE: PRT
<213> ORGANISM: Homo sapiens

<400> SEQUENCE: 33

Tyr Pro Val Tyr Gln Pro Val Gly Pro
1               5

<210> SEQ ID NO 34
<211> LENGTH: 9
<212> TYPE: PRT
<213> ORGANISM: Homo sapiens

<400> SEQUENCE: 34

Tyr Gly Phe Val Asn Tyr Val Thr Ala
1               5

<210> SEQ ID NO 35
<211> LENGTH: 9
<212> TYPE: PRT
<213> ORGANISM: Homo sapiens

<400> SEQUENCE: 35

Phe Val Glu Ile Leu Ile Pro Val Ala
1               5

<210> SEQ ID NO 36
<211> LENGTH: 9
<212> TYPE: PRT
<213> ORGANISM: Homo sapiens

<400> SEQUENCE: 36

Phe Pro Lys Glu Thr Phe Glu Gly Pro
1               5

<210> SEQ ID NO 37
<211> LENGTH: 9
<212> TYPE: PRT
<213> ORGANISM: Homo sapiens

<400> SEQUENCE: 37

Ser Ala Pro Val Asn Phe Ile Ser Ala
1               5

<210> SEQ ID NO 38
<211> LENGTH: 9
<212> TYPE: PRT
<213> ORGANISM: Homo sapiens
```

```
<400> SEQUENCE: 38

Phe Leu Trp Pro Glu Ala Phe Leu Tyr
1               5

<210> SEQ ID NO 39
<211> LENGTH: 9
<212> TYPE: PRT
<213> ORGANISM: Homo sapiens

<400> SEQUENCE: 39

Tyr Val Pro Glu His Trp Glu Tyr Tyr
1               5

<210> SEQ ID NO 40
<211> LENGTH: 9
<212> TYPE: PRT
<213> ORGANISM: Homo sapiens

<400> SEQUENCE: 40

Lys Leu Asp Leu Leu Glu Gln Glu Tyr
1               5

<210> SEQ ID NO 41
<211> LENGTH: 9
<212> TYPE: PRT
<213> ORGANISM: Homo sapiens

<400> SEQUENCE: 41

Thr Thr Asp Gly Tyr Leu Leu Arg Leu
1               5

<210> SEQ ID NO 42
<211> LENGTH: 9
<212> TYPE: PRT
<213> ORGANISM: Homo sapiens

<400> SEQUENCE: 42

Asp Thr Glu Phe Pro Asn Phe Lys Tyr
1               5

<210> SEQ ID NO 43
<211> LENGTH: 9
<212> TYPE: PRT
<213> ORGANISM: Homo sapiens

<400> SEQUENCE: 43

Ala Thr Asp Gly Lys Val Leu Leu Trp
1               5

<210> SEQ ID NO 44
<211> LENGTH: 9
<212> TYPE: PRT
<213> ORGANISM: Homo sapiens

<400> SEQUENCE: 44

Asp Gly Leu Leu Arg Val Leu Thr Val
1               5

<210> SEQ ID NO 45
<211> LENGTH: 9
<212> TYPE: PRT
<213> ORGANISM: Homo sapiens
```

```
<400> SEQUENCE: 45

Asp Ala Pro Leu Asn Ile Arg Ser Ile
1               5

<210> SEQ ID NO 46
<211> LENGTH: 9
<212> TYPE: PRT
<213> ORGANISM: Homo sapiens

<400> SEQUENCE: 46

Asp Gly Leu Arg Asp Leu Pro Ser Ile
1               5

<210> SEQ ID NO 47
<211> LENGTH: 9
<212> TYPE: PRT
<213> ORGANISM: Homo sapiens

<400> SEQUENCE: 47

Asp Gly Tyr Val Val Lys Glu Thr Ile
1               5

<210> SEQ ID NO 48
<211> LENGTH: 9
<212> TYPE: PRT
<213> ORGANISM: Homo sapiens

<400> SEQUENCE: 48

Asp Gly Arg Leu Val Ile Asn Arg Val
1               5

<210> SEQ ID NO 49
<211> LENGTH: 9
<212> TYPE: PRT
<213> ORGANISM: Homo sapiens

<400> SEQUENCE: 49

Asp Ala Tyr Pro Gln Arg Ile Lys Phe
1               5

<210> SEQ ID NO 50
<211> LENGTH: 9
<212> TYPE: PRT
<213> ORGANISM: Homo sapiens

<400> SEQUENCE: 50

Ile Ile Tyr Pro Thr Pro Lys Val Val
1               5

<210> SEQ ID NO 51
<211> LENGTH: 9
<212> TYPE: PRT
<213> ORGANISM: Homo sapiens

<400> SEQUENCE: 51

Val Pro Pro Leu Val Pro Lys Val Leu
1               5

<210> SEQ ID NO 52
<211> LENGTH: 9
<212> TYPE: PRT
<213> ORGANISM: Homo sapiens
```

<400> SEQUENCE: 52

Thr Pro Glu Ser Lys Ile Arg Phe Val
1               5

<210> SEQ ID NO 53
<211> LENGTH: 9
<212> TYPE: PRT
<213> ORGANISM: Homo sapiens

<400> SEQUENCE: 53

Val Ala Leu Leu Val Gly Glu Lys Val
1               5

<210> SEQ ID NO 54
<211> LENGTH: 9
<212> TYPE: PRT
<213> ORGANISM: Homo sapiens

<400> SEQUENCE: 54

Tyr Ile Ile Glu Arg Glu Pro Leu Ile
1               5

<210> SEQ ID NO 55
<211> LENGTH: 9
<212> TYPE: PRT
<213> ORGANISM: Homo sapiens

<400> SEQUENCE: 55

Phe Tyr Pro Glu Leu Lys Leu Ala Tyr
1               5

<210> SEQ ID NO 56
<211> LENGTH: 9
<212> TYPE: PRT
<213> ORGANISM: Homo sapiens

<400> SEQUENCE: 56

His Phe Leu Asp Arg His Leu Val Phe
1               5

<210> SEQ ID NO 57
<211> LENGTH: 9
<212> TYPE: PRT
<213> ORGANISM: Homo sapiens

<400> SEQUENCE: 57

Tyr Leu Pro Ala Leu Lys Val Glu Tyr
1               5

<210> SEQ ID NO 58
<211> LENGTH: 9
<212> TYPE: PRT
<213> ORGANISM: Homo sapiens

<400> SEQUENCE: 58

Leu Pro Leu Asp Ile Gln Ile Phe Tyr
1               5

<210> SEQ ID NO 59
<211> LENGTH: 9
<212> TYPE: PRT
<213> ORGANISM: Homo sapiens

<400> SEQUENCE: 59

Ala Leu Ser Asp Leu Ala Leu His Phe
1               5

<210> SEQ ID NO 60
<211> LENGTH: 9
<212> TYPE: PRT
<213> ORGANISM: Homo sapiens

<400> SEQUENCE: 60

Gly Leu Asp Asp Lys Leu Leu His Tyr
1               5

<210> SEQ ID NO 61
<211> LENGTH: 9
<212> TYPE: PRT
<213> ORGANISM: Homo sapiens

<400> SEQUENCE: 61

Gly Leu Pro Asp Leu Val Ala Lys Tyr
1               5

<210> SEQ ID NO 62
<211> LENGTH: 9
<212> TYPE: PRT
<213> ORGANISM: Homo sapiens

<400> SEQUENCE: 62

Tyr Pro Val Tyr Gln Pro Val Gly Pro
1               5

<210> SEQ ID NO 63
<211> LENGTH: 9
<212> TYPE: PRT
<213> ORGANISM: Homo sapiens

<400> SEQUENCE: 63

Tyr Gly Phe Val Asn Tyr Val Thr Ala
1               5

<210> SEQ ID NO 64
<211> LENGTH: 9
<212> TYPE: PRT
<213> ORGANISM: Homo sapiens

<400> SEQUENCE: 64

Phe Val Glu Ile Leu Ile Pro Val Ala
1               5

<210> SEQ ID NO 65
<211> LENGTH: 9
<212> TYPE: PRT
<213> ORGANISM: Homo sapiens

<400> SEQUENCE: 65

Phe Pro Lys Glu Thr Phe Glu Gly Pro
1               5

<210> SEQ ID NO 66
<211> LENGTH: 9
<212> TYPE: PRT
<213> ORGANISM: Homo sapiens

<400> SEQUENCE: 66

Ser Ala Pro Val Asn Phe Ile Ser Ala
1               5